United States Patent
Beatty et al.

(10) Patent No.: US 12,071,411 B2
(45) Date of Patent: Aug. 27, 2024

(54) INHIBITORS OF HIF-2α AND METHODS OF USE THEREOF

(71) Applicant: ARCUS BIOSCIENCES, INC., Hayward, CA (US)

(72) Inventors: Joel Worley Beatty, San Mateo, CA (US); Samuel Lawrie Drew, Millbrae, CA (US); Matthew Epplin, San Francisco, CA (US); Jeremy Fournier, Fremont, CA (US); Balint Gal, Hayward, CA (US); Clayton Hardman, San Francisco, CA (US); Artur Karenovich Mailyan, Livermore, CA (US); Kenneth Victor Lawson, San Francisco, CA (US); Manmohan Reddy Leleti, Dublin, CA (US); Dongdong Liu, Fremont, CA (US); Guillaume Mata, Berkeley, CA (US); Maša Podunavac, Hayward, CA (US); Jay Patrick Powers, Sisters, OR (US); Brandon Reid Rosen, San Mateo, CA (US); Kai Yu, Hayward, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

(21) Appl. No.: 18/050,557

(22) Filed: Oct. 28, 2022

(65) Prior Publication Data
US 2023/0159466 A1 May 25, 2023

Related U.S. Application Data

(60) Provisional application No. 63/380,221, filed on Oct. 19, 2022, provisional application No. 63/345,120, filed on May 24, 2022, provisional application No. 63/273,283, filed on Oct. 29, 2021.

(51) Int. Cl.
| | | |
|---|---|---|
| *C07D 231/56* | (2006.01) | |
| *C07D 405/04* | (2006.01) | |
| *C07D 405/06* | (2006.01) | |
| *C07D 409/04* | (2006.01) | |
| *C07D 409/06* | (2006.01) | |
| *C07D 413/06* | (2006.01) | |

(52) U.S. Cl.
CPC ......... *C07D 231/56* (2013.01); *C07D 405/04* (2013.01); *C07D 405/06* (2013.01); *C07D 409/04* (2013.01); *C07D 409/06* (2013.01); *C07D 413/06* (2013.01)

(58) Field of Classification Search
CPC .. C07D 231/56; C07D 405/04; C07D 405/06; C07D 409/04; C07D 409/06; C07D 413/06
See application file for complete search history.

(56) References Cited

U.S. PATENT DOCUMENTS

| | | |
|---|---|---|
| 2016/0185777 A1 | 6/2016 | Hartman et al. |
| 2017/0158691 A1 | 6/2017 | Hartman et al. |

FOREIGN PATENT DOCUMENTS

| | | |
|---|---|---|
| WO | 99/06375 A1 | 2/1999 |
| WO | 99/18080 A1 | 4/1999 |
| WO | 00/69846 A1 | 11/2000 |
| WO | 02/20492 A1 | 3/2002 |
| WO | 2010/049366 A1 | 5/2010 |
| WO | 2010/072352 A1 | 7/2010 |
| WO | 2012/087782 A1 | 6/2012 |
| WO | 2015/188369 A1 | 12/2015 |
| WO | 2016/004807 A2 | 1/2016 |
| WO | 2016/144825 A1 | 9/2016 |
| WO | 2021/009566 A1 | 1/2021 |
| WO | 2021/188769 A1 | 9/2021 |
| WO | 2021/249463 A1 | 12/2021 |
| WO | 2022/063115 A1 | 3/2022 |

OTHER PUBLICATIONS

International Search Report and Written Opinion mailed Feb. 10, 2023 corresponding to PCT/US2022/078842 filed Oct. 28, 2022; 12 pages.

*Primary Examiner* — Rebecca L Anderson
(74) *Attorney, Agent, or Firm* — Foley & Lardner LLP; Brittany J. Perla

(57) ABSTRACT

The present disclosure is directed to compounds that are inhibitors of HIF-2α having a structure according to Formula I, and compositions containing those compounds. Methods of using the compounds for the treatment of diseases, disorders, or conditions are also described.

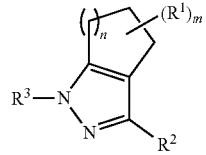

(Formula I)

31 Claims, No Drawings

INHIBITORS OF HIF-2α AND METHODS OF USE THEREOF

CROSS-REFERENCES TO RELATED APPLICATIONS

This application claims the benefit of priority under 35 U.S.C. § 119(e) to U.S. Provisional Application Ser. No. 63/273,283 filed Oct. 29, 2021, 63/345,120 filed May 24, 2022, and 63/380,221 filed Oct. 19, 2022, the disclosure of each of which is incorporated herein by reference in its entirety.

BACKGROUND

The following discussion is provided to aid the reader in understanding the disclosure and is not admitted to describe or constitute prior art thereto.

Hypoxia-inducible factor (HIF) transcription factors play an integral role in cellular response to low oxygen availability. HIFs are heterodimeric transcription factors consisting of a common constitutive subunit called the aryl hydrocarbon receptor nuclear translocator (ARNT, or HIF-β) and one of three HIF-α subunits. Under normal conditions, the α-subunits are hydroxylated at conserved proline residues by prolyl-4-hydroxylases, and subsequently targeted for degradation by the von Hippel-Lindau ubiquitin E3 ligase complex. However, under hypoxic conditions, HIF-α accumulates and enters the nucleus to activate the expression of genes that regulate metabolism, angiogenesis, cell proliferation and survival, immune evasion, and inflammatory response.

Of the three different α-subunit isoforms, HIF-1α, HIF-2α and the less characterized HIF-3α, HIF-1α and HIF-2α overexpression have been associated with poor clinical outcomes in patients with various cancers. Specifically, HIF-2α has been found to be a marker of poor prognosis in glioblastoma, neuroblastoma, head and neck squamous carcinoma, and non-small cell lung cancer. Hypoxia is also prevalent in many acute and chronic inflammatory disorders, such as inflammatory bowel disease and rheumatoid arthritis.

In view of the significant role of HIF-2α in cancer, inflammation and other disorders, there is a need in the art for HIF-2α inhibitors. The present invention addresses this need and provides related advantages as well.

SUMMARY

In one aspect, the present disclosure relates to compounds that inhibit the activity of the hypoxia-inducible factor (HIF) transcription factors, particularly HIF-2α. The compounds are represented by Formula I:

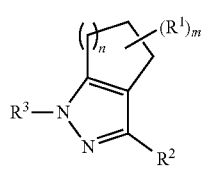

(Formula I)

wherein n, m, $R^1$, $R^2$, and $R^3$ have the meanings provided herein below.

In another aspect, this disclosure is directed to methods of inhibiting HIF-2α function in a subject comprising administering to the subject an effective amount of a compound described herein.

In yet another aspect, this disclosure provides methods for treating a disease, disorder, or condition mediated at least in part by HIF-2α in a subject, comprising administering to the subject a therapeutically effective amount of a HIF-2α inhibitor described herein. Diseases, disorders, and conditions mediated by HIF-2α include Von Hippel-Lindau (VHL) disease, cancer, an immune-related disease, disorder, or condition, an inflammatory-related disease, disorder, or condition, cardiovascular disease, kidney disease, or a metabolic disease. Certain aspects of the present disclosure further comprise the administration of one or more additional therapeutic agents as set forth herein below.

In another aspect, this disclosure is directed to a combination of a HIF-2α inhibitor described herein and one or more additional therapeutic agents.

DETAILED DESCRIPTION OF THE DISCLOSURE

Before the present disclosure is further described, it is to be understood that the disclosure is not limited to the particular embodiments set forth herein, and it is also to be understood that the terminology used herein is for the purpose of describing particular embodiments only, and is not intended to be limiting.

Definitions

Unless otherwise defined, all terms of art, notations and other scientific terms or terminology used herein are intended to have the meanings commonly understood by those of skill in the art to which this disclosure pertains.

The term "about" is used herein has its original meaning of approximately and is to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, if the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "alkyl", by itself or as part of another substituent, means, unless otherwise stated, a saturated monovalent hydrocarbon radical, having, in some embodiments, one to eight (e.g., $C_1$-$C_8$ alkyl), or one to six (e.g., $C_1$-$C_6$ alkyl), or one to three (e.g., $C_1$-$C_3$ alkyl), or two to eight (e.g., $C_2$-$C_8$ alkyl), or two to six (e.g., $C_2$-$C_6$ alkyl), or two to four (e.g., $C_2$-$C_4$ alkyl), or two to three carbon atoms (e.g., $C_2$-$C_3$ alkyl) respectively. The term "alkyl" encompasses straight and branched-chain hydrocarbon groups. Examples of alkyl groups include, but are not limited to, methyl, ethyl, n-propyl, iso-propyl, n-butyl, iso-butyl, tert-butyl, sec-butyl, n-pentyl, 2,2-dimethylpropyl, 3-methylbutyl, sec-pentyl, 2-methylbutyl, iso-hexyl, sec-hexyl, tert-hexyl, and the like. In some embodiments, the alkyl groups are $C_1$-$C_6$ alkyl groups. In some embodiments, the alkyl groups are $C_2$-$C_6$ alkyl groups. In some embodiments, the alkyl groups are $C_1$-$C_3$ alkyl groups.

The term "alkylene" refers to a straight or branched, saturated, hydrocarbon radical having, in some embodiments, one to six (e.g., $C_{1-6}$ alkylene), or one to four (e.g., $C_1$-$C_4$ alkylene), or one to three (e.g., $C_1$-$C_3$ alkylene), or two to three (e.g., $C_2$-$C_3$ alkylene) carbon atoms, and linking at least two other groups, i.e., a divalent hydrocarbon radical. When two moieties are linked to the alkylene they can be linked to the same carbon atom (i.e., geminal), or different carbon atoms of the alkylene group. For instance, a straight chain alkylene can be the bivalent radical of —$(CH_2)_n$—, where n is 1, 2, 3, 4, 5 or 6 (i.e., a $C_1$-$C_6$ alkylene). Representative alkylene groups include, but are not limited to, methylene, ethylene, propylene, iso-propylene, butylene, iso-butylene, sec-butylene, tert-butylene, pentylene, iso-pentylene, sec-pentylene, tert-pentylene, hexylene and the like. In some embodiments, the alkylene groups are $C_1$-$C_3$ alkylene groups (e.g., methylene, ethylene, propylene, and iso-propylene).

As used herein, the term "alkoxy" refers to an alkyl group, as defined herein, that is attached to the remainder of the molecule via an oxygen atom (e.g., —O—($C_1$-$C_{12}$ alkyl), —O—($C_1$-$C_8$ alkyl), —O—($C_1$-$C_6$ alkyl), or —O—($C_1$-$C_3$ alkyl). Non-limiting examples of alkoxy groups include methoxy, ethoxy, n-propoxy, iso-propoxy, n-butoxy, sec-butoxy, n-pentoxy, n-hexoxy, and the like. In some embodiments, the alkoxy is a —O—($C_1$-$C_3$ alkyl) group, e.g., methoxy, ethoxy, n-propoxy, isopropoxy.

The term "cycloalkyl" refers to a monocyclic, bicyclic or polycyclic hydrocarbon ring system having, in some embodiments, 3 to 14 carbon atoms (e.g., $C_3$-$C_{14}$ cycloalkyl), or 3 to 10 carbon atoms (e.g., $C_3$-$C_{10}$ cycloalkyl), or 3 to 8 carbon atoms (e.g., $C_3$-$C_8$ cycloalkyl), or 3 to 6 carbon atoms (e.g., $C_3$-$C_6$ cycloalkyl) or 4 to 6 carbon atoms (e.g., $C_4$-$C_6$ cycloalkyl), or 5 to 6 carbon atoms (e.g., $C_5$-$C_6$ cycloalkyl). Cycloalkyl groups can be saturated or characterized by one or more points of unsaturation (i.e., carbon-carbon double and/or triple bonds), provided that the points of unsaturation do not result in an aromatic system. Examples of monocyclic cycloalkyl groups include, but are not limited to, cyclopropyl, cyclobutyl, cyclopentyl, cyclohexyl, cyclohexenyl, cyclohexynyl, cycloheptyl, cycloheptenyl, cycloheptadienyl, cyclooctyl, cyclooctenyl, cyclooctadienyl and the like. The rings of bicyclic and polycyclic cycloalkyl groups can be fused, bridged, or spirocyclic. Non-limiting examples of bicyclic, spirocyclic and polycyclic hydrocarbon groups include bicyclo[3.1.0]hexane, bicyclo[2.2.1]heptane, bicyclo[2.2.2]octane, adamantyl, indanyl, spiro[5.5]undecane, spiro[2.2]pentane, spiro[2.2]pentadiene, spiro[2.3]hexane, spiro[3.3]heptane, spiro[2.5]octane, spiro[2.2]pentadiene, and the like. In some embodiments, the cycloalkyl groups of the present disclosure are monocyclic $C_3$-$C_6$ cycloalkyl moieties (e.g., cyclopropyl, cyclobutyl, cyclopentyl, or cyclohexyl), or bicyclic $C_6$-$C_8$ cycloalkyl moieties (e.g., spiro[2.3]hexane, spiro[3.3]heptane, or bicyclo[3.1.0]hexane).

The term "heterocycloalkyl" refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 3 to 8 members (e.g., 3- to 8-membered heterocycle), or 3 to 6 members (e.g., 3- to 6-membered heterocycle), or 4 to 6 members (e.g., 4- to 6-membered heterocycle), and having from one to five, one to four, one to three, one to two or one heteroatom selected from nitrogen (N), oxygen (O), and sulfur (S). In some embodiments, the nitrogen and sulfur atoms of the heterocycloalkyl group are optionally oxidized (e.g., N-oxide ($N^+$—$O^-$), sulfoxide (S=O), or sulfone (S(=O)$_2$)), and the nitrogen atom(s) are optionally quaternized. Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, thietane, sulfolane, isothiazolidine, isothiazolidine 1,1-dioxide, pyrrolidine, imidazolidine, pyrazolidine, dioxolane, phthalimide, piperidine, 1,4-dioxane, morpholine, thiomorpholine, thiomorpholine-S-oxide, thiomorpholine-S,S-oxide, piperazine, 3,4,5,6-tetrahydropyridazine, pyran, tetrahydropyran, decahydroisoquinoline, 3-pyrroline, thiopyran, tetrahydrofuran, tetrahydrothiophene, quinuclidine, 2,6-diazaspiro[3.3]heptane, 2-azaspiro[3.3]heptane, 1-oxaspiro[3.3]heptane, 6-azaspiro[3.4]octane, 2-thiaspiro[3.3]heptane 2,2-dioxide, and the like. A heterocycloalkyl group can be attached to the remainder of the molecule through a ring carbon atom, or a ring heteroatom, when chemically permissible. In some embodiments, the heterocycloalkyl groups of the present disclosure are monocyclic 3- to 6-membered heterocycloalkyl moieties, or bicyclic 6- to 8-membered heterocycloalkyl moieties having one or two heteroatom or heteroatom groups selected from N, O, S, S=O and S(=O)$_2$ (e.g., aziridine, oxetane, piperidine, piperazine, morpholine, pyrrolidine, imidazolidine, pyrazolidine, tetrahydrofuran, tetrahydropyran, sulfolane, thietane, thietane 1-oxide, thietane 1,1-dioxide, 2-thiaspiro[3.3]heptane 2,2-dioxide). In some embodiments, the heterocycloalkyl group is a monocyclic 3- to 6-membered heterocycloalkyl moiety, or a bicyclic 6- to 8-membered heterocycloalkyl moiety having one or two heteroatom or heteroatom groups selected from O and S(=O)$_2$, (e.g., oxetane, tetrahydrofuran, tetrahydropyran, sulfolane, thietane 1,1-dioxide, or 2-thiaspiro[3.3]heptane 2,2-dioxide).

The term "heteroaryl" refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two, or one heteroatom selected from nitrogen (N), oxygen (O), sulfur (S). In some embodiments, the nitrogen and sulfur atoms are optionally oxidized (e.g., N-oxide ($N^+$—$O^-$), sulfoxide (S=O), or sulfone (S(=O)$_2$)), and the nitrogen atom(s) are optionally quaternized. A heteroaryl group can be attached to the remainder of the molecule through a carbon atom or a heteroatom of the heteroaryl group, when chemically permissible. Non-limiting examples of heteroaryl groups include pyridyl, pyridazinyl, pyrazinyl, pyrimindinyl, triazinyl, purinyl, thienopyridinyl, thienopyrimidinyl, pyrazolopyrimidinyl, imidazopyridines, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. In some embodiments, the heteroaryl groups of the present disclosure are monocyclic 5- to 6-membered heterocycloalkyl moieties having one to three heteroatoms selected from N, O and S (e.g., pyridinyl, pyrimidinyl, pyridazinyl, triazolyl, imidazolyl, pyrazolyl, oxazolyl, or thiazolyl).

As used herein, a wavy line, "⌇", that intersects a single, double or triple bond in any chemical structure depicted herein, represents that the point of attachment of the single, double, or triple bond to the remainder of the molecule is through either one of the atoms that make up the single, double or triple bond. Additionally, a bond extending from a substituent to the center of a ring (e.g., a phenyl ring) is meant to indicate attachment of that substituent to the ring at any of the available ring vertices, i.e., such that attachment of the substituent to the ring results in a chemically stable arrangement.

The terms "halo" or "halogen," by themselves or as part of another substituent, mean, unless otherwise stated, a fluorine, chlorine, bromine, or iodine atom. Additionally, terms such as "haloalkyl," refer to alkyl groups, as defined herein, that are substituted with one or more halogen(s). For example, the term "$C_1$-$C_6$ haloalkyl" is meant to include trifluoromethyl, difluoromethyl, fluoromethyl, 2,2,2-trifluoroethyl, 4-chlorobutyl, 3-bromopropyl, and the like. In some embodiments, the haloalkyl is a $C_1$-$C_6$ alkyl, or a $C_1$-$C_3$ alkyl substituted with 1-3 halo. In some embodiments, the haloalkyl is —$CF_3$.

The compounds of the present disclosure (e.g., a compound of Formula I, Formula II, Formula IIa, Formula IIa-1, Formula IIb, Formula IIb-1, Formula III, Formula IIIa, Formula IIIa-1, Formula IIIb, Formula IIIb-1, Formula IIIc, Formula IIIc-1, Formula IIId, Formula IIId-1, Formula IIIe, Formula IIIe-1, Formula IIIf, or Formula IIIf-1 as described herein) can be present in their neutral form, or as a pharmaceutically acceptable salt, isomer, polymorph or solvate thereof.

As referred to herein, "pharmaceutically acceptable salt" is meant to include salts of the compounds according to this disclosure that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

The present disclosure contemplates compounds which are in a prodrug form. Prodrugs of the compounds described herein are those compounds that readily undergo chemical changes to provide the compounds of the present disclosure. Generally, a prodrug contains a moiety that is cleaved in vivo resulting in a compound of the present disclosure.

This disclosure also contemplates isomers of the compounds described herein (e.g., stereoisomers). For example, certain compounds of the present disclosure possess asymmetric carbon atoms (chiral centers); the racemates, diastereomers, and enantiomers of which are all intended to be encompassed within the scope of the present disclosure. Stereoisomeric forms may be defined, in terms of absolute stereochemistry, as (R) or (S), and/or depicted uses dashes and/or wedges. When a stereochemical depiction (e.g., using dashes, ⸱⸱⸱⸱⸱⸱⸱⸱⸱⸱⸱, and/or wedges, ▬▬▬▬ ) is shown in a chemical structure, or a stereochemical assignment (e.g., using (R) and (S) notation) is made in a chemical name, it is meant to indicate that the denoted stereoisomer is present and substantially free of one or more other isomer(s) (e.g., enantiomers and diastereomers, when present), unless the context dictates otherwise. "Substantially free of" other isomer(s) indicates at least a 70/30 ratio of the indicated isomer to the other isomer(s), more preferably 80/20, 90/10, or 95/5 or more. In some embodiments, the indicated isomer will be present in an amount of at least 99%. A chemical bond to an asymmetric carbon that is depicted as a solid line (▬▬▬▬▬) indicates that all possible stereoisomers (e.g., stereoisomers identified using a dash or a wedge) at that carbon atom are included. In such instances, the compound may be present as a racemic mixture, scalemic mixture, or a mixture of diastereomers.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere herein. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure. In some embodiments, the compounds according to this disclosure are characterized by one or more deuterium atoms.

The terms "patient" or "subject" are used interchangeably to refer to a human or a non-human animal (e.g., a mammal).

The terms "treat", "treating", treatment" and the like refer to a course of action that eliminates, reduces, suppresses, mitigates, ameliorates, or prevents the worsening of, either temporarily or permanently, a disease, disorder or condition to which the term applies, or at least one of the symptoms associated therewith. Treatment includes alleviation of symptoms, diminishment of extent of disease, inhibiting (e.g., arresting the development or further development of the disease, disorder or condition or clinical symptoms association therewith) an active disease, delaying or slowing of disease progression, improving the quality of life, and/or prolonging survival of a subject as compared to expected survival if not receiving treatment or as compared to a published standard of care therapy for a particular disease.

The term "in need of treatment" as used herein refers to a judgment made by a physician or other caregiver that a subject requires, will require, or will benefit from treatment. This judgment is made based on a variety of factors that are in the realm of the physician's or caregiver's expertise.

The terms "prevent", "preventing", "prevention", "prophylaxis" and the like refer to a course of action initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state. Prevention also refers to a course of action initiated in a subject after the subject has been treated for a disease, disorder, condition or a symptom associated therewith in order to prevent relapse of that disease, disorder, condition or symptom The term "in need of prevention" as used herein refers to a judgment made by a physician or other caregiver that a subject requires or will benefit from preventative care. This judgment is made based on a variety of factors that are in the realm of a physician's or caregiver's expertise. In one embodiment, those in need of prevention may be prone to have the disease, condition or disorder to be prevented due to a genetic predisposition.

The phrase "therapeutically effective amount" or "effective amount" refers to the amount of an agent (e.g., a compound of Formula (I)) that achieves measurable and beneficial effect, such as the amelioration, elimination, reduction or lessening of one or more symptoms associated with a disease, disorder or condition when administered to a subject. A "therapeutically effective amount" also refers to the amount of an agent that is administered to a subject that is capable of reducing, slowing or stopping the progression and/or proliferation of a disease, disorder or condition. The therapeutically effective amount can be ascertained by measuring relevant physiological effects, and it can be adjusted in connection with the dosing regimen and diagnostic analysis of the subject's condition, and the like. By way of example, measurement of the serum level of a compound according to this disclosure (or, e.g., a metabolite thereof) at a particular time post-administration may be indicative of whether a therapeutically effective amount has been used.

The terms "inhibitor of HIF-2α" and "HIF-2α inhibitor" may be used interchangeably, and refer to the ability of a molecule to decrease the function or activity of HIF-2α either directly or indirectly. Inhibitors of HIF-2α may interfere with protein dimerization, thereby decreasing the transcriptional activity of HIF-2α.

"Substantially pure" indicates that a component (e.g., a compound according to this disclosure) makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

Compounds provided herein may have advantageous pharmacokinetic profiles including, for example, hepatocyte stability, clearance, PXR agonism, and inhibition against CYP.

Compounds provided herein may have low serum fold shift values. Serum fold shift values reflect the ratio of the potency (i.e., IC50) against HIF-2α in 100% serum to the potency against HIF-2α in serum free conditions. In one embodiment, the compounds described herein are characterized by a serum fold shift value of less than or equal to about 25, less than or equal to about 24, less than or equal to about 23, less than or equal to about 22, less than or equal to about 21, less than or equal to about 20, such as a serum fold shift value of less than or equal to about 20, less than or equal to about 19, less than or equal to about 18, less than or equal to about 17, less than or equal to about 16, less than or equal to about 15, less than or equal to about 14, less than or equal to about 13, less than or equal to about 12, less than or equal to about 11, less than or equal to about 10, less than or equal to about 9, less than or equal to about 8, less than or equal to about 7, less than or equal to about 6, less than or equal to about 5, less than or equal to about 4, less than or equal to about 3, or less than or equal to about 2. In one embodiment, the serum fold shift value is less than or equal to about 10. In another embodiment, the serum fold shift value is less than or equal to about 5.

Compounds of the Disclosure

The present disclosure relates to compounds that inhibit the activity of the hypoxia-inducible factor (HIF) transcription factors, particularly HIF-2α.

In one aspect, this disclosure is directed to a compound, or a pharmaceutically acceptable salt thereof, having a structure according to Formula I:

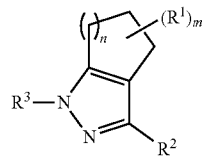

(Formula I)

wherein:
n is 1 or 2;
m is 2, 3, 4, 5, 6, 7, or 8, provided that when n is 1, m is 2, 3, 4, 5, or 6;
each $R^1$ is independently selected from the group consisting of halo, —OH, and —O—($C_1$-$C_3$ alkyl);

R² selected from the group consisting of —C₁-C₆ alkyl, —CN, and —S(O)₂—(C₁-C₃ alkyl), wherein the —C₁-C₆ alkyl and —S(O)₂—(C₁-C₃ alkyl) are substituted with 0-3 halo;

R³ is selected from the group consisting of —C₁-C₂ alkyl substituted with 1-3 R⁴, —C₃-C₆ alkyl, —C₃-C₈ cycloalkyl, -3- to 7-membered heterocycloalkyl having 1-3 heteroatom or heteroatom groups selected from N, O, S, S(═O), and S(═O)₂, —Y—(C₃-C₆ cycloalkyl), —Y—O—(C₃-C₆ cycloalkyl), —Y-(3- to 6-membered heterocycloalkyl) having 1-3 heteroatom or heteroatom groups selected from N, O, S, S(═O), and S(═O)₂, —X-(phenyl), and —Y-(5- to 6-membered heteroaryl) having 1-3 heteroatoms selected from N, O, and S, wherein the —C₃-C₆ alkyl, —C₃-C₆ cycloalkyl, -3- to 7-membered heterocycloalkyl, —Y—(C₃-C₆ cycloalkyl), —Y—O—(C₃-C₆ cycloalkyl), —Y-(3- to 6-membered heterocycloalkyl), —X-(phenyl), and —Y-(5- to 6-membered heteroaryl), are substituted with 0-3 R⁴;

each R⁴ is independently selected from halo, —C₁-C₆ alkyl, —CN, —C₁-C₆ haloalkyl, —OH, —O—(C₁-C₆ alkyl), —Y—O—(C₁-C₆ alkyl), —S—(C₁-C₆ alkyl), —S(O)—(C₁-C₆ alkyl) and —S(O)₂—(C₁-C₆ alkyl), wherein the —O—(C₁-C₆ alkyl), —Y—O—(C₁-C₆ alkyl), —S—(C₁-C₆ alkyl), —S(O)—(C₁-C₆ alkyl) and —S(O)₂—(C₁-C₆ alkyl) are substituted with 0-3 halo;

X is —C₂-C₃ alkylene-; and

Y is —C₁-C₃ alkylene-.

In one aspect, this disclosure is directed to a compound, or a pharmaceutically acceptable salt or solvate thereof, having a structure according to Formula I:

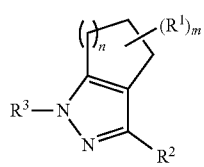

(Formula I)

wherein:

n is 1 or 2;

m is 2, 3, 4, 5, 6, 7, or 8, provided that when n is 1, m is 2, 3, 4, 5, or 6;

each R¹ is independently selected from the group consisting of halo, —OH, and —O—(C₁-C₃ alkyl);

R² selected from the group consisting of —C₁-C₆ alkyl, —CN, and —S(O)₂—(C₁-C₃ alkyl), wherein the —C₁-C₆ alkyl and —S(O)₂—(C₁-C₃ alkyl) are substituted with 0-3 halo;

R³ is selected from the group consisting of —C₁-C₂ alkyl substituted with 1-3 R⁴, —C₃-C₆ alkyl, —C₃-C₆ cycloalkyl, —Y—(C₃-C₆ cycloalkyl), —Y—O—(C₃-C₆ cycloalkyl), —Y-(3- to 6-membered heterocycloalkyl) having 1-3 heteroatom or heteroatom groups selected from N, O, S, S(═O), S(═O)₂, and —Y-(5- to 6-membered heteroaryl) having 1-3 heteroatoms selected from N, O, and S, wherein the —C₃-C₆ alkyl, —C₃-C₆ cycloalkyl, —Y—(C₃-C₆ cycloalkyl), —Y—O—(C₃-C₆ cycloalkyl), —Y-(3- to 6-membered heterocycloalkyl), and —Y-(5- to 6-membered heteroaryl) are substituted with 0-3 R⁴;

each R⁴ is independently selected from halo, —C₁-C₆ alkyl, —CN, —C₁-C₆ haloalkyl, —OH, —O—(C₁-C₆ alkyl), —S—(C₁-C₆ alkyl), and —S(O)₂—(C₁-C₆ alkyl), wherein the —O—(C₁-C₆ alkyl), —S—(C₁-C₆ alkyl), and —S(O)₂—(C₁-C₆ alkyl) are substituted with 0-3 halo; and Y is —C₁-C₃ alkylene-.

In one or more embodiments, this disclosure is directed to a compound according to Formula I, wherein R³ is selected from the group consisting of —C₁-C₂ alkyl substituted with 1-3 R⁴, —C₃-C₆ alkyl, —C₃-C₈ cycloalkyl, -3- to 7-membered heterocycloalkyl having 1-3 heteroatom or heteroatom groups selected from N, O, S, S(═O), and S(═O)₂, —Y—(C₃-C₆ cycloalkyl), —Y—O—(C₃-C₆ cycloalkyl), —Y-(3- to 6-membered heterocycloalkyl) having 1-3 heteroatom or heteroatom groups selected from N, O, S, S(═O), and S(═O)₂, —X-(phenyl), and —Y-(5-membered heteroaryl) having 1-3 heteroatoms selected from N, O, and S, wherein the —C₃-C₆ alkyl, —C₃-C₆ cycloalkyl, -3- to 7-membered heterocycloalkyl, —Y—(C₃-C₆ cycloalkyl), —Y—O—(C₃-C₆ cycloalkyl), —Y-(3- to 6-membered heterocycloalkyl), —X-(phenyl), and —Y-(5-membered heteroaryl), are substituted with 0-3 R⁴.

In some embodiments, m is 2, 3, or 4. In some embodiments, m is 2. In some embodiments, m is 3. In some embodiments, m is 4.

In one or more embodiments, the compound according to Formula I has a structure according to Formula II:

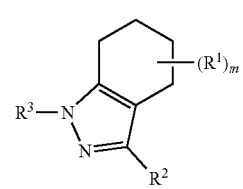

(Formula II)

wherein m, R¹, R², and R³ have the meanings provided for Formula I.

In one or more embodiments, the compound according to Formula I, or Formula II has a structure according to Formula IIa, or Formula IIa-1:

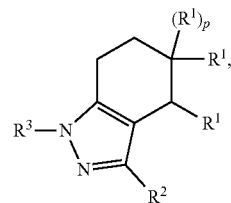

(Formula IIa)

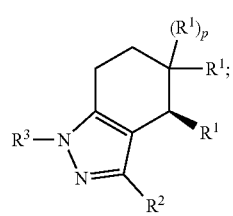

(Formula IIa-1)

wherein p is 0 or 1; and the remainder of the groups have the meanings provided for Formula I.

In some embodiments, the compound of Formula I, Formula II, or Formula IIa has a structure according to Formula IIb or Formula IIb-1:

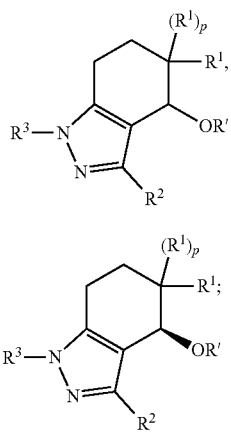

(Formula IIb)

(Formula IIb-1)

wherein: p is 0 or 1; R' is H or —$C_1$-$C_3$ alkyl; and the remainder of the groups have the meanings provided for Formula I.

In some embodiments of the compound of Formula IIb, or Formula IIb-1, R' is H.

In some embodiments of the compound of Formula IIb, or Formula IIb-1, each $R^1$ is halo.

In one or more embodiments, the compound according to Formula I has a structure according to Formula III:

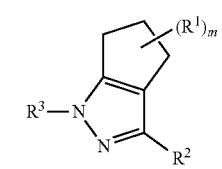

(Formula III)

wherein m, $R^1$, $R^2$, and $R^3$ have the meanings provided for Formula I.

In one or more embodiments, the compound according to Formula I, or Formula III has a structure according to Formula IIIa, or Formula IIIa-1:

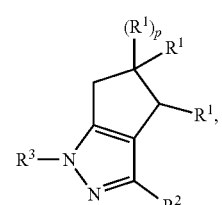

(Formula IIIa)

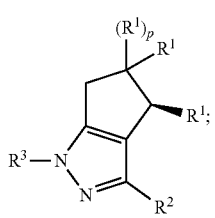

(Formula IIIa-1)

wherein p is 0 or 1, and the remainder of the groups have the meanings provided for Formula I.

In some embodiments, the compound according to Formula I, Formula III, or Formula IIIa has a structure according to Formula IIIb, or Formula IIIb-1:

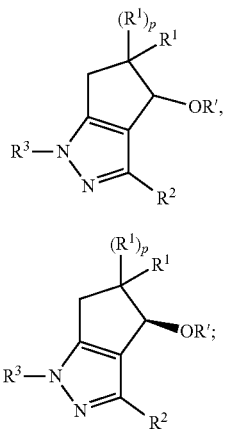

(Formula IIIb)

(Formula IIIb-1)

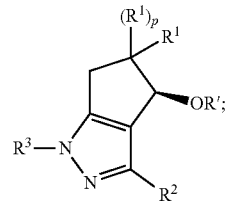

wherein: p is 0 or 1; R' is H or —$C_1$-$C_3$ alkyl; and the remainder of the groups have the meanings provided for Formula I.

In some embodiments, the compound according to Formula I, or Formula III has a structure according to Formula IIIc or Formula IIIc-1:

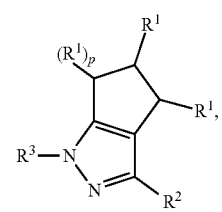

(Formula IIIc)

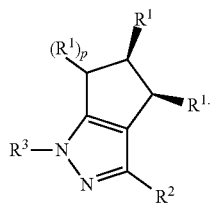

(Formula IIIc-1)

wherein p is 0 or 1, and the remainder of the groups have the meanings provided for Formula I.

In some embodiments, the compound according to Formula I, Formula III, or Formula IIIc has a structure according to Formula IIId or Formula IIId-1:

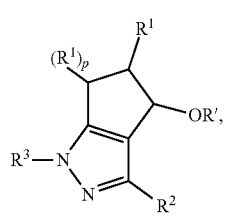

(Formula IIId)

-continued

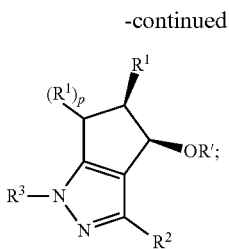

(Formula IIId-1)

wherein: p is 0 or 1; R' is H or —C$_1$-C$_3$ alkyl; and the remainder of the groups have the meanings provided for Formula I.

In some embodiments, the compound according to Formula I, or Formula III has a structure according to Formula IIIe or Formula IIIe-1:

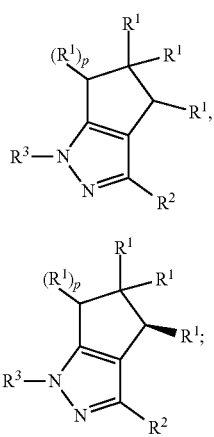

(Formula IIIe)

(Formula IIIe-1)

wherein p is 0 or 1, and the remainder of the groups have the meanings provided for Formula I.

In some embodiments, the compound according to Formula I, or Formula III has a structure according to Formula IIIf or Formula IIIf-1:

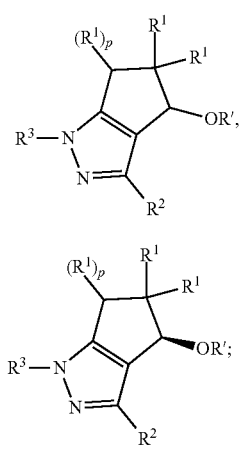

(Formula IIIf)

(Formula IIIf-1)

wherein: p is 0 or 1; R' is H or —C$_1$-C$_3$ alkyl; and the remainder of the groups have the meanings provided for Formula I.

In some embodiments of the compound of Formula IIIb, R' is H.

In some embodiments of the compound of Formula IIIb, each R$^1$ is halo.

In some embodiments of the compound of Formula IIIb, Formula IIIb-1, Formula IIId, Formula IIId-1, Formula IIIf, or Formula IIIf-1, R' is H.

In some embodiments of the compound of Formula IIIb, Formula IIIb-1, Formula IIId, Formula IIId-1, Formula IIIf, or Formula IIIf-1, each R$^1$ is halo.

In some embodiments of the compound of Formula IIa, Formula IIa-1, Formula IIb, Formula IIb-1, Formula IIIa, Formula IIIa-1, Formula IIIb, Formula IIIb-1, Formula IIId, Formula IIId-1, Formula IIIf, or Formula IIIf-1, p is 1.

In one or more embodiments, this disclosure is directed to a compound of Formula I, wherein: each R$^1$ is independently halo or —OH; R$^2$ is —C$_1$-C$_6$ alkyl substituted with 0-3 halo; R$^3$ is —C$_1$-C$_6$ alkyl, —C$_3$-C$_6$ cycloalkyl, or —Y—(C$_3$-C$_6$ cycloalkyl), each of which is substituted with 1-3 R$^4$; each R$^4$ is independently halo, —C$_1$-C$_6$ haloalkyl, —O—(C$_1$-C$_6$ alkyl), —S—(C$_1$-C$_6$ alkyl), or —S(O)$_2$—(C$_1$-C$_6$ alkyl), wherein the —O—(C$_1$-C$_6$ alkyl), —S—(C$_1$-C$_6$ alkyl), and —S(O)$_2$—(C$_1$-C$_6$ alkyl) are substituted with 0-3 halo; and Y is —C$_1$-C$_3$ alkylene-. In some embodiments, R$^2$ is —C$_1$-C$_6$ alkyl substituted with 1-3 halo.

In one or more embodiments, this disclosure is directed to a compound of Formula I, wherein: each R$^1$ is independently halo or —OH; R$^2$ is —C$_1$-C$_6$ alkyl substituted with 0-3 halo; R$^3$ is —C$_1$-C$_6$ alkyl, —C$_3$-C$_8$ cycloalkyl, oxygen containing 6-membered heterocycloalkyl, or —Y—(C$_3$-C$_6$ cycloalkyl), each of which is substituted with 1-3 R$^4$; each R$^4$ is independently halo, —C$_1$-C$_6$ haloalkyl, —O—(C$_1$-C$_6$ alkyl), —Y—O—(C$_1$-C$_6$ alkyl), —S—(C$_1$-C$_6$ alkyl), or —S(O)$_2$—(C$_1$-C$_6$ alkyl), wherein the —O—(C$_1$-C$_6$ alkyl), —Y—O—(C$_1$-C$_6$ alkyl), —S—(C$_1$-C$_6$ alkyl), and —S(O)$_2$—(C$_1$-C$_6$ alkyl) are substituted with 0-3 halo; and Y is —C$_1$-C$_3$ alkylene-.

In some embodiments of the compound of Formula I, each R$^4$ is independently selected from the group consisting of halo, —CN, —O—(C$_1$-C$_3$ alkyl), —S—(C$_1$-C$_3$ alkyl), and —S(O)$_2$—(C$_1$-C$_3$ alkyl), wherein the —O—(C$_1$-C$_3$ alkyl), —S—(C$_1$-C$_3$ alkyl), and —S(O)$_2$—(C$_1$-C$_3$ alkyl) are substituted with 0-3 halo. In some embodiments, each R$^4$ is independently selected from the group consisting of halo, —O—(C$_1$-C$_3$ alkyl), —S—(C$_1$-C$_3$ alkyl), and —S(O)$_2$—(C$_1$-C$_3$ alkyl), wherein the —O—(C$_1$-C$_3$ alkyl), —S—(C$_1$-C$_3$ alkyl), and —S(O)$_2$—(C$_1$-C$_3$ alkyl) are substituted with 0-3 halo, wherein the remaining groups have the meanings provided for Formula I. In some embodiments, each R$^4$ is independently selected from —F, —CN, —OCH$_3$, —OCF$_2$H, —OCF$_3$, —SCF$_3$, and —S(O)$_2$CF$_3$. In some embodiments, each R$^4$ is independently selected from —F, —OCH$_3$, —OCF$_2$H, —OCF$_3$, —SCF$_3$, and —S(O)$_2$CF$_3$. In some embodiments, the compound has a structure according to Formula II, Formula IIa, Formula IIa-1, Formula IIb, or Formula IIb-1.

In some embodiments of the compound of Formula I, each R$^4$ is independently halo, —C$_1$-C$_6$ haloalkyl, —O—(C$_1$-C$_6$ alkyl), or —Y—O—(C$_1$-C$_6$ alkyl), wherein the —O—(C$_1$-C$_6$ alkyl) and —Y—O—(C$_1$-C$_6$ alkyl) are substituted with 0-3 halo, and the remainder groups have the meanings provided for Formula I. In some embodiments each R$^4$ is independently halo, —C$_1$-C$_6$ haloalkyl, or —O—(C$_1$-C$_6$ alkyl) substituted with 0-3 halo. In some embodiments, each R$^4$ is independently —F, —CF$_3$, —OCH$_3$, or —OCF$_3$, or —CH(CH$_3$)—O—CF$_3$. In some embodiments, each R$^4$ is independently —F, —CF$_3$, —OCH$_3$, or —OCF$_3$.

In some embodiments, the compound is a compound of Formula III, IIIa, IIIb, IIIb-1, IIIc, IIIc-1, IIId, IIId-1, IIIe, IIIe-1, IIIf, or IIIf-1.

In some embodiments of the compound of Formula I, $R^3$ is selected from the group consisting of:

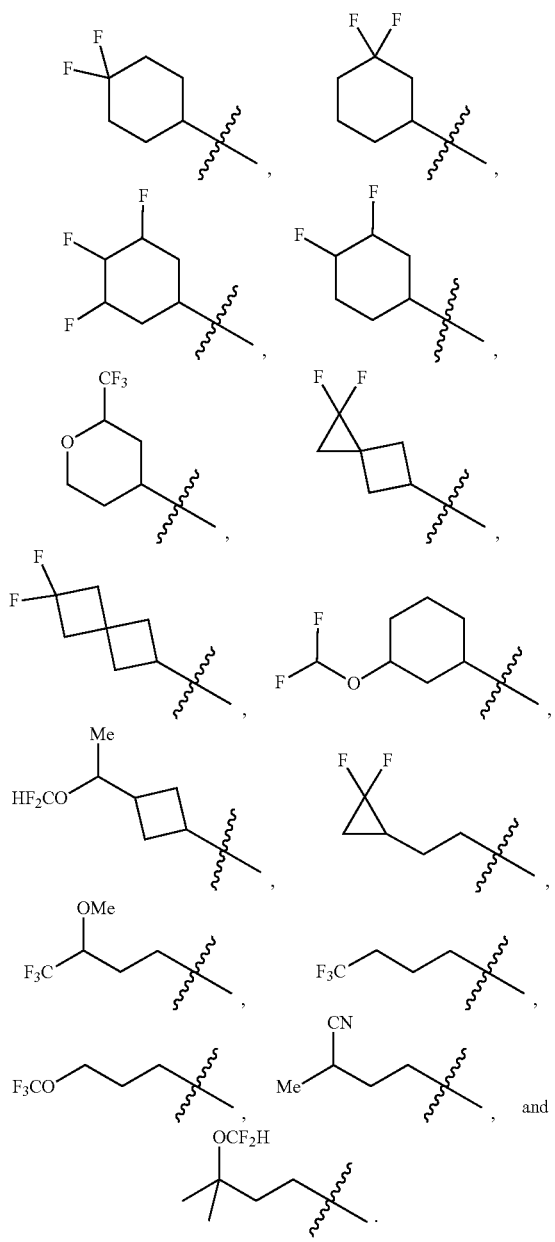

In some embodiments, the compound is a compound of Formula III, IIIa, IIIb, IIIb-1, IIIc, IIIc-1, IIId, IIId-1, IIIe, IIIe-1, IIIf, or IIIf-1.

In one or more embodiments, this disclosure is directed to a compound of Formula I, wherein: each $R^1$ is independently halo or —OH; $R^2$ is —$C_1$-$C_6$ alkyl substituted with 0-3 halo; $R^3$ is —$C_1$-$C_6$ alkyl, —$C_3$-$C_6$ cycloalkyl, or —Y—($C_3$-$C_6$ cycloalkyl), each of which is substituted with 1-3 $R^4$; each $R^4$ is independently selected from halo, —CN, —$C_1$-$C_6$ haloalkyl, —OH, —O—($C_1$-$C_6$ alkyl), and —S(O)$_2$—($C_1$-$C_6$ alkyl), wherein the —O—($C_1$-$C_6$ alkyl), and —S(O)$_2$—($C_1$-$C_6$ alkyl) are substituted with 0-3 halo; and Y is —$C_1$-$C_3$ alkylene-. In some embodiments, $R^2$ is —$C_1$-$C_6$ alkyl substituted with 1-3 halo. In some embodiments, the compound is a compound of Formula III, IIIa, IIIa, IIIb, IIIc, IIId, IIIe, or IIIf.

In one or more embodiments, this disclosure is directed to a compound of Formula I, wherein: each $R^1$ is independently halo or —OH; $R^2$ is —$C_1$-$C_6$ alkyl substituted with 0-3 halo, or —S(O)$_2$—($C_1$-$C_3$ alkyl); $R^3$ is —$C_1$-$C_6$ alkyl, —$C_3$-$C_8$ cycloalkyl, -3- to 7-membered heterocycloalkyl substituted with 1-2 heteroatom or heteroatom groups selected from O and S(=O)$_2$, —Y—($C_3$-$C_6$ cycloalkyl), —Y-(3- to 6-membered heterocycloalkyl) having one heteroatom or heteroatom group selected from O and S(=O)$_2$, —X-(phenyl), or —Y-(5- to 6-membered heteroaryl) having 1-2 heteroatoms selected from N, O, and S, each of which is substituted with 0-3 $R^4$; each $R^4$ is independently selected from halo, —CN, —$C_1$-$C_6$ haloalkyl, —OH, —O—($C_1$-$C_6$ alkyl), —Y—O—($C_1$-$C_6$ alkyl), —S(O)—($C_1$-$C_6$ alkyl), and —S(O)$_2$—($C_1$-$C_6$ alkyl), wherein the —O—($C_1$-$C_6$ alkyl), —Y—O—($C_1$-$C_6$ alkyl), —S(O)—($C_1$-$C_6$ alkyl), and —S(O)$_2$—($C_1$-$C_6$ alkyl) are substituted with 0-3 halo; X is —$C_2$-$C_3$ alkylene-; and Y is —$C_1$-$C_3$ alkylene-. In some embodiments, $R^2$ is —$C_1$-$C_6$ alkyl substituted with 1-3 halo. In some embodiments, the compound is a compound of Formula III, IIIa, IIIb, IIIc, IIId, IIIe, or IIIf.

In one or more embodiments, this disclosure is directed to a compound of Formula I, wherein: each $R^1$ is independently halo or —OH; $R^2$ is —$C_1$-$C_6$ alkyl substituted with 0-3 halo, or —S(O)$_2$—($C_1$-$C_3$ alkyl); $R^3$ is —$C_1$-$C_6$ alkyl substituted with 1-3 $R^4$, —$C_3$-$C_6$ cycloalkyl, 6- to 7-membered heterocycloalkyl having one heteroatom or heteroatom group selected from O and S(=O)$_2$, —$C_1$-$C_2$ alkylene-($C_3$-$C_4$ cycloalkyl), —$C_1$-$C_2$ alkylene-(4- to 5-membered heterocycloalkyl) having 1 heteroatom or heteroatom group selected from O and S(=O)$_2$, —$C_2$-$C_3$ alkylene-(phenyl), and —$C_1$-$C_2$ alkylene-(5-membered heteroaryl) having 1-2 heteroatoms selected from N, O, and S, wherein the —$C_3$-$C_6$ cycloalkyl, -6 to 7-membered heterocycloalkyl, —$C_1$-$C_2$ alkylene-($C_3$-$C_4$ cycloalkyl), —$C_1$-$C_2$ alkylene-(4- to 5-membered heterocycloalkyl), —$C_2$-$C_3$ alkylene-(phenyl), and —$C_1$-$C_2$ alkylene-(5-membered heteroaryl) are substituted with 0-3 $R^4$; each $R^4$ is independently selected from halo, —CN, —$C_1$-$C_6$ haloalkyl, —OH, —O—($C_1$-$C_6$ alkyl), —($C_1$-$C_2$ alkylene)-O—($C_1$-$C_6$ alkyl), —S(O)—($C_1$-$C_6$ alkyl), and —S(O)$_2$—($C_1$-$C_6$ alkyl), wherein the —O—($C_1$-$C_6$ alkyl), —($C_1$-$C_2$ alkylene)-O—($C_1$-$C_6$ alkyl), —S(O)—($C_1$-$C_6$ alkyl), and —S(O)$_2$—($C_1$-$C_6$ alkyl) are substituted with 0-3 halo. In some embodiments, the compound is a compound of Formula III, IIIa, IIIb, IIIc, IIId, IIIe, or IIIf.

In some embodiments of the compound of Formula I, $R^3$ is selected from the group consisting of:

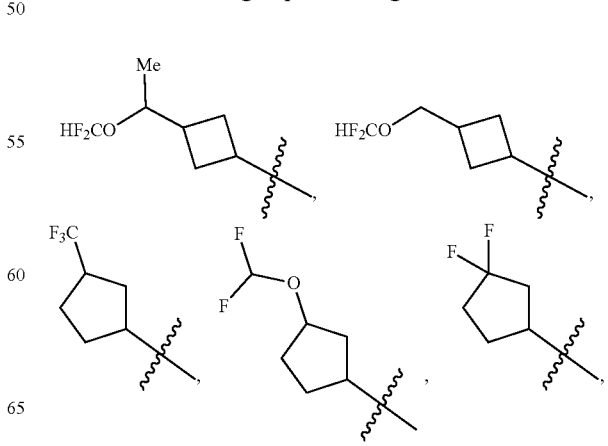

-continued
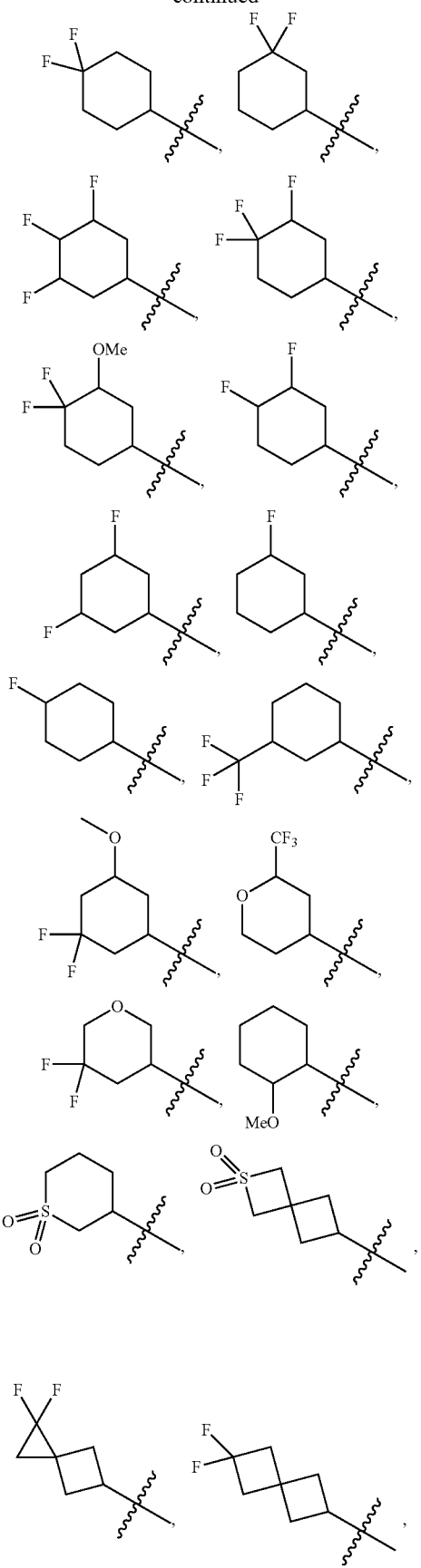
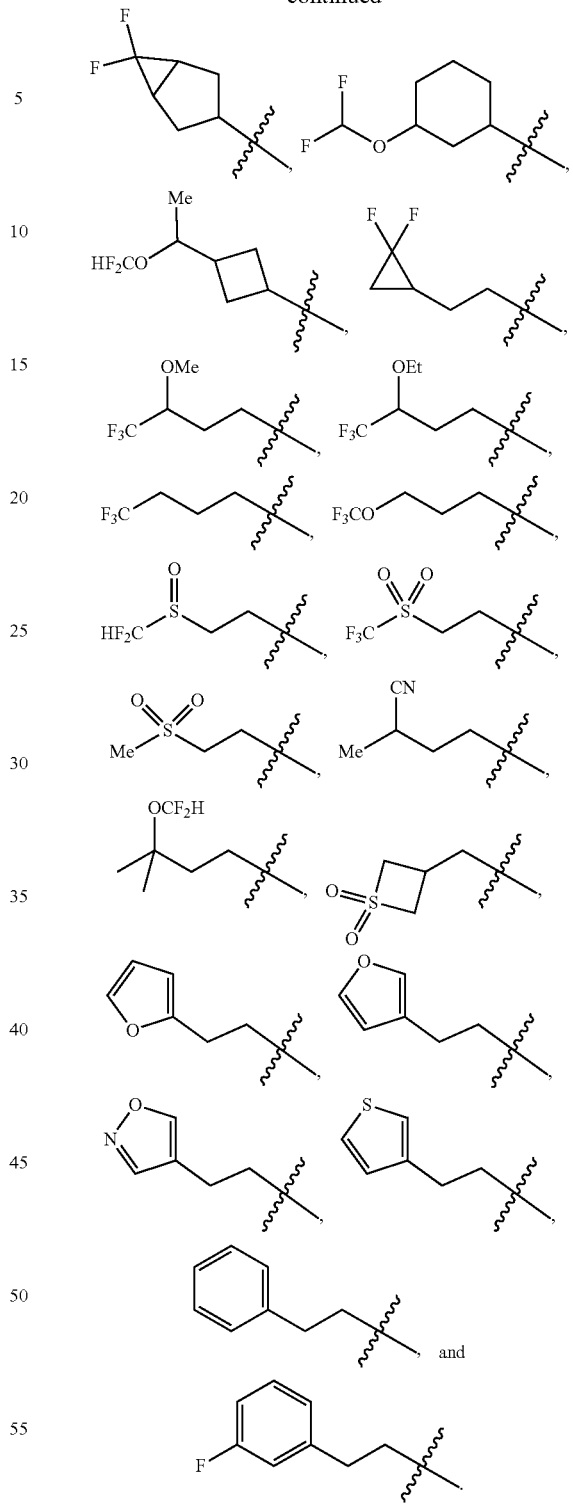
In some embodiments, the compound is a compound of Formula III, IIIa, IIIb, IIIb-1, IIIc, IIIc-1, IIId, IIId-1, IIIe, IIIe-1, IIIf, or IIIf-1.
In some embodiments of the compound of Formula I, $R^3$ is —$C_1$-$C_2$ alkyl substituted with 1-3 $R^4$, or —$C_3$-$C_6$ alkyl substituted with 0-3 $R^4$. In some embodiments, $R^3$ is selected from

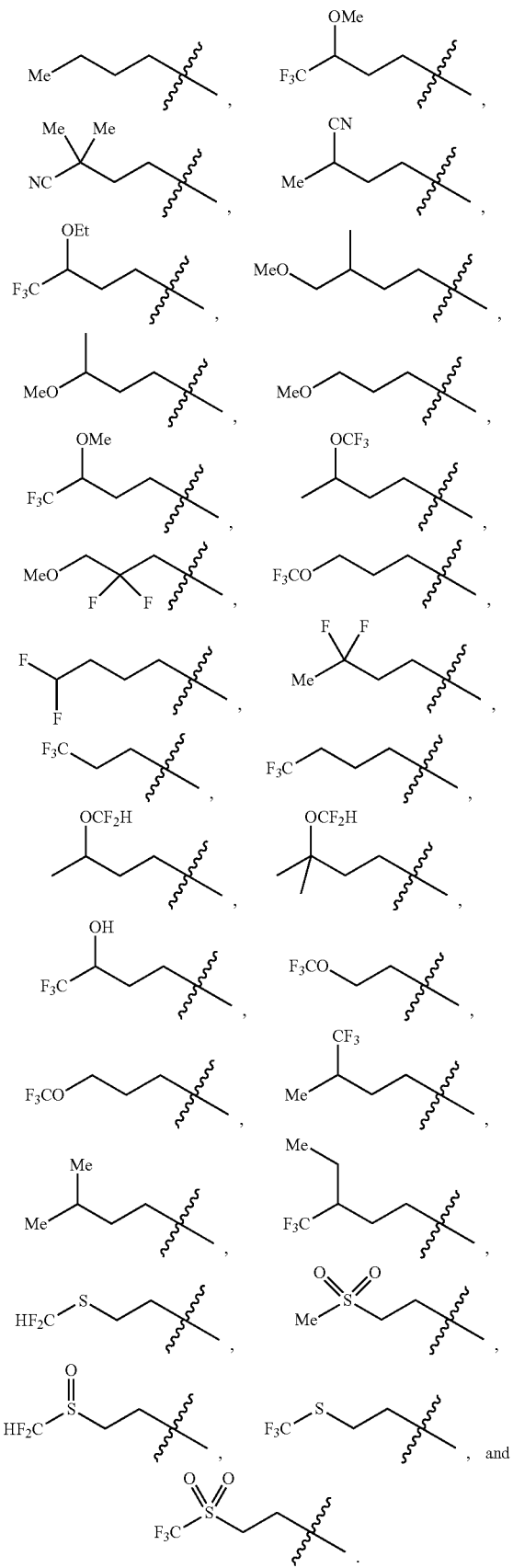
In some embodiments of the compound of Formula I, $R^3$ is —$C_3$-$C_8$ cycloalkyl substituted with 0-3 $R^4$. In some embodiments, $R^3$ is —$C_4$-$C_7$ cycloalkyl substituted with 0-3 $R^4$.
In some embodiments, $R^3$ is selected from the group consisting of
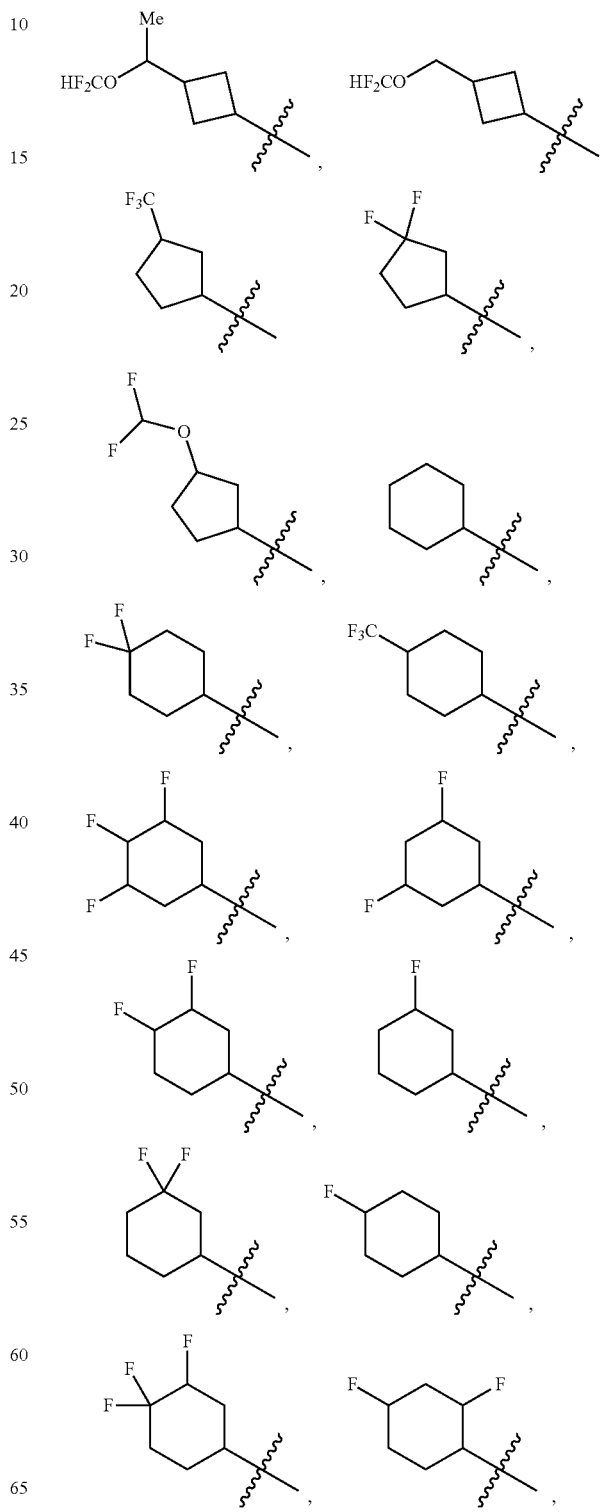

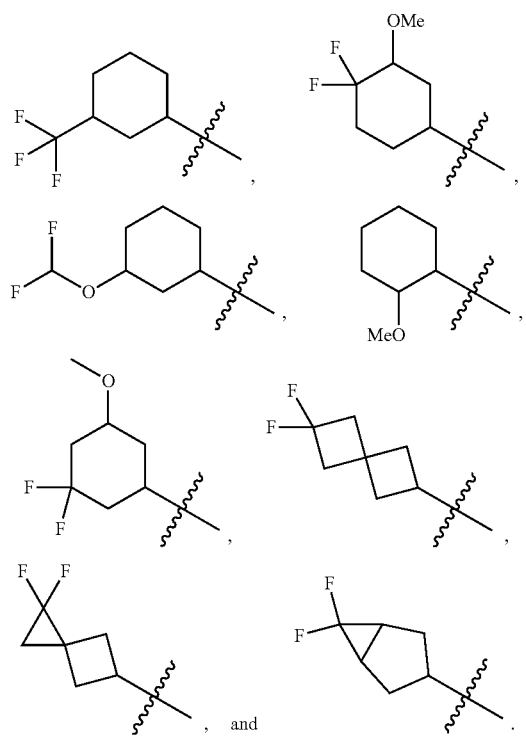

, and

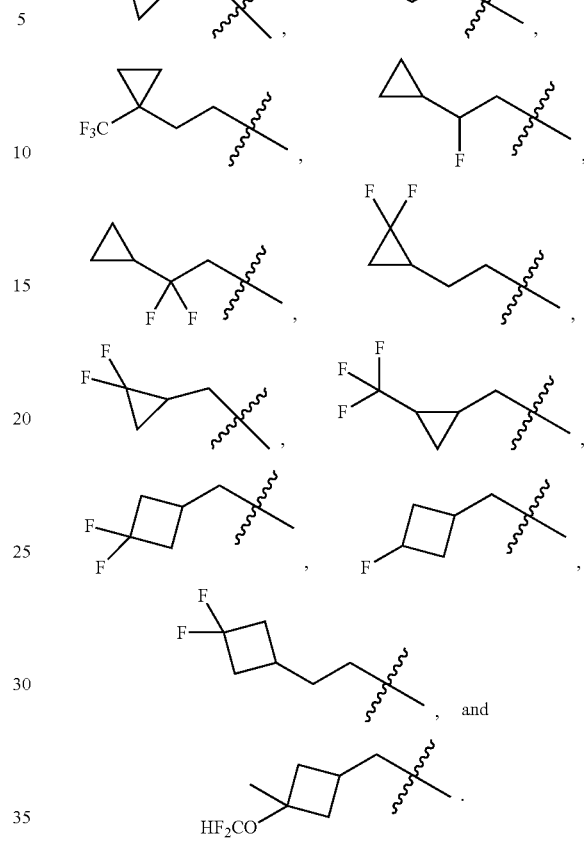

, and

In some embodiments of the compound of Formula I, $R^3$ is a -3- to 7-membered heterocycloalkyl having 1-3 heteroatom or heteroatom groups selected from N, O, S, S(=O), and S(=O)$_2$, wherein said heterocycloalkyl is substituted with 0-3 $R^4$. In some embodiments, $R^3$ is a 6- to 7-membered heterocycloalkyl having one heteroatom or heteroatom group selected from O and S(=O)$_2$, wherein said heterocycloalkyl is substituted with 0-2 $R^4$. In some embodiments, $R^3$ is tetrahydropyranyl substituted with 0-2 $R^4$. In some embodiments, $R^3$ is a 6- to 7-membered heterocycloalkyl selected from the group consisting of

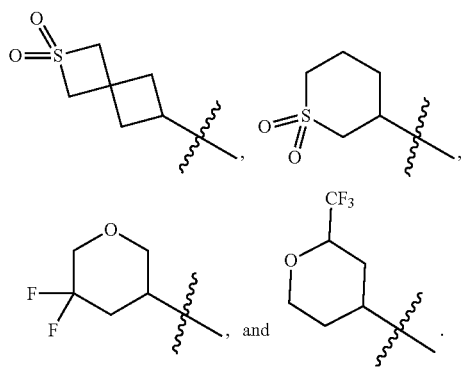

, and

In some embodiments of the compound of Formula I, $R^3$ is —Y—(C$_3$-C$_6$ cycloalkyl) substituted with 0-3 $R^4$, wherein Y is —C$_1$-C$_3$ alkylene-. In some embodiments, $R^3$ is —C$_1$-C$_2$ alkylene-(C$_3$-C$_4$ cycloalkyl) substituted with 0-3 $R^4$. In some embodiments, $R^3$ is —C$_1$-C$_2$ alkylene-(C$_3$-C$_4$ cycloalkyl) substituted with 0-2 $R^4$. In some embodiments, $R^3$ is selected from the group consisting of In some embodiments of the compound of Formula I, $R^3$ is —Y—O—(C$_3$-C$_6$ cycloalkyl) substituted with 0-3 $R^4$, wherein Y is —C$_1$-C$_3$ alkylene-. In some embodiments, $R^3$ is —(C$_2$ alkylene)-O—C$_3$ cycloalkyl substituted with 0-2 $R^4$. In one embodiment, $R^3$ is

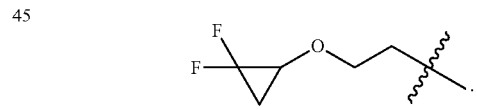

In some embodiments of the compound of Formula I, $R^3$ is —Y-(3- to 6-membered heterocycloalkyl) having 1-3 heteroatom or heteroatom groups selected from N, O, S, S(=O), and S(=O)$_2$, wherein said heterocycloalkyl is substituted with 0-3 $R^4$, and Y is —C$_1$-C$_3$ alkylene-. In some embodiments, $R^3$ is —C$_1$-C$_2$ alkylene-(4- to 5-membered heterocycloalkyl) having 1 heteroatom or heteroatom group selected from O and S(=O)$_2$, wherein said —C$_1$-C$_2$ alkylene-(4- to 5-membered heterocycloalkyl) is substituted with 0-3 R4. In some embodiments, $R^3$ is —C$_1$-C$_2$ alkylene-(4- to 5-membered heterocycloalkyl) having 1 heteroatom or heteroatom group selected from O and S(=O)$_2$, wherein said —C$_1$-C$_2$ alkylene-(4- to 5-membered heterocycloalkyl) is substituted with 0-1 $R^4$. In some embodiments, $R^3$ is selected from the group consisting of

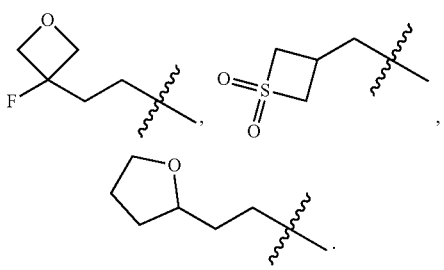

In some embodiments of the compound of Formula I, $R^3$ is —X-(phenyl) substituted with 0-3 $R^4$, wherein X is —$C_2$-$C_3$ alkylene-. In some embodiments, $R^3$ is —$C_2$-$C_3$ alkylene-(phenyl) substituted with 0-3 $R^4$. In some embodiments, $R^3$ is —$C_2$-$C_3$ alkylene-(phenyl) substituted with 0-1 $R^4$. In some embodiments, $R^3$ is

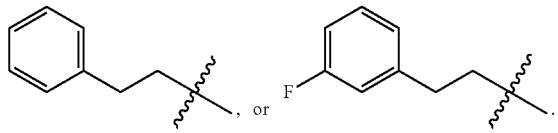 [SMILES: *CCc1ccccc1 ; *CCc1cccc(F)c1]

In some embodiments of the compound of Formula I, $R^3$ is —Y-(5- to 6-membered heteroaryl) having 1-3 heteroatoms selected from N, O, and S, wherein said —Y-(5- to 6-membered heteroaryl) is substituted with 0-3 $R^4$, and Y is —$C_1$-$C_3$ alkylene. In some embodiments, $R^3$ is —$C_1$-$C_2$ alkylene-(5-membered heteroaryl) having 1-2 heteroatoms selected from N, O, and S, wherein said heteroaryl is substituted with 0-3 $R^4$. In some embodiments, $R^3$ is —$C_1$-$C_2$ alkylene-(5-membered heteroaryl) having 1-2 heteroatoms selected from N, O, and S, wherein said heteroaryl is substituted with 0-1 $R^4$. In some embodiments, $R^3$ is

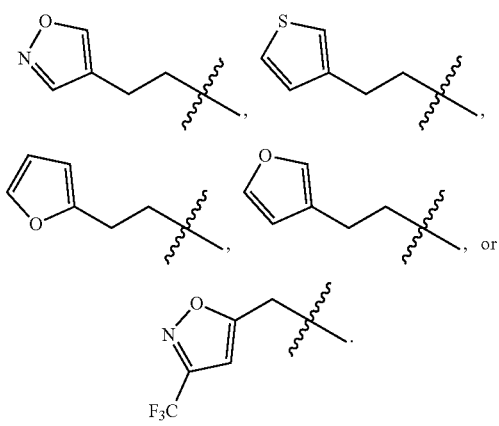

In some embodiments of the compound of Formula I, $R^3$ is phenyl or 5- to 6-membered heteroaryl having 1-2 heteroatoms selected from N, O, and S, wherein said phenyl or 5- to 6-membered heteroaryl are substituted with 0-3 $R^4$. In some embodiments, $R^3$ is phenyl or pyridyl substituted with 0-2 $R^4$. In some embodiments, $R^3$ is

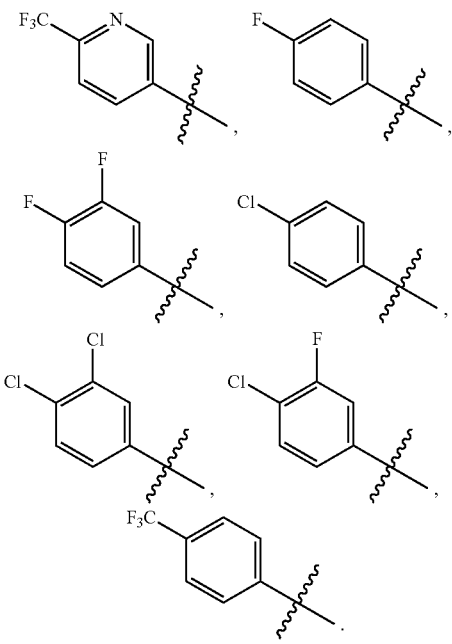

In one or more embodiments of the compound of Formula I, $R^2$ is —$CF_3$.

In one or more embodiments of the compound of Formula I, at least one $R^1$ is —F.

In one or more embodiments of the compound of Formula I, at least one $R^1$ is —OH.

In some embodiments, the compound of Formula I has a structure according to Formula II, Formula IIa, Formula IIa-1, Formula IIb, Formula IIb-1, Formula III, Formula IIIa, Formula IIIa-1, Formula IIIb, Formula IIIb-1, Formula IIIc, Formula IIIc-1, Formula IIId, Formula IIId-1, Formula IIIe, Formula IIIe-1, Formula IIIf, or Formula IIIf-1.

In some aspects, this disclosure is directed to a compound, or a pharmaceutically acceptable salt thereof, having a structure according to Formula I:

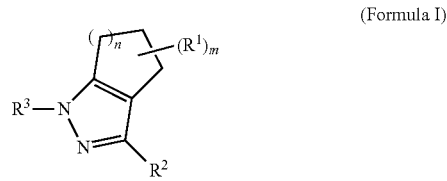

(Formula I)

wherein:
n is the integer 1 or 2;
m is an integer selected from the group consisting of 2, 3, 4, 5, 6, 7, and 8, provided that when n is 1, m is not 7 or 8;
each $R^1$ is independently selected from the group consisting of halo, —OH, and —O—($C_1$-$C_3$ alkyl);
$R^2$ selected from the group consisting of —$C_1$-$C_6$ alkyl, —CN, and —S(O)$_2$—($C_1$-$C_3$ alkyl), wherein the —$C_1$-$C_6$ alkyl and —S(O)$_2$—($C_1$-$C_3$ alkyl) are substituted with 0-3 halo;
$R^3$ is selected from the group consisting of —$C_1$-$C_2$ alkyl substituted with 1-3 $R^4$, —$C_3$-$C_6$ alkyl, —$C_3$-$C_8$ cycloalkyl, -3- to 7-membered heterocycloalkyl having 1-3 heteroatom or heteroatom groups selected from N, O, S, S(=O), and S(=O)$_2$, —Y—(C$_3$-C$_6$ cycloalkyl), —Y—O—(C$_3$-C$_6$ cycloalkyl), —Y-(3- to 6-membered heterocycloalkyl) having 1-3 heteroatom or heteroatom groups selected from N, O, S, S(=O), and S(=O)$_2$, —X-(phenyl), and —Y-(5- to 6-membered heteroaryl) having 1-3 heteroatoms selected from N, O, and S, wherein the —C$_3$-C$_6$ alkyl, —C$_3$-C$_6$ cycloalkyl, -3- to 7-membered heterocycloalkyl, —Y—(C$_3$-C$_6$ cycloalkyl), —Y—O—(C$_3$-C$_6$ cycloalkyl), —Y-(3- to 6-membered heterocycloalkyl), —X-(phenyl), and —Y-(5- to 6-membered heteroaryl), are substituted with 0-3 R$^4$;

each R$^4$ is independently selected from halo, —C$_1$-C$_6$ alkyl, —CN, —C$_1$-C$_6$ haloalkyl, —OH, —O—(C$_1$-C$_6$ alkyl), —Y—O—(C$_1$-C$_6$ alkyl), —S—(C$_1$-C$_6$ alkyl), —S(O)—(C$_1$-C$_6$ alkyl) and —S(O)$_2$—(C$_1$-C$_6$ alkyl), wherein the —O—(C$_1$-C$_6$ alkyl), —Y—O—(C$_1$-C$_6$ alkyl), —S—(C$_1$-C$_6$ alkyl), —S(O)—(C$_1$-C$_6$ alkyl), and —S(O)$_2$—(C$_1$-C$_6$ alkyl) are optionally substituted with 1-3 halo;

X is —C$_2$-C$_3$ alkylene-; and

Y is —C$_1$-C$_3$ alkylene-.

In one or more embodiments, the compound, or pharmaceutically acceptable salt or solvate thereof, according to this disclosure is selected from the compounds provided in Table 1, or any stereoisomer thereof. In one or more embodiments, the compound, or pharmaceutically acceptable salt or solvate thereof, according to this disclosure is selected from the compounds provided in Table 1.

In Table 1, below, when the absolute stereochemistry for particular Example/elution fraction has not yet been determined, the entry lists two example numbers. Example numbers ending in "a" or "b" refer to elution fractions that have more than one isomer.

TABLE 1

| Example | Structure |
|---------|-----------|
| 1 | |
| 2 | |
| 3 | |
| 4 | 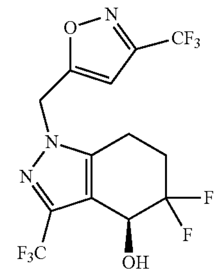 [SMILES: O[C@H]1c2c(C(F)(F)F)nn(Cc3cc(C(F)(F)F)no3)c2CCC1(F)F] |
| 5 | 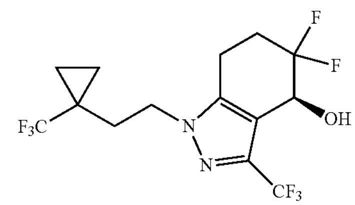 [SMILES: O[C@H]1c2c(C(F)(F)F)nn(CCC3(C(F)(F)F)CC3)c2CCC1(F)F] |
| 6 | 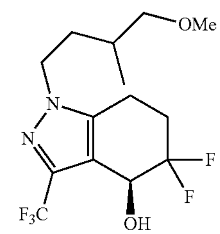 [SMILES: COCC(C)CCn1nc(C(F)(F)F)c2c1CCC(F)(F)[C@H]2O] |
| 7 | 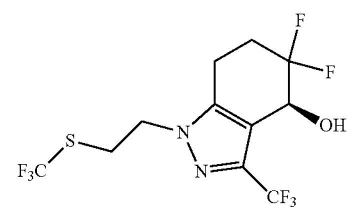 [SMILES: O[C@H]1c2c(C(F)(F)F)nn(CCSC(F)(F)F)c2CCC1(F)F] |
| 8 | 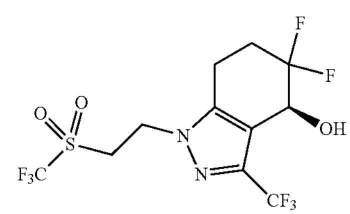 [SMILES: O=S(=O)(CCn1nc(C(F)(F)F)c2c1CCC(F)(F)[C@H]2O)C(F)(F)F] |
| 9 | 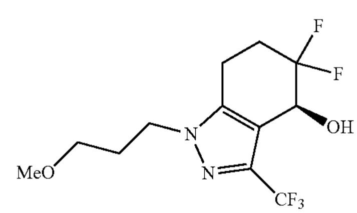 [SMILES: COCCCn1nc(C(F)(F)F)c2c1CCC(F)(F)[C@H]2O] |
| 10 | 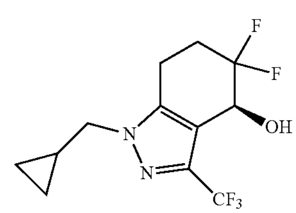 [SMILES: O[C@H]1c2c(C(F)(F)F)nn(CC3CC3)c2CCC1(F)F] |

TABLE 1-continued

| Example | Structure |
|---------|-----------|
| 11 | 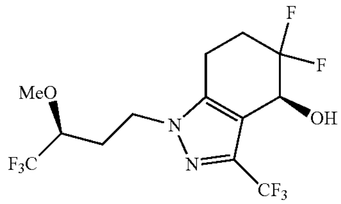 [SMILES: CO[C@@H](CCn1nc(C(F)(F)F)c2c1CCC(F)(F)[C@H]2O)C(F)(F)F] |
| 12 | 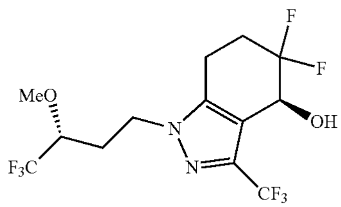 [SMILES: CO[C@H](CCn1nc(C(F)(F)F)c2c1CCC(F)(F)[C@H]2O)C(F)(F)F] |
| 13 | 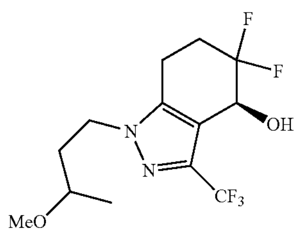 [SMILES: COC(C)CCn1nc(C(F)(F)F)c2c1CCC(F)(F)[C@H]2O] |
| 14 | 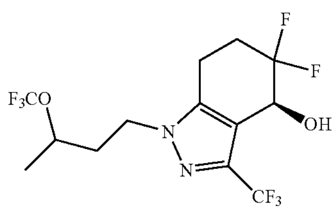 [SMILES: CC(CCn1nc(C(F)(F)F)c2c1CCC(F)(F)[C@H]2O)OC(F)(F)F] |
| 15 | 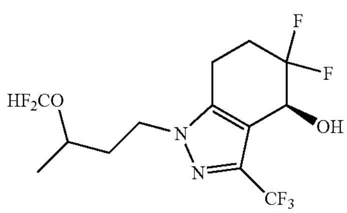 |
| 16 | 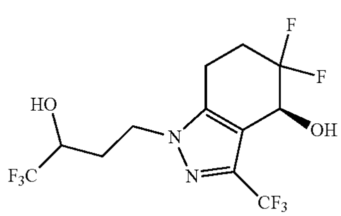 [SMILES: OC(CCn1nc(C(F)(F)F)c2c1CCC(F)(F)[C@H]2O)C(F)(F)F] |
| 17 | 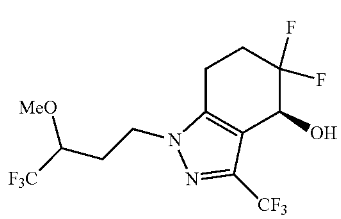 [SMILES: COC(CCn1nc(C(F)(F)F)c2c1CCC(F)(F)[C@H]2O)C(F)(F)F] |
| 18 | |
| 19 | |
| 20 | |
| 21 | |
| 22 | |
| 23/24 | |
| 23/24 | |

TABLE 1-continued

| Example | Structure |
|---|---|
| 25 | (structure) |
| 26/27 | (structure) |
| 26/27 | (structure) |
| 28 | (structure) |
| 29 | (structure) |
| 30 | (structure) |
| 31 | (structure) |
| 32 | (structure) |
| 33 | (structure) |
| 34 | (structure) |
| 35 | (structure) |
| 36 | (structure) |
| 37 | (structure) |
| 38 | (structure) |

TABLE 1-continued

| Example | Structure |
|---------|-----------|
| 39 | 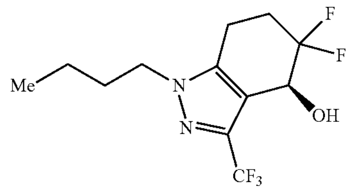 [SMILES: CCCCn1nc(C(F)(F)F)c2c1CCC(F)(F)[C@H]2O] |
| 40 | 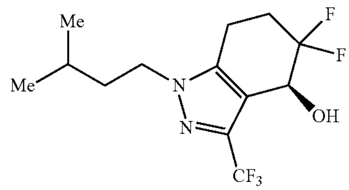 [SMILES: CC(C)CCn1nc(C(F)(F)F)c2c1CCC(F)(F)[C@H]2O] |
| 41 | 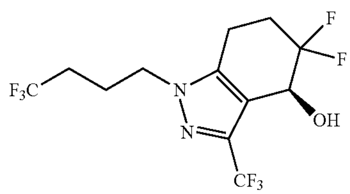 |
| 42 | 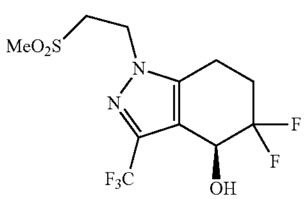 [SMILES: CS(=O)(=O)CCn1nc(C(F)(F)F)c2c1CCC(F)(F)[C@H]2O] |
| 43 | 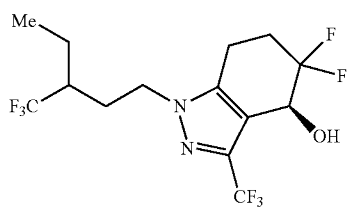 [SMILES: CCC(CCn1nc(C(F)(F)F)c2c1CCC(F)(F)[C@H]2O)C(F)(F)F] |
| 44 | 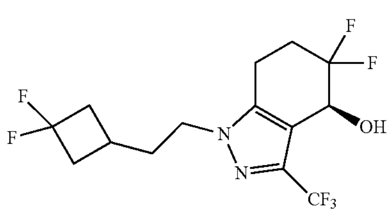 |
| 45 | 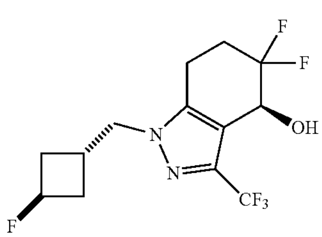 [SMILES: O[C@H]1c2c(C(F)(F)F)nn(C[C@H]3C[C@H](F)C3)c2CCC1(F)F] |
| 46 | 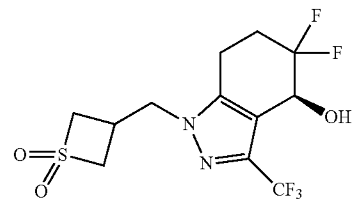 [SMILES: O=S1(=O)CC(Cn2nc(C(F)(F)F)c3c2CCC(F)(F)[C@H]3O)C1] |
| 47 | 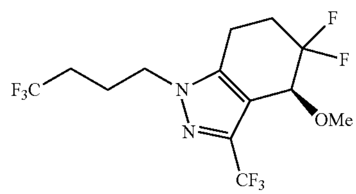 [SMILES: CO[C@H]1c2c(C(F)(F)F)nn(CCCC(F)(F)F)c2CCC1(F)F] |
| 48 | 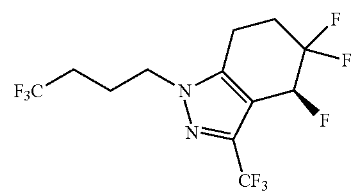 [SMILES: F[C@H]1c2c(C(F)(F)F)nn(CCCC(F)(F)F)c2CCC1(F)F] |
| 49 | 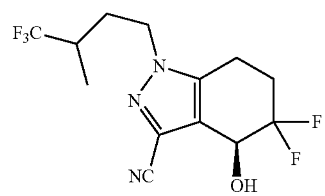 [SMILES: CC(CCn1nc(C#N)c2c1CCC(F)(F)[C@H]2O)C(F)(F)F] |
| 50 | 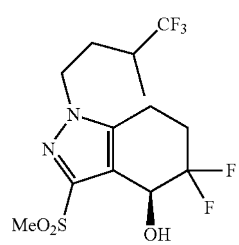 [SMILES: CC(CCn1nc(S(C)(=O)=O)c2c1CCC(F)(F)[C@H]2O)C(F)(F)F] |
| 51 | 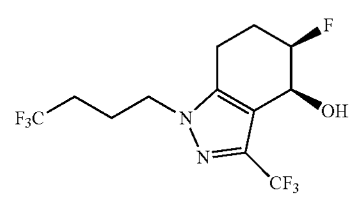 [SMILES: O[C@H]1c2c(C(F)(F)F)nn(CCCC(F)(F)F)c2CC[C@H]1F] |
| 52 | 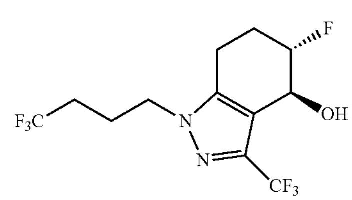 [SMILES: O[C@H]1c2c(C(F)(F)F)nn(CCCC(F)(F)F)c2CC[C@@H]1F] |

TABLE 1-continued

| Example | Structure |
|---------|-----------|
| 53 | 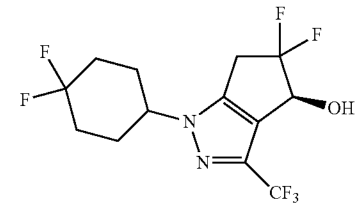 |
| 54 | 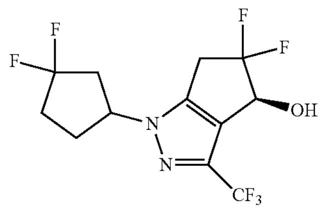 [SMILES: O[C@H]1c2c(C(F)(F)F)nn(C3CCC(F)(F)C3)c2CC1(F)F] |
| 55 | 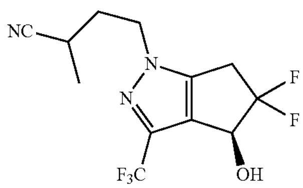 [SMILES: CC(C#N)CCn1nc(C(F)(F)F)c2c1CC(F)(F)[C@H]2O] |
| 56 | 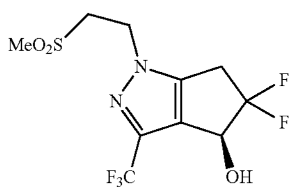 [SMILES: CS(=O)(=O)CCn1nc(C(F)(F)F)c2c1CC(F)(F)[C@H]2O] |
| 57 | 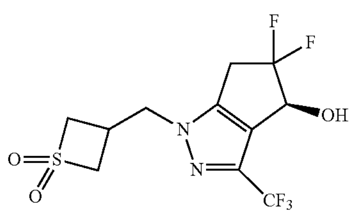 [SMILES: O=S1(=O)CC(Cn2nc(C(F)(F)F)c3c2CC(F)(F)[C@H]3O)C1] |
| 58 | 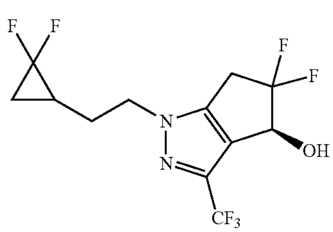 [SMILES: O[C@H]1c2c(C(F)(F)F)nn(CCC3CC3(F)F)c2CC1(F)F] |
| 59 | 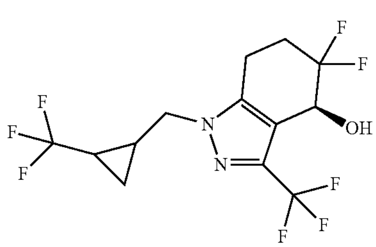 [SMILES: O[C@H]1c2c(C(F)(F)F)nn(CC3CC3C(F)(F)F)c2CCC1(F)F] |
| 60 | |
| 61 | |
| 62 | |
| 63 | |
| 64 | |
| 65 | |
| 66 | |

TABLE 1-continued

| Example | Structure |
|---|---|
| 67 | (structure) |
| 68 | (structure) |
| 69a | (structure) |
| 69b | (structure) |
| 70 | (structure) |
| 71 | (structure) |
| 72/73 | (structure) |
| 72/73 | (structure) |
| 74 | (structure) |
| 75 | (structure) |
| 76 | (structure) |
| 77 | (structure) |

TABLE 1-continued
| Example | Structure |
|---|---|
| 78 | 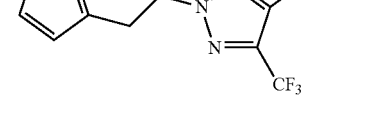 |
| 79 | 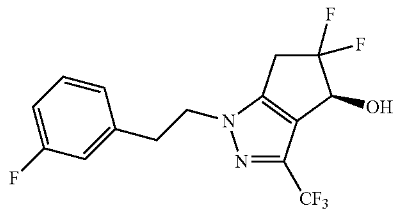 [SMILES: O[C@H]1c2c(C(F)(F)F)nn(CCc3cccc(F)c3)c2CC1(F)F] |
| 80 | 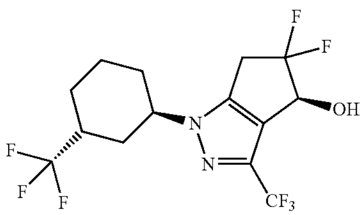 |
| 81 | 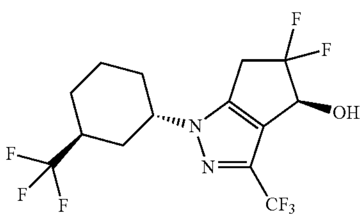 [SMILES: O[C@H]1c2c(C(F)(F)F)nn([C@H]3CCC[C@H](C(F)(F)F)C3)c2CC1(F)F] |
| 82 | 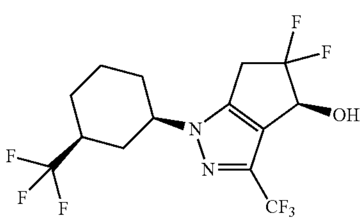 [SMILES: O[C@H]1c2c(C(F)(F)F)nn([C@@H]3CCC[C@H](C(F)(F)F)C3)c2CC1(F)F] |
| 83 | 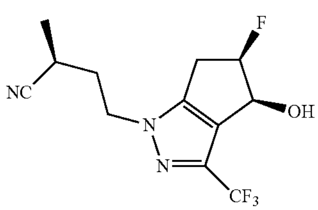 [SMILES: C[C@H](C#N)CCn1nc(C(F)(F)F)c2c1C[C@@H](F)[C@H]2O] |
| 84 | 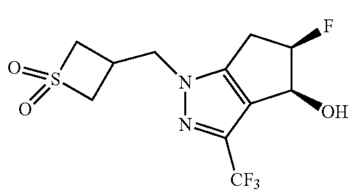 [SMILES: O=S1(=O)CC(Cn2nc(C(F)(F)F)c3c2C[C@@H](F)[C@H]3O)C1] |
| 85 | 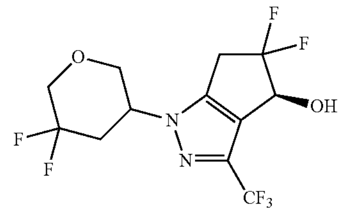 [SMILES: O[C@H]1c2c(C(F)(F)F)nn(C3COCC(F)(F)C3)c2CC1(F)F] |
| 86 | 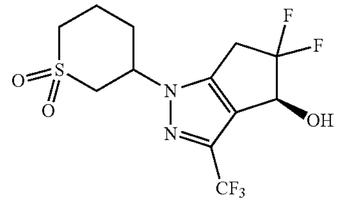 [SMILES: O=S1(=O)CCCC(n2nc(C(F)(F)F)c3c2CC(F)(F)[C@H]3O)C1] |
| 87 | 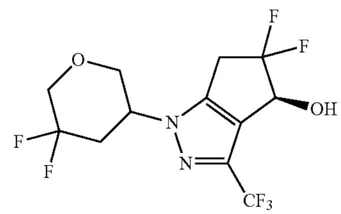 [SMILES: O[C@H]1c2c(C(F)(F)F)nn(C3COCC(F)(F)C3)c2CC1(F)F] |
| 88 | 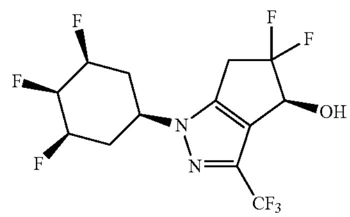 [SMILES: O[C@H]1c2c(C(F)(F)F)nn([C@H]3C[C@@H](F)[C@@H](F)[C@@H](F)C3)c2CC1(F)F] |
| 89 | 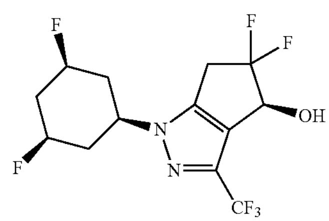 [SMILES: O[C@H]1c2c(C(F)(F)F)nn([C@@H]3C[C@H](F)C[C@H](F)C3)c2CC1(F)F] |
| 90a | 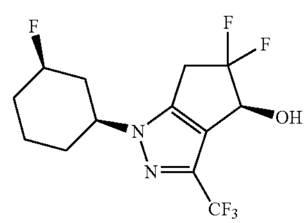 [SMILES: O[C@H]1c2c(C(F)(F)F)nn([C@H]3CCC[C@@H](F)C3)c2CC1(F)F] |
| 90b | 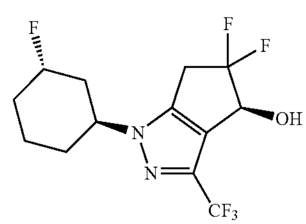 [SMILES: O[C@H]1c2c(C(F)(F)F)nn([C@H]3CCC[C@H](F)C3)c2CC1(F)F] |

TABLE 1-continued

| Example | Structure |
|---------|-----------|
| 91a | (structure) |
| 91b | (structure) |
| 92/93 | (structure) |
| 92/93 | (structure) |
| 94/95 | (structure) |
| 94/95 | (structure) |
| 96 | (structure) |
| 97/98 | (structure) |
| 97/98 | (structure) |
| 99 | (structure) |
| 100 | (structure) |
| 101 | (structure) |
| 102 | (structure) |
| 103 | (structure) |

TABLE 1-continued

| Example | Structure |
|---|---|
| 104 | (structure) |
| 105 | (structure) |
| 106 | (structure) |
| 107a | (structure) |
| 107b | (structure) |
| 108a | (structure) |
| 108b | (structure) |
| 109a | (structure) |
| 109b | (structure) |
| 110a | (structure) |
| 110b | (structure) |
| 111a | (structure) |
| 111b | (structure) |

TABLE 1-continued

| Example | Structure |
|---|---|
| 112a | 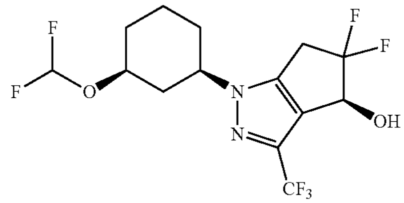 [SMILES: O[C@H]1c2c(C(F)(F)F)nn([C@@H]3CCC[C@H](OC(F)F)C3)c2CC1(F)F] |
| 112b | 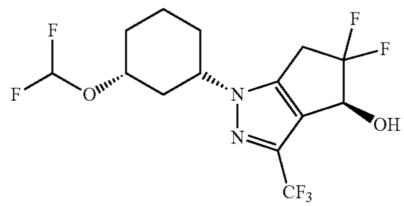 |
| 113 | 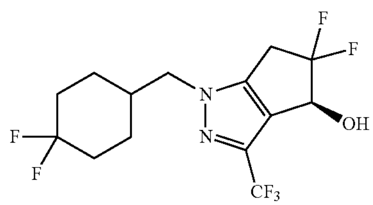 [SMILES: O[C@H]1c2c(C(F)(F)F)nn(CC3CCC(F)(F)CC3)c2CC1(F)F] |
| 114 | 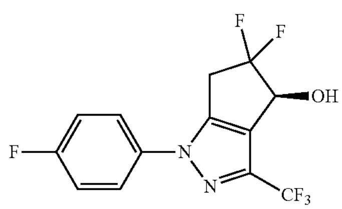 [SMILES: O[C@H]1c2c(C(F)(F)F)nn(-c3ccc(F)cc3)c2CC1(F)F] |
| 115 | 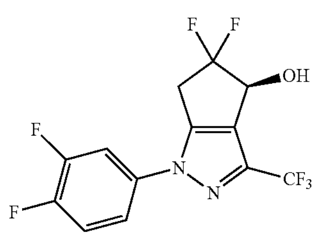 [SMILES: O[C@H]1c2c(C(F)(F)F)nn(-c3ccc(F)c(F)c3)c2CC1(F)F] |
| 116 | 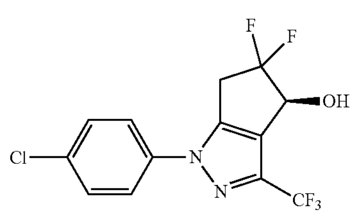 [SMILES: O[C@H]1c2c(C(F)(F)F)nn(-c3ccc(Cl)cc3)c2CC1(F)F] |
| 117 | 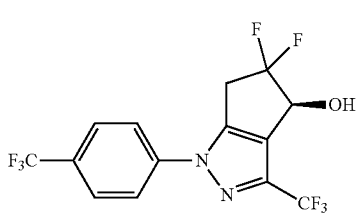 |
| 118 | |
| 119 | |
| 120 | |
| 121 | |
| 122 | |
| 123 | |
| 124 | |

TABLE 1-continued

| Example | Structure |
|---|---|
| 125/126 | (structure) |
| 125/126 | (structure) |
| 127 | (structure) |
| 128 | (structure) |
| 129/130 | (structure) |
| 129/130 | (structure) |
| 131 | (structure) |
| 132 | (structure) |
| 133 | (structure) |
| 134 | (structure) |
| 135 | (structure) |
| 136/137 | (structure) |

TABLE 1-continued

| Example | Structure |
|---------|-----------|
| 136/137 | 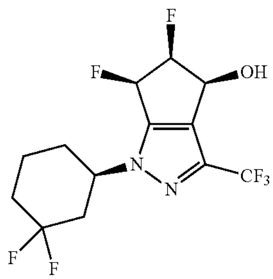 [SMILES: O[C@H]1c2c(C(F)(F)F)nn([C@@H]3CCCC(F)(F)C3)c2[C@@H](F)[C@H]1F] |
| 138 | 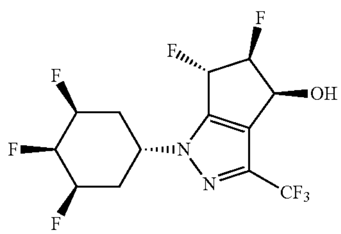 [SMILES: O[C@H]1c2c(C(F)(F)F)nn([C@@H]3C[C@@H](F)[C@@H](F)[C@@H](F)C3)c2[C@H](F)[C@H]1F] |
| 139 | 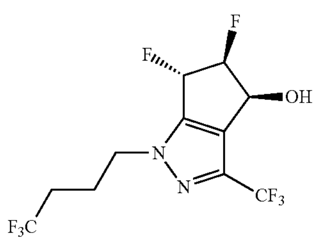 [SMILES: O[C@H]1c2c(C(F)(F)F)nn(CCCC(F)(F)F)c2[C@H](F)[C@H]1F] |
| 140 | 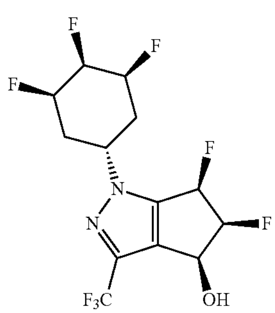 [SMILES: O[C@H]1c2c(C(F)(F)F)nn([C@@H]3C[C@@H](F)[C@@H](F)[C@@H](F)C3)c2[C@@H](F)[C@H]1F] |
| 141/142 | 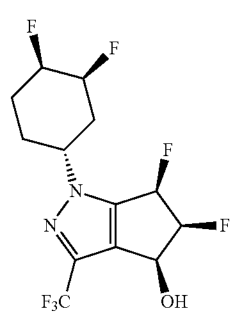 [SMILES: O[C@H]1c2c(C(F)(F)F)nn([C@@H]3CC[C@@H](F)[C@@H](F)C3)c2[C@@H](F)[C@H]1F] |
| 143 | |
| 144/145 | |
| 144/145 | |
| 146/147 | |

TABLE 1-continued

| Example | Structure |
|---|---|
| 146/147 | (structure) |
| 148/149 | (structure) |
| 148/149 | (structure) |
| 150/151 | (structure) |
| 150/151 | (structure) |
| 152 | (structure) |
| 153 | (structure) |
| 154 | (structure) |
| 155 | (structure) |
| 156 | (structure) |
| 157 | (structure) |

Therapeutic and Prophylactic Uses

The present disclosure encompasses the use of the HIF-2α inhibitors described herein in the preparation of a medicament for the treatment or prevention of diseases, disorders, and/or conditions amenable to inhibition of HIF-2α.

In some embodiments, the HIF-2α inhibitors described herein are administered to a subject in need thereof in an amount effective to prevent, reverse, stop or slow the progression of HIF-2α-mediated dysregulation, for example, those diseases, disorders, and/or conditions associated with HIF-2α overexpression and/or dysregulation, as well as those diseases, disorders, and/or conditions in which local or systemic HIF-2α associated hypoxia is prevalent. For example, diseases, disorders, and/or conditions responsive to HIF-2α inhibition may be characterized by (i) increased HIF-2α expression in one or more suitable samples as compared to a similar sample from a healthy control or another disease, disorder and/or condition not responsive to HIF-2α inhibition, (ii) increased HIF-2α expression as compared to HIF-1α expression in one or more suitable samples as compared to a similar sample from a healthy control or another disease, disorder and/or condition not responsive to HIF-2α inhibition, (iii) increased expression of genes regulated by HIF-2α in one or more suitable samples as compared to a similar sample from a healthy control or another disease, disorder and/or condition not responsive to HIF-2α inhibition, or (iv) any combination thereof. A suitable sample may be a tissue, blood, or lymph sample comprising tumor cells, immune cells, etc., or an enriched or purified sample of cells obtained from tissue, blood, or lymph; etc. In various embodiments, the disease, disorder, and/or condition may be Von Hippel-Lindau (VHL) disease, cancer, an immune-related disease, disorder or condition, or an inflammatory-related disease, disorder or condition, cardiovascular disease, kidney disease, or a metabolic disease.

In some embodiments, the compounds described herein are useful in treating a subject having a HIF-2α-stabilizing defect. Under normoxic conditions, the α-subunit is hydroxylated at conserved proline residues by prolyl-4-hydroxylases, and subsequently targeted for degradation by the von Hippel-Lindau ubiquitin E3 ligase complex. HIF-2α-stabilizing defects, caused by gene deletion(s), mutation(s), epigenetic silencing, posttranslational modifications, and the like, result in increased stabilization of HIF-2α and abnormally activate the expression of genes that regulate metabolism, angiogenesis, cell proliferation and survival, immune evasion, and inflammatory response. For example, HIF-stabilizing mutations have been detected in the von Hippel-Lindau gene (VHL), as well as in other genes, such as succinate dehydrogenase (SDHB, SDHC, SDHD), fumarate hydratase (FH), Egl nine homolog 1 (EGLN1), and transcription elongation factor B subunit 1 (TCEB1), as well as the gene that encodes HIF-2α itself, EPAS1. A subject that has a HIF-2α-stabilizing defect may have a disease, disorder, or condition associated with HIF-2α dysregulation, or may have an increased risk of developing said disease, disorder, or condition as compared to a subject without the HIF-2α-stabilizing defect.

In some embodiments, the HIF-2α inhibitors described herein are useful in treating a subject having Von Hippel-Lindau (VHL) disease or having a genetic mutation or gene deletion associated with VHL disease. In further embodiments, the subject also has cancer, or a benign tumor or cyst. VHL-related cancers include but are not limited to, renal carcinoma (typically clear cell renal cell carcinoma), pancreatic neuroendocrine tumor, tumors of adrenal gland, and pheochromocytoma. VHL-related benign cysts and tumors include but are not limited to kidney cysts, pancreatic cysts, epididymal cystadenomas, broad ligament cystadenomas, endolymphatic sac tumors, hemangioblastomas, and retinal angiomas. In one embodiment, the subject has VHL disease and associated renal cell carcinoma, central nervous system hemangioblastomas, or pancreatic neuroendocrine tumors.

Oncology-related Disorders. In one or more embodiments, the compounds described herein are useful in the treatment and/or prophylaxis of cancer (e.g., carcinomas, sarcomas, leukemias, lymphomas and myelomas). In certain embodiments, the cancer is metastatic, or at risk of becoming metastatic. Alternatively, or in addition, the cancer may be recurrent or no longer responding to treatment. Exemplary types of cancer contemplated by this disclosure include cancer of the genitourinary tract (e.g., bladder, kidney, renal cell, penile, prostate, testicular, Von Hippel-Lindau disease, etc.), uterus, cervix, ovary, peritoneal, fallopian tube, breast, gastrointestinal tract (e.g., esophagus, oropharynx, stomach, small or large intestines, colon, or rectum), bone, bone marrow, skin (e.g., melanoma), head and neck, liver, gallbladder, bile ducts, heart, lung, pancreas, salivary gland, adrenal gland, thyroid, brain (e.g., gliomas), ganglia, central nervous system (CNS), peripheral nervous system (PNS), the hematopoietic system (i.e., hematological malignancies), and the immune system (e.g., spleen or thymus).

In some embodiments, the compounds according to this disclosure are useful in the treatment and/or prophylaxis of hematological malignancies. Exemplary types of cancer affecting the hematopoietic system include leukemias, lymphomas and myelomas, including acute myeloid leukemia, adult T-cell leukemia, T-cell large granular lymphocyte leukemia, acute lymphoblastic leukemia, chronic lymphocytic leukemia, chronic myelogenous leukemia, acute monocytic leukemia, Hodgkin's and Non-Hodgkin's lymphoma, Diffuse large B Cell lymphoma, and multiple myeloma.

In another embodiment, the compounds according to this disclosure are useful in the treatment and/or prophylaxis of solid tumors, such as, for example, ovarian cancer, endometrial cancer, breast cancer, lung cancer (small cell or non-small cell), colon cancer, prostate cancer, cervical cancer, biliary cancer, pancreatic cancer, gastric cancer, esophageal cancer, hepatocellular carcinoma (liver cancer), renal cell carcinoma (kidney cancer), head-and-neck tumors, mesothelioma, melanoma, sarcomas, and brain tumors (e.g., gliomas, such as astrocytoma, oligodendroglioma and glioblastomas). The solid tumor may also be an advanced solid tumor, for example a malignant solid tumor that spread to other anatomic sites (metastatic), is recurrent, is no longer responding to treatment, or any combination thereof.

In some embodiments, the cancer is colorectal, bile duct, gallbladder, liver or pancreatic cancer.

In some embodiments, the cancer is bile duct, bladder, breast, colorectal, esophageal, gastric, lung, neuroendocrine, ovarian, pancreatic, or renal cell cancer.

In some embodiments, the cancer is a lung cancer, genitourinary cancer, gastrointestinal cancer, neuroendocrine cancer.

In some embodiments, the cancer is brain cancer, breast cancer, ovarian cancer, kidney cancer, liver cancer, lung cancer, neuroendocrine cancer, or pancreatic cancer.

In some embodiments, the cancer is breast cancer. In further embodiments, the breast cancer is ERα-positive breast cancer, HER2 positive breast cancer, HER2 overexpressing breast cancer, or any combination thereof.

In some embodiments, the cancer is kidney cancer. In further embodiments, the kidney cancer is renal cell carcinoma. In still further embodiments, the renal cell carcinoma is clear cell renal carcinoma.

In some embodiments, the cancer is lung cancer. In further embodiments, the lung cancer is non-small cell lung cancer (NSCLC). In still further embodiments, the NSCLC is lung squamous cell carcinoma or lung adenocarcinoma.

In some embodiments, the cancer is pancreatic cancer. In further embodiments, the pancreatic cancer is pancreatic neuroendocrine tumor or pancreatic adenocarcinoma.

In some embodiments, the cancer is neuroendocrine tumor. In further embodiments, the neuroendocrine tumor is pancreatic neuroendocrine tumor, pheochromocytoma, paraganglioma, or a tumor of the adrenal gland.

In some embodiments, the cancer is brain cancer. In further embodiments, the brain cancer is a glioma. In still further embodiments, the glioma is an astrocytoma, an oligodendroglioma, or a glioblastoma.

In some embodiments, the cancer is biliary tract neoplasm, colon adenocarcinoma, colorectal neoplasm, glioblastoma, hepatocellular carcinoma, lung squamous cell carcinoma, lung adenocarcinoma, pancreatic adenocarcinoma, pancreatic ductal adenocarcinoma, pancreatic neuroendocrine tumor, paraganglioma, pheochromocytoma, or renal cell carcinoma.

The present disclosure also provides methods of treating or preventing other cancer-related diseases, disorders or conditions. The use of the term(s) cancer-related diseases, disorders and conditions is meant to refer broadly to conditions that are associated, directly or indirectly, with cancer, and includes, e.g., angiogenesis, precancerous conditions such as dysplasia, and non-cancerous proliferative diseases disorders or conditions, such as benign proliferative breast disease and papillomas. For clarity, the term(s) cancer-related disease, disorder and condition do not include cancer per se.

The methods of the present disclosure may be practiced in an adjuvant setting. "Adjuvant setting" refers to a clinical setting in which a subject has a history of a proliferative disease, particularly cancer, and generally (but not necessarily) has been responsive to therapy, which includes, but is not limited to, surgery, radiotherapy, and/or chemotherapy. However, because of a history of the proliferative disease, these subjects are considered to be at risk of relapse and/or disease progression. Treatment or administration in the "adjuvant setting" refers to a subsequent mode of treatment. Generally, adjuvant therapy is given in addition to the primary treatment to decrease the risk of the disease or condition recurring. In some embodiments, provided herein is a method for treating or effecting prophylaxis of cancer including administering to a subject having or at risk of cancer a therapeutically effective amount of any of the compounds disclosed herein in an adjuvant setting.

The methods provided herein may also be practiced in a "neoadjuvant setting," that is, the method may be carried out before the primary therapy. In some aspects, the subject has previously been treated. In other aspects, the subject has not previously been treated. In some aspects, the primary treatment is a first line therapy. In some embodiments, provided herein is a method for treating or effecting prophylaxis of cancer including administering to a subject having or at risk of having cancer a therapeutically effective amount of any of the compounds disclosed herein in a neoadjuvant setting.

The methods described herein may be indicated as first line, second line, third line, or greater treatments.

In some embodiments, the present disclosure provides methods for treating a proliferative condition, cancer, tumor, or precancerous condition with the HIF-2α inhibitors according to this disclosure and at least one additional therapeutic agent, examples of which are set forth elsewhere herein.

Immune- and Inflammatory-related Disorders. In one or more embodiments, the compounds described herein are useful in the treatment and/or prophylaxis of immune-related or inflammatory-related diseases, disorders and conditions. In various embodiments, the immune- or inflammatory-related disease, disorder or condition is arthritis, kidney failure, lupus, asthma, psoriasis, colitis, pancreatitis, allergies, fibrosis, surgical complications (e.g., where inflammatory cytokines prevent healing), anemia, fibromyalgia, Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), chronic obstructive pulmonary disease (COPD), atherosclerosis, allergic contact dermatitis, atopic dermatitis or other form of eczema, systemic sclerosis, transplantation, multiple sclerosis, reflux esophagitis, or gastroesophageal reflux disease.

In some embodiments, the subject has an acute inflammatory disease, disorder or condition.

In some embodiments, the subject has chronic inflammatory disease, disorder, or condition. In further embodiments, the chronic inflammatory disease, disorder, or condition is an eosinophilic gastrointestinal disorder, arthritis, eczema, inflammatory bowel disease, lupus, psoriasis, or systemic sclerosis. In still further embodiments, the chronic inflammatory disorder is Crohn's disease, ulcerative colitis, psoriasis or rheumatoid arthritis. In still further embodiments, the chronic inflammatory disorder is an allergic disease, disorder, or condition. In further embodiments, the allergic disease, disorder or condition is anti-histamine refractory chronic spontaneous urticaria, allergic asthma, atopic dermatitis In some embodiments, the compounds described herein are useful in the treatment of cardiovascular disease. In further embodiments, the cardiovascular disease is aortic valve stenosis, asthma, arteriosclerosis, atherosclerosis, cardiac ischemia, cardiac fibrosis, chronic obstructive pulmonary disease (COPD), congestive heart failure, pulmonary fibrosis, pulmonary hypertension, or stroke. In still further embodiments, the cardiovascular disease is pulmonary arterial hypertension.

In some embodiments, the compounds described herein are useful in the treatment of metabolic disease. In further embodiments, the metabolic disease is insulin resistance, diabetes, or obesity.

In some embodiments the subject has kidney disease. In further embodiments, the kidney disease is chronic kidney disease. In still further embodiments, the kidney disease is kidney failure.

In particular embodiments of the present disclosure, the HIF-2α inhibitors described herein are used to increase or enhance an immune response to an antigen by providing adjuvant activity. In a particular embodiment, at least one antigen or vaccine is administered to a subject in combination with at least one HIF-2α inhibitor of the present disclosure to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one HIF-2α inhibitor of the present disclosure.

Selection of patients. In some instances, the methods according to this disclosure may be provided in selected patients, for example subjects identified as having, e.g., overexpression of genes associated with HIF-2α signaling or having high microsatellite instability or high tumor mutational burden. In some instances, the subject is identified as having an oncogene driven cancer that has a mutation in at least one gene associated with the cancer. In some embodiments, patients are identified as having a high expression of EPAS1 (the gene encoding HIF-2α) and/or a high HIF-2/HIF-1 ratio. In another embodiment, patients are identified as having a high hypoxia score. In one embodiment, patients are identified as having high PD-1 and/or PD-L1 expression.

Routes of Administration

In some embodiments, pharmaceutical compositions containing a compound according to this disclosure may be in a form suitable for oral administration. Oral administration may involve swallowing the formulation thereby allowing the compound to be absorbed into the bloodstream in the gastrointestinal tract. Alternatively, oral administration may involve buccal, lingual or sublingual administration, thereby allowing the compound to be absorbed into the blood stream through oral mucosa.

In another embodiment, the pharmaceutical compositions containing a compound according to this disclosure may be in a form suitable for parenteral administration. Forms of parenteral administration include, but are not limited to, intravenous, intraarterial, intramuscular, intradermal, intraperitoneal, intrathecal, intracisternal, intracerebral, intracerebroventricular, intraventricular, and subcutaneous. Pharmaceutical compositions suitable for parenteral administration may be formulated using suitable aqueous or non-aqueous carriers. Depot injections, which are generally administered subcutaneously or intramuscularly, may also be utilized to release the compounds disclosed herein over a defined period of time.

Other routes of administration are also contemplated by this disclosure, including, but not limited to, nasal, vaginal, intraocular, rectal, topical (e.g., transdermal), and inhalation.

Particular embodiments of the present disclosure contemplate oral administration or parenteral administration.

Pharmaceutical Compositions

The HIF-2α inhibitors of the present disclosure may be in the form of compositions suitable for administration to a subject. In general, such compositions are pharmaceutical compositions comprising a HIF-2α inhibitor according to this disclosure and one or more pharmaceutically acceptable excipients. In certain embodiments, the HIF-2α inhibitor may be present in a therapeutically effective amount. The pharmaceutical compositions may be used in the methods of the present disclosure; thus, for example, the pharmaceutical compositions comprising a HIF-2α inhibitor according to this disclosure can be administered to a subject in order to practice the therapeutic and prophylactic methods and uses described herein.

The pharmaceutical compositions of the present disclosure can be formulated to be compatible with the intended method or route of administration. Routes of administration may include those known in the art. Exemplary routes of administration are oral and parenteral. Furthermore, the pharmaceutical compositions may be used in combination with one or more other therapeutically active agents or compounds as described herein in order to treat or prevent the diseases, disorders and conditions as contemplated by the present disclosure. In one embodiment, the one or more other therapeutically active agents or compounds contemplated by this disclosure are included in the same pharmaceutical composition that comprises the HIF-2α inhibitor according to this disclosure. In another embodiment, the one or more other additional active therapeutic agents are in a composition that is separate from the pharmaceutical composition comprising the HIF-2α inhibitor according to this disclosure.

In one aspect, the compounds described herein may be administered orally. Oral administration may be via, for example, capsule or tablets. In making the pharmaceutical compositions that include the compound of Formula (I), or a pharmaceutically acceptable salt thereof, the tablet or capsule typically includes at least one pharmaceutically acceptable excipient, such as, for example, bulking agents, lubricating agents, wetting agents, emulsifying agents, suspending agents, dispersing agents, preserving agents, sweeteners, flavoring agents, colorants, and the like. An oral dosage form may be formulated as a solution or suspension.

In another aspect, the compounds described herein may be administered parenterally, for example by intravenous injection. A pharmaceutical composition appropriate for parenteral administration may be formulated in solution for injection or may be reconstituted for injection in an appropriate system such as a physiological solution. Such solutions may include sterile water for injection, salts, buffers, and tonicity excipients in amounts appropriate to achieve isotonicity with the appropriate physiology.

The pharmaceutical compositions described herein may be stored in an appropriate sterile container or containers. In some embodiments, the container is designed to maintain stability for the pharmaceutical composition over a given period of time.

Combination Therapy

The present disclosure contemplates the use of the HIF-2α inhibitors described herein alone or in combination with one or more additional active therapeutic agents, optionally in combination with another treatment modality, for example, before or after surgery, a bone marrow transplant, etc. In embodiments comprising one or more additional active therapeutic agents, each agent may target a different, but complementary, mechanism of action. The additional active therapeutic agents can be small chemical molecules; macromolecules such as proteins, antibodies, peptibodies, peptides, DNA, RNA or fragments of such macromolecules; or cellular or gene therapies. The use of the HIF-2α inhibitors described herein in combination with one or more additional active therapeutic agents may have a synergistic therapeutic or prophylactic effect on the underlying disease, disorder, or condition. In addition or alternatively, the combination therapy may allow for a dose reduction of one or more of the agents, thereby ameliorating, reducing or eliminating adverse effects associated with one or more of the agents.

The active therapeutic agents used in such combination therapy can be formulated as a single composition or as separate compositions. If administered separately, each therapeutic agent in the combination can be given at or around the same time, or at different times. Furthermore, the therapeutic agents are administered "in combination" even if they have different forms of administration (e.g., oral capsule and intravenous), they are given at different dosing intervals, one therapeutic agent is given at a constant dosing regimen while another is titrated up, titrated down or discontinued, or each therapeutic agent in the combination is independently titrated up, titrated down, increased or decreased in dosage, or discontinued and/or resumed during a patient's course of therapy. If the combination is formulated as separate compositions, in some embodiments, the separate compositions are provided together in a kit.

Cancer Therapeutic Agents

The present disclosure contemplates the use of the HIF-2α inhibitors described herein in combination with one or more additional active therapeutic agent useful in the treatment of cancer.

In some embodiments, one or more of the additional therapeutic agents is a chemotherapeutic agent. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, pomalidomide, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab paclitaxel, and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors such as irinotecan, topotecan, etoposide, mitoxantrone, teniposide; difluoromethylornithine (DMFO); retinoic acid; esperamicins; capecitabine; anthracyclines and pharmaceutically acceptable salts, acids or derivatives of any of the above. In certain embodiments, combination therapy comprises a chemotherapy regimen that includes one or more chemotherapeutic agents. In one embodiment, combination therapy comprises a chemotherapeutic regimen comprising FOLFOX (folinic acid, fluorouracil, and oxaliplatin), FOLFIRI (e.g., folinic acid, fluorouracil, and irinotecan), a taxane (e.g., docetaxel, paclitaxel, nab-paclitaxel, etc.), CAPOX (capecitabine and oxaliplatin), irinotecan, a platinum-based chemotherapeutic agent, and/or gemcitabine.

In some embodiments, one or more of the additional therapeutic agents is a radiopharmaceutical. A radiopharmaceutical is a form of internal radiation therapy in which a source of radiation (i.e., one or more radionuclide) is put inside a subject's body. The radiation source can be in solid or liquid form. Non-limiting examples of radiopharmaceuticals include sodium iodide I-131, radium-223 dichloride, lobenguane iodine-131, radioiodinated vesicles (e.g., saposin C-dioleoylphosphatidylserine (SapC-DOPS) nanovesicles), various forms of brachytherapy, and various forms of targeted radionuclides. Targeted radionuclides comprise a radionuclide associated (e.g., by covalent or ionic interactions) with a molecule ("a targeting agent") that specifically binds to a target on a cell, typically a cancer cell or an immune cell. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (i.e., an antigen enriched but not specific to a cancer cell), a tumor-specific antigen (i.e., an antigen with minimal to no expression in normal tissue), or a neo-antigen (i.e., an antigen specific to the genome of a cancer cell generated by non-synonymous mutations in the tumor cell genome). Non-limiting examples of targeted radionuclides include radionuclides attached to: somatostatin or peptide analogs thereof (e.g., 177Lu-Dotatate, etc.); prostate specific membrane antigen or peptide analogs thereof (e.g., 177Lu-PSMA-617, 225Ac-PSMA-617, 177Lu-PSMA-I&T, 177Lu-MIP-1095, etc.); a receptor's cognate ligand, peptide derived from the ligand, or variants thereof (e.g., 188Re-labeled VEGF125-136 or variants thereof with higher affinity to VEGF receptor, etc.); antibodies targeting tumor antigens (e.g., 131I-tositumomab, 90Y-ibritumomab tiuxetan, CAM-H2-I131 (Precirix NV), I131-omburtamab, etc.).

In some embodiments, one or more of the additional therapeutic agents is a hormone therapy. Hormone therapies act to regulate or inhibit hormonal action on tumors. Examples of hormone therapies include, but are not limited to: selective estrogen receptor degraders such as fulvestrant, GDC-9545, SAR439859, RG6171, AZD9833, rintodestrant, ZN-c5, LSZ102, D-0502, LY3484356, SHR9549; selective estrogen receptor modulators such as tamoxifen, raloxifene, 4-hydroxytamoxifen, trioxifene, keoxifene, toremifene; aromatase inhibitors such as anastrozole, exemestane, letrozole and other aromatase inhibiting 4(5)-imidazoles; gonadotropin-releasing hormone agonists such as nafarelin, tiptorelin, goserelin; gonadotropin-releasing hormone antagonists such as degarelix; antiandrogens such as abiraterone, enzalutamide, apalutamide, darolutamide, flutamide, nilutamide, bicalutamide, leuprolide; 5α-reductase inhibitors such as finasteride, dutasteride; and the like. In certain embodiments, combination therapy comprises administration of a hormone or related hormonal agent. In one embodiment, combination therapy comprises administration of enzalutamide.

In some embodiments, one or more of the additional therapeutic agents is an epigenetic modulator. An epigenetic modulator alters an epigenetic mechanism controlling gene expression, and may be, for example, an inhibitor or activator of an epigenetic enzyme. Non-limiting examples of epigenetic modulators include DNA methyltransferase (DNMT) inhibitors, hypomethylating agents, and histone deacetylase (HDAC) inhibitors. In one or more embodiments, the HIF-2α inhibitors according to this disclosure are combined with DNA methyltransferase (DNMT) inhibitors or hypomethylating agents. Exemplary DNMT inhibitors include decitabine, zebularine and azacitadine. In one or more embodiments, combinations of the HIF-2α inhibitors according to this disclosure with a histone deacetylase (HDAC) inhibitor is also contemplated. Exemplary HDAC inhibitors include vorinostat, givinostat, abexinostat, panobinostat, belinostat and trichostatin A.

In some embodiments, one or more of the additional therapeutic agents is an ATP-adenosine axis-targeting agent. ATP-adenosine axis-targeting agents alter signaling mediated by adenine nucleosides and nucleotides (e.g., adenosine, AMP, ADP, ATP), for example by modulating the level of adenosine or targeting adenosine receptors. Adenosine and ATP, acting at different classes of receptors, often have opposite effects on inflammation, cell proliferation and cell death. For instance, ATP and other adenine nucleotides have antitumor effects via activation of the PS2Y1 receptor subtype, while accumulation of adenosine in the tumor microenvironment has been shown to inhibit the antitumor function of various immune cells and to augment the immunosuppressive activity of myeloid and regulatory T cells by binding to cell surface adenosine receptors. In certain embodiments, an ATP-adenosine axis-targeting agent is an inhibitor of an ectonucleotidase involved in the conversion of ATP to adenosine or an antagonist of adenosine receptor. Ectonucleotidases involved in the conversion of ATP to adenosine include the ectonucleotide triphosphate diphosphohydrolase 1 (ENTPD1, also known as CD39 or Cluster of Differentiation 39) and the ecto-5'-nucleotidase (NT5E or 5NT, also known as CD73 or Cluster of Differentiation 73). Exemplary small molecule CD73 inhibitors include CB-708, ORIC-533, LY3475070 and AB680. Exemplary anti-CD39 and anti-CD73 antibodies include ES002, TTX-030, IPH-5201, SRF-617, CPI-006, oleclumab (MEDI9447), NZV930, IPH5301, GS-1423, uliledlimab (TJD5, TJ004309), AB598, and BMS-986179. In one embodiment, the present disclosure contemplates combination of the HIF-2α inhibitors described herein with a CD73 inhibitor such as those described in WO 2017/120508, WO 2018/067424, WO 2018/094148, and WO 2020/046813. In further embodiments, the CD73 inhibitor is quemliclustat (AB680). Adenosine can bind to and activate four different G-protein coupled receptors: $A_1R$, $A_{2A}R$, $A_{2B}R$, and $A_3R$. $A_2R$ antagonists include etrumadenant, inupadenant, taminadenant, caffeine citrate, NUV-1182, TT-702, DZD-2269, INCB-106385, EVOEXS-21546, AZD-4635, imaradenant, RVU-330, ciforadenant, PBF-509, PBF-999, PBF-1129, and CS-3005. In some embodiments, the present disclosure contemplates the combination of the HIF-2α inhibitors described herein with an $A_{2A}R$ antagonist, an $A_{2B}R$ antagonist, or an antagonist of $A_{2A}R$ and $A_{2B}R$. In some embodiments, the present disclosure contemplates the combination of the HIF-2α inhibitors described herein with the adenosine receptor antagonists described in WO 2018/136700, WO 2018/204661, WO 2018/213377, or WO 2020/023846, WO 2020/102646. In one embodiment, the adenosine receptor antagonist is etrumadenant.

In some embodiments, one or more of the additional therapeutic agents is a targeted therapy. In one aspect, a targeted therapy may comprise a chemotherapeutic agent, a radionuclide, a hormone therapy, or another small molecule drug attached to a targeting agent. The targeting agent may be a small molecule, a saccharide (inclusive of oligosaccharides and polysaccharides), an antibody, a lipid, a protein, a peptide, a non-natural polymer, or an aptamer. In some embodiments, the targeting agent is a saccharide (inclusive of oligosaccharides and polysaccharides), a lipid, a protein, or a peptide and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In some embodiments, the targeting agent is an antibody and the target is a tumor-associated antigen (enriched but not specific to a cancer cell), a tumor-specific antigen (minimal to no expression in normal tissue), or a neo-antigen (an antigen specific to the genome of a cancer cell generated by non-synonymous mutations in the tumor cell genome). In other aspects, a targeted therapy may inhibit or interfere with a specific protein that helps a tumor grow and/or spread. Non-limiting examples of such targeted therapies include signal transduction inhibitors, RAS signaling inhibitors, inhibitors of oncogenic transcription factors, activators of oncogenic transcription factor repressors, angiogenesis inhibitors, immunotherapeutic agents, ATP-adenosine axis-targeting agents, AXL inhibitors, CDK-4/6 inhibitors, PARP inhibitors, PAK4 inhibitors, PI3K inhibitors, CD39 inhibitors, CD73 inhibitors, A2R antagonists, TIGIT antagonists, and PD-1 antagonists. ATP-adenosine axis-targeting agents are described above, while other agents are described in further detail below.

In some embodiments, one or more of the additional therapeutic agents is a signal transduction inhibitor. Signal transduction inhibitors are agents that selectively inhibit one or more steps in a signaling pathway. Signal transduction inhibitors (STIs) contemplated by the present disclosure include but are not limited to: (i) BCR-ABL kinase inhibitors (e.g., imatinib); (ii) epidermal growth factor receptor tyrosine kinase inhibitors (EGFR TKIs), including small molecule inhibitors (e.g., gefitinib, erlotinib, afatinib, icotinib, and osimertinib), and anti-EGFR antibodies; (iii) inhibitors of the human epidermal growth factor (HER) family of transmembrane tyrosine kinases, e.g., HER-2/neu receptor inhibitors (e.g., trastuzumab and HER-3 receptor inhibitors); (iv) vascular endothelial growth factor receptor (VEGFR) inhibitors including small molecule inhibitors (e.g., axitinib, sunitinib and sorafenib), VEGF kinase inhibitors (e.g., lenvatinib, cabozantib, XL092, etc.) and anti-VEGF antibodies (e.g., bevacizumab); (v) inhibitors of AKT family kinases or the AKT pathway (e.g., rapamycin); (vi) inhibitors of serine/threonine-protein kinase B-Raf (BRAF), such as, for example, vemurafenib, dabrafenib and encorafenib; (vii) inhibitors of rearranged during transfection (RET), including, for example, selpercatinib and pralsetinib; (viii) tyrosine-protein kinase Met (MET) inhibitors (e.g., tepotinib, tivantinib, cabozantinib, XL092, and crizotinib); (ix) anaplastic lymphoma kinase (ALK) inhibitors (e.g., ensartinib, ceritinib, lorlatinib, crizotinib, and brigatinib); (x) inhibitors of the RAS signaling pathway (e.g., inhibitors of KRAS, HRAS, RAF, MEK, ERK) as described elsewhere herein; (xi) FLT-3 inhibitors (e.g., gilteritinib); (xii) inhibitors of Trop-2, such as, for example, the antibody drug conjugate sacituzumab govitecan-hziy; (xiii) inhibitors of the JAK/STAT pathway, e.g., JAK inhibitors including tofacitinib and ruxolitinib, or STAT inhibitors such as napabucasin; (xiv) inhibitors of NF-kB; (xv) cell cycle kinase inhibitors (e.g., flavopiridol); (xvi) phosphatidyl inositol kinase (PI3K) inhibitors; (xix) protein kinase B (AKT) inhibitors (e.g., capivasertib, miransertib), and (xx) inhibitors of CDK-4 and/or CDK-6 (e.g., abemaciclib, palbociclib, ribociclib, trilaciclib, etc.). In one or more embodiments, the additional therapeutic agent comprises an inhibitor of CDK-4, CDK-6, EGFR, VEGFR, HER-2, HER-3, BRAF, RET, MET, ALK, RAS (e.g., KRAS, MEK, ERK), FLT-3, JAK, STAT, NF-kB, PI3K, AKT, or any combinations thereof.

In some embodiments, one or more of the additional therapeutic agents is a RAS signaling inhibitor. Oncogenic mutations in the RAS family of genes, e.g., HRAS, KRAS, and NRAS, are associated with a variety of cancers. For example, mutations of G12C, G12D, G12V, G12A, G13D, Q61H, G13C and G12S, among others, in the KRAS family of genes have been observed in multiple tumor types. Direct and indirect inhibition strategies have been investigated for the inhibition of mutant RAS signaling. Indirect inhibitors target effectors other than RAS in the RAS signaling pathway, and include, but are not limited to, inhibitors of RAF, MEK, ERK, PI3K, PTEN, SOS (e.g., SOS1), mTORC1, SHP2 (PTPN11), and AKT. Non-limiting examples of indirect inhibitors under development include RMC-4630, RMC-5845, RMC-6291, RMC-6236, JAB-3068, JAB-3312, TNO155, RLY-1971, BI1701963. Direct inhibitors of RAS mutants have also been explored, and generally target the KRAS-GTP complex or the KRAS-GDP complex. Exemplary direct RAS inhibitors under development include, but are not limited to, sotorasib (AMG510), MRTX849, mRNA-5671 and ARS1620. In some embodiments, the one or more RAS signaling inhibitors are selected from the group consisting of RAF inhibitors, MEK inhibitors, ERK inhibitors, PI3K inhibitors, PTEN inhibitors, SOS1 inhibitors, mTORC1 inhibitors, SHP2 inhibitors, and AKT inhibitors. In other embodiments the one or more RAS signaling inhibitors directly inhibit RAS mutants.

In some embodiments one or more of the additional therapeutic agents is an inhibitor of a phosphatidylinositol 3-kinase (PI3K), particularly an inhibitor of the PI3Kγ isoform. PI3Kγ inhibitors can stimulate an anti-cancer immune response through the modulation of myeloid cells, such as by inhibiting suppressive myeloid cells, dampening immune-suppressive tumor-infiltrating macrophages or by stimulating macrophages and dendritic cells to make cytokines that contribute to effective T-cell responses thereby decreasing cancer development and spread. Exemplary PI3Kγ inhibitors include copanlisib, duvelisib, AT-104, ZX-101, tenalisib, eganelisib, SF-1126, AZD3458, and pictilisib. In some embodiments, the HIF-2α inhibitors according to this disclosure are combined with one or more PI3Kγ inhibitors described in WO 2020/0247496A1.

In some embodiments, one or more of the additional therapeutic agents is an inhibitor of arginase. Arginase has been shown to be either responsible for or participate in inflammation-triggered immune dysfunction, tumor immune escape, immunosuppression and immunopathology of infectious disease. Exemplary arginase compounds include CB-1158 and OAT-1746. In some embodiments, the HIF-2α inhibitors according to this disclosure are combined with one or more arginase inhibitors described in WO/2019/173188 and WO 2020/102646.

In some embodiments, one or more of the additional therapeutic agents is an inhibitor of an oncogenic transcription factor or an activator of an oncogenic transcription factor repressor. Suitable agents may act at the expression level (e.g., RNAi, siRNA, etc.), through physical degradation, at the protein/protein level, at the protein/DNA level, or by binding in an activation/inhibition pocket. Non-limiting examples include inhibitors of one or more subunit of the MLL complex (e.g., HDAC, DOT1L, BRD4, Menin, LEDGF, WDR5, KDM4C (JMJD2C) and PRMT1), inhibitors of hypoxia-inducible factor (HIF) transcription factor, and the like.

In some embodiments, one or more of the additional therapeutic agents is an inhibitor of anexelekto (AXL). The AXL signaling pathway is associated with tumor growth and metastasis, and is believed to mediate resistance to a variety of cancer therapies. There are a variety of AXL inhibitors under development that also inhibit other kinases in the TAM family (i.e., TYRO3, MERTK), as well as other receptor tyrosine kinases including MET, FLT3, RON and AURORA, among others. Exemplary multikinase inhibitors include sitravatinib, rebastinib, glesatinib, gilteritinib, merestinib, cabozantinib, foretinib, XL092, BMS777607, LY2801653, S49076, GSK1363089, and RXDX-106. AXL specific inhibitors have also been developed, e.g., small molecule inhibitors including DS-1205, SGI-7079, SLC-391, TP-0903 (i.e., dubermatinib), BGB324 (i.e., bemcentinib), and DP3975; anti-AXL antibodies such as ADCT-601; and antibody drug conjugates (ADCs) such as BA3011. Another strategy to inhibit AXL signaling involves targeting AXL's ligand, GAS6. For example, AVB-500 is under development as is a Fc fusion protein that binds the GAS6 ligand thereby inhibiting AXL signaling.

In some embodiments, one or more of the additional therapeutic agents is an inhibitor of p21-activated kinase 4 (PAK4). PAK4 overexpression has been shown across a variety of cancer types, notably including those resistant to PD-1 therapies. While no PAK4 inhibitors have been approved, some are in development, and exhibit dual PAK4/NAMPT inhibitor activity, e.g., ATG-019 and KPT-9274. In some embodiments, the compounds according to this disclosure are combined with a PAK4 selective inhibitor. In some embodiments, the compounds according to this disclosure are combined with a PAK4/NAMPT dual inhibitor, e.g., ATG-019 or KPT-9274.

In some embodiments, one or more of the additional therapeutic agents is a cyclin-dependent kinase (CDK) inhibitor. In certain embodiments, the inhibitor is a CDK4 and/or CDK6 inhibitor. Exemplary CDK4 and/or CDK-6 inhibitors may include abemaciclib, palbociclib, ribociclib, and trilaciclib In some embodiments, one or more of the additional therapeutic agents is (i) an agent that inhibits the enzyme poly (ADP-ribose) polymerase (e.g., olaparib, niraparib and rucaparib, etc.); (ii) an inhibitor of the Bcl-2 family of proteins (e.g., venetoclax, navitoclax, etc.); (iii) an inhibitor of MCL-1; (iv) an inhibitor of the CD47-SIRPα pathway (e.g., the anti-CD47 antibody, magrolimab, etc.); (v) an isocitrate dehydrogenase (IDH) inhibitor, e.g., IDH-1 or IDH-2 inhibitor (e.g., ivosidenib, enasidenib, etc.).

In some embodiments, one or more of the additional therapeutic agents is an immunotherapeutic agent. Immunotherapeutic agents treat a disease by stimulating or suppressing the immune system. Immunotherapeutic agents useful in the treatment of cancers typically elicit or amplify an immune response to cancer cells. Non-limiting examples of suitable immunotherapeutic agents include: immunomodulators; cellular immunotherapies; vaccines; gene therapies; ATP-adenosine axis-targeting agents; immune checkpoint modulators. ATP-adenosine axis-targeting agents are described above. Immunomodulators, cellular immunotherapies, vaccines, gene therapies, and immune checkpoint modulators are described further below.

In some embodiments, one or more of the additional therapeutic agents is an immunotherapeutic agent, more specifically a cytokine or chemokine, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); an organic or inorganic adjuvant that activates antigen-presenting cells and promote the presentation of antigen epitopes on major histocompatibility complex molecules agonists including, but not limited to Toll-like receptor (TLR) agonists, antagonists of the mevalonate pathway, agonists of STING; indoleamine 2,3-dioxygenase 1 (IDO1) inhibitors and immune-stimulatory oligonucleotides, as well as other T-cell adjuvants.

In some embodiments, one or more of the additional therapeutic agents is an immunotherapeutic agent, more specifically a cellular therapy. Cellular therapies are a form of treatment in which viable cells are administered to a subject. In certain embodiments, one or more of the additional therapeutic agents is a cellular immunotherapy that activates or suppresses the immune system. Cellular immunotherapies useful in the treatment of cancers typically elicit or amplify an immune response. The cells can be autologous or allogenic immune cells (e.g., monocytes, macrophages, dendritic cells, NK cells, T-cells, etc.) collected from one or more subject. Alternatively, the cells can be "(re)programmed" allogenic immune cells produced from immune precursor cells (e.g., lymphoid progenitor cells, myeloid progenitor cells, common dendritic cell precursor cells, stem cells, induced pluripotent stem cells, etc.). In some embodiments, such cells may be an expanded subset of cells with distinct effector functions and/or maturation markers (e.g., adaptive memory NK cells, tumor infiltrating lymphocytes, immature dendritic cells, monocyte-derived dendritic cells, plasmacytoid dendritic cells, conventional dendritic cells (sometimes referred to as classical dendritic cells), M1 macrophages, M2 macrophages, etc.), may be genetically modified to target the cells to a specific antigen and/or enhance the cells' anti-tumor effects (e.g., engineered T cell receptor (TCR) cellular therapies, chimeric antigen receptor (CAR) cellular therapies, lymph node homing of antigen-loaded dendritic cells, etc.), may be engineered to express of have increased expression of a tumor-associated antigen, or may be any combination thereof. Non-limiting types of cellular therapies include CAR-T cell therapy, CAR-NK cell therapy, TCR therapy, and dendritic cell vaccines. Exemplary cellular immunotherapies include sipuleucel-T, tisagenlecleucel, lisocabtagene maraleucel, idecabtagene vicleucel, brexucabtagene autoleucel, and axicabtagene ciloleucel, as well as CTX110, JCAR015, JCAR017, MB-CART19.1, MB-CART20.1, MB-CART2019.1, Uni-CAR02-T-CD123, BMCA-CAR-T, JNJ-68284528, BNT211, and NK-92/5.28.z.

In some embodiments, one or more of the additional therapeutic agents is an immunotherapeutic agent, more specifically a gene therapy. Gene therapies comprise recombinant nucleic acids administered to a subject or to a subject's cells ex vivo in order to modify the expression of an endogenous gene or to result in heterologous expression of a protein (e.g., small interfering RNA (siRNA) agents, double-stranded RNA (dsRNA) agents, micro RNA (miRNA) agents, viral or bacterial gene delivery, etc.), as well as gene editing therapies that may or may not comprise a nucleic acid component (e.g., meganucleases, zinc finger nucleases, TAL nucleases, CRISPR/Cas nucleases, etc.), oncolytic viruses, and the like. Non-limiting examples of gene therapies that may be useful in cancer treatment include Gendicine® (rAd-p53), Oncorine® (rAD5-H101), talimogene laherparepvec, Mx-dnG1, ARO-HIF2 (Arrowhead), CTX110 (CRISPR Therapeutics), CTX120 (CRISPR Therapeutics), and CTX130 (CRISPR Therapeutics).

In some embodiments, one or more of the additional therapeutic agents is an immunotherapeutic agent, more specifically an agent that modulates an immune checkpoint. Immune checkpoints are a set of inhibitory and stimulatory pathways that directly affect the function of immune cells (e.g., B cells, T cells, NK cells, etc.). Immune checkpoints engage when proteins on the surface of immune cells recognize and bind to their cognate ligands. The present invention contemplates the use of HIF-2α inhibitors described herein in combination with agonists of stimulatory or co-stimulatory pathways and/or antagonists of inhibitory pathways. Agonists of stimulatory or co-stimulatory pathways and antagonists of inhibitory pathways may have utility as agents to overcome distinct immune suppressive pathways within the tumor microenvironment, inhibit T regulatory cells, reverse/prevent T cell anergy or exhaustion, trigger innate immune activation and/or inflammation at tumor sites, or combinations thereof.

In some embodiments, one or more of the additional therapeutic agents is an immune checkpoint inhibitor. As used herein, the term "immune checkpoint inhibitor" refers to an antagonist of an inhibitory or co-inhibitory immune checkpoint. Immune checkpoint inhibitors may antagonize an inhibitory or co-inhibitory immune checkpoint by interfering with receptor-ligand binding and/or altering receptor signaling. Examples of immune checkpoints (ligands and receptors), some of which are selectively upregulated in various types of cancer cells, that can be antagonized include PD-1 (programmed cell death protein 1); PD-L1 (PD1 ligand); BTLA (B and T lymphocyte attenuator); CTLA-4 (cytotoxic T-lymphocyte associated antigen 4); TIM-3 (T-cell membrane protein 3); LAG-3 (lymphocyte activation gene 3); TIGIT (T cell immunoreceptor with Ig and ITIM domains); CD276 (B7-H3); PD-L2 (programmed cell death 1 ligand 2); Galectin 9; CEACAM-1 (carcinoembryonic antigen-related cell adhesion molecule 1); CD69 (cluster of differentiation 69); Galectin-1; CD113 (poliovirus receptor-related 3; nectin-3); GPR56 (G protein-coupled receptor 56); VISTA (V-domain Ig suppressor of T cell activation); natural killer cell receptor 2B4 (cluster of differentiation 244); CD48 (cluster of differentiation 48); GARP (glycoprotein-A repetitions predominant protein); PD1H (programmed death-1 homolog); LAIR1 (leukocyte associated immunoglobulin like receptor 1); TIM-1 (T-cell membrane protein 1); and TIM-4 (T cell membrane protein 3); and Killer Inhibitory Receptors, which can be divided into two classes based on their structural features: i) killer cell immunoglobulin-like receptors (KIRs), and ii) C-type lectin receptors (members of the type II transmembrane receptor family). Also contemplated are other less well-defined immune checkpoints that have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

In some embodiments, an immune checkpoint inhibitor is a CTLA-4 antagonist. In further embodiments, the CTLA-4 antagonist can be an antagonistic CTLA-4 antibody. Suitable antagonistic CTLA-4 antibodies include, for example, monospecific antibodies such as ipilimumab or tremelimumab, as well as bispecific antibodies such as MEDI5752 and KN046.

In some embodiments, an immune checkpoint inhibitor is a PD-1 antagonist. In further embodiments, the PD-1 antagonist can be an antagonistic PD-1 antibody. Suitable antagonistic PD-1 antibodies include, for example, monospecific antibodies such as budigalimab, camrelizumab, cosibelimab, dostarlimab, emiplimab, ezabenlimab (BI-754091), MEDI-0680 (AMP-514; WO2012/145493), nivolumab, pembrolizumab, pidilizumab (CT-011), pimivalimab, retifanlimab, sasanlimab, spartalizumab, sintilimab, tislelizumab, toripalimab, and zimberelimab; as well as bi-specific antibodies such as LY3434172. In still further embodiments, the PD-1 antagonist can be a recombinant protein composed of the extracellular domain of PD-L2 (B7-DC) fused to the Fc portion of IgG1 (AMP-224). In certain embodiments, an immune checkpoint inhibitor is zimberelimab.

In some embodiments, an immune checkpoint inhibitor is a PD-L1 antagonist. In further embodiments, the PD-L1 antagonist can be an antagonistic PD-L1 antibody. Suitable antagonistic PD-L1 antibodies include, for example, monospecific antibodies such as avelumab, atezolizumab, durvalumab, BMS-936559, and envafolimab as well as bi-specific antibodies such as LY3434172 and KN046.

In some embodiments, an immune checkpoint inhibitor is a TIGIT antagonist. In further embodiments, the TIGIT antagonist can be an antagonistic TIGIT antibody. Suitable antagonistic anti-TIGIT antibodies include monospecific antibodies such as AGEN1327, antibody disclosed in WO2021/247591, BMS 986207, COM902, AB308, domvanalimab, EOS-448, etigilimab, IBI-929, JS006, M6223, ociperlimab, SEA-TGT, tiragolumab, vibostolimab; as well as bi-specific antibodies such as AGEN1777 and AZD2936. In certain embodiments, an immune checkpoint inhibitor is domvanalimab or antibody disclosed in WO2021/247591.

In some embodiments, an immune checkpoint inhibitor is a LAG-3 antagonist. In further embodiments, the LAG-3 antagonist can be an antagonistic LAG-3 antibody. Suitable antagonistic LAG-3 antibodies include, for example, BMS-986016 (WO10/19570, WO14/08218), or IMP-731 or IMP-321 (WO08/132601, WO09/44273). In certain embodiments, an immune checkpoint inhibitor is a B7-H3 antagonist. In further embodiments, the B7-H3 antagonist is an antagonistic B7-H3 antibody. Suitable antagonist B7-H3 antibodies include, for example, MGA271 (WO11/109400), omburtamab, enoblituzumab, DS-7300a, ABBV-155, and SHR-A1811.

In some embodiments, one or more of the additional therapeutic agents activates a stimulatory or co-stimulatory immune checkpoint. Examples of stimulatory or co-stimulatory immune checkpoints (ligands and receptors) include B7-1, B7-2, CD28, 4-1BB (CD137), 4-1BBL, ICOS, ICOS-L, OX40, OX40L, GITR, GITRL, CD70, CD27, CD40, DR3 and CD2.

In some embodiments, an agent that activates a stimulatory or co-stimulatory immune checkpoint is a CD137 (4-1BB) agonist. In further embodiments, the CD137 agonist can be an agonistic CD137 antibody. Suitable CD137 antibodies include, for example, urelumab and PF-05082566 (WO12/32433). In some embodiments, an agent that activates a stimulatory or co-stimulatory immune checkpoint is a GITR agonist. In further embodiments, the GITR agonist can be an agonistic GITR antibody. Suitable GITR antibodies include, for example, BMS-986153, BMS-986156, TRX-518 (WO06/105021, WO09/009116) and MK-4166 (WO11/028683). In some embodiments, an agent that activates a stimulatory or co-stimulatory immune checkpoint is an OX40 agonist. In further embodiments, the OX40 agonist can be an agonistic OX40 antibody. Suitable OX40 antibodies include, for example, MEDI-6383, MEDI-6469, MEDI-0562, PF-04518600, GSK3174998, BMS-986178, and MOXR0916. In some embodiments, an agent that activates a stimulatory or co-stimulatory immune checkpoint is a CD40 agonist. In further embodiments, the CD40 agonist can be an agonistic CD40 antibody. In some embodiments, an agent that activates a stimulatory or co-stimulatory immune checkpoint is a CD27 agonist. In further embodiments, the CD27 agonist can be an agonistic CD27 antibody. Suitable CD27 antibodies include, for example, varlilumab.

In some embodiments, one or more of the additional therapeutic agents is an agent that inhibits or depletes immune-suppressive immune cells. For example, to inhibit or deplete immunosuppressive macrophages or monocytes the agent may be CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13/169264).

In some embodiments, each additional therapeutic agent can independently be a chemotherapeutic agent, a radiopharmaceutical, a hormone therapy, an epigenetic modulator, a targeted agent, an immunotherapeutic agent, a cellular therapy, or a gene therapy. For example, in one embodiment, the present disclosure contemplates the use of the HIF-2α inhibitors described herein in combination with one or more chemotherapeutic agents and optionally one or more additional therapeutic agents, wherein each additional therapeutic agent is independently a radiopharmaceutical, a hormone therapy, a targeted agent, an immunotherapeutic agent, a cellular therapy, or a gene therapy. In another embodiment, the present disclosure contemplates the use of the HIF-2α inhibitors described herein in combination with one or more chemotherapeutic agents and optionally one or more additional therapeutic agents, wherein each additional therapeutic agent is independently a targeted agent, an immunotherapeutic agent, or a cellular therapy. In another embodiment, the present disclosure contemplates the use of HIF-2α inhibitors of the present disclosure in combination with one or more chemotherapeutic agents and one or more inhibitors independently selected from (i) BCR-ABL kinase inhibitor; (ii) an EGFR inhibitor (e.g., EGFR TKI or anti-EGFR antibody); (iii) HER-2/neu receptor inhibitor; (iv) an anti-angiogenic agent (e.g., anti-VEGF antibody, VEGFR TKI, VEGF kinase inhibitors, etc.); (v) AKT inhibitor; (vi) BRAF inhibitor; (vii) RET inhibitor; (viii) MET inhibitor; and (ix) ALK inhibitor; and optionally one or more additional therapeutic agents, wherein each additional therapeutic agent is independently a targeted agent, an immunotherapeutic agent, or a cellular therapy. In another embodiment, the present disclosure contemplates the use of the HIF-2α inhibitors described herein in combination with one or more immunotherapeutic agents and optionally one or more additional therapeutic agent, wherein each additional therapeutic agent is independently a radiopharmaceutical, a hormone therapy, a targeted agent, a chemotherapeutic agent, a cellular therapy, or a gene therapy. In another embodiment, the present disclosure contemplates the use of the HIF-2α inhibitors described herein in combination with one or more immunotherapeutic agents and optionally one or more additional therapeutic agents, wherein each additional therapeutic agent is independently a chemotherapeutic agent, a targeted agent, or a cellular therapy. In another embodiment, the present disclosure contemplates the use of the HIF-2α inhibitors described herein in combination with one or more immune checkpoint inhibitors and/or one or more ATP-adenosine axis-targeting agents, and/or one or more tyrosine kinase inhibitors, and optionally one or more additional therapeutic agents, wherein each additional therapeutic agent is independently a chemotherapeutic agent, a targeted agent, an immunotherapeutic agent, or a cellular therapy. In another embodiment, the present disclosure contemplates the use of the HIF-2α inhibitors of the present disclosure in combination with one or more immune checkpoint inhibitors and/or one or more ATP-adenosine axis-targeting agents, and one or more inhibitors independently selected from (i) BCR-ABL kinase inhibitor; (ii) an EGFR inhibitor (e.g., EGFR TKI or anti-EGFR antibody); (iii) HER-2/neu receptor inhibitor; (iv) an anti-angiogenic agent (e.g., anti-VEGF antibody, VEGFR TKI, VEGF kinase inhibitors, etc.); (v) AKT inhibitor; (vi) BRAF inhibitor; (vii) RET inhibitor; (viii) MET inhibitor; (ix) ALK inhibitor, (x) AXL inhibitor, and (xi) an inhibitor of CDK-4 and/or CDK-6. In further embodiments of the above (a) the targeted agent can be a PI3K inhibitor, an arginase inhibitor, an AXL inhibitor, or a PAK4 inhibitor; a VEGFR inhibitor; an inhibitor of CDK-4 and/or CDK-6, or an anti-angiogenic agent; (b) the immunotherapeutic agent is an ATP-adenosine axis-targeting agent or an immune checkpoint inhibitor; (c) the ATP-adenosine axis-targeting agent is an $A2_AR$ and/or $A2_BR$ antagonist, a CD73 inhibitor, or a CD39 inhibitor; (d) the ATP-adenosine axis-targeting agent is etrumadenant, quemliclustat, or AB598; (e) the immunotherapeutic agent is an anti-PD-1 antagonist antibody or an anti-TIGIT antagonist antibody; (f) the immunotherapeutic agent is zimberelimab, domvanalimab, or AB308; or (g) any combination thereof. In still further embodiments of the above, the present disclosure contemplates the use of the HIF-2α inhibitors described herein in combination with domvanalimab, etrumadenant, quemliclustat, zimberelimab, AB308, or any combination thereof.

Selection of the additional therapeutic agent(s) may be informed by current standard of care for a particular cancer and/or mutational status of a subject's cancer and/or stage of disease. Detailed standard of care guidelines are published, for example, by National Comprehensive Cancer Network (NCCN). See, for instance, NCCN CRC v3.2021, NCCN Hepatobilliary v4.2021, NCCN Kidney Cancer, v2.2022, NCCN NSCLC v5.2021, NCCN PDAC v2.2021.

Other Therapeutic Agents

In another aspect, the present disclosure contemplates the use of HIF-2α inhibitors of this disclosure in combination with one or more additional active therapeutic agent useful in the treatment of immune- and/or inflammatory-related diseases, disorders or conditions.

In some embodiments, one or more additional therapeutic active agent is a non-steroidal anti-inflammatory drug (NSAID), a cyclooxygenase-2 (COX-2) inhibitor, or a steroid.

In some embodiments, one or more additional therapeutic active agent is a JAK inhibitor.

In some embodiments, one or more additional therapeutic active agent is an immune checkpoint inhibitor. Suitable immune checkpoint inhibitors are described above.

In some embodiments, one or more additional therapeutic active agent is cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, infliximab, adalimumab, anti-TNF antibody fragments (e.g., CDP870), and soluble p55 or p75 TNF receptors, derivatives thereof, p75TNFRIgG (entanercept) or p55TNFR1gG (lenercept), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the HIF-2α inhibitors described herein include interferon β-1a; interferon-β-1b, glatiramer acetate; hyperbaric oxygen; intravenous immunoglobulin; cladribine; and antibodies to, or antagonists of, other human cytokines or growth factors (e.g., antibodies to CD40 ligand and CD80).

The present disclosure also contemplates the use of the HIF-2α inhibitors described herein in combination with one or more additional active therapeutic agent useful in the treatment of cardiovascular and/or metabolic-related diseases, disorders and conditions.

Dosing

The HIF-2α inhibitors of the present disclosure may be administered to a subject in an amount that is dependent upon, for example, the goal of administration (e.g., the degree of resolution desired); the age, weight, sex, and health and physical condition of the subject to which the HIF-2α inhibitor is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with absorption, distribution, metabolism and excretion (ADME), taking into consideration the route of administration and other factors.

In certain embodiments, the HIF-2α inhibitors contemplated by the present disclosure may be administered (e.g., orally, parenterally, etc.) at dosage levels of about 0.01 mg/kg to about 50 mg/kg, or about 1 mg/kg to about 25 mg/kg, of subject body weight per day, one or more times a day, a week, or a month, to obtain the desired therapeutic effect. In some embodiments, the dosage may be delivered independent of the subject's body weight at the dosage levels described above (e.g., a fixed-dosage that results in about 0.01 mg/kg to about 50 mg/kg).

In certain embodiments, the HIF-2α inhibitors of the present disclosure are administered (e.g., orally, parenterally, etc.) at fixed dosage levels of about 1 mg to about 1000 mg, particularly 1, 3, 5, 10, 15, 20, 25, 50, 75, 100, 150, 200, 250, 300, 350, 400, 450, 500, 550, 600, 650, 700, 750, 800, 850, 900, 950, or 1000 mg. In some embodiments, the HIF-2α inhibitor is administered at a dose between about 100 mg to about 1000 mg. In some embodiments, the HIF-2α inhibitor is administered at a dose between about 100 mg to about 500 mg. In some embodiments, the HIF-2α inhibitor is administered at a dose between about 500 mg to about 1000 mg. In some embodiments, the HIF-2α inhibitor is administered at a dose between about 100 mg to about 350 mg. In some embodiments, the HIF-2α inhibitor is administered at a dose between about 350 mg to about 500 mg. In some embodiments, the HIF-2α inhibitor is administered at a dose between about 500 mg to about 750 mg. In some embodiments, the HIF-2α inhibitor is administered at a dose between about 750 mg to about 1000 mg.

In some embodiments, the HIF-2α inhibitor according to the present disclosure is administered one or more times a day, a week, or a month to obtain a desired effect. In some embodiments, the HIF-2α inhibitor is administered once or twice a day. In one embodiment, the HIF-2α inhibitor is administered twice daily. In another embodiment, the HIF-2α inhibitor is administered once daily.

In certain embodiments, the dosage of the HIF-2α inhibitors is contained in a "unit dosage form". The phrase "unit dosage form" refers to physically discrete units, each unit containing a predetermined amount of the HIF-2α inhibitors, either alone or in combination with one or more additional agents, sufficient to produce the desired effect. It will be appreciated that the parameters of a unit dosage form will depend on the particular agent and the effect to be achieved.

EXPERIMENTAL

The following examples are put forth so as to provide those of ordinary skill in the art with a complete disclosure and description of how to make and use the present disclosure, and are not intended to limit the scope of what the inventors regard as their invention. Additional compounds within the scope of this disclosure may be made using methods based on those illustrated in these examples, or based on other methods known in the art. Efforts have been made to ensure accuracy with respect to numbers used (e.g., amounts, temperature, etc.), but some experimental errors and deviations should be accounted for.

All reactions were performed using a Teflon-coated magnetic stir bar at the indicated temperature and were conducted under an inert atmosphere when stated. All chemicals were used as received. Reactions were monitored by TLC (silica gel 60 with fluorescence F254, visualized with a short wave/long wave UV lamp) and/or LCMS (Agilent 1100 or 1200 series LCMS with UV detection at 254 or 280 nm using a binary solvent system [0.1% formic acid in MeCN/0.1% formic acid in H$_2$O] using one of the following columns: Agilent Eclipse Plus C18 [3.5 µm, 4.6 mm i.d.×100 mm], Waters XSelect HSS C18 [3.5 µm, 2.1 mm i.d.×75 mm]). Flash chromatography was conducted on silica gel using an automated system (CombiFlash RF+ manufactured by Teledyne ISCO), with detection wavelengths of 254 and 280 nm, and optionally equipped with an evaporative light scattering detector. Reverse phase preparative HPLC was conducted on an Agilent 1260 or 1290 Infinity series HPLC. Samples were eluted using a binary solvent system (MeCN/H$_2$O with an acid modifier as needed—for example 0.1% TFA or 0.1% formic acid) with gradient elution on a Gemini C18 110 Å column (21.2 mm i.d.×250 mm) with variable wavelength detection. Final compounds obtained through preparative HPLC were concentrated through lyophilization. All reported yields are isolated yields. All assayed compounds were purified to ≥95% purity as determined by $^1$H NMR or LCMS (Agilent 1100 or 1200 series LCMS with UV detection at 254 or 280 nm using a binary solvent system [0.1% formic acid in MeCN/0.1% formic acid in H$_2$O] using one of the following columns: Agilent Eclipse Plus C18 [3.5 µm, 4.6 mm i.d.×100 mm], Waters XSelect HSS C18 [3.5 µm, 2.1 mm i.d.×75 mm]) 1H NMR spectra were recorded on a Varian 400 MHz NMR spectrometer equipped with an Oxford AS400 magnet or a Bruker AVANCE NEO 400 MHz NMR. Chemical shifts (δ) are reported as parts per million (ppm) relative to residual undeuterated solvent as an internal reference. The abbreviations s, br s, d, t, q, dd, dt, ddd, dddd, dddt, and m stand for singlet, broad singlet, doublet, triplet, quartet, doublet of doublets, doublet of triplets, doublet of doublet of doublets, doublet of doublet of doublet of triplets, doublet of doublet of doublets of doublets and multiplet, respectively.

Unless indicated otherwise, temperature is in degrees Celsius (° C.), and pressure is at or near atmospheric. Standard abbreviations are used, including the following: rt or r.t.=room temperature; min=minute(s); h or hr=hour(s); ng=nanogram; µg=microgram; mg=milligram; g=gram; kg=kilogram; µl or µL=microliter; ml or mL=milliliter; l or L=liter; µM=micromolar; mM=millimolar; M=molar; mol=mole; mmol=millimole; aq.=aqueous; calcd=calculated; sat. or satd.=saturated; equiv.=equivalent(s); psi=pounds per square inch; mbar=millibar; DCM and CH$_2$Cl$_2$=dichloromethane; CDCl$_3$=chloroform-d; CCl$_4$=carbon tetrachloride; MTBE=methyl tert-butyl ether; THF=tetrahydrofuran; THP=tetrahydropyran; Et$_2$O=diethyl ether; EtOAc=ethyl acetate; DCE=1,2-dichloroethane; DME=dimethoxyethane; ACN and CH$_3$CN=acetonitrile; NMP=N-methyl-2-pyrrolidone; DMF=N,N-dimethylformamide; DMSO=dimethyl sulfoxide; EtOH=ethanol; MeOH=methanol; H$_2$=hydrogen gas; N$_2$=nitrogen gas; PPh$_3$=triphenyl phosphine; AIBN=azobisisobutyronitrile; CAN=ceric ammonium nitrate; DIBAL-H=diisobutylammonium hydride; DAST=diethylaminosulfur trifluoride=DIAD=diisopropyl azodicarboxylate; BzCl=benzoyl chloride; AgOTf=silver trifluoromethanesulfonate; AgClO$_4$=silver perchlorate; TBSOTf=tert-butyldimethylsilyl trifluoromethanesulfonate; TFAA=trifluoracetic anhydride; DHP=3,4-dihydropyran; TMSCHN$_2$=trimethylsilyldiazomethane; TMSCF$_3$=trifluormethyltrimethyl silane; TMSCF$_2$H=difluoromethyltrimethylsilane; TMSCF$_2$Br=(bromodifluoromethyl)trimethylsilane; TBDPSCl=tert-butyl(chloro)diphenylsilane; TBAF=tetra-n-butylammonium fluoride; 3HF·TEA=triethylamine trihydrofluoride; mCPBA=meta-chloroperoxybenzoic acid; NBS=N-bromosuccinimide; Na$_2$SO$_4$=sodium sulfate; MgSO$_4$=magnesium sulfate; CsF=cesium fluoride; Cs$_2$CO$_3$=cesium carbonate; NaHCO$_3$=sodium bicarbonate; NH$_4$OH=ammonium hydroxide; NH$_3$=ammonia; Et$_3$N=triethyl amine; KOH=potassium hydroxide; NaOH=sodium hydroxide; Na$_2$S$_2$O$_3$=sodium thiosulfate; NaBH4=sodium borohydride; LiOH·H$_2$O=lithium hydroxide monohydrate; KOAc=potassium acetate; TsOH·H$_2$O=p-toluenesulfonic acid monohydrate; TsNHNH$_2$=p-toluenesulfonhydrazide; pTsOH·H$_2$O=p-toluenesulfonic acid monohydrate; HBF$_4$=tetrafluoroboric acid; OsO$_4$=osmium tetroxide; TFA=trifluoroacetic acid; HCO$_2$H=formic acid; SiO$_2$=silicon dioxide; DMAP=4-dimethylaminopyridine; DMP=Dess-Martin periodinane; NFSI=N-fluorobenzenesulfonimide; H$_2$SO$_4$=sulfuric acid; CuCl=copper(I) chloride; CuSCN=copper(I) thiocyanate; (CyCAAC)Rh(COD)Cl=[2-[2,6-bis(1-methylethyl)phenyl]-3,3-dimethyl-2-azaspiro[4.5]dec-1-ylidene]chloro[(1,2,5,6-η)-1,5-cyclooctadiene]Rhodium; [RuCl((R)-BINAP)(p-cymene)]Cl=Chloro[(R)-(+)-2,2'-bis(diphenylphosphino)-1,1'-binaphthyl](p-cymene)ruthenium(II) chloride; RuCl(p- cymene)[(R,R)-TsDPEN]=[N-[(1R,2R)-2-(Amino-κN)-1,2-diphenylethyl]-4-methylbenzenesulfonamidato-κN] chloro [(1,2,3,4,5,6-η)-1-methyl-4-(1-methylethyl)benzene]-ruthenium; PMB=p-methoxybenzyl; MHz=megahertz; Hz=hertz; ppm=parts per million; ESI MS=electrospray ionization mass spectrometry; NMR=nuclear magnetic resonance; TLC=thin layer chromatography; LCMS=liquid chromatography-mass spectrometry.

Example 1: 4-[(4S)-5,5-Difluoro-4-hydroxy-3-(trifluoromethyl)-6,7-dihydro-4H-indazol-1-yl]-2,2-dimethylbutanenitrile resulting mixture was heated at reflux for 1 h. After cooling down to room temperature, the reaction was quenched with NaHCO₃ sat., the organic phase was separated, and the aqueous layer was extracted with DCM. The combined organic phase was dried over Na₂SO₄, concentrated and the crude residue was purified by column chromatography (SiO₂, EtOAc in hexanes, 30 to 60%) to give 5-fluoro-3-(trifluoromethyl)-1,5,6,7-tetrahydroindazol-4-one (2.94 g, 54% yield).

Step d: To a solution of 5-fluoro-3-(trifluoromethyl)-1,5,6,7-tetrahydroindazol-4-one (2.90 g, 13.1 mmol, 1.0 equiv.) in THF (131 mL, 0.1M) was added DHP (1.8 mL, 19.6 mmol, 1.5 equiv.) and pTsOH·H₂O (248 mg, 1.31 mmol, 0.1

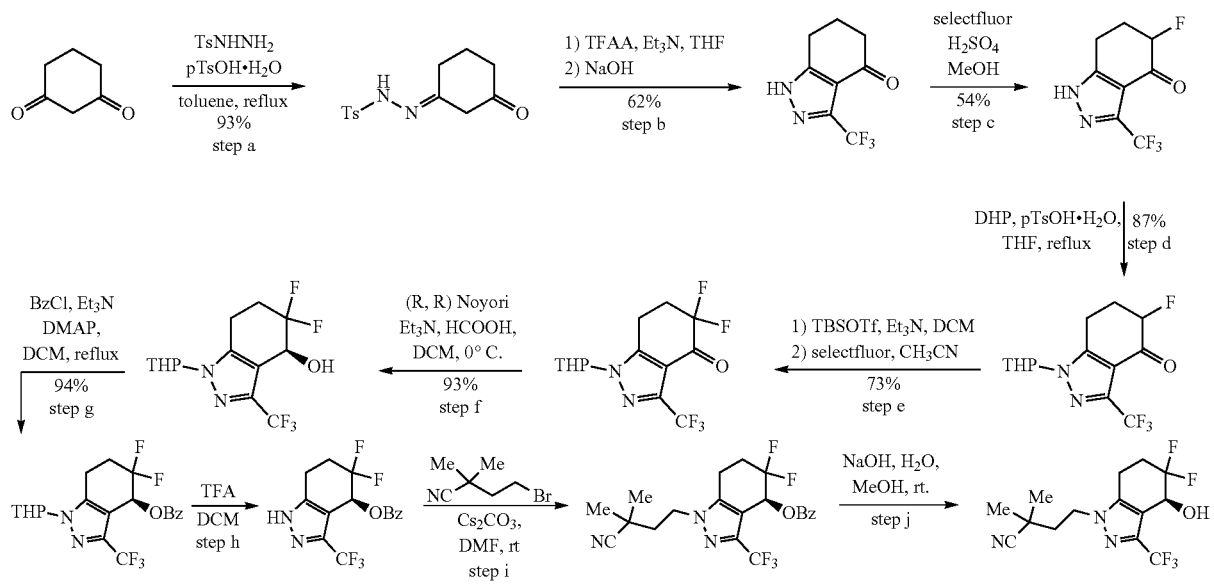

Step a: Cyclohexane-1,3-dione (5 g, 44.6 mmol, 1.0 equiv.), TsNHNH₂ (8.3 g, 44.6 mmol, 1.0 equiv.) and pTsOH·H₂O (85 mg, 0.45 mmol, 0.01 equiv.) were dissolved in toluene (297 mL, 0.15 M) and the mixture was stirred at 110° C. for 30 minutes. After cooling down to rt, the reaction mixture was filtered and the solid washed with MTBE to afford 4-methyl-N-[(E)-(3-oxocyclohexylidene)amino]benzenesulfonamide (11.63 g, 93%).

Step b: The product of step a (11.4 g, 40.7 mmol, 1.0 equiv.) was suspended in THF (204 mL, 0.2M) and Et₃N (14 mL, 102 mmol, 2.5 equiv.) followed by TFAA (5.7 mL, 40.7 mmol, 1.0 equiv.) were added and the mixture was stirred at 50° C. for 3 h. After cooling down to rt, 40 mL of 1M aq. NaOH and 40 mL of MeOH were added, and the mixture was stirred at rt overnight. The reaction was quenched with sat. aq. NH₄Cl solution, the organic phase was separated, and the aqueous layer was extracted with EtOAc. The combined organic phase was dried over Na₂SO₄, concentrated and the crude residue was purified by column chromatography (SiO₂, EtOAc in hexanes, 20 to 60%) to give 3-(trifluoromethyl)-1,5,6,7-tetrahydroindazol-4-one (5.19 g, 62% yield).

Step c: To the product of step b (5.05 g, 24.7 mmol, 1.0 equiv.) in MeOH (124 mL, 0.2M) was added Selectfluor (9.63 g, 27.2 mmol, 1.1 equiv.) and concentrated H₂SO₄ (0.1 mL). The resulting mixture was heated at reflux for 3 h. After cooling down to room temperature, 0.3 M aq. H₂SO₄ solution (10 mL) was added to the reaction mixture. The equiv.) and the mixture was refluxed overnight. The reaction was quenched with NaHCO₃ sat., the organic phase was separated, and the aqueous layer was extracted with EtOAc. The combined organic phase was dried over Na₂SO₄, concentrated and the crude residue was purified by column chromatography (SiO₂, EtOAc in hexanes, 20 to 60%) to give 5-fluoro-1-(oxan-2-yl)-3-(trifluoromethyl)-6,7-dihydro-5H-indazol-4-one (3.49 g, 87% yield).

Step e: To a solution of the product from step d (3.40 g, 11.1 mmol, 1.0 equiv.) and Et₃N (9.1 mL, 66.6 mmol, 6.0 equiv.) in DCM (28 mL, 0.4M) was added TBSOTf (5.1 mL, 22.2 mmol, 2.0 equiv.) dropwise at 0° C. The resulting solution was stirred at 0° C. for 1.5 h, and then quenched with sat. aq. NaHCO₃ solution. The organic phase was separated, and the aqueous phase was extracted with DCM, the combined organic phase was then washed with brine, dried over Na₂SO₄ and concentrated to afford the silyl enol ether. The crude material was then dissolved in MeCN (55 mL, 0.2M) and Selectfluor (5.90 g, 16.7 mmol, 1.5 equiv.) was added portion-wise at room temperature. The resulting mixture was stirred at room temperature for 30 min, then water and DCM were added, and the aqueous phase was extracted with DCM. The combined organic phase was dried over Na₂SO₄, concentrated and the crude residue was purified by column chromatography (SiO₂, EtOAc in hexanes, 30 to 60%) to give 5,5-difluoro-1-(oxan-2-yl)-3-(trifluoromethyl)-6,7-dihydroindazol-4-one (2.63 g, 73% yield).

Step f: To a solution of the product from step e (1.70 g, 5.24 mmol, 1.0 equiv.) in DCM (26 mL, 0.2M) was added HCO₂H (0.59 mL, 15.7 mmol, 3.0 equiv.) and Et₃N (1.4 mL, 10.5 mmol, 2.0 equiv.). After cooling down the solution to 0° C., RuCl(p-cymene)[(R,R)-TsDPEN] (100 mg, 0.16 mmol, 0.03 equiv.) was added and the resulting mixture was kept in the fridge overnight. The reaction was quenched with sat. aq. NaHCO₃ solution, the organic phase was separated, and the aqueous layer was extracted with DCM. The combined organic phase was dried over Na₂SO₄, concentrated and the crude residue was purified by column chromatography (SiO₂, EtOAc in hexanes, 10 to 40%) to give (4S)-5,5-difluoro-1-(oxan-2-yl)-3-(trifluoromethyl)-6,7-dihydro-4H-indazol-4-ol (1.58 g, 93% yield).

Step g: The product from step f (1.53 g, 4.69 mmol, 1.0 equiv.) was dissolved in DCM (31 mL, 0.15M) and Et₃N (1.3 mL, 9.38 mmol, 2 equiv.), BzCl (0.82 mL, 7.04 mmol, 1.5 equiv.) and DMAP (57 mg, 0.47 mmol, 0.1 equiv.) were added. The reaction mixture was refluxed overnight and quenched with sat. aq. NH₄Cl solution. The organic phase was separated, the aqueous layer was extracted with DCM, the combined organic phase was dried over Na₂SO₄, concentrated and the crude residue was purified by column chromatography (SiO₂, EtOAc in hexanes, 0 to 40%) to give [(4S)-5,5-difluoro-1-(oxan-2-yl)-3-(trifluoromethyl)-6,7-dihydro-4H-indazol-4-yl] benzoate (1.90 g, 94% yield).

Step h: The product of step g (1.85 g, 4.30 mmol, 1.0 equiv.) was dissolved in DCM:TFA (5:1, 21.5 mL, 0.2M) and the reaction mixture was stirred at rt for 4 h. The reaction was quenched with NaHCO₃ sat., the organic phase was separated, the aqueous layer was extracted with DCM, the combined organic phase was dried over Na₂SO₄, concentrated and the crude residue was purified by column chromatography (SiO₂, EtOAc in hexanes, 20 to 50%) to give [(4S)-5,5-difluoro-3-(trifluoromethyl)-1,4,6,7-tetrahydroindazol-4-yl] benzoate (1.26 mg, 85% yield).

Step i: The product from step h (85 mg, 0.245 mmol, 1.0 equiv.) was dissolved in DMF (1.2 mL). To this solution was added 4-bromo-2,2-dimethylbutanenitrile (52 mg, 0.294 mmol, 1.2 equiv.) and Cs₂CO₃ (160 mg, 0.490 mmol, 2.0 equiv.). The reaction was stirred at ambient room temperature for 48 h, or until LCMS indicated the complete consumption of starting material. The reaction was diluted with H₂O and extracted with EtOAc. The aqueous layer was separated and back extracted with additional EtOAc. The organic layers were combined, washed with water, brine, and dried over MgSO₄. Concentration under reduced pressure and purification by flash chromatography (SiO₂, hexanes to 30% EtOAc) furnished [(4S)-1-(3-cyano-3-methylbutyl)-5,5-difluoro-3-(trifluoromethyl)-6,7-dihydro-4H-indazol-4-yl] benzoate (63 mg, 58% yield).

Step j: The product from step i (60 mg, 0.136 mmol, 1.0 equiv.) was dissolved in MeOH (1.4 mL). To this mixture was added 1M aq. NaOH solution (0.68 mL, 0.68 mmol, 5.0 equiv.) and the reaction was stirred for 1 h, or until the consumption of starting material by LCMS. The reaction was quenched with sat. aq. NH₄Cl solution and diluted with EtOAc. The aqueous layer was separated and back extracted with additional EtOAc. The organic layers were combined, washed with water, brine, and dried over MgSO₄. Concentration under reduced pressure and purification by flash chromatography (SiO₂, hexanes to 40% EtOAc) furnished the title compound as a pale yellow oil (10.7 mg, 23% yield). ¹H NMR (400 MHz, CDCl₃) δ 4.88 (q, J=5.7 Hz, 1H), 4.26-4.19 (m, 2H), 2.99-2.80 (m, 2H), 2.65-2.45 (m, 2H), 2.37-2.22 (m, 1H), 2.19-2.08 (m, 2H), 1.40 (d, J=5.9 Hz, 6H). ESI MS [M+H]⁺ for C₁₄H₁₆F₅N₃O, calcd 338.1, found 338.0.

Example 2: (4S)-1-[(3,3-difluorocyclobutyl)methyl]-5,5-difluoro-3-(trifluoromethyl)-6,7-dihydro-4H-indazol-4-ol

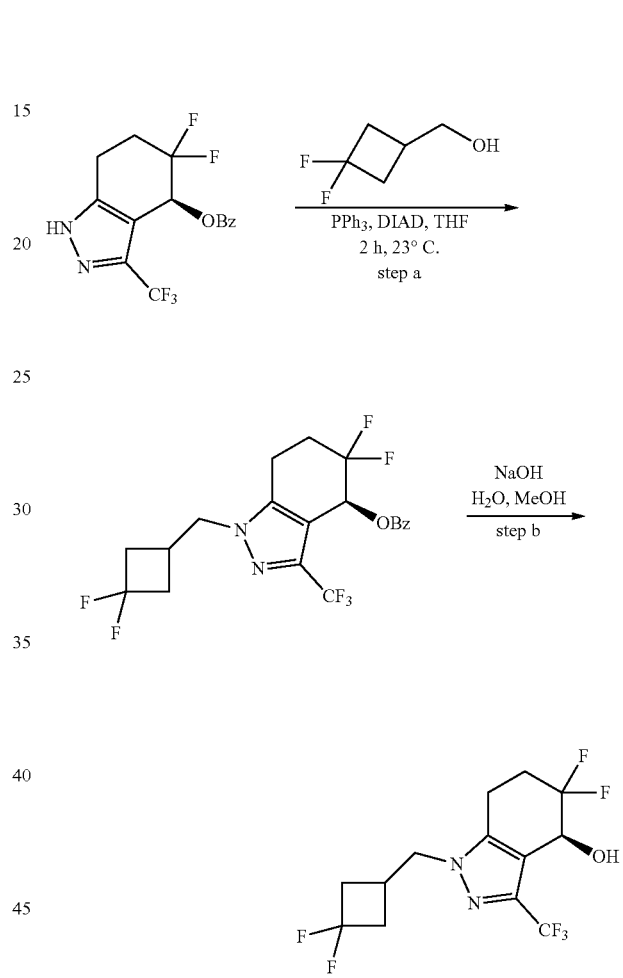

Step a: To a solution of [(4S)-5,5-difluoro-3-(trifluoromethyl)-1,4,6,7-tetrahydroindazol-4-yl] benzoate (200 mg, 0.578 mmol, 1.0 equiv.) in THF (5.8 mL) was added PPh₃ (273 mg, 1.04 mmol, 1.8 equiv.) then (3,3-difluorocyclobutyl)methanol (141 mg, 1.15 mmol, 2.0 equiv.). DIAD (0.23 mL, 1.15 mmol, 2.0 equiv.) was then added dropwise and the mixture was stirred at 23° C. for 2 h. After concentration, the crude residue was purified by column chromatography (SiO₂, EtOAc in hexanes, 0 to 35%) to afford the desired compound (92 mg, 35% yield).

Step b: The deprotection step was carried out as described for Example 1 to furnish the title compound. ¹H NMR (400 MHz, CDCl₃) δ 4.85 (q, J=5.7 Hz, 1H), 4.14-4.04 (m, 2H), 2.89-2.74 (m, 2H), 2.74-2.62 (m, 4H), 2.61-2.41 (m, 1H), 2.41-2.20 (m, 3H). ESI MS [M+H]⁺ for C₁₃H₁₄F₇N₂O, calcd 347.1, found 347.0.

Example 3: 4-[(4S)-5,5-difluoro-4-hydroxy-3-(trifluoromethyl)-6,7-dihydro-4H-indazol-1-yl]-2-methylbutanenitrile

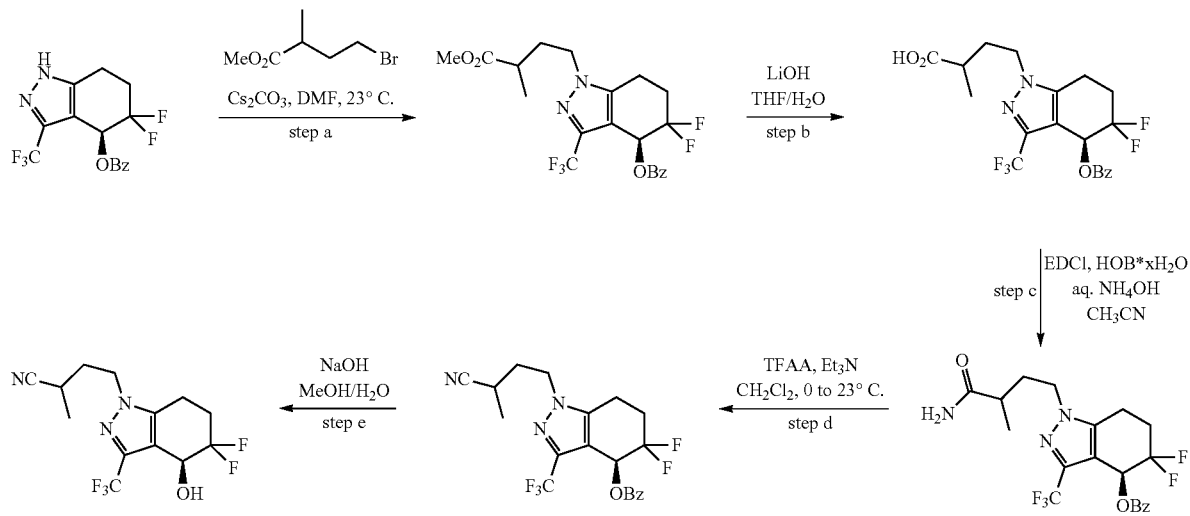

Step a: [(4S)-5,5-Difluoro-1-(4-methoxy-3-methyl-4-oxobutyl)-3-(trifluoromethyl)-6,7-dihydro-4H-indazol-4-yl] benzoate (1.0 g, 2.17 mmol, 77% yield) was prepared according to the general protocol described for Example 1, step i using [(4S)-5,5-difluoro-3-(trifluoromethyl)-1,4,6,7-tetrahydroindazol-4-yl] benzoate (1.0 g, 2.9 mmol) and methyl 4-bromo-2-methylbutanoate (0.7 g, 3.6 mmol) as the alkylating reagent.

Step b: The methyl ester from step a (200.0 mg, 0.43 mmol) was dissolved in THF (2.0 mL) and a solution of LiOH·H$_2$O (91.0 mg, 2.2 mmol) in water (1 mL) was added at ambient temperature. The resulting mixture was vigorously stirred and monitored by TLC analysis. Upon complete consumption of the starting material the reaction was acidified with 1M aq. hydrochloric acid to pH ~3 and the product was extracted with EtOAc (3×7 mL). Combined organic extract was washed with brine, dried over Na$_2$SO$_4$ and concentrated to dryness to produce the desired carboxylic acid (194.0 mg, 0.43 mmol, 100% yield) as a colorless oil.

Step c: N-(3-dimethylaminopropyl)-N'-ethylcarbodiimide hydrochloride (108.0 mg, 0.57 mmol) and 1-hydroxybenzotriazole hydrate (95.0 mg, 0.57 mmol, contains 20 wt. % of water) were added to a solution of the carboxylic acid from step b (194.0 mg, 0.43 mmol) in CH$_3$CN (2.2 mL). The resulting solution was stirred for 1 h before aq. NH$_4$OH (1.0 mL, 28.0-30.0% NH$_3$ basis) was added in one portion. The reaction mixture was stirred at ambient temperature overnight, then partitioned between EtOAc (10.0 mL) and water (10.0 mL). The aqueous phase was separated and additionally extracted with EtOAc (2×10 mL). The combined organic extract was washed with brine (25 mL), dried over Na$_2$SO$_4$ and concentrated to dryness under reduced pressure. The resulting crude primary amide was used for the next step without additional purification.

Step d: The amide from step c was dissolved in dichloromethane, triethylamine (300 µL, 2.15 mmol) was added, and the reaction mixture was cooled to 0° C. Trifluoroacetic anhydride (180 µL, 1.3 mmol) was added dropwise, and the resulting colorless solution was stirred at 0° C. for 1 h. Once TLC analysis indicated complete consumption of the staring material the reaction was diluted with dichloromethane (20.0 mL), washed with 1M aq. hydrochloric acid (15.0 mL), sat. aq. NaHCO$_3$ (15.0 mL) and brine (15.0 mL). The organic extract was dried over Na$_2$SO$_4$ and concentrated to dryness under reduced pressure. The dry residue was fractionated by column chromatography (SiO$_2$, hexanes/EtOAc gradient) to provide the desired nitrile as a colorless oil (155.0 mg, 0.37 mmol, 87% yield).

Step e: To a solution of the nitrile from step d (155.0 mg, 0.37 mmol) in MeOH (7.5 mL) was added aq. 1M NaOH solution (1.9 mL, 1.9 mmol) at ambient temperature. The resulting mixture was stirred for 1 h. Once TLC analysis indicated complete consumption of the starting material the reaction was diluted with EtOAc (35.0 mL) and aq. 1M NaOH solution (40.0 mL). The organic phase was separated and washed again with aq. 1M NaOH solution (2×20.0 mL) and brine (30.0 mL) to remove the residual benzoic acid. The combined organic phase was dried over Na$_2$SO$_4$, concentrated to dryness, and the crude residue was purified by column chromatography (SiO$_2$, hexanes/EtOAc gradient) to give the title compound (64.0 mg, 55% yield) as a colorless oil. $^1$H NMR (400 MHz, CDCl$_3$) δ 4.85 (br. s, 1H), 4.29-4.08 (m, 2H), 3.08-2.76 (m, 2H), 2.76-2.67 (m, 1H), 2.67-2.42 (m, 2H), 2.38-2.19 (m, 2H), 2.16-1.99 (m, 1H), 1.36 (d, J=7.1 Hz, 3H). ESI MS [M+H]$^+$ for C$_{13}$H$_{14}$F$_5$N$_3$O, calcd 324.1, found 324.2.

Example 4: (4S)-5,5-difluoro-3-(trifluoromethyl)-1-[[3-(trifluoromethyl)-1,2-oxazol-5-yl]methyl]-6,7-dihydro-4H-indazol-4-ol

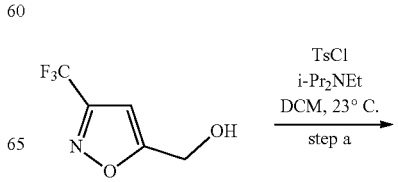

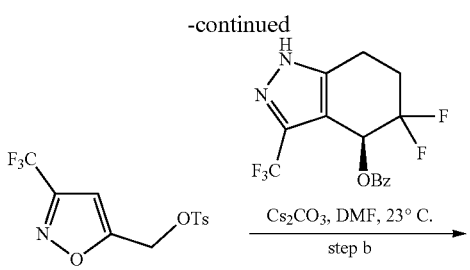

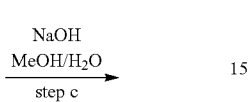

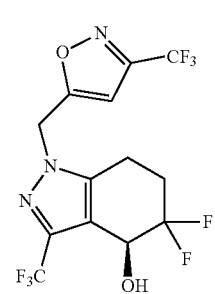

Step a: Tosyl chloride (290.0 mg, 1.5 mmol) was added to a mixture of [3-(trifluoromethyl)-1,2-oxazol-5-yl]methanol (0.25 g, 1.5 mmol) and iPr$_2$NEt (0.5 mL, 3 mmol) in dichloromethane (7.5 mL) at room temperature. The resulting mixture was stirred for 3 h. Then the reaction was diluted with dichloromethane (20.0 mL), washed with aq. 1 M hydrochloric acid (30.0 mL) and brine (30.0 mL). The organic extract was dried over Na$_2$SO$_4$ and concentrated to dryness under reduced pressure. The dry residue was fractionated by column chromatography (SiO$_2$, hexanes/EtOAc gradient) to produce [3-(trifluoromethyl)-1,2-oxazol-5-yl] methyl 4-methylbenzenesulfonate (250.0 mg, 0.78 mmol, 92% yield) as a colorless oil.

Step b: The tosylate from step a (250.0 mg, 0.78 mmol) was added to a mixture of [(4S)-5,5-difluoro-3-(trifluoromethyl)-1,4,6,7-tetrahydroindazol-4-yl] benzoate (225.0 mg, 0.65 mmol) and Cs$_2$CO$_3$ (420.0 mg, 1.3 mmol) in DMF (3.3 mL) at ambient temperature. The resulting mixture was vigorously stirred for 1 h. Once TLC analysis indicated complete consumption of the alkylating reagent the reaction was diluted with EtOAc (30.0 mL), washed with sat. aq. NH$_4$Cl (20.0 mL), water (2×20.0 mL) and brine (20.0 mL). The organic extract was dried over Na$_2$SO$_4$ and concentrated to dryness under reduced pressure. The dry residue was fractionated by column chromatography (SiO$_2$, hexanes/EtOAc gradient) to produce the corresponding alkylated product (210.0 mg, 0.42 mmol, 65% yield) as a colorless oil.

Step c: To a solution of the product of step b (210.0 mg, 0.42 mmol) in MeOH (8.4 mL) was added aq. 1M NaOH solution (2.1 mL, 2.1 mmol) at ambient temperature. The resulting mixture was stirred for 1 h. Once TLC analysis indicated complete consumption of the starting material the reaction was diluted with EtOAc (40.0 mL) and aq. 1M NaOH solution (40.0 mL). The organic phase was separated and washed again with aq. 1M NaOH solution (2×30.0 mL) and brine (30.0 mL) to remove the residual benzoic acid. The combined organic phase was dried over Na$_2$SO$_4$, concentrated to dryness, and the crude product was purified by column chromatography (SiO$_2$, hexanes/EtOAc gradient) to give the title compound (160.0 mg, 96% yield) as a colorless oil. $^1$H NMR (400 MHz, CDCl$_3$) δ 6.54 (s, 1H), 5.42 (s, 2H), 5.02-4.70 (m, 1H), 3.12-2.73 (m, 3H), 2.73-2.42 (m, 1H), 2.41-2.22 (m, 1H). ESI MS [M+H]$^+$ for C$_{13}$H$_9$F$_8$N$_3$O$_2$, calcd 392.1, found 392.1.

Example 5: (4S)-5,5-difluoro-3-(trifluoromethyl)-1-[2-[1-(trifluoromethyl)cyclopropyl]ethyl]-6,7-dihydro-4H-indazol-4-ol

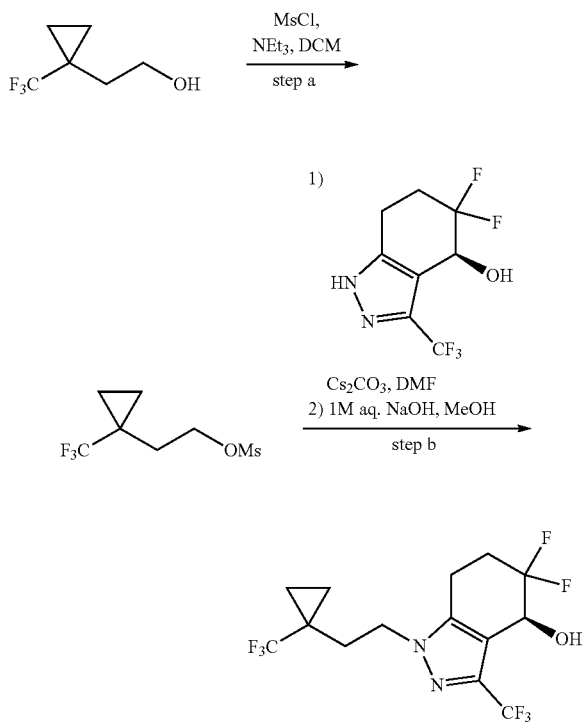

Step a: 2-[1-(Trifluoromethyl)cyclopropyl]ethanol (44 mg, 0.29 mmol, 1.0 equiv.) was dissolved in DCM (1.5 mL, 0.2M). Triethylamine (80 μL, 0.57 mmol, 2.0 equiv.) was added followed by methanesulfonyl chloride (34 μL, 0.44 mmol, 1.5 equiv.). The reaction was stirred at room temperature for 1 hour, at which point it was complete by TLC. The reaction was quenched with 1.0 M HCl (10 mL) and extracted with DCM (2×10 mL). The combined organics were dried over Na$_2$SO$_4$, filtered, and concentrated in vacuo. The crude residue was used directly in the subsequent alkylation without further purification.

Step b: The alkylation was carried out as described for Example 1 using the mesylate prepared in step a. The benzoyl deprotection was also carried out as described for Example 1. $^1$H NMR (400 MHz, Chloroform-d) δ 4.87 (s, 1H), 4.18 (t, J=7.8 Hz, 2H), 2.99-2.74 (m, 2H), 2.60-2.44 (m, 1H), 2.40-2.23 (m, 1H), 2.22-2.05 (m, 2H), 1.06-0.94 (m, 2H), 0.64-0.48 (m, 2H). ESI MS [M+H]$^+$ for C$_{14}$H$_{14}$F$_8$N$_2$O, calcd 379.1, found 379.1.

Example 6: (4S)-5,5-difluoro-1-(4-methoxy-3-methylbutyl)-3-(trifluoromethyl)-6,7-dihydro-4H-indazol-4-ol

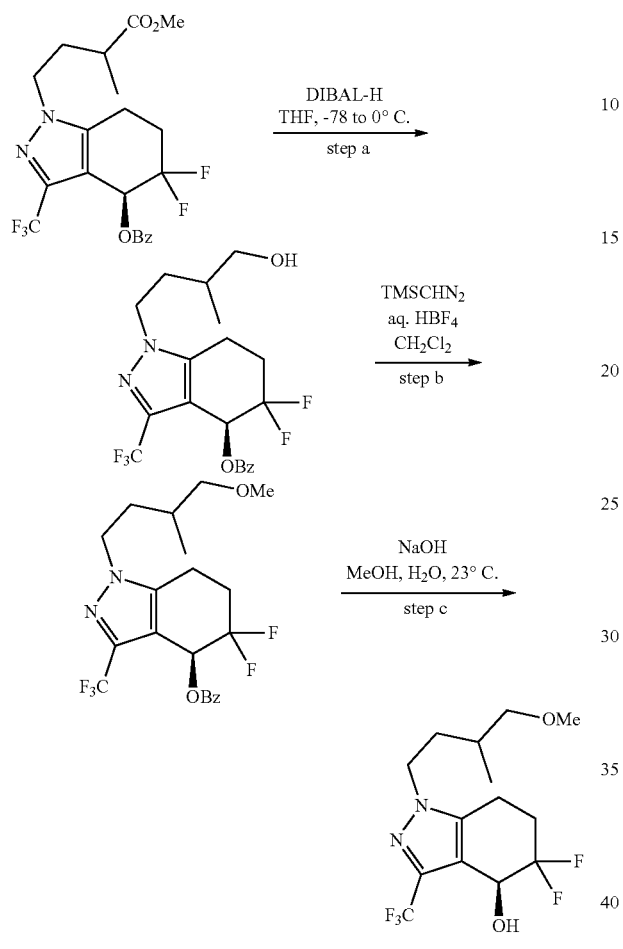

The starting material was prepared according to protocol described in the synthesis of Example 3.

Step a: The methyl ester (0.8 g, 1.74 mmol) was dissolved in THF (17.4 mL), and the resulting solution was cooled to −78° C. under nitrogen atmosphere. 1M DIBAL-H solution in THF (7.7 mL, 7.7 mmol) was added dropwise over 10 min. The resulting mixture was stirred at −78° C. for 2 h, then allowed to warm to 0° C. and stirred for additional 2 h. The reaction was quenched by addition of MeOH (1.0 mL) at 0° C. The resulting solution was diluted with EtOAc (40.0 mL) and saturated aqueous Rochelle's salt (20.0 mL), then vigorously stirred for 2 h. The organic phase was separated, and the aqueous phase was additionally extracted with EtOAc (2×20 mL). The combined organic phase was washed with brine, dried over $Na_2SO_4$ and concentrated to dryness. The crude residue was fractionated by column chromatography ($SiO_2$, hexanes/EtOAc gradient) to give the desired alcohol (460.0 mg, 1.1 mmol, 63% yield) as a colorless oil.

Step b: The alcohol from step a (100.0 mg, 0.24 mmol) was dissolved in dichloromethane (2.4 mL) and aq. 48% $HBF_4$ (31.0 μL, 0.24 mmol) was added. The mixture was cooled to 0° C. before a 2M solution of $TMSCHN_2$ in $Et_2O$ (1.0 mL, 1.92 mmol) was added to the reaction mixture. The cooling bath was removed, and the residue was stirred at ambient temperature overnight. The resulting solution was diluted with dichloromethane (15.0 mL), washed with sat. aq. $NaHCO_3$ (20.0 mL), dried over $Na_2SO_4$ and concentrated to dryness. The dry residue was fractionated by column chromatography ($SiO_2$, hexanes/EtOAc gradient) to give corresponding methyl ether (55.0 mg, 0.12 mmol, 51% yield) as a colorless oil.

Step c: To a solution of the product of step b (55.0 mg, 0.12 mmol) in MeOH (2.5 mL) was added aq. 1M NaOH solution (0.6 mL, 0.6 mmol) at ambient temperature. The resulting mixture was stirred for 1 h. Once TLC analysis indicated complete consumption of the starting material the reaction was diluted with EtOAc (15.0 mL) and aq. 1M NaOH solution (15.0 mL). The organic phase was separated and washed again with aq. 1M NaOH solution (2×10.0 mL) and brine (15.0 mL) to remove the residual benzoic acid. The combined organic phase was dried over $Na_2SO_4$, concentrated to dryness, and the crude product was purified by column chromatography ($SiO_2$, hexanes/EtOAc gradient) to give the title compound (43.0 mg, 100% yield) as a colorless oil. $^1$H NMR (400 MHz, $CDCl_3$) δ 4.84 (s, 1H), 4.07 (t, J=7.7 Hz, 2H), 3.29 (s, 3H), 3.28-3.12 (m, 2H), 2.95-2.70 (m, 3H), 2.62-2.40 (m, 1H), 2.33-2.16 (m, 1H), 1.98-1.85 (m, 1H), 1.83-1.62 (m, 2H), 0.93 (dd, J=6.6, 1.8 Hz, 3H). ESI MS $[M+H]^+$ for $C_{14}H_{19}F_5N_2O_2$, calcd 343.1, found 343.3.

Example 7: (4S)-5,5-difluoro-3-(trifluoromethyl)-1-[2-(trifluoromethylsulfanyl)ethyl]-6,7-dihydro-4H-indazol-4-ol

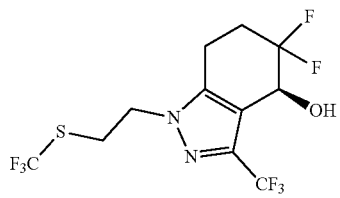 [SMILES: O[C@H]1c2c(C(F)(F)F)nn(CCSC(F)(F)F)c2CCC1(F)F]

The title compound was prepared in a similar fashion to that described for Example 5 from 2-(trifluoromethylsulfanyl)ethanol. $^1$H NMR (400 MHz, $CDCl_3$) δ 4.93-4.79 (m, 1H), 4.29 (t, J=6.8 Hz, 2H), 3.36 (t, J=6.8 Hz, 2H), 2.97-2.77 (m, 2H), 2.68 (s, 1H), 2.65-2.42 (m, 1H), 2.39-2.21 (m, 1H). ESI MS $[M+H]^+$ for $C_{11}H_{10}F_8N_2OS$, calcd 370.0, found 370.1.

Example 8: (4S)-5,5-difluoro-3-(trifluoromethyl)-1-[2-(trifluoromethylsulfonyl)ethyl]-6,7-dihydro-4H-indazol-4-ol

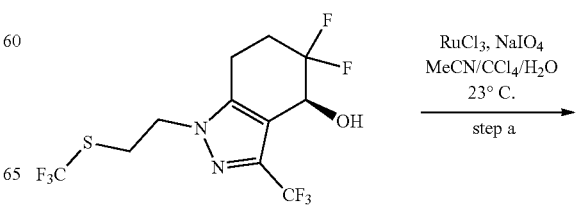

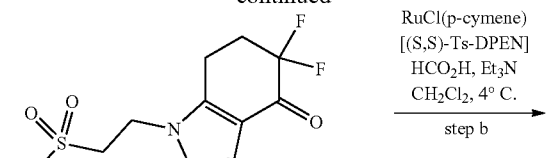

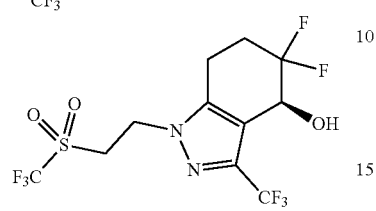

Step a: Ruthenium trichloride (4 mg, 0.016 mmol) and sodium periodate (0.15 g, 0.68 mmol) were added to a solution of (4S)-5,5-difluoro-3-(trifluoromethyl)-1-[2-(trifluoromethylsulfanyl)ethyl]-6,7-dihydro-4H-indazol-4-ol (61 mg, 0.14 mmol) in a mixture of MeCN (0.6 mL), CCl$_4$ (0.6 mL) and water (1.3 mL). The reaction was stirred at the room temperature for 1 h, then it was diluted with dichloromethane (5.0 mL) and aq. sat. Na$_2$S$_2$O$_3$ (5.0 mL). The organic phase was separated, and the aqueous solution was additionally extracted with dichloromethane (2×5 mL). The combined organic solution was washed with brine (5 mL), dried over Na$_2$SO$_4$ and concentrated under reduced pressure. The crude residue was purified by column chromatography (EtOAc in hexanes, 0 to 70%) to give the corresponding trifluoromethylsulfone (63 mg, 0.16 mmol, 95% yield) as colorless oil.

Step b: Product of step a (63 mg, 0.16 mmol) was dissolved in CH$_2$Cl$_2$ (0.8 mL), and the solution was cooled to 0° C. Formic acid (18 µL, 0.47 mmol) and triethylamine (44 µL, 0.31 mmol) were added sequentially and the solution was purged with nitrogen for 10 min. RuCl(p-cymene)[(R,R)-Ts-DPEN] (3 mg, 0.0047 mmol) was added and the resulting mixture was stirred at 4° C. for 16 h. Upon completion (TLC monitoring), the reaction mixture was diluted with dichloromethane (5.0 mL), washed with sat. aq. NaHCO$_3$ (5 mL) and brine (5.0 mL), dried over Na$_2$SO$_4$ and concentrated under reduced pressure. The residue was purified using column chromatography on silica gel column chromatography (EtOAc in hexanes, 0 to 50%) to give the final product (52 mg, 0.13 mmol, 82% yield) as colorless oil. $^1$H NMR (400 MHz, CDCl$_3$) δ 4.87 (q, J=5.7 Hz, 1H), 4.55 (t, J=6.5 Hz, 2H), 4.01-3.78 (m, 2H), 3.05-2.79 (m, 2H), 2.67-2.43 (m, 2H), 2.40-2.22 (m, 1H). ESI MS [M+H]$^+$ for C$_{11}$H$_{10}$F$_8$N$_2$O$_3$S, calcd 402.0, found 402.0.

Example 9: (4S)-5,5-difluoro-1-(3-methoxypropyl)-3-(trifluoromethyl)-6,7-dihydro-4H-indazol-4-ol

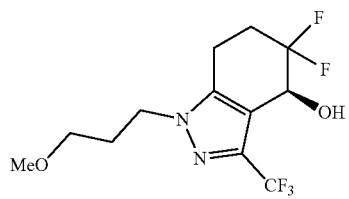 [SMILES: COCCCn1nc(C(F)(F)F)c2c1CCC(F)(F)[C@H]2O]

The title compound was prepared in a similar fashion to Example 1 from 1-bromo-3-methoxypropane. $^1$H NMR (400 MHz, CDCl$_3$) δ 4.87-4.76 (m, 1H), 4.09 (t, J=6.8 Hz, 2H), 3.31-3.19 (m, 4H), 3.16-3.06 (m, 1H), 2.86 (ddd, J=16.6, 6.9, 2.5 Hz, 1H), 2.75 (ddd, J=16.7, 10.7, 6.3 Hz, 1H), 2.59-2.36 (m, 1H), 2.29-2.16 (m, 1H), 2.07 (tddd, J=6.9, 6.1, 5.3, 0.8 Hz, 2H). ESI MS [M+H]$^+$ for C$_{12}$H$_{15}$F$_5$N$_2$O$_2$, calcd 314.1, found 314.1.

Example 10: (4S)-1-(cyclopropylmethyl)-5,5-difluoro-3-(trifluoromethyl)-6,7-dihydro-4H-indazol-4-ol

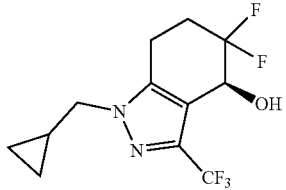 [SMILES: O[C@H]1c2c(C(F)(F)F)nn(CC3CC3)c2CCC1(F)F]

The title compound was prepared in a similar fashion to Example 1 from bromomethylcyclopropane. $^1$H NMR (400 MHz, CDCl$_3$) δ 4.88 (t, J=6.3 Hz, 1H), 3.99-3.84 (m, 2H), 2.99-2.70 (m, 3H), 2.67-2.41 (m, 1H), 2.37-2.19 (m, 1H), 1.33-1.14 (m, 1H), 0.72-0.54 (m, 2H), 0.46-0.28 (m, 2H). ESI MS [M+H]$^+$ for C$_{12}$H$_{13}$F$_5$N$_2$O, calcd 296.1, found 296.0.

Example 11: (4S)-5,5-difluoro-1-[(3S)-4,4,4-trifluoro-3-methoxybutyl]-3-(trifluoromethyl)-6,7-dihydro-4H-indazol-4-ol

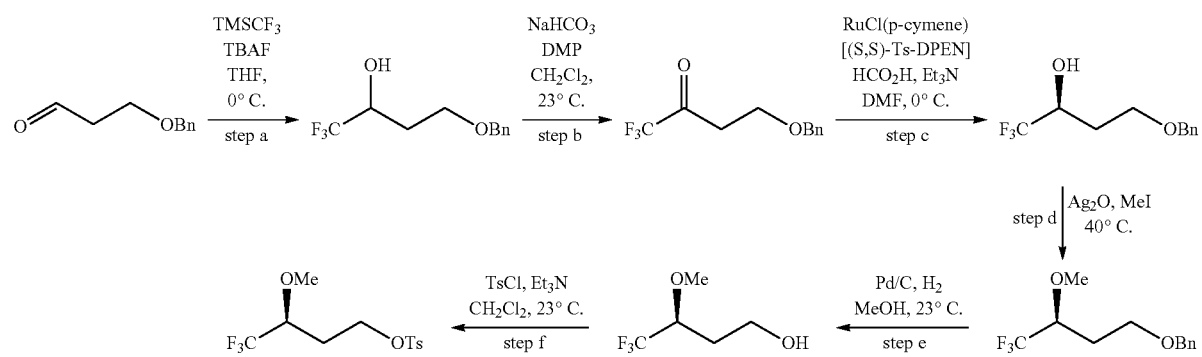

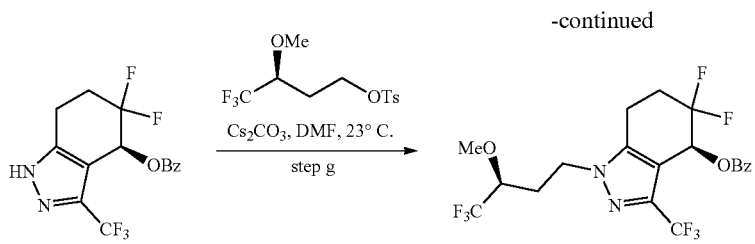 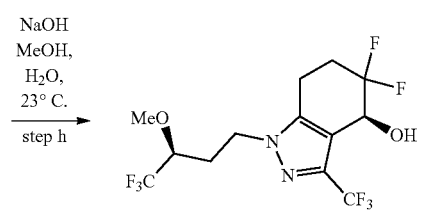

Step a: TMSCF₃ (13.5 mL, 91.35 mmol) and TBAF (1M in THF, 60.9 mL, 60.9 mmol) were sequentially added to the solution of 3-phenylmethoxypropanal (10.0 g, 60.9 mmol) in THF (300.0 mL) at 0° C. The resulting mixture was stirred at 0° C. and monitored by TLC analysis. Upon complete consumption of the starting material the reaction was diluted with EtOAc (300.0 mL), washed with water (3×200.0 mL), then with brine (200.0 mL). The organic phase was separated, dried over Na₂SO₄, filtered, and concentrated to dryness under reduced pressure. The dry residue was fractionated by column chromatography (SiO₂, EtOAc in hexanes, 0 to 50%) to provide desired alcohol (13.1 g, 51.8 mmol, 85% yield) as a colorless oil.

Step b: Dess-Martin periodinane (20.1 g, 47.4 mmol) was slowly added in two portions to the solution of the alcohol from step a (10.1 g, 43.1 mmol) and NaHCO₃ (7.9 g, 94.8 mmol) in CH₂Cl₂ (216.0 mL) at 0° C. Upon complete addition the reaction was warmed up to 23° C. and stirred for 1 h. Then the reaction was quenched by addition of sat. aq. NaHCO₃ (100.0 mL) and sat. aq. Na₂SO₃ (100.0 mL). The resulting biphasic mixture was vigorously stirred for 20 min. The organic layer was separated, and the aqueous phase was additionally extracted with CH₂Cl₂ (2×100.0 mL). Combined organic phase was dried over Na₂SO₄, filtered, and concentrated to dryness under reduced pressure. The dry residue was fractionated by column chromatography (SiO₂, EtOAc in hexanes, 0 to 60%) to provide the corresponding trifluoromethylketone (9.0 g, 38.8 mmol, 90% yield) as a colorless oil.

Step c: The trifluoromethylketone from step b (5.40 g, 23.3 mmol) was dissolved in DMF (116.0 mL) and cooled to 0° C. Triethylamine (12.9 mL, 93.0 mmol) and formic acid (5.30 mL, 0.14 mmol) were then added sequentially. The solution was degassed by sparging with nitrogen gas for 10 min followed by an addition of RuCl(p-cymene)[(S,S)-Ts-DPEN] (0.59 g, 0.93 mmol). The resulting solution was stirred at 4° C. for 16 h. Once TLC analysis indicated complete conversion of the starting material, the mixture was diluted with EtOAc (150.0 mL), washed with water (3×100.0 mL), aq. sat. NaHCO₃ (100.0 mL) and brine (100.0 mL). The organic phase was dried over Na₂SO₄, filtered, and concentrated to dryness under reduced pressure. The dry residue was fractionated by column chromatography (SiO₂, EtOAc in hexanes, 0 to 60%) to provide the corresponding chiral alcohol (4.76 g, 20.3 mmol, 87% yield) as a colorless oil.

Step d: Methyl iodide (12.0 mL, 0.19 mmol) was added to the suspension of the alcohol from step c (4.50 g, 19.2 mmol) and Ag₂O (13.4 g, 57.6 mmol) in 1,2-dichloroethane (19.0 mL) at 0° C. The resulting suspension was stirred at 60° C. for 48 h. The reaction mixture was cooled to ambient temperature and filtered through a celite pad. The celite pad was additionally washed with EtOAc (20.0 mL) and the combined filtrate was concentrated to dryness under reduced pressure. The dry residue was fractionated by column chromatography (SiO₂, EtOAc in hexanes, 0 to 35%) to provide the desired methyl ether (1.50 g, 6.04 mmol, 31% yield) as a colorless oil.

Step e: The benzyl ether from step d (1.50 g, 6.0 mmol) was dissolved in MeOH (60.0 mL), and the resulting solution was placed under nitrogen atmosphere. Palladium on carbon (0.15 g, 10 wt %, 10% Pd) was added to the reaction vial and the nitrogen atmosphere was replaced with hydrogen using rubber balloon (1 atm). The mixture was vigorously stirred under an atmosphere of hydrogen for 16 h. The resulting suspension was filtered through a celite pad, washed with EtOAc, and concentrated to dryness under reduced pressure. The resulting crude primary alcohol (0.94 g) was used for the next step without further purification.

Step f: Tosyl chloride (1.10 g, 5.65 mmol) was added to the solution of product of step e (0.94 g) and triethylamine (1.10 mL, 5.94 mmol) in CH₂Cl₂ (29.0 mL) at 0° C. The reaction was allowed to warm up to 23° C. and stirred for 16 h. Then 50 μL of morpholine was added in order to quench the residual tosyl chloride. The solution was washed with 1M HCl (5.0 mL). The organic phase was separated, and the aqueous phase was additionally extracted with CH₂Cl₂ (2×10.0 mL). Combined organic phase was dried over Na₂SO₄, filtered, and concentrated to dryness under reduced pressure. The dry residue was fractionated by column chromatography (SiO₂, EtOAc in hexanes, 0 to 50%) to provide the corresponding tosylate (0.62 g, 2.0 mmol, 33% yield over 2 steps) as a white solid.

Step g: The methyl ether (0.26 g, 0.534 mmol, 67% yield) was prepared in a similar fashion described for Example 1 using the product of step f ([(3S)-4,4,4-trifluoro-3-methoxybutyl] 4-methylbenzenesulfonate) as the alkylating reagent.

Step h: To a solution of the methyl ether from step g (0.26 g, 0.534 mmol) in MeOH (11.0 mL) was added aq. 1M NaOH solution (2.70 mL, 2.70 mmol) at an ambient temperature. The resulting mixture was stirred for 3 h. Once TLC analysis indicated complete consumption of the starting material, the reaction was quenched with sat. NH₄Cl. The organic phase was separated, and the aqueous layer was extracted with EtOAc (2×5.0 mL). The combined organic phase was dried over Na₂SO₄, concentrated and the crude residue was purified by column chromatography (SiO₂, EtOAc in hexanes, 0 to 50%) to give the title compound (0.19 g, 0.497 mmol, 93% yield) as a colorless oil. ¹H NMR (400 MHz, CDCl₃) δ 4.89 (q, J=5.6 Hz, 1H), 4.24 (ddd, J=14.9, 8.7, 6.5 Hz, 1H), 4.13 (ddt, J=14.5, 7.4, 4.2 Hz, 1H), 3.62-3.44 (m, 4H), 2.97-2.78 (m, 2H), 2.69-2.45 (m, 2H), 2.28 (dddd, J=18.0, 10.6, 8.6, 4.6 Hz, 2H), 2.15-1.99 (m, 1H). ESI MS [M+H]⁺ for $C_{13}H_{14}F_8N_2O_2$, calcd 382.1, found 382.2.

Example 12: (4S)-5,5-difluoro-1-[(3R)-4,4,4-trifluoro-3-methoxybutyl]-3-(trifluoromethyl)-6,7-dihydro-4H-indazol-4-ol

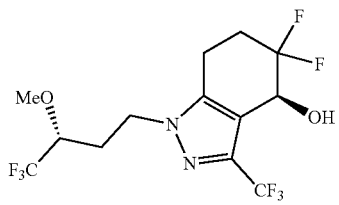 [SMILES: CO[C@H](CCn1nc(C(F)(F)F)c2c1CCC(F)(F)[C@H]2O)C(F)(F)F]

The title compound was prepared according to the protocol described for Example 11 using RuCl(p-cymene)[(R,R)-Ts-DPEN] in step c. $^1$H NMR (400 MHz, CDCl$_3$) δ 4.89 (q, J=5.9 Hz, 1H), 4.25 (ddd, J=15.0, 8.6, 6.6 Hz, 1H), 4.14 (ddd, J=13.2, 7.1, 4.5 Hz, 1H), 3.64-3.43 (m, 4H), 2.97-2.74 (m, 2H), 2.65-2.43 (m, 2H), 2.39-2.16 (m, 1H), 2.15-2.02 (m, 1H). ESI MS [M+H]$^+$ for C$_{13}$H$_{14}$F$_8$N$_2$O$_2$, calcd 382.1, found 382.1.

Example 13: (4S)-5,5-difluoro-1-(3-methoxybutyl)-3-(trifluoromethyl)-6,7-dihydro-4H-indazol-4-ol extract was dried over Na$_2$SO$_4$, filtered, and concentrated to dryness under reduced pressure. The dry residue was fractionated by column chromatography (SiO$_2$, EtOAc in hexanes, 0 to 80%) to provide desired ketone (0.63 g, 1.51 mmol, 57% yield) as a colorless oil.

Step c: Sodium borohydride (46.0 mg, 1.2 mmol) was added to the solution of the ketone from step b (0.50 g, 1.20 mmol) in MeOH (6.0 mL) at 0° C. The reaction mixture was allowed to warm to room temperature and was stirred for an additional 15 min. Then it was diluted with water (1.0 mL), and MeOH was evaporated under reduced pressure. The residue was mixed with EtOAc (10.0 mL) and washed with water (5.0 mL). The organic phase was separated, dried over Na$_2$SO$_4$, filtered, and concentrated to dryness under reduced pressure. The dry residue was fractionated by column chromatography (SiO$_2$, EtOAc in hexanes, 0 to 100%) to provide desired alcohol (0.45 g, 1.08 mmol, 90% yield) as a colorless oil.

Step d: Aqueous trifluoroboric acid (48 wt. % in water, 44.0 μL, 0.239 mmol) and TMSCHN$_2$ (1.40 mL, 2.87 mmol, 2M in hexanes) were added to a solution of the alcohol from the step c (0.1 g, 0.239 mmol) in CH$_2$Cl$_2$ (2.4 mL) at 0° C. Once the reaction was warmed up to room temperature, TLC analysis indicated complete reaction. The mixture was quenched with aq. sat. NaHCO$_3$ (2.0 mL) and extracted with CH$_2$Cl$_2$ (2×5.0 mL). The combined organic extract was

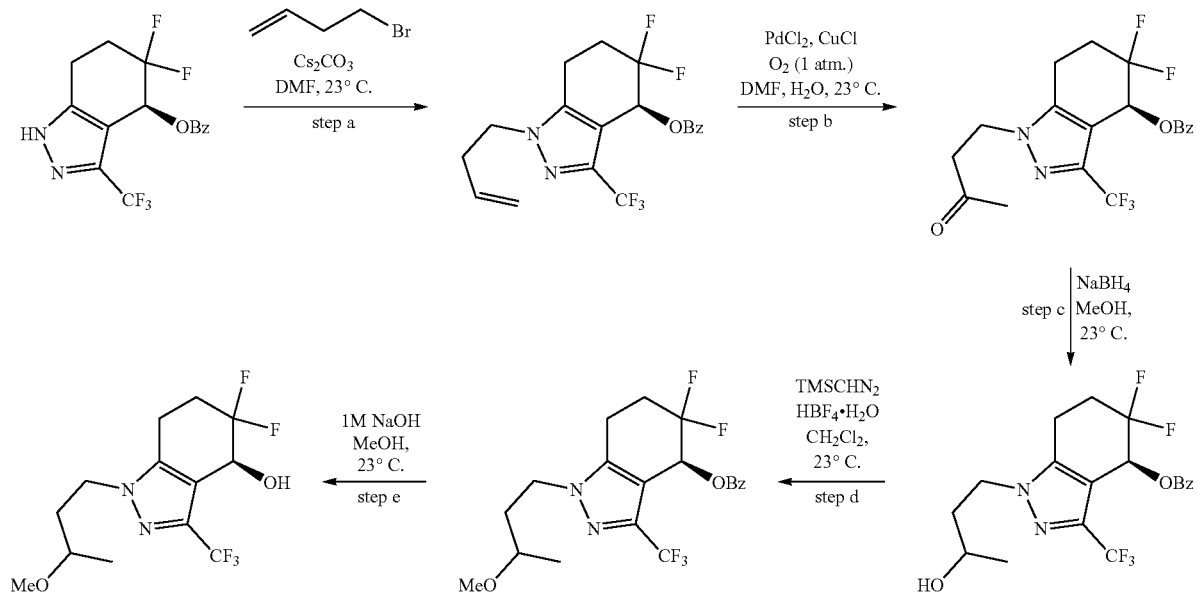

Step a: The olefin was prepared in a similar fashion to that described for Example 1 using 4-bromobut-1-ene as the alkylating reagent.

Step b: A 30 mL screw-cap vial was charged with PdCl$_2$ (47.0 mg, 0.265 mmol), and CuCl (0.26 g, 2.65 mmol) under nitrogen atmosphere. A mixture of DMF/H$_2$O (3.5 mL/0.5 mL) was added and oxygen gas was bubbled through suspension as it was stirred vigorously for 1 h. The olefin from step a (1.06 g, 2.65 mmol) was added to the reaction and oxygen was bubbled through the reaction mixture for additional 0.5 h. The bubbling needle was then removed and the solution was stirred for 3 h in a sealed vial. The mixture was diluted with EtOAc (10.0 mL) and washed with sat. aq. NH$_4$Cl (2×10.0 mL) and brine (10.0 mL). The organic dried over Na$_2$SO$_4$, filtered, and concentrated to dryness. The dry residue was fractionated by column chromatography (SiO$_2$, EtOAc in hexanes, 0 to 60%) to provide the desired methyl ether (91 mg, 0.21 mmol, 88% yield) as a colorless oil.

Step e: To a solution of the methyl ether from step d (91.0 mg, 0.21 mmol) in MeOH (4.2 mL) was added aq. 1M NaOH solution (1.1 mL, 1.10 mmol) at ambient temperature. The resulting mixture was stirred for 3 h. Once TLC analysis indicated complete consumption of the starting material, the reaction was quenched with sat. NH$_4$Cl. The organic phase was separated, and the aqueous layer was extracted with EtOAc (2×5.0 mL). The combined organic phase was dried over Na$_2$SO$_4$, concentrated and the crude residue was purified by column chromatography (SiO$_2$, EtOAc in hexanes, 0 to 70%) to give the title compound (55 mg, 0.167 mmol, 80% yield) as a colorless oil. $^1$H NMR (400 MHz, CDCl$_3$) δ 4.89 (d, J=6.4 Hz, 1H), 4.12 (h, J=5.7, 5.0 Hz, 2H), 3.27 (dd, J=5.5, 1.9 Hz, 3H), 3.19 (dtt, J=15.0, 5.7, 2.9 Hz, 1H), 2.98-2.73 (m, 2H), 2.68-2.42 (m, 2H), 2.27 (q, J=7.8, 6.7 Hz, 1H), 2.17-2.00 (m, 1H), 1.87 (dddd, J=16.0, 8.8, 4.3, 2.0 Hz, 1H), 1.14 (dd, J=6.2, 1.8 Hz, 3H). ESI MS [M+H]$^+$ for C$_{13}$H$_{17}$F$_5$N$_2$O$_2$, calcd 328.1, found 328.0.

Example 14: (4S)-5,5-difluoro-1-[3-(trifluoromethoxy)butyl]-3-(trifluoromethyl)-6,7-dihydro-4H-indazol-4-ol

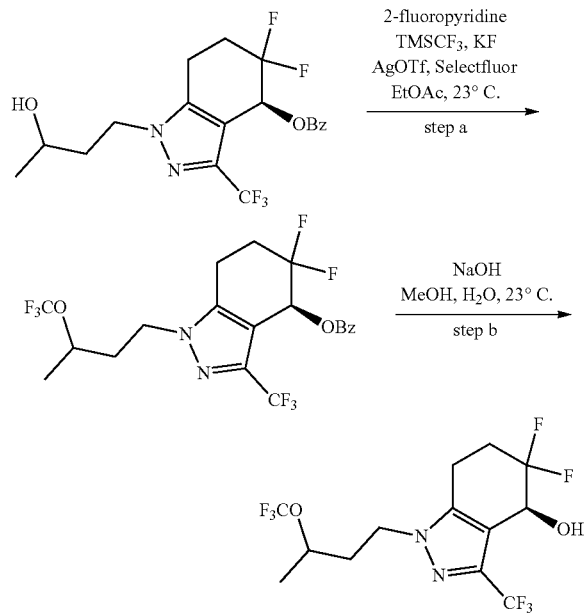

The alcohol starting material was prepared according to the protocol described for the synthesis of Example 13.

Step a: 2-Fluoropyridine (74 μL, 0.86 mmol) and TMSCF$_3$ (0.13 mL, 0.86 mmol) were added sequentially to a suspension of the alcohol starting material (0.12 g, 0.29 mmol), AgOTf (0.22 g, 0.86 mmol), Selectfluor (0.15 g, 0.43 mmol) and KF (67 mg, 1.15 mmol) in EtOAc (1.5 mL). The reaction was stirred for 16 h at 23° C., then concentrated to dryness under reduced pressure. The dry residue was fractionated by column chromatography (SiO$_2$, EtOAc in hexanes, 0 to 50%) to provide desired ether (20 mg, 0.041 mmol, 14% yield) as colorless oil.

Step b: To a solution of the trifluoromethyl ether from step a (20.0 mg, 0.041 mmol) in MeOH (0.8 mL) was added aq. 1M NaOH solution (0.21 mL, 0.21 mmol) at ambient temperature. The resulting mixture was stirred for 3 h. Once TLC analysis indicated complete consumption of the starting material, the reaction was quenched with sat. NH$_4$Cl. The organic phase was separated, and the aqueous layer was extracted with EtOAc (2×3.0 mL). The combined organic phase was dried over Na$_2$SO$_4$, concentrated and the crude residue was purified by column chromatography (EtOAc in hexanes, 0 to 40%) to give the title compound (11.0 mg, 0.0029 mmol, 70% yield) as a colorless oil. $^1$H NMR (400 MHz, CDCl$_3$) δ 4.87 (q, J=5.7 Hz, 1H), 4.37 (dq, J=9.6, 4.7, 3.5 Hz, 1H), 4.11 (t, J=7.3 Hz, 2H), 3.04-2.73 (m, 2H), 2.65-2.43 (m, 2H), 2.28 (dtd, J=15.6, 7.9, 3.1 Hz, 2H), 2.12 (h, J=6.7, 5.3 Hz, 1H), 1.39 (dd, J=6.5, 2.6 Hz, 3H). ESI MS [M+H]$^+$ for C$_{13}$H$_{14}$F$_8$N$_2$O$_2$, calcd 328.1, found 328.0.

Example 15: (4S)-1-[3-(difluoromethoxy)butyl]-5,5-difluoro-3-(trifluoromethyl)-6,7-dihydro-4H-indazol-4-ol The alcohol starting material was prepared according to the protocol described for the synthesis of Example 13.

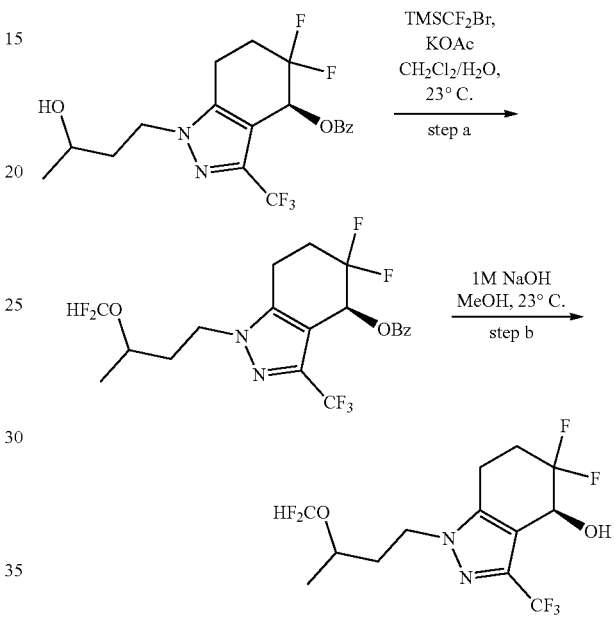

Step a: TMSCF$_2$Br (0.18 mL, 1.15 mmol) and KOAc (0.22 g, 2.3 mmol) were added to the solution of the alcohol (0.12 g, 0.29 mmol) in CH$_2$Cl$_2$ (0.14 mL) and water (0.14 mL). The reaction was stirred for 2 h at 23° C. Then it was diluted with CH$_2$Cl$_2$ (2.0 mL) and washed with water (2×4 mL). The combined organic phase was dried over Na$_2$SO$_4$, concentrated and the crude residue was purified by column chromatography (SiO$_2$, EtOAc in hexanes, 0 to 40%) to give the final product (0.13 g, 0.278 mmol, 97% yield) as a colorless oil.

Step b: 1M aq. NaOH solution (1.40 mL, 1.40 mmol) was added at room temperature to a solution of the difluoromethyl ether from step a (0.13 mg, 0.278 mmol) in MeOH (5.60 mL). The resulting mixture was stirred for 3 h. Once TLC analysis indicated complete consumption of the starting material, the reaction was quenched with sat. NH$_4$Cl. The organic phase was separated, and the aqueous layer was extracted with EtOAc (2×5.0 mL). The combined organic phase was dried over Na$_2$SO$_4$, concentrated and the crude residue was purified by column chromatography (SiO$_2$, EtOAc in hexanes, 0 to 50%) to give the title compound (90 mg, 0.247 mmol, 89% yield) as colorless oil. $^1$H NMR (400 MHz, CDCl$_3$) δ 6.23 (t, J=75.2 Hz, 1H), 4.87 (q, J=5.4 Hz, 1H), 4.24 (dq, J=12.1, 4.5, 3.0 Hz, 1H), 4.11 (t, J=7.4 Hz, 2H), 3.01-2.70 (m, 2H), 2.65-2.42 (m, 2H), 2.37-2.14 (m, 2H), 2.04 (q, J=7.7, 5.9 Hz, 1H), 1.32 (dd, J=6.3, 2.2 Hz, 3H). ESI MS [M+H]$^+$ for C$_{13}$H$_{15}$F$_7$N$_2$O$_2$, calcd 364.1, found 364.1.

Example 16: (4S)-5,5-difluoro-1-(4,4,4-trifluoro-3-hydroxybutyl)-3-(trifluoromethyl)-6,7-dihydro-4H-indazol-4-ol

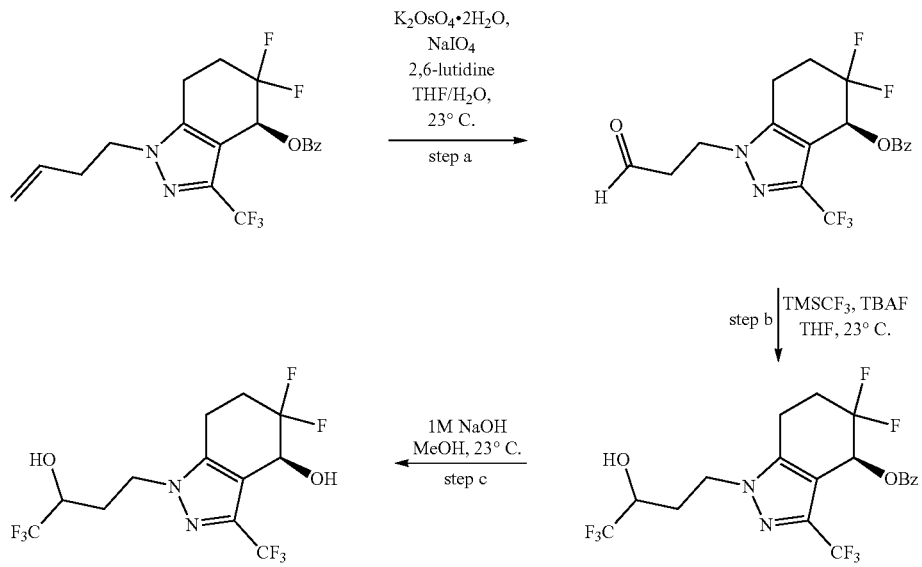

The olefin starting material was prepared in a similar fashion to that described for Example 1 using 4-bromobut-1-ene as the alkylating reagent.

Step a: Potassium osmate(VI) dihydrate (67 mg, 0.18 mmol), NaIO$_4$ (1.5 g, 7.2 mmol) and 2,6-lutidine (0.42 mL, 3.6 mmol) were added to a solution of the olefin (0.70 g, 1.8 mmol) in THF (9.0 mL) and water (9.0 mL). The solution was stirred for 1 h at 23° C. Upon completion (TLC analysis), the reaction was diluted with CH$_2$Cl$_2$ (20.0 mL) and washed with sat. aq. NaHCO$_3$ (5.0 mL) and brine (10.0 mL). The combined organic phase was dried over Na$_2$SO$_4$, filtered, and concentrated to dryness under reduced pressure. The dry residue was fractionated by column chromatography (SiO$_2$, EtOAc in hexanes, 0 to 70%) to provide the corresponding aldehyde (0.41 g, 1.02 mmol, 56% yield) as colorless oil.

Step b: TMSCF$_3$ (0.20 mL, 1.34 mmol) and TBAF (1M in THF, 0.89 mL, 0.89 mmol) were sequentially added to the solution of the product from the step a (0.36 g, 0.89 mmol) in THF (5.0 mL) at 0° C. The resulting mixture was stirred at 0° C. and monitored by TLC analysis. After 30 min the reaction was diluted with EtOAc (15.0 mL), washed with water (3×5.0 mL) and brine (5.0 mL). The organic extract was dried over Na$_2$SO$_4$, filtered, and concentrated to dryness under reduced pressure. The dry residue was fractionated by column chromatography (SiO$_2$, EtOAc in hexanes, 0 to 60%) to provide the desired alcohol (0.26 g, 0.55 mmol, 62% yield) as a colorless oil.

Step c: To a solution of the product from step b (50.0 mg, 0.106 mmol) in MeOH (2.1 mL) was added aq. 1M NaOH solution (0.53 mL, 0.53 mmol) at ambient temperature. The resulting mixture was stirred for 3 h. Once TLC analysis indicated complete consumption of the starting material, the reaction was quenched with sat. NH$_4$Cl. The organic phase was separated, and the aqueous layer was extracted with EtOAc (2×3 mL). The combined organic phase was dried over Na$_2$SO$_4$, concentrated and the crude residue was purified by column chromatography (EtOAc in hexanes, 0 to 100%) to give the title compound (30 mg, 0.082 mmol, 77% yield) as colorless oil. $^1$H NMR (400 MHz, CDCl$_3$) δ 4.88 (s, 1H), 4.29 (dddd, J=12.1, 9.5, 5.6, 2.8 Hz, 1H), 4.19 (dt, J=14.1, 5.4 Hz, 1H), 3.94 (d, J=22.7 Hz, 1H), 3.38 (d, J=5.1 Hz, 1H), 2.99-2.71 (m, 3H), 2.66-2.43 (m, 1H), 2.31 (ddddd, J=18.8, 12.7, 9.3, 6.2, 3.1 Hz, 2H), 2.10 (dqd, J=15.0, 5.2, 3.5 Hz, 1H). ESI MS [M+H]$^+$ for C$_{12}$H$_{12}$F$_8$N$_2$O$_2$, calcd 368.1, found 368.2.

Example 17: (4S)-5,5-difluoro-1-(4,4,4-trifluoro-3-methoxybutyl)-3-(trifluoromethyl)-6,7-dihydro-4H-indazol-4-ol

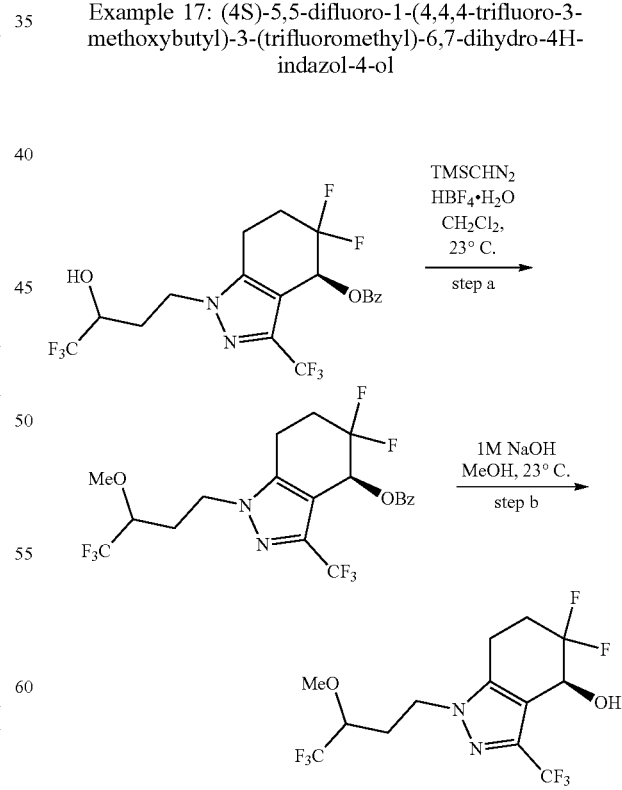

The alcohol starting material was prepared according to the protocol described for Example 16.

Step a: Trifluoroboric acid (48 wt. %, in water, 50 μL, 0.275 mmol) and TMSCHN₂ (1.1 mL, 2.2 mmol, 2M in hexanes) were added to the solution of the alcohol (0.13 g, 0.275 mmol) in CH₂Cl₂ (2.75 mL) at 0° C. Then the cooling bath was removed and the reaction was left to stir for 20 h at 23° C. Once TLC analysis indicated complete consumption of the starting material, the mixture was quenched with sat. aq. NaHCO₃ (2.0 mL), and the product was extracted with CH₂Cl₂ (2×5.0 mL). The combined organic phase was dried over Na₂SO₄, filtered, and concentrated to dryness. The dry residue was fractionated by column chromatography (SiO₂, EtOAc in hexanes, 0 to 70%) to provide the corresponding ether (22.0 mg, 0.045 mmol, 16% yield) as a colorless oil.

Step b: To a solution of the methyl ether from step a (22 mg, 0.045 mmol) in MeOH (0.90 mL) was added aq. 1M NaOH solution (0.23 mL, 0.23 mmol) at ambient temperature. The resulting mixture was stirred for 3 h. Once TLC analysis indicated complete consumption of the starting material, the reaction was quenched with sat. NH₄Cl. The organic phase was separated, and the aqueous layer was extracted with EtOAc (2×2.0 mL). The combined organic phase was dried over Na₂SO₄, concentrated and the crude residue was purified by column chromatography (SiO₂, EtOAc in hexanes, 0 to 80%) to give the title compound (13.3 mg, 0.035 mmol, 77% yield) as colorless oil. ¹H NMR (400 MHz, CDCl₃) δ 4.89 (q, J=5.9 Hz, 1H), 4.25 (ddd, J=15.0, 8.6, 6.6 Hz, 1H), 4.14 (ddd, J=13.2, 7.1, 4.5 Hz, 1H), 3.64-3.43 (m, 4H), 2.97-2.74 (m, 2H), 2.65-2.43 (m, 2H), 2.39-2.16 (m, 1H), 2.15-2.02 (m, 1H). ESI MS [M+H]⁺ for C₁₃H₁₄F₈N₂O₂, calcd 382.1, found 382.0.

Example 18: (4S)-1-[2-(difluoromethylsulfanyl) ethyl]-5,5-difluoro-3-(trifluoromethyl)-6,7-dihydro-4H-indazol-4-ol

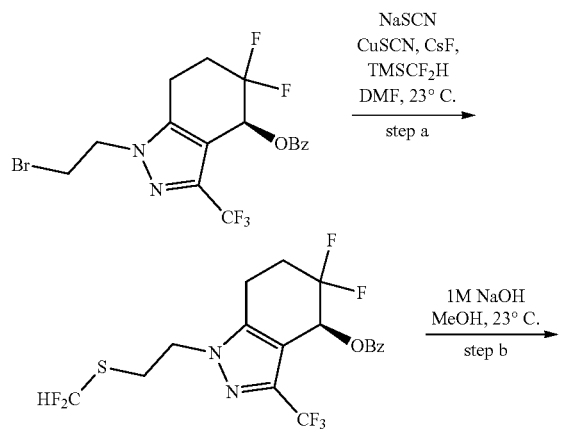

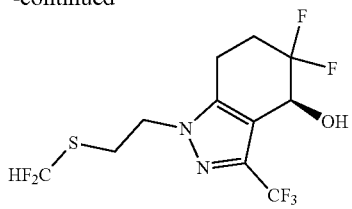

The alkylbromide starting material was prepared in a similar fashion to that described for Example 1 using a large excess of 1,2-dibromoethane (20 equiv.) as the alkylating reagent in NMP.

Step a: Sodium thiocyanate (0.17 g, 2.14 mmol) was added to a solution of alkylbromide starting material (0.65 g, 1.43 mmol) in DMF (3.0 mL). The resulting mixture was stirred at 60° C. for 2 h. Once cooled to the room temperature, CuSCN (0.24 g, 1.90 mmol), CsF (1.20 g, 7.60 mmol), and TMSCF₂H (0.32 mL, 3.80 mmol) were added, and reaction was stirred for additional 24 h. The reaction was diluted with EtOAc (5.0 mL), washed with water (3×5.0 mL) and brine (5.0 mL). The organic phase was dried over Na₂SO₄, concentrated and the crude residue was purified by column chromatography (SiO₂, EtOAc in hexanes, 0 to 70%) to give the sulfide (0.15 g, 0.33 mmol, 34% yield) as a colorless oil.

Step b: To a solution of the product from step a (0.15 g, 0.33 mmol) in MeOH (8.5 mL) was added aq. 1M NaOH solution (2.2 mL, 2.2 mmol) at ambient temperature. The resulting mixture was stirred for 3 h. Once TLC analysis indicated complete consumption of the starting material, the reaction was quenched with sat. aq. NH₄Cl. The organic phase was separated, and the aqueous layer was extracted with EtOAc (2×5.0 mL). The combined organic phase was dried over Na₂SO₄, concentrated and the crude residue was purified by column chromatography (SiO₂, EtOAc in hexanes, 0 to 50%) to give the title compound (87 mg, 0.24 mmol, 72% yield) as a colorless oil. ¹H NMR (400 MHz, CDCl₃) δ 6.78 (t, J=55.5 Hz, 1H), 4.88 (q, J=5.7 Hz, 1H), 4.29 (t, J=6.8 Hz, 2H), 3.29 (t, J=6.8 Hz, 2H), 3.02-2.78 (m, 2H), 2.69-2.44 (m, 2H), 2.39-2.20 (m, 1H). ESI MS [M+H]⁺ for C₁₁H₁₁F₇N₂OS, calcd 352.0, found 352.1.

Example 19: (4S)-1-[[3-(difluoromethoxy)-3-methylcyclobutyl]methyl]-5,5-difluoro-3-(trifluoromethyl)-6,7-dihydro-4H-indazol-4-ol

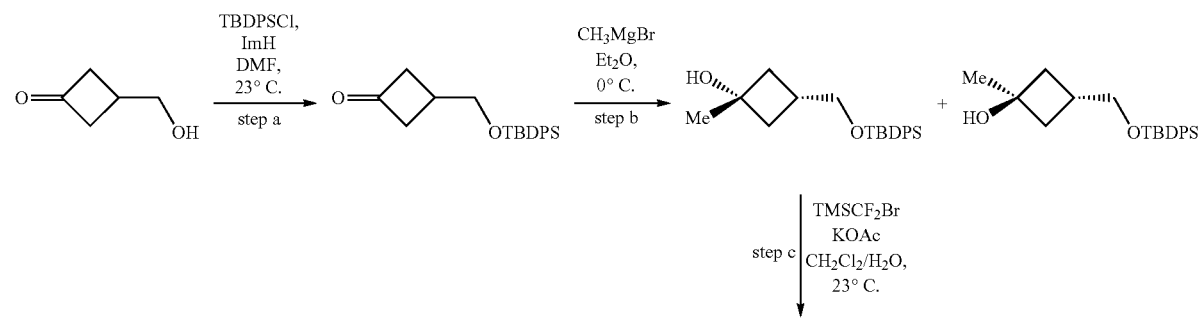

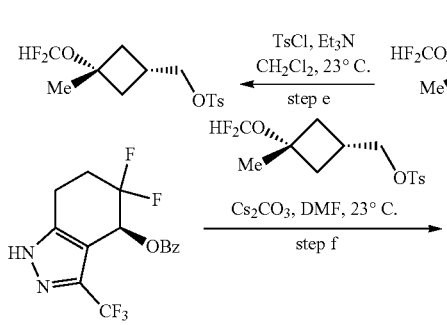
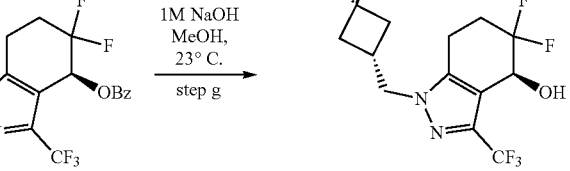

Step a: TBDPSCl (7.80 mL, 30 mmol) was added to a solution of 3-(hydroxymethyl)cyclobutan-1-one (2.50 g, 25 mmol) and imidazole (3.9 g, 57.4 mmol) in DMF (30 mL) at 0° C. After 5 min the reaction was warmed up to room temperature and stirred for 1 h. Upon completion, the reaction was diluted with CH$_2$Cl$_2$ (30.0 mL), washed with water (3×10.0 mL), sat. aq. NaHCO$_3$ (20.0 mL) and brine (20.0 mL). The organic solution was dried over Na$_2$SO$_4$, filtered, and concentrated to dryness under reduced pressure. The dry residue was fractionated by column chromatography (SiO$_2$, EtOAc in hexanes, 0 to 15%) to provide the desired silyl ether (3.0 g, 8.90 mmol, 35% yield) as a colorless oil.

Step b: Methylmagnesium bromide (3.40 mL, 11.5 mmol, 3.40 M in 2-methyltetrahydrofuran) was added to the solution of the cyclobutanone from step a (3.0 g, 8.90 mmol) in diethyl ether (44.0 mL) at 0° C. The resulting solution was stirred at 0° C. for 1 h. Upon completion by TLC analysis, the reaction was quenched by addition of aq. sat. NH$_4$Cl (10.0 mL) and diluted with EtOAc (100.0 mL). The layers were separated, and the organic phase was washed with brine (70.0 mL), dried over Na$_2$SO$_4$, filtered, and concentrated to dryness under reduced pressure. The dry residue was fractionated by column chromatography (SiO$_2$, EtOAc in hexanes, 0 to 20%) to provide the corresponding tertiary alcohol (1.8 g, 5.08 mmol, 57% yield) as a colorless oil.

Step c: TMSCF$_2$Br (5.6 mL, 36 mmol) and KOAc (3.5 g, 36 mmol) were added to the solution of tertiary alcohol from step b (1.6 g, 4.5 mmol) in a mixture of dichloromethane (3.0 mL) and water (3.0 mL). The reaction was vigorously stirred for 3 days at 23° C. Then it was diluted with dichloromethane (5.0 mL), and the organic layer was separated. The solution was washed with water (2×5.0 mL), dried over Na$_2$SO$_4$ and concentrated to dryness under reduced pressure. The crude product was purified by column chromatography (SiO$_2$ EtOAc in hexanes, 0 to 20%) to give the difluoromethyl ether (1.64 g, 4.05 mmol, 90% yield) as colorless oil.

Step d: TBAF (6.0 mL, 6.0 mmol, 1M in THF) was added to the solution of the product from step c (1.76 g, 4.35 mmol) in THF (20.0 mL) at 0° C. The resulting mixture was stirred at room temperature for 30 min. Upon completion, the mixture was partitioned between Et$_2$O and water. The organic layer was washed with water (3×30.0 mL) and brine (30.0 mL), dried over MgSO$_4$, filtered, and concentrated to dryness under reduced pressure. The dry residue was used for the next step without further purification.

Step e: Tosyl chloride (0.79 g, 4.35 mmol) was added to the solution of the product of step d and triethylamine (0.60 mL, 4.35 mmol) in CH$_2$Cl$_2$ (22.0 mL) at 0° C. The reaction was warmed up to 23° C. and stirred overnight. Upon completion 50 μL of morpholine was added to quench the remaining tosyl chloride. After 10 min the reaction mixture was diluted with dichloromethane (20.0 mL) and washed with aq. 1M HCl (20.0 mL). The layers were separated, and the aqueous phase was additionally extracted with CH$_2$Cl$_2$ (2×10.0 mL). The combined organic phase was dried over Na$_2$SO$_4$, filtered, and concentrated to dryness under reduced pressure. The dry residue was fractionated by column chromatography (SiO$_2$, EtOAc in hexanes, 0 to 30%) to provide the inseparable mixture of tert-butyldiphenylsilanol and the desired tosylate (1.30 g) that was used for the next step without additional purification.

Step f: The difluoromethyl ether (0.17 g, 0.34 mmol, 44% yield) was prepared in a similar fashion to that described for Example 1 using the product from step e as the alkylating reagent.

Step g: To a solution of the product from step f (0.17 g, 0.34 mmol) in MeOH (6.9 mL) was added aq. 1M NaOH solution (1.7 mL, 1.7 mmol) at ambient temperature. The resulting mixture was stirred for 3 h. Once TLC analysis indicated complete consumption of the starting material, the reaction was quenched with sat. aq. NH$_4$Cl. The organic phase was separated, and the aqueous phase was additionally extracted with EtOAc (2×10.0 mL). The combined organic phase was dried over Na$_2$SO$_4$, concentrated and the crude residue was purified by column chromatography (SiO$_2$, EtOAc in hexanes, 0 to 50%) to give the title compound (0.10 g, 0.26 mmol, 74% yield) as colorless oil. $^1$H NMR (400 MHz, CDCl$_3$) δ 6.17 (t, J=75.8 Hz, 1H), 4.87 (q, J=5.7 Hz, 1H), 4.08 (dd, J=7.1, 1.4 Hz, 2H), 2.95-2.72 (m, 2H), 2.65-2.43 (m, 3H), 2.37-2.22 (m, 3H), 2.15 (dtd, J=12.3, 6.8, 2.7 Hz, 2H), 1.50 (s, 3H). ESI MS [M+H]$^+$ for C$_{15}$H$_{17}$F$_7$N$_2$O$_2$, calcd 390.1, found 390.0.

Example 20: (4S)-1-[2-(2,2-difluorocyclopropyl)ethyl]-5,5-difluoro-3-(trifluoromethyl)-4,5,6,7-tetrahydro-1H-indazol-4-ol

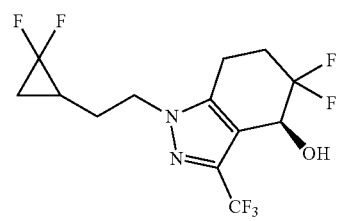 [SMILES: O[C@H]1c2c(C(F)(F)F)nn(CCC3CC3(F)F)c2CCC1(F)F]

The title compound was prepared in a similar fashion to that described for Example 1 from 2-(2-bromoethyl)-1,1-difluorocyclopropane. $^1$H NMR (400 MHz, Chloroform-d) δ 4.86 (q, J=5.6 Hz, 1H), 4.10 (tt, J=7.1, 2.4 Hz, 2H), 2.94-2.72 (m, 2H), 2.62 (d, J=3.9 Hz, 1H), 2.59-2.39 (m, 1H), 2.35-2.20 (m, 1H), 2.17-2.04 (m, 1H), 1.96-1.83 (m, 1H), 1.49-1.35 (m, 2H), 0.90 (td, J=13.0, 3.6 Hz, 1H). ESI MS [M+H]$^+$ for $C_{13}H_{13}F_7N_2O$, calcd 347.1, found 347.0.

Example 21: (4S)-5,5-difluoro-1-[2-(3-fluorooxetan-3-yl)ethyl]-3-(trifluoromethyl)-4,5,6,7-tetrahydro-1H-indazol-4-ol

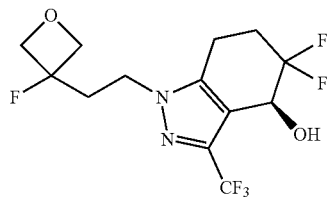

The title compound was prepared in a similar fashion to that described for Example 2 from 2-(3-fluorooxetan-3-yl)ethanol. $^1$H NMR (400 MHz, Chloroform-d) δ 4.85 (q, J=5.7 Hz, 1H), 4.73-4.54 (m, 2H), 4.38-4.10 (m, 4H), 2.92-2.70 (m, 2H), 2.66-2.62 (m, 1H), 2.63-2.40 (m, 3H), 2.32-2.20 (m, 1H). ESI MS [M+H]$^+$ for $C_{13}H_{14}F_6N_2O_2$, calcd 345.1, found 345.0.

Example 22: (4S)-1-(2-cyclopropylethyl)-5,5-difluoro-3-(trifluoromethyl)-4,5,6,7-tetrahydro-1H-indazol-4-ol

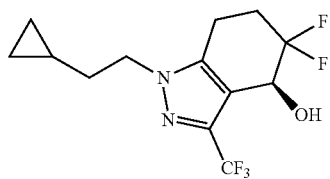 [SMILES: O[C@H]1c2c(C(F)(F)F)nn(CCC3CC3)c2CCC1(F)F]

The title compound was prepared in a similar fashion to that described for Example 1 using 2-bromomethylcyclopropane as the alkylating reagent. $^1$H NMR (400 MHz, Chloroform-d) δ 4.87 (q, J=5.7 Hz, 1H), 4.17-4.00 (m, 2H), 2.93-2.74 (m, 2H), 2.61-2.42 (m, 2H), 2.33-2.19 (m, 1H), 1.82-1.63 (m, 2H), 0.64-0.51 (m, 1H), 0.46-0.35 (m, 2H), 0.03--0.10 (m, 2H). ESI MS [M+H]$^+$ for $C_{13}H_{15}F_5N_2O$, calcd 311.1, found 311.1.

Example 23 and 24: (4S)-1-{[(1R)-2,2-difluorocyclopropyl]methyl}-5,5-difluoro-3-(trifluoromethyl)-4,5,6,7-tetrahydro-1H-indazol-4-ol and (4S)-1-{[(1S)-2,2-difluorocyclopropyl]methyl}-5,5-difluoro-3-(trifluoromethyl)-4,5,6,7-tetrahydro-1H-indazol-4-ol

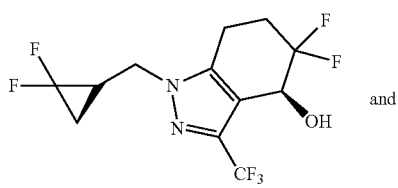

and

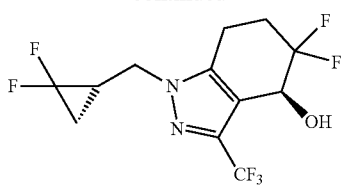

The title compounds were prepared in a similar fashion to that described for Example 1 using 2-(bromomethyl)-1,1-difluorocyclopropane as the alkylating reagent. The diastereomers were separable by flash chromatography (SiO$_2$, hexanes to 30% EtOAc).

First eluting isomer (DIAST-1): $^1$H NMR (400 MHz, Chloroform-d) δ 4.93-4.83 (m, 1H), 4.18 (dd, J=15.0, 6.5 Hz, 1H), 4.07 (dd, J=14.5, 7.7 Hz, 1H), 2.90 (dd, J=16.5, 6.8 Hz, 1H), 2.77 (ddd, J=16.7, 10.8, 6.6 Hz, 1H), 2.66-2.42 (m, 2H), 2.37-2.21 (m, 1H), 2.13 (tt, J=13.7, 6.6 Hz, 1H), 1.67-1.51 (m, 1H), 1.40-1.19 (m, 1H). ESI MS [M+H]$^+$ for $C_{12}H_{11}F_7N_2O$, calcd 333.1, found 333.1.

Second eluting isomer (DIAST-2): $^1$H NMR (400 MHz, Chloroform-d) δ 4.98-4.75 (m, 1H), 4.18 (dd, J=14.7, 6.7 Hz, 1H), 4.08 (dd, J=14.9, 7.8 Hz, 1H), 2.88-2.74 (m, 2H), 2.61 (s, 1H), 2.59-2.40 (m, 1H), 2.36-2.21 (m, 1H), 2.12 (td, J=11.6, 5.6 Hz, 1H), 1.66-1.53 (m, 1H), 1.32-1.20 (m, 1H). ESI MS [M+H]$^+$ for $C_{12}H_{11}F_7N_2O$, calcd 333.1, found 333.1.

Example 25: (4S)-1-[2-(2,2-difluorocyclopropoxy)ethyl]-5,5-difluoro-3-(trifluoromethyl)-4,5,6,7-tetrahydro-1H-indazol-4-ol

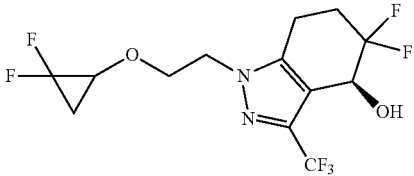 [SMILES: O[C@H]1c2c(C(F)(F)F)nn(CCOC3CC3(F)F)c2CCC1(F)F]

The title compound was prepared in a similar fashion to that described for Example 1 from 2-(2-bromoethoxy)-1,1-difluorocyclopropane. $^1$H NMR (400 MHz, Chloroform-d) δ 4.85 (q, J=5.7 Hz, 1H), 4.27-4.16 (m, 2H), 4.00-3.85 (m, 2H), 3.54 (tq, J=7.6, 2.6 Hz, 1H), 3.04-2.71 (m, 2H), 2.58 (s, 1H), 2.55-2.37 (m, 1H), 2.31-2.16 (m, 1H), 1.45 (ddd, J=16.9, 8.7, 6.5 Hz, 1H), 1.22-1.09 (m, 1H). ESI MS [M+H]$^+$ for $C_{13}H_{13}F_7N_2O_2$, calcd 363.1, found 363.0.

Example 26 and 27: (4S)-1-[(2S)-2-cyclopropyl-2-fluoroethyl]-5,5-difluoro-3-(trifluoromethyl)-4,5,6,7-tetrahydro-1H-indazol-4-ol and (4S)-1-[(2R)-2-cyclopropyl-2-fluoroethyl]-5,5-difluoro-3-(trifluoromethyl)-4,5,6,7-tetrahydro-1H-indazol-4-ol

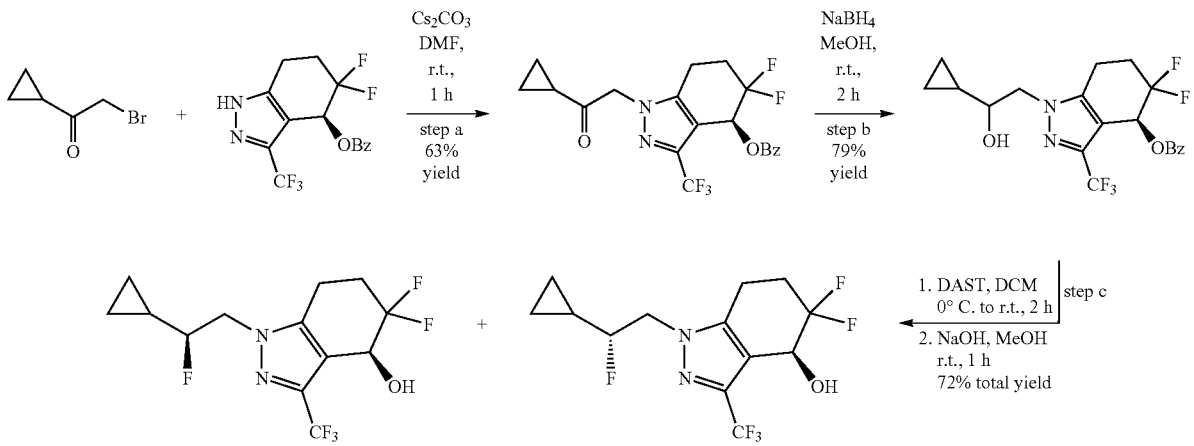

Step a: To a solution of 2-bromo-1-cylcopropylethanone (142 mg, 0.87 mmol, 1.5 equiv.) and [(4S)-5,5-difluoro-3-(trifluoromethyl)-1,4,6,7-tetrahydroindazol-4-yl] benzoate (200 mg, 0.58 mmol, 1.0 equiv.) in DMF (4.0 mL) was added $Cs_2CO_3$ (378 mg, 1.16 mmol, 2.0 equiv.). The resulting mixture was stirred at room temperature for 1 h and then diluted with EtOAc and $H_2O$. The organic phase was separated and washed with $H_2O$ twice and brine sequentially. The organic solution was then dried with $Na_2SO_4$, filtered and concentrated. Purification by flash chromatography ($SiO_2$, 0 to 50% EtOAc/Hexanes) furnished the ketone product as a colorless oil (157 mg, 0.37 mmol, 63% yield).

Step b: To a solution of the product from step a (78.3 mg, 0.183 mmol, 1.0 equiv.) in methanol (1.8 mL) was added $NaBH_4$ (27.6 mg, 0.731 mmol, 4.0 equiv.) at 0° C. The resulting solution was stirred at room temperature for 2 h and then quenched with $H_2O$ and extracted with EtOAc twice. The organic solution was washed with brine, dried with $Na_2SO_4$, filtered and concentrated. Purification by flash chromatography ($SiO_2$, 0 to 40% EtOAc/Hexanes) furnished the alcohol product as a colorless oil (dr 1:1, 61.4 mg, 0.142 mmol, 79% yield).

Step c: To a solution of the product from step b (61.4 mg, 0.143 mmol, 1.0 equiv.) in DCM (1.4 mL) was added DAST (27.1 mg, 22 µL, 0.168 mmol, 1.2 equiv.) at 0° C. The resulting solution was then stirred at room temperature for 2 h and then quenched with saturated $NaHCO_3$ aqueous solution. The mixture was then extracted with DCM twice. The combined organic phase was washed with brine, dried with $Na_2SO_4$, filtered and concentrated. The crude was then redissolved in methanol (2 mL) and treated with NaOH (1M aq., 1 mL). The resulting mixture was stirred at room temperature for 1 h before extracted with EtOAc and concentrated. The crude product was then purified by flash chromatography ($SiO_2$, 0 to 40% EtOAc/Hexanes) furnishing two diastereomers separated: (4S)-1-[(2S)-2-cyclopropyl-2-fluoroethyl]-5,5-difluoro-3-(trifluoromethyl)-4,5,6,7-tetrahydro-1H-indazol-4-ol (17.0 mg, 51.8 µmol, 36% yield over 2 steps) and (4S)-1-[(2R)-2-cyclopropyl-2-fluoroethyl]-5,5-difluoro-3-(trifluoromethyl)-4,5,6,7-tetrahydro-1H-indazol-4-ol (16.7 mg, 50.9 µmol, 36% yield over 2 steps).

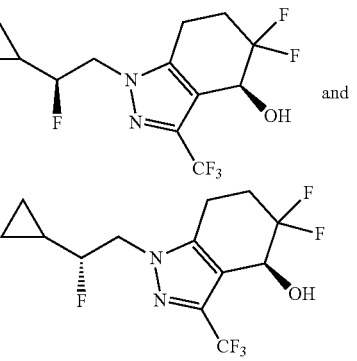

First eluting isomer (DIAST-1): $^1$H NMR (400 MHz, Chloroform-d) δ 4.88 (q, J=5.8 Hz, 1H), 4.45-4.06 (m, 3H), 3.00 (ddd, J=16.5, 6.8, 2.4 Hz, 1H), 2.81 (ddd, J=16.7, 10.9, 6.4 Hz, 1H), 2.65-2.42 (m, 2H), 2.34-2.19 (m, 1H), 1.02 (ddt, J=14.3, 10.9, 5.4 Hz, 1H), 0.76-0.61 (m, 2H), 0.58-0.49 (m, 1H), 0.42-0.31 (m, 1H). ESI MS [M+H]$^+$ for $C_{13}H_{14}F_6N_2O$, calcd 329.1, found 329.1.

Second eluting isomer (DIAST-2): $^1$H NMR (400 MHz, Chloroform-d) δ 4.89 (q, J=5.8 Hz, 1H), 4.48-4.06 (m, 3H), 2.97-2.85 (m, 2H), 2.63-2.41 (m, 2H), 2.27 (dtt, J=18.0, 8.7, 4.0 Hz, 1H), 1.04 (ddt, J=11.8, 8.2, 4.1 Hz, 1H), 0.75-0.61 (m, 2H), 0.59-0.49 (m, 1H), 0.45-0.36 (m, 1H). ESI MS [M+H]$^+$ for $C_{13}H_{14}F_6N_2O$, calcd 329.1, found 329.1.

Example 28: (4S)-1-(2-cyclopropyl-2,2-difluoroethyl)-5,5-difluoro-3-(trifluoromethyl)-4,5,6,7-tetrahydro-1H-indazol-4-ol

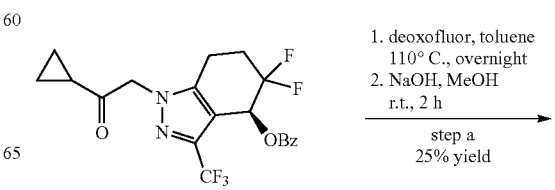

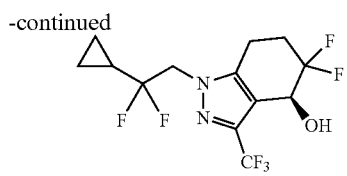

Step a: To a solution of ketone product prepared during the preparation of Example 26 (43.0 mg, 0.10 mmol) in toluene (0.20 mL) was added deoxofluor (2.7 M in toluene, 0.19 mL, 0.50 mmol, 5.0 equiv.). The resulting solution was then heated at 110° C. for overnight and then cooled back to room temperature and quenched with saturated NaHCO₃ aqueous solution. The mixture was then extracted with EtOAc twice. The combined organic phase was washed with brine, dried with Na₂SO₄, filtered and concentrated. The crude material was purified by flash chromatography (SiO₂, 0 to 30% EtOAc/Hex) furnishing the difluorinated intermediate (14.9 mg). The intermediate was then dissolved in methanol (2 mL) and treated with NaOH (1M aq., 1 mL). The resulting mixture was stirred at room temperature for 2 h before extracted with EtOAc and concentrated. The crude material was then purified by flash chromatography (SiO₂, 0 to 30% EtOAc/Hexanes) furnishing the title compound (8.7 mg, 25 µmol, 25% yield over 2 steps). $^1$H NMR (400 MHz, Chloroform-d) δ 4.89 (q, J=5.8 Hz, 1H), 4.48 (td, J=11.9, 3.9 Hz, 2H), 3.00-2.77 (m, 2H), 2.64-2.41 (m, 2H), 2.28 (dt, J=14.3, 7.6 Hz, 1H), 1.34-1.17 (m, 1H), 0.70-0.46 (m, 4H). ESI MS [M+H]$^+$ for $C_{13}H_{13}F_7N_2O$, calcd 347.1, found 347.1.

Example 29: (4S)-1-(2,2-difluorobutyl)-5,5-difluoro-3-(trifluoromethyl)-6,7-dihydro-4H-indazol-4-ol reaction mixture was stirred at 70° C. for 16 hours. After cooling to room temperature, the reaction was carefully quenched by the addition of saturated aqueous NaHCO₃ solution, and the mixture was diluted with EtOAc. After the layers were separated, the aqueous was extracted twice more with EtOAc. The combined organics were dried over Na₂SO₄ and concentrated. The crude material was purified by column chromatography using a gradient of 0 to 50% EtOAc in hexanes to yield 48 mg of [(4S)-1-(2,2-difluorobutyl)-5,5-difluoro-3-(trifluoromethyl)-6,7-dihydro-4H-indazol-4-yl] benzoate.

Step d: The deprotection step was conducted in a similar fashion to that described for Example 1. $^1$H NMR (400 MHz, Chloroform-d) δ 4.88 (app q, J=5.5 Hz, 1H), 4.38 (t, J=12.0 Hz, 2H), 3.04-2.77 (m, 2H), 2.67-2.36 (m, 2H), 2.37-2.19 (m, 1H), 2.01-1.79 (m, 2H), 1.07 (t, J=7.5 Hz, 3H). ESI MS [M+H]$^+$ for $C_{12}H_{14}F_7N_2O$, calcd 335.1, found 335.1.

Example 30: (4S)-5,5-difluoro-1-[3-(trifluoromethoxy)propyl]-3-(trifluoromethyl)-6,7-dihydro-4H-indazol-4-ol

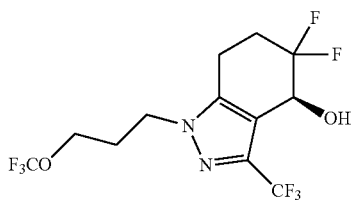

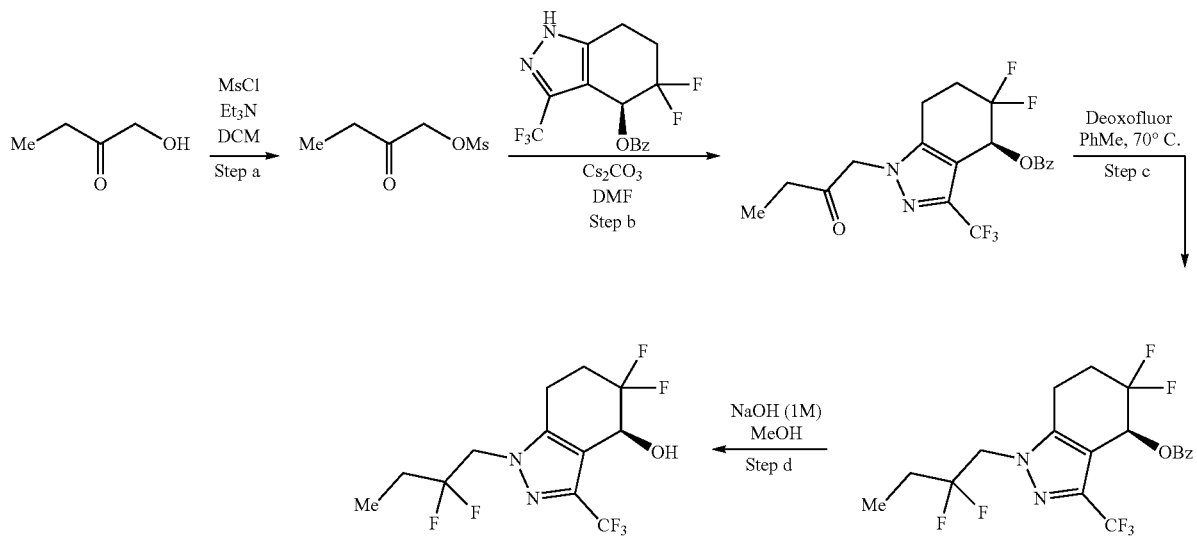

Step a: The mesylate intermediate was prepared in a similar fashion to that described for Example 5.

Step b: The ketone intermediate was prepared in a similar fashion to that described for Example 1.

Step c: To 100 mg of [(4S)-5,5-difluoro-1-(2-oxobutyl)-3-(trifluoromethyl)-6,7-dihydro-4H-indazol-4-yl] benzoate was added 1 mL of DeoxoFluor (50% wt. in toluene), and The title compound was prepared in a similar fashion to that described for Example 5 from 3-(trifluoromethoxy)propan-1-ol. $^1$H NMR (400 MHz, Chloroform-d) δ 4.92-4.85 (m, 1H), 3.95 (td, J=5.7, 1.7 Hz, 2H), 2.98-2.73 (m, 2H), 2.65-2.46 (m, 2H), 2.30 (m, 3H). ESI MS [M+H]$^+$ for $C_{12}H_{13}F_8N_2O_2$, calcd 369.1, found 369.1.

Example 31: (4S)-1-(4,4-difluorobutyl)-5,5-difluoro-3-(trifluoromethyl)-6,7-dihydro-4H-indazol-4-ol

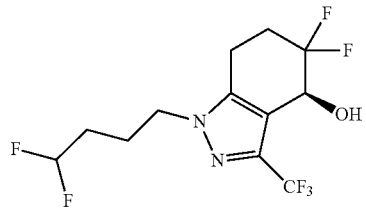 [SMILES: O[C@H]1c2c(C(F)(F)F)nn(CCCC(F)F)c2CCC1(F)F]

The title compound was prepared in a similar fashion to that described for Example 2 from 4,4-difluorobutan-1-ol. $^1$H NMR (400 MHz, Chloroform-d) δ 5.85 (tdd, J=56.4, 5.9, 3.0 Hz, 1H), 4.88 (q, J=5.5 Hz, 1H), 4.27-3.96 (m, 2H), 2.94-2.74 (m, 2H), 2.68-2.43 (m, 1H), 2.28 (dq, J=14.4, 7.8 Hz, 1H), 2.12-1.99 (m, 3H), 1.88 (ttd, J=18.0, 10.4, 9.6, 5.3 Hz, 2H). ESI MS [M+H]$^+$ for $C_{12}H_{14}F_7N_2O$, calcd 335.1, found 335.1.

Example 32: (4S)-1-(3,3-difluorobutyl)-5,5-difluoro-3-(trifluoromethyl)-6,7-dihydro-4H-indazol-4-ol

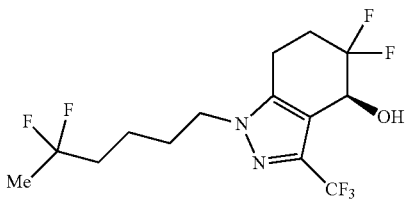 [SMILES: CC(F)(F)CCCCn1nc(C(F)(F)F)c2c1CCC(F)(F)[C@H]2O]

The title compound was prepared in a similar fashion to Example 5 from 3,3-difluorobutan-1-ol. $^1$H NMR (400 MHz, Chloroform-d) δ 4.88 (q, J=5.7 Hz, 1H), 4.24 (t, J=7.4 Hz, 2H), 2.98-2.75 (m, 2H), 2.66-2.19 (m, 4H), 1.62 (t, J=18.6 Hz, 3H). ESI MS [M+H]$^+$ for $C_{12}H_{14}F_7N_2O$, calcd 335.1, found 335.1.

Example 33: (4S)-5,5-difluoro-3-(trifluoromethyl)-1-(3,3,3-trifluoropropyl)-6,7-dihydro-4H-indazol-4-ol

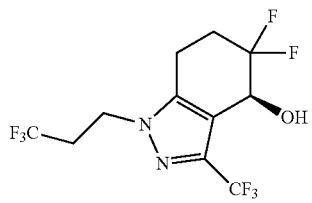 [SMILES: O[C@H]1c2c(C(F)(F)F)nn(CCC(F)(F)F)c2CCC1(F)F]

The title compound was prepared in a similar fashion to that described for Example 2 from 3,3,3-trifluoropropan-1-ol. $^1$H NMR (400 MHz, Chloroform-d) δ 4.88 (q, J=5.7 Hz, 1H), 4.26 (t, J=7.2 Hz, 2H), 2.95-2.67 (m, 3H), 2.66-2.44 (m, 2H), 2.38-2.22 (m, 1H). ESI MS [M+H]$^+$ for $C_{11}H_{11}F_8N_2O$, calcd 339.1, found 339.1.

Example 34: (4S)-5,5-difluoro-1-[2-(oxolan-2-yl)ethyl]-3-(trifluoromethyl)-6,7-dihydro-4H-indazol-4-ol

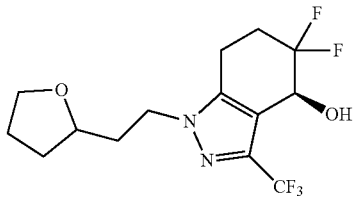 [SMILES: O[C@H]1c2c(C(F)(F)F)nn(CCC3CCCO3)c2CCC1(F)F]

The title compound was prepared in a similar fashion to Example 2 from 2-(oxolan-2-yl)ethanol. $^1$H NMR (400 MHz, Chloroform-d) δ 4.87-4.79 (m, 1H), 4.16-4.08 (m, 2H), 3.91-3.78 (m, 1H), 3.72-3.58 (m, 2H), 2.88-2.81 (m, 2H), 2.59-2.40 (m, 1H), 2.29-2.19 (m, 1H), 2.19-2.09 (m, 1H), 2.01-1.91 (m, 1H), 1.91-1.79 (m, 3H), 1.53-1.40 (m, 1H). ESI MS [M+H]$^+$ for $C_{14}H_{17}F_5N_2O_2$, calcd 341.1, found 341.1.

Example 35: (4S)-1-cyclohexyl-5,5-difluoro-3-(trifluoromethyl)-6,7-dihydro-4H-indazol-4-ol

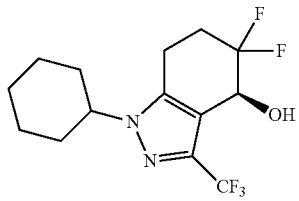 [SMILES: O[C@H]1c2c(C(F)(F)F)nn(C3CCCCC3)c2CCC1(F)F]

The title compound was prepared in a similar fashion to Example 2 from cyclohexanol. $^1$H NMR (400 MHz, Chloroform-d) δ 4.86 (t, J=6.3 Hz, 1H), 3.96-3.83 (m, 1H), 2.93-2.73 (m, 2H), 2.61-2.41 (m, 2H), 2.31-2.18 (m, 1H), 1.90 (qd, J=10.4, 9.2, 3.6 Hz, 6H), 1.42-1.22 (m, 4H). ESI MS [M+H]$^+$ for $C_{14}H_{17}F_5N_2O$, calcd 325.1, found 325.1.

Example 36: (4S)-1-(4,4-difluorocyclohexyl)-5,5-difluoro-3-(trifluoromethyl)-6,7-dihydro-4H-indazol-4-ol

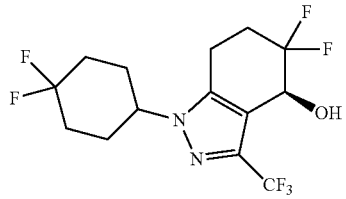 [SMILES: O[C@H]1c2c(C(F)(F)F)nn(C3CCC(F)(F)CC3)c2CCC1(F)F]

The title compound was prepared in a similar fashion to Example 2 from 4,4-difluorocyclohexan-1-ol. $^1$H NMR (400 MHz, Chloroform-d) δ 4.87 (s, 1H), 4.12-4.03 (m, 1H), 2.92-2.73 (m, 2H), 2.60 (s, 1H), 2.59-2.42 (m, 1H), 2.37-2.20 (m, 5H), 2.02-1.76 (m, 4H). ESI MS [M+H]$^+$ for $C_{14}H_{15}F_7N_2O$, calcd 361.1, found 361.0.

Example 37: (4S)-5,5-difluoro-3-(trifluoromethyl)-1-[4-(trifluoromethyl)cyclohexyl]-6,7-dihydro-4H-indazol-4-ol

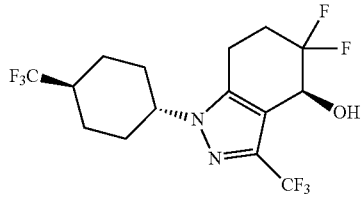

The title compound was prepared in a similar fashion to Example 2 from (cis)-4-(trifluoromethyl)cyclohexan-1-ol. $^1$H NMR (400 MHz, Chloroform-d) δ 4.87 (s, 1H), 3.92 (ddd, J=15.8, 9.4, 7.3 Hz, 1H), 2.92-2.73 (m, 2H), 2.63-2.43 (m, 2H), 2.32-2.21 (m, 1H), 2.21-2.09 (m, 3H), 2.07-1.97 (d, J=3.4 Hz, 3H), 1.54-1.41 (m, 2H). ESI MS [M+H]$^+$ for $C_{15}H_{16}F_8N_2O$, calcd 393.1, found 393.0.

Example 38: (4S)-5,5-difluoro-3-(trifluoromethyl)-1-(4,4,4-trifluoro-3-methylbutyl)-6,7-dihydro-4H-indazol-4-ol

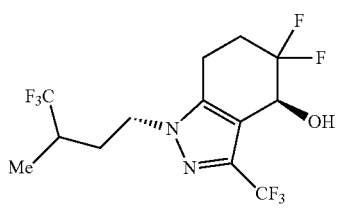

The title compound was prepared in a similar fashion to Example 5 from 4,4,4-trifluoro-3-methylbutan-1-ol. $^1$H NMR (400 MHz, Chloroform-d) δ 4.86 (s, 1H), 4.09 (t, J=7.7 Hz, 2H), 2.90-2.73 (m, 2H), 2.63-2.44 (m, 2H), 2.33-2.10 (m, 3H), 1.99-1.87 (m, 1H), 1.16 (dd, J=6.9, 1.4 Hz, 3H). ESI MS [M+H]$^+$ for $C_{13}H_{14}F_8N_2O$, calcd 367.1, found 367.0.

Example 39: (4S)-1-butyl-5,5-difluoro-3-(trifluoromethyl)-6,7-dihydro-4H-indazol-4-ol

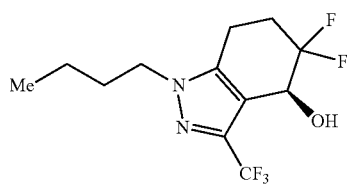 [SMILES: CCCCn1nc(C(F)(F)F)c2c1CCC(F)(F)[C@H]2O]

The title compound was prepared in a similar fashion to Example 1 from 1-bromobutane. $^1$H NMR (400 MHz, Chloroform-d) δ 4.88 (t, J=6.4 Hz, 1H), 4.01 (t, J=7.4 Hz, 2H), 2.94-2.72 (m, 2H), 2.67-2.43 (m, 2H), 2.34-2.19 (m, 1H), 1.89-1.74 (m, 2H), 1.41-1.26 (m, 2H), 0.94 (t, J=7.3 Hz, 3H). ESI MS [M+H]$^+$ for $C_{12}H_{15}F_5N_2O$, calcd 299.1, found 299.2.

Example 40: (4S)-5,5-difluoro-1-(3-methylbutyl)-3-(trifluoromethyl)-6,7-dihydro-4H-indazol-4-ol

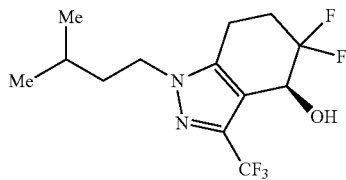 [SMILES: CC(C)CCn1nc(C(F)(F)F)c2c1CCC(F)(F)[C@H]2O]

The title compound was prepared in a similar fashion to Example 1 from 1-bromo-3-methylbutane. $^1$H NMR (400 MHz, Chloroform-d) δ 4.88 (t, J=6.4 Hz, 1H), 4.02 (t, J=7.8 Hz, 2H), 2.92-2.74 (m, 2H), 2.69-2.44 (m, 1H), 2.36-2.18 (m, 1H), 1.71 (q, J=7.2 Hz, 2H), 1.67-1.54 (m, 1H), 0.95 (d, J=6.4 Hz, 6H). ESI MS [M+H]$^+$ for $C_{13}H_{17}F_5N_2O$, calcd 313.1, found 313.2.

Example 41: (4S)-5,5-difluoro-1-(4,4,4-trifluorobutyl)-3-(trifluoromethyl)-6,7-dihydro-4H-indazol-4-ol

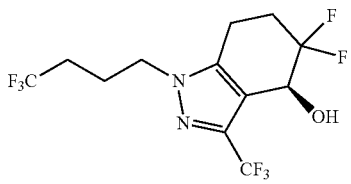 [SMILES: O[C@H]1c2c(C(F)(F)F)nn(CCCC(F)(F)F)c2CCC1(F)F]

The title compound was prepared in a similar fashion to Example 1 from (1,1,1-trifluoro-4-iodobutane). $^1$H NMR (400 MHz, Chloroform-d) δ 4.88 (t, J=6.3 Hz, 1H), 4.09 (t, J=6.5 Hz, 2H), 2.91-2.74 (m, 2H), 2.65-2.42 (m, 1H), 2.35-2.22 (m, 1H), 2.22-2.07 (m, 4H). ESI MS [M+H]$^+$ for $C_{12}H_{12}F_8N_2O$, calcd 353.1, found 353.2.

Example 42: (4S)-5,5-difluoro-1-(2-methylsulfonylethyl)-3-(trifluoromethyl)-6,7-dihydro-4H-indazol-4-ol

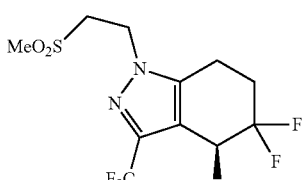

The title compound was prepared in a similar fashion to that described for Example 1 from 1-bromo-2-methylsulfonylethane. $^1$H NMR (400 MHz, CD$_3$OD) δ 4.68 (t, J=6.5 Hz, 1H), 4.53 (t, J=6.4 Hz, 2H), 3.72 (ddd, J=6.9, 6.0, 0.7 Hz, 2H), 3.06 (ddd, J=16.8, 6.7, 2.4 Hz, 1H), 2.89 (ddd, J=17.0, 10.7, 6.6 Hz, 1H), 2.79 (s, 3H), 2.58-2.34 (m, 1H), 2.33-2.15 (m, 1H). ESI MS [M+H]$^+$ for $C_{11}H_{13}F_5N_2O_3S$, calcd 349.1, found 349.1.

Example 43: (4S)-5,5-difluoro-3-(trifluoromethyl)-1-[3-(trifluoromethyl)pentyl]-6,7-dihydro-4H-indazol-4-ol

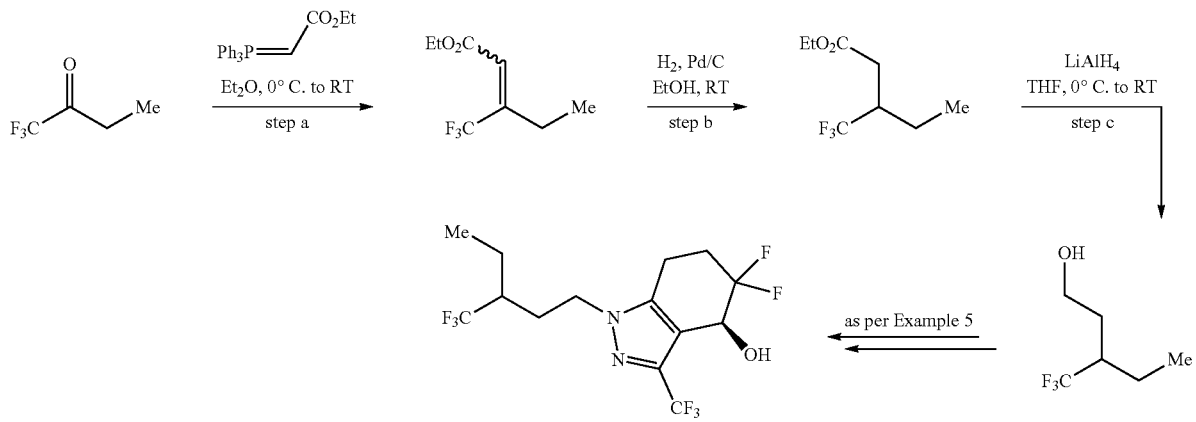

Step a: (Carbethoxymethylene)triphenylphosphorane (25 g, 71.8 mmol, 1.02 equiv.) was dissolved in Et$_2$O (140 mL) and the solution was cooled to 0° C. 1,1,1-trifluorobutan-2-one (8.9 g, 70.4 mmol, 1.0 equiv.) was added dropwise and the reaction was stirred for 72 hours at room temperature. The reaction mixture was filtered and directly concentrated in vacuo (700 mbar, 40° C.). The crude residue was purified by vacuum distillation to afford the product (4.86 g, 35% yield).

Step b: Ethyl (E,Z)-3-(trifluoromethyl)pent-2-enoate (4.86 g, 24.8 mmol, 1.0 equiv.) was dissolved in EtOH (100 mL, 0.25 M). Pd/C (500 mg, 10% wt) was added and the reaction was shaken under 50 psi of H$_2$ for 16 hours. The reaction mixture was sparged with N$_2$, filtered over Celite, and concentrated in vacuo (200 mbar, 40° C.). The crude residue was used in the subsequent step without further purification.

Step c: Ethyl 3-(trifluoromethyl)pentanoate (1.36 g, 6.87 mmol, 1.0 equiv.) was dissolved in THF (34 mL, 0.2 M) and the solution was cooled to 0° C. LiAlH$_4$ (2.0 M in THF, 6.9 mL, 13.7 mmol, 2.0 equiv.) was added dropwise and the reaction was stirred at room temperature for 16 hours. The reaction mixture was cooled to 0° C. and quenched with water (1.5 mL). 1.0 M NaOH (5 mL) was added, and the reaction mixture was stirred at room temperature for 15 minutes. MgSO$_4$ was added and the reaction mixture was stirred at room temperature for an additional 15 minutes. The reaction mixture was then filtered over celite and the crude solution of the product alcohol in THF was used directly in the subsequent mesylation without further purification.

The title compound was prepared in 3 additional steps in a similar fashion to that described for Example 5. $^1$H NMR (400 MHz, Chloroform-d) δ 4.93-4.84 (m, 1H), 4.10 (t, J=6.5 Hz, 2H), 2.92-2.73 (m, 2H), 2.67-2.42 (m, 2H), 2.36-2.22 (m, 1H), 2.20-1.91 (m, 3H), 1.86-1.64 (m, 1H), 1.55-1.41 (m, 1H), 0.99 (t, J=6.4 Hz, 3H). ESI MS [M+H]$^+$ for C$_{14}$H$_{16}$F$_8$N$_2$O, calcd 381.1, found 381.1.

Example 44: (4S)-1-[2-(3,3-difluorocyclobutyl)ethyl]-5,5-difluoro-3-(trifluoromethyl)-6,7-dihydro-4H-indazol-4-ol

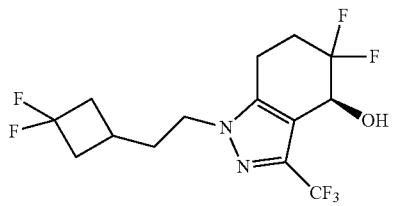 [SMILES: O[C@H]1c2c(C(F)(F)F)nn(CCC3CC(F)(F)C3)c2CCC1(F)F]

The title compound was prepared in a similar fashion to Example 5 from 2-(3,3-difluorocyclobutyl)ethanol. $^1$H NMR (400 MHz, CDCl$_3$) δ 4.93-4.81 (m, 1H), 4.05-3.94 (m, 2H), 2.88-2.72 (m, 2H), 2.72-2.44 (m, 4H), 2.34-2.20 (m, 1H), 2.17-2.00 (m, 5H). ESI MS [M+H]$^+$ for C$_{14}$H$_{16}$F$_7$N$_2$O, calcd 361.1, found 361.0.

Example 45: (4S)-5,5-difluoro-1-[(3-fluorocyclobutyl)methyl]-3-(trifluoromethyl)-6,7-dihydro-4H-indazol-4-ol

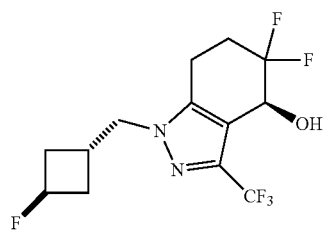

The title compound was prepared in a similar fashion to Example 5 from (3-fluorocyclobutyl)methanol. $^1$H NMR (400 MHz, CDCl$_3$) δ 5.21-5.00 (m, 1H), 4.87 (q, J=5.7 Hz, 1H), 4.04 (d, J=7.8 Hz, 2H), 2.91-2.81 (m, 2H), 2.81-2.76 (m, 1H), 2.62-2.46 (m, 2H), 2.45-2.30 (m, 2H), 2.29-2.21 (m, 3H). ESI MS [M+H]$^+$ for C$_{13}$H$_{15}$F$_6$N$_2$O, calcd 329.1, found 329.0.

Example 46: (4S)-1-[(1,1-dioxothietan-3-yl)methyl]-5,5-difluoro-3-(trifluoromethyl)-6,7-dihydro-4H-indazol-4-ol

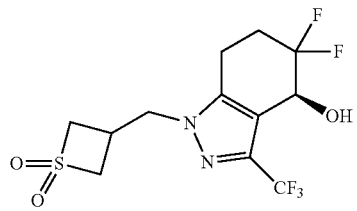 [SMILES: O=S1(=O)CC(Cn2nc(C(F)(F)F)c3c2CCC(F)(F)[C@H]3O)C1]

The title compound was prepared in a similar fashion to Example 5 from (1,1-dioxothietan-3-yl)methanol. $^1$H NMR (400 MHz, CDCl$_3$) δ 4.87 (q, J=5.6 Hz, 1H), 4.32-4.24 (m, 4H), 3.87-3.76 (m, 2H), 3.30-3.18 (m, 1H), 2.94-2.76 (m, 2H), 2.64-2.43 (m, 2H), 2.36-2.23 (m, 1H). ESI MS [M+H]$^+$ for $C_{12}H_{14}F_5N_2O_3S$, calcd 361.1, found 361.0.

Example 47: (4S)-5,5-difluoro-4-methoxy-1-(4,4,4-trifluorobutyl)-3-(trifluoromethyl)-6,7-dihydro-4H-indazole

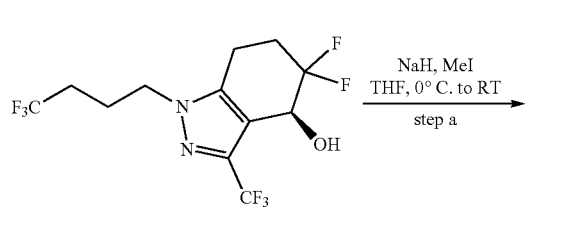

Step a: (4S)-5,5-difluoro-1-(4,4,4-trifluorobutyl)-3-(trifluoromethyl)-6,7-dihydro-4H-indazol-4-ol (17 mg, 0.05 mmol, 1.0 equiv.) was dissolved in THF (0.5 mL) and the solution was cooled to 0° C. NaH (5 mg, 0.21 mmol, 4.2 equiv.) was added and the reaction mixture was stirred for 10 minutes at 0° C. MeI (17 µL, 0.25 mmol, 5.0 equiv.) was then added and the reaction was stirred for 16 hours at room temperature. The reaction was quenched with saturated aqueous NH$_4$Cl (15 mL) and extracted with EtOAc (2×10 mL). The combined organics were dried over Na$_2$SO$_4$, filtered, and concentrated in vacuo. The crude residue was purified by flash column chromatography (silica gel, 25% EtOAc in hexanes) to afford the title compound (15 mg, 82% yield). $^1$H NMR (400 MHz, CDCl$_3$) δ 4.39 (t, J=5.5 Hz, 1H), 4.07 (t, J=7.0 Hz, 2H), 3.63 (s, 3H), 2.89-2.71 (m, 2H), 2.64-2.44 (m, 1H), 2.34-2.21 (m, 1H), 2.21-2.07 (m, 4H). ESI MS [M+H]$^+$ for $C_{13}H_{14}F_8N_2O$, calcd 367.1, found 367.2.

Example 48: (4S)-4,5,5-trifluoro-1-(4,4,4-trifluorobutyl)-3-(trifluoromethyl)-6,7-dihydro-4H-indazole

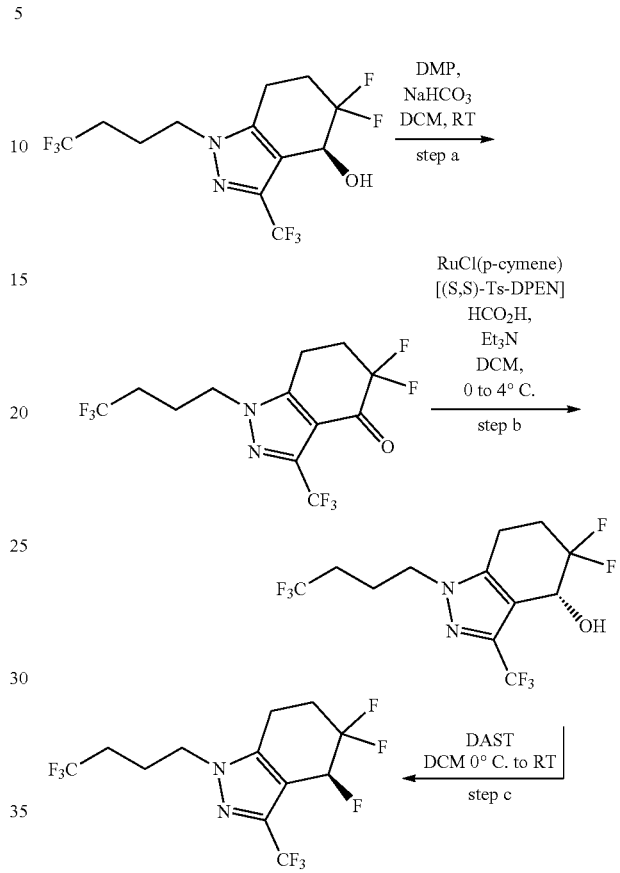

Step a: (4S)-5,5-difluoro-1-(4,4,4-trifluorobutyl)-3-(trifluoromethyl)-6,7-dihydro-4H-indazol-4-ol (50 mg, 0.14 mmol, 1.0 equiv.) was dissolved in DCM (0.7 mL, 0.2 M) and NaHCO$_3$ (46 mg, 0.56 mmol, 4.0 equiv.) was added followed by DMP (180 mg, 0.42 mmol, 3.0 equiv.). The reaction was stirred for 4 hours at room temperature. The reaction was quenched with saturated aqueous Na$_2$S$_2$O$_3$ (10 mL) and saturated aqueous NaHCO$_3$ (10 mL) and extracted with DCM (2×10 mL). The combined organics were dried over Na$_2$SO$_4$, filtered, and concentrated in vacuo. The crude residue was moved directly into step b without further purification.

Step b: The crude residue from step a (assume 0.14 mmol) was dissolved in DCM (1.4 mL, 0.1 M) and the solution was cooled to 0° C. HCO$_2$H (16 µL, 0.42 mmol, 3.0 equiv.), Et$_3$N (39 µL, 0.28 mmol, 2.0 equiv.), and RuCl(p-cymene)[(S,S)-Ts-DPEN] (5 mg, 0.007 mmol, 0.05 equiv.) were added sequentially and the reaction was stirred at 4° C. under N$_2$ for 16 hours. The reaction was quenched with saturated aqueous NaHCO$_3$ (15 mL) and extracted with DCM (2×10 mL). The combined organics were dried over Na$_2$SO$_4$, filtered, and concentrated in vacuo. The crude residue was purified by flash column chromatography (silica gel, 0-50% EtOAc in hexanes) to afford the product (35 mg, 71% over 2 steps).

Step c: (4R)-5,5-difluoro-1-(4,4,4-trifluorobutyl)-3-(trifluoromethyl)-6,7-dihydro-4H-indazol-4-ol (19 mg, 0.05 mmol, 1.0 equiv.) was dissolved in DCM (0.5 mL, 0.1 M)

and the solution was cooled to 0° C. DAST (33 µL, 0.25 mmol, 5.0 equiv.) was added and the reaction was stirred at room temperature for 16 hours. The reaction was quenched with saturated aqueous NaHCO$_3$ (15 mL) and extracted with DCM (2×10 mL). The combined organics were dried over Na$_2$SO$_4$, filtered, and concentrated in vacuo. The crude residue was purified by flash column chromatography (25% EtOAc in hexanes) to afford the product (10 mg, 56% yield). $^1$H NMR (400 MHz, Chloroform-d) δ 5.47 (dt, J=52.9, 5.2 Hz, 1H), 4.17-4.08 (m, 2H), 3.00-2.70 (m, 2H), 2.63-2.34 (m, 2H), 2.25-2.10 (m, 4H). ESI MS [M+H]$^+$ for C$_{12}$H$_{11}$F$_9$N$_2$, calcd 355.1, found 355.1.

Example 49: (4S)-5,5-difluoro-4-hydroxy-1-(4,4,4-trifluoro-3-methylbutyl)-6,7-dihydro-4H-indazole-3-carbonitrile

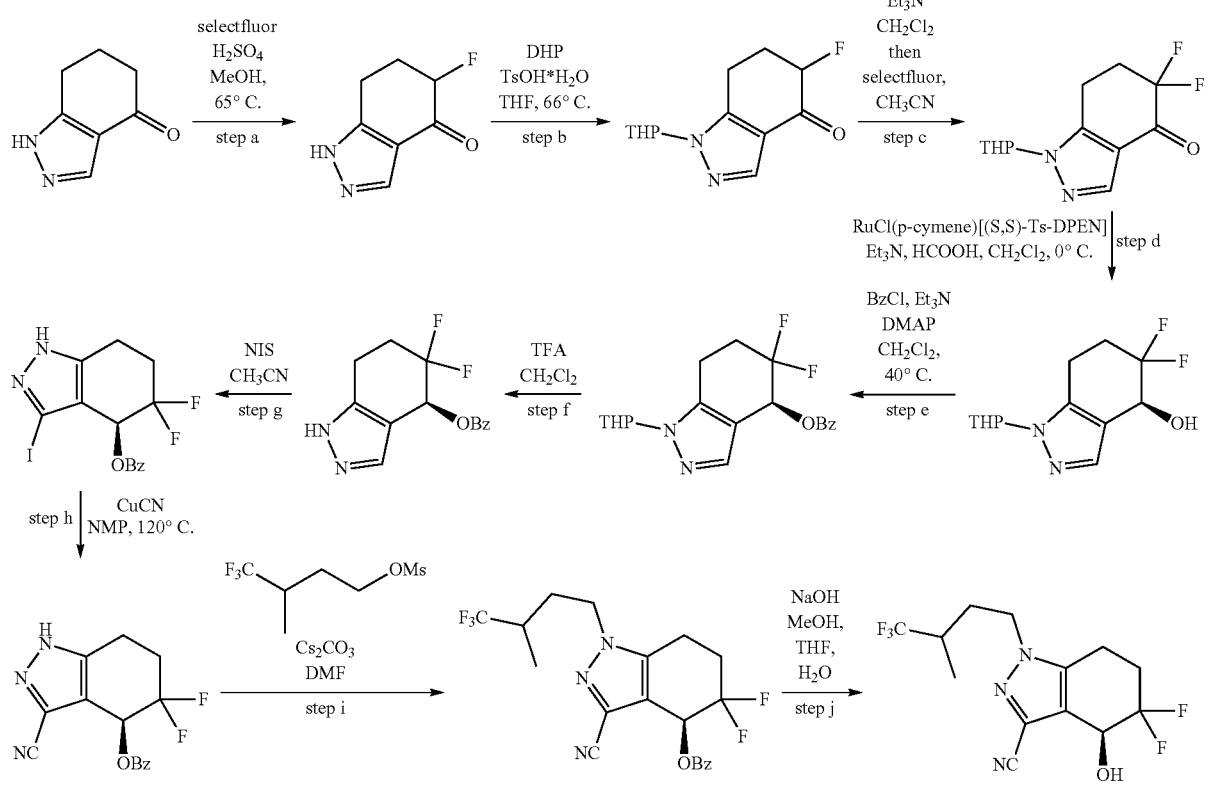

Step a: To a solution of 1,5,6,7-tetrahydroindazol-4-one (1.16 g, 8.5 mmol) in MeOH (43.0 mL) was added Selectfluor (3.32 g, 9.4 mmol) and concentrated H$_2$SO$_4$ (50.0 µL). The resulting mixture was heated at reflux for 3 h. After cooling down to room temperature, 0.3 M aq. H$_2$SO$_4$ (10 mL) was added to the reaction mixture. The resulting solution was heated at reflux for 1 h. After cooling down to room temperature, the reaction was carefully quenched with aq. sat. NaHCO$_3$ (100.0 mL) and diluted with dichloromethane (100.0 mL). The organic phase was separated, and the aqueous layer was additionally extracted with dichloromethane (2×50.0 mL). The combined organic phase was dried over Na$_2$SO$_4$ and concentrated to dryness under reduced pressure to yield the corresponding α-fluorinated ketone compound. The crude product was used for the next step without further purification.

Step b: To a solution of the crude α-fluorinated ketone from step a in THF (85.0 mL) was added DHP (1.2 mL, 12.8 mmol) and TsOH·H$_2$O (162 mg, 0.85 mmol), and the reaction mixture was refluxed overnight. The resulting solution was diluted with EtOAc (150.0 mL) and washed with aq. sat. NaHCO$_3$ (100.0 mL). The organic phase was separated, and the aqueous layer was additionally extracted with EtOAc (2×70.0 mL). The combined organic extract was dried over Na$_2$SO$_4$, concentrated to dryness under reduced pressure and the crude product was purified by column chromatography (SiO$_2$, hexanes/EtOAc gradient) to give the title compound (690.0 mg, 2.9 mmol, 34% yield over two steps) as a colorless oil.

Step c: To a solution of the product from step b (630.0 mg, 2.6 mmol) and Et$_3$N (2.2 mL, 15.8 mmol) in dichloromethane (13.0 mL), TBSOTf (1.2 mL, 5.3 mmol) was added dropwise at 0° C. The resulting solution was stirred at 0° C. for 1.5 h, then diluted with dichloromethane (30.0 mL) and then quenched with sat. aq. NaHCO$_3$. The organic phase was separated, and the aqueous phase was additionally extracted with dichloromethane (2×10.0 mL). The combined organic phase was washed with brine (50.0 mL), dried over Na$_2$SO$_4$ and concentrated to dryness under reduced pressure to afford the crude silyl enol ether. This material was dissolved in acetonitrile (13.0 mL) and Selectfluor (1.4 g, 4.0 mmol) was added portion-wise over 5 min at room temperature. The resulting mixture was stirred at room temperature for 0.5 h, then water (20.0 mL) and dichloromethane (40.0 mL) were added. The organic phase was separated, and the aqueous phase was additionally extracted with dichloromethane (2×15.0 mL). The combined organic solution was dried over Na$_2$SO$_4$, concentrated to dryness under reduced pressure and the crude product was purified by column chromatography (SiO$_2$, hexanes/EtOAc gradient) to give the corresponding α,α-difluoroketone compound (660.0 mg, 2.57 mmol, 97% yield) as a colorless oil.

Step d: To a solution of α,α-difluoroketone from step c (520.0 mg, 2.6 mmol) in dichloromethane (10.0 mL) was added formic acid (230.0 μL, 6.1 mmol) and triethylamine (560.0 μL, 4.1 mmol). The resulting solution was cooled to 0° C., RuCl(p-cymene)[(R,R)-TsDPEN] (39.0 mg, 0.06 mmol) was added in one portion, and the resulting mixture was maintained at +4° C. overnight. Once TLC analysis indicated complete disappearance of the starting material, the mixture was diluted with dichloromethane (30.0 mL) and washed with aq. sat. NaHCO$_3$ solution (25.0 mL), dried over Na$_2$SO$_4$ and concentrated to dryness under reduced pressure to provide the crude α,α-difluorohydrin. The crude product was used for the next step without purification.

Step e: The alcohol from step d was dissolved in dichloromethane (20.0 mL), then Et$_3$N (560.0 μL, 4.1 mmol), DMAP (24 mg, 0.2 mmol) and benzoyl chloride (350.0 μL, 3.1 mmol) were added sequentially. The reaction mixture was refluxed overnight. Upon confirming complete reaction by TLC, the mixture was diluted with dichloromethane (30.0 mL) and quenched with aq. sat. NH$_4$Cl (20.0 mL). The organic phase was separated, dried over Na$_2$SO$_4$ and concentrated to dryness under reduced pressure. The crude residue was purified by column chromatography (SiO$_2$, hexanes/EtOAc gradient) to give the corresponding benzoylated alcohol (0.77 g, 2.1 mmol, 95% yield over two steps).

Step f: The product of step e (0.75 g, 2.1 mmol) was dissolved in trifluoroacetic acid/dichloromethane mixture (1:5, 10.0 mL), and the solution was stirred at ambient temperature for 4 h. Upon complete THP group removal (TLC control) the reaction was diluted with dichloromethane (30.0 mL), washed with water (50.0 mL) and aq. sat. NaHCO$_3$ (30.0 mL). The organic extract was dried over Na$_2$SO$_4$, concentrated to dryness under reduced pressure and the crude residue was purified by column chromatography (SiO$_2$, hexanes/EtOAc gradient) to give the corresponding benzoylated alcohol (0.43 g, 1.55 mmol, 74% yield).

Step g: The tetrahydroindazole from step f (0.40 g, 1.4 mmol) and N-iodosuccinimide (0.42 g, 1.9 mmol) were dissolved in acetonitrile (7.2 mL), and the reaction mixture was refluxed overnight. Then the mixture was cooled to ambient temperature, diluted with EtOAc (25.0 mL) and washed with aq. sat. Na$_2$S$_2$O$_3$ (15.0 mL). The organic phase was separated, dried over Na$_2$SO$_4$ and concentrated to dryness under reduced pressure. The crude residue was purified by column chromatography (SiO$_2$, hexanes/EtOAc gradient) to give the corresponding iodotetrahydroindazole (0.49 g, 1.21 mmol, 84% yield).

Step h: A mixture of iodotetrahydroindazole (160.0 mg, 0.40 mmol) and copper (I) cyanide (71.0 mg, 0.80 mmol) in N-methylpyrrolidone (1.0 mL) was placed in 1 dram vial equipped with magnetic stirring bar and septum. The mixture was degassed under vacuum and backfilled with nitrogen twice and heated at 120° C. for 14 h. Upon complete reaction (TLC monitoring) the reaction was cooled to room temperature, diluted with EtOAc (20.0 mL) and washed with aq. sat. NH$_4$Cl (15.0 mL), water (15.0 ml) and brine (15.0 mL). The organic phase was separated, dried over anhydrous sodium sulfate and concentrated to dryness under reduced pressure. The crude residue was purified by column chromatography (SiO$_2$, hexanes/EtOAc gradient) to give the corresponding cyanotetrahydroindazole (69.0 mg, 0.23 mmol, 58% yield).

Step i: The alkylating reagent (4,4,4-trifluoro-3-methylbutyl) methanesulfonate (prepared in a similar fashion to that described in Example 5 from 4,4,4-trifluoro-3-methylbutan-1-ol) (60.0 mg, 0.27 mmol) was added to a mixture of cyanotetrahydroindazole from step h (69.0 mg, 0.23 mmol) and Cs$_2$CO$_3$ (150.0 mg, 0.45 mmol) in DMF (1.0 mL) at ambient temperature. The resulting mixture was vigorously stirred for 1 h. Once TLC analysis indicated complete consumption of the alkylating reagent the reaction was diluted with EtOAc (20.0 mL), washed with sat. aq. NH$_4$Cl (20.0 mL), water (2×15.0 mL) and brine (15.0 mL). The organic extract was dried over Na$_2$SO$_4$ and concentrated to dryness under reduced pressure. The dry residue was fractionated by column chromatography (SiO$_2$, hexanes/EtOAc gradient) to produce the corresponding alkylated product (48.0 mg, 0.11 mmol, 49% yield) as a white solid.

Step j: To a solution of the alkylation product of step i (48.0 mg, 0.11 mmol) in MeOH (2.2 mL) and THF (1.0 mL) was added aq. 1M NaOH solution (0.6 mL, 0.56 mmol) at ambient temperature. The resulting mixture was stirred for 1 h. Once TLC analysis indicated complete consumption of the starting material the reaction was diluted with EtOAc (15.0 mL) and aq. 1M NaOH solution (15.0 mL). The organic phase was separated and washed again with aq. 1M NaOH solution (2×10.0 mL) and brine (15.0 mL) to remove the residual benzoic acid. The combined organic phase was dried over Na$_2$SO$_4$, concentrated to dryness, and the crude product was purified by column chromatography (SiO$_2$, hexanes/EtOAc gradient) to give the title compound (2.1 mg, 0.006 mmol, 6% yield) as a colorless oil. Additionally, a corresponding ester product derived from nitrile hydrolysis was isolated (25.0 mg, 0.07 mmol). $^1$H NMR (400 MHz, CDCl$_3$) δ 4.88 (t, J=6.7 Hz, 1H), 4.11 (td, J=7.5, 2.4 Hz, 2H), 2.93-2.70 (m, 3H), 2.63-2.38 (m, 1H), 2.37-2.09 (m, 3H), 2.01-1.88 (m, 1H), 1.17 (dd, J=6.8, 1.0 Hz, 3H). ESI MS [M+H]$^+$ for C$_{13}$H$_{14}$F$_5$N$_3$O, calcd 324.1, found 324.2.

Example 50: (4S)-5,5-difluoro-3-methylsulfonyl-1-(4,4,4-trifluoro-3-methylbutyl)-6,7-dihydro-4H-indazol-4-ol

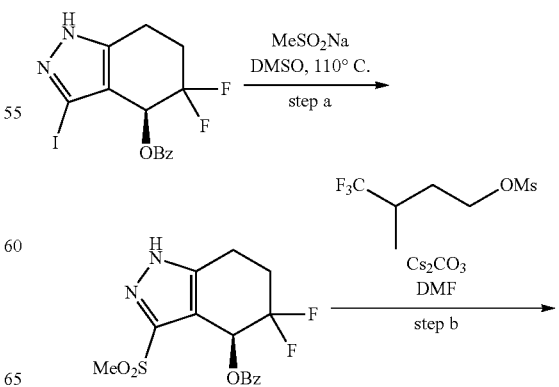

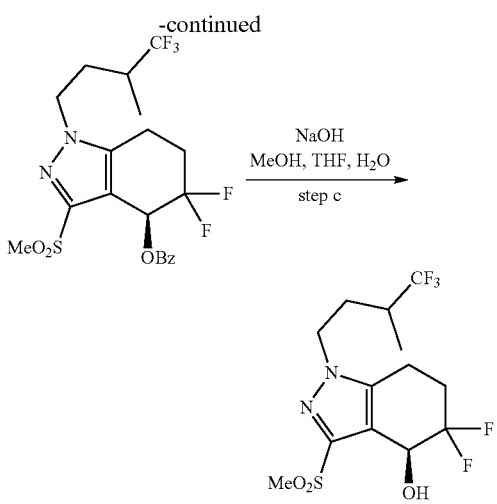

The starting material was prepared according to the protocol described in the synthesis of Example 49.

Step a: The iodopyrazole starting material (100.0 mg, 0.25 mmol), sodium methanesulfinate (76.0 mg, 0.74 mmol) and cupper (I) iodide (140.0 mg, 0.74 mmol) were mixed together in dimethyl sulfoxide (1.0 mL) and placed in 1 dram vial. The vessel was degassed under vacuum and backfilled with nitrogen twice. The reaction mixture was heated at 100° C. for 2.5 h. Once TLC analysis of an aliquot indicated a complete consumption of the starting material the reaction was cooled to ambient temperature. The resulting solution was diluted with EtOAc (20.0 mL), washed with sat. aq. NH$_4$Cl (10.0 mL), water (15.0 mL) and brine (15.0 mL). The organic phase was separated, dried over Na$_2$SO$_4$ and concentrated to dryness under reduced pressure. The crude residue was fractionated by column chromatography (SiO$_2$, CH$_2$Cl$_2$/EtOAc gradient) to give the desired sulfone (34.0 mg, 0.1 mmol, 39% yield) as a white solid.

Step b: The alkylating reagent (4,4,4-trifluoro-3-methylbutyl) methanesulfonate (prepared in a similar fashion to that described in Example 5 from 4,4,4-trifluoro-3-methylbutan-1-ol) (25.0 mg, 0.11 mmol) was added to a mixture of sulfone from step a (34.0 mg, 0.11 mmol) and Cs$_2$CO$_3$ (62.0 mg, 0.19 mmol) in DMF (0.5 mL) at ambient temperature. The resulting mixture was vigorously stirred for 1 h. Once TLC analysis indicated complete consumption of the alkylating reagent the reaction was diluted with EtOAc (15.0 mL), washed with sat. aq. NH$_4$Cl (15.0 mL), water (2×10.0 mL) and brine (10.0 mL). The organic extract was dried over Na$_2$SO$_4$ and concentrated to dryness under reduced pressure. The dry residue was fractionated by column chromatography (SiO$_2$, hexanes/EtOAc gradient) to produce the corresponding alkylated product (35.0 mg, 0.07 mmol, 76% yield) as a colorless oil.

Step c: To a solution of the alkylation product of step b (35.0 mg, 0.07 mmol) in MeOH (1.5 mL) and THF (1.0 mL) was added aq. 1M NaOH solution (0.4 mL, 0.36 mmol) at ambient temperature. The resulting mixture was stirred for 1 h. Once TLC analysis indicated complete consumption of the starting material the reaction was diluted with EtOAc (15.0 mL) and aq. 1M NaOH solution (15.0 mL). The organic phase was separated and washed again with aq. 1M NaOH solution (2×10.0 mL) and brine (15.0 mL) to remove the residual benzoic acid. The combined organic phase was dried over Na$_2$SO$_4$, concentrated to dryness, and the crude product was purified by column chromatography (SiO$_2$, hexanes/EtOAc gradient) to give the title compound (25.0 mg, 91% yield) as a colorless oil. $^1$H NMR (400 MHz, CDCl$_3$) δ 5.09 (ddd, J=7.5, 5.8, 1.4 Hz, 1H), 4.24-4.05 (m, 2H), 3.20 (s, 3H), 3.00-2.72 (m, 2H), 2.60-2.38 (m, 1H), 2.37-2.10 (m, 2H), 2.11-1.85 (m, 1H), 1.17 (dd, J=6.9, 2.0 Hz, 3H). ESI MS [M+H]$^+$ for C$_{13}$H$_{17}$F$_5$N$_2$O$_3$S, calcd 377.1, found 377.1.

Example 51: (4S,5R)-5-fluoro-1-(4,4,4-trifluorobutyl)-3-(trifluoromethyl)-4,5,6,7-tetrahydroindazol-4-ol

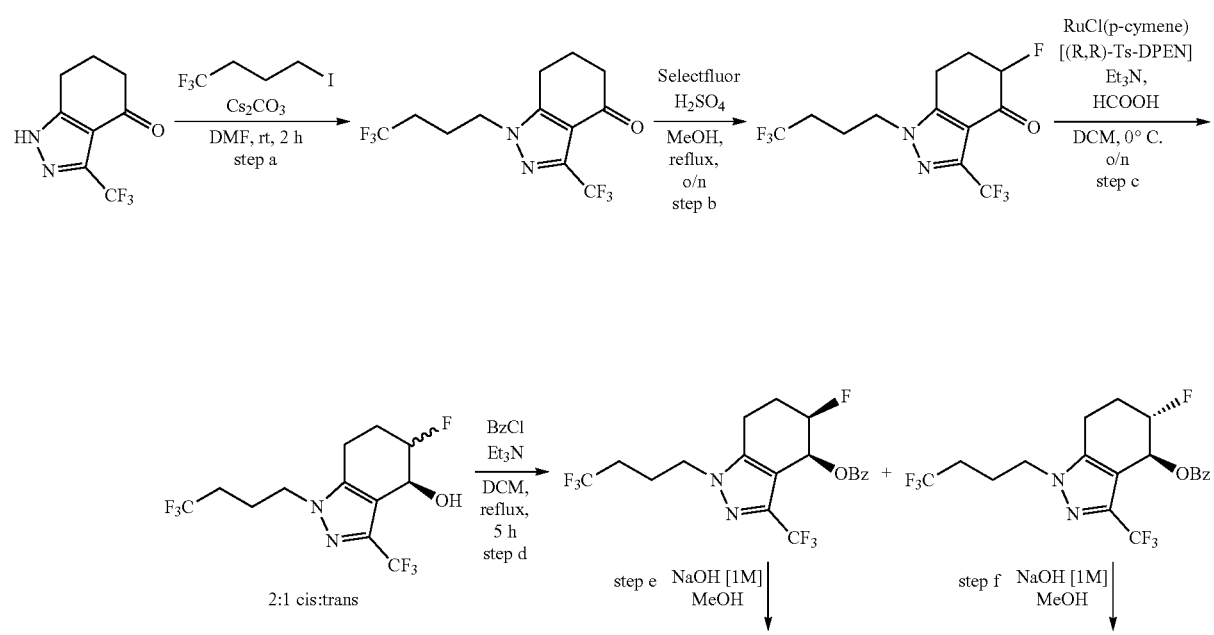

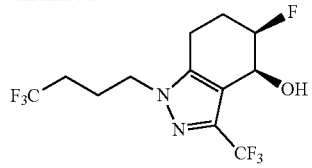
Example 51

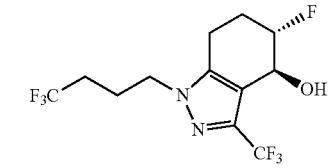
Example 52

Step a: To 3-(trifluoromethyl)-1,5,6,7-tetrahydroindazol-4-one (2.04 g, 10.0 mmol, 1.0 eq) in DMF (0.5 M, 20 mL) at room temperature was added $Cs_2CO_3$ (4.89 g, 15.0 mmol, 1.5 eq) followed by 1,1,1-trifluoro-4-iodobutane (1.47 mL, 12.0 mmol, 1.2 eq) and the mixture was stirred at room temperature for 2 hours. Upon completion, the reaction was quenched with satd. $NH_4Cl$ and diluted with ethyl acetate. The layers were separated and the aqueous layer was extracted with ethyl acetate. The combined organic layers were washed with water (2×) and then dried over $Na_2SO_4$, filtered, and concentrated. The crude residue was purified via flash column chromatography (ISCO, Redisep 40 g column, 0-100% EA/Hex gradient) to afford 1-(4,4,4-trifluorobutyl)-3-(trifluoromethyl)-6,7-dihydro-5H-indazol-4-one as a red oil (2.25 g, 72%).

Step b: To the product of step a (2.00 g, 6.37 mmol, 1.0 eq) in MeOH (0.4 M, 16 mL) at room temperature was added Selectfluor (2.48 g, 7.01 mmol, 1.1 eq) followed by conc. $H_2SO_4$ (34 μL, 0.64 mmol, 0.1 eq) and the mixture was heated to reflux overnight. Upon completion, the reaction was cooled to room temperature, quenched with satd. $NaHCO_3$, and diluted with ethyl acetate. The layers were separated and the aqueous layer was extracted with ethyl acetate. The combined organic layers were washed with water (2×) and then dried over $Na_2SO_4$, filtered, and concentrated to afford 5-fluoro-1-(4,4,4-trifluorobutyl)-3-(trifluoromethyl)-6,7-dihydro-5H-indazol-4-one as a red oil (1.72 g, 82%).

Step c: To the product of step b (332 mg, 1.00 mmol, 1.0 eq) in DCM (0.1 M, 10 mL) at room temperature was added $Et_3N$ (277 μL, 2.00 mmol, 2.0 eq) followed by formic acid (113 μL, 3.00 mmol, 3.0 eq). The mixture was degassed for ~10 minutes, cooled to 0° C., RuCl(p-cymene)[(R,R)-Ts-DPEN] (32 mg, 0.050 mmol, 0.05 eq) was added, and the mixture was stirred at 0° C. overnight. Upon completion, the reaction was concentrated and purified via flash column chromatography (ISCO, Redisep 12 g column, 0-60% EA/Hex gradient) to afford (4S,5R)-5-fluoro-1-(4,4,4-trifluorobutyl)-3-(trifluoromethyl)-4,5,6,7-tetrahydroindazol-4-ol and (4S,5S)-5-fluoro-1-(4,4,4-trifluorobutyl)-3-(trifluoromethyl)-4,5,6,7-tetrahydroindazol-4-ol (247 mg, 74%) as an inseparable mixture of diastereomers (~2:1 cis:trans).

Step d: To the products of step c (100 mg, 0.30 mmol, 1.0 eq) and DMAP (9.0 mg, 0.075 mmol, 0.25 eq) in DCM (0.1 M, 3.0 mL) at room temperature were added $Et_3N$ (83 μL, 0.60 mmol, 2.0 eq) followed by benzoyl chloride (42 μL, 0.36 mmol, 1.2 eq) and the mixture was heated to reflux for 5 hours. Upon completion, the reaction was cooled to room temperature and quenched with 1 M HCl. The layers were separated, and the aqueous layer was extracted with DCM. The combined organic layers were dried over $Na_2SO_4$, filtered, and concentrated. The crude residue was purified via flash column chromatography (ISCO, Redisep 12 g column, 0-60% EA/Hex gradient) to afford [(4S,5R)-5-fluoro-1-(4,4,4-trifluorobutyl)-3-(trifluoromethyl)-4,5,6,7-tetrahydroindazol-4-yl] benzoate as a clear oil (61 mg, 47%) and [(4S,5S)-5-fluoro-1-(4,4,4-trifluorobutyl)-3-(trifluoromethyl)-4,5,6,7-tetrahydroindazol-4-yl]benzoate as a clear oil (35 mg, 27%).

Step e: To [(4S,5R)-5-fluoro-1-(4,4,4-trifluorobutyl)-3-(trifluoromethyl)-4,5,6,7-tetrahydroindazol-4-yl] benzoate (61 mg, 0.14 mmol, 1.0 eq) in MeOH (2.25 mL, ~0.05 M total) at room temperature was added 1 M NaOH (0.75 mL, 0.75 mmol, 5.4 eq) and the mixture was stirred at room temperature overnight. Upon completion, the reaction was quenched with satd. $NH_4Cl$ and diluted with ethyl acetate. The layers were separated, and the aqueous layer was extracted with ethyl acetate. The combined organic layers were dried over $Na_2SO_4$, filtered, and concentrated. The crude residue was purified via flash column chromatography (ISCO (ELS), Redisep 4 g column, 0-60% EA/Hex gradient) to afford (4S,5R)-5-fluoro-1-(4,4,4-trifluorobutyl)-3-(trifluoromethyl)-4,5,6,7-tetrahydroindazol-4-ol (41 mg, 88%).

$^1$H NMR (400 MHz, Chloroform-d) δ 5.01 (d, J=10.2 Hz, 1H), 4.86 (ddt, J=47.2, 10.3, 3.2 Hz, 1H), 4.08 (t, J=6.7 Hz, 2H), 2.84 (dddd, J=16.4, 6.0, 4.3, 1.6 Hz, 1H), 2.64 (ddd, J=16.2, 9.2, 6.3 Hz, 1H), 2.56-2.37 (m, 2H), 2.23-1.98 (m, 5H). $^{19}$F NMR (376 MHz, $CDCl_3$) δ -61.41, -66.01, -195.35. ESI MS [M+H]f for $C_{12}H_{14}F_7N_2O$, calcd 335.1, found 335.1.

Example 52: (4S,5S)-5-fluoro-1-(4,4,4-trifluorobutyl)-3-(trifluoromethyl)-4,5,6,7-tetrahydroindazol-4-ol Step f: To [(4S,5S)-5-fluoro-1-(4,4,4-trifluorobutyl)-3-(trifluoromethyl)-4,5,6,7-tetrahydroindazol-4-yl] benzoate (35 mg, 0.080 mmol, 1.0 eq) in MeOH (2.25 mL, ~0.025 M total) at room temperature was added 1 M NaOH (0.75 mL, 0.75 mmol, 9.4 eq) and the mixture was stirred at room temperature overnight. Upon completion, the reaction was quenched with satd. $NH_4Cl$ and diluted with ethyl acetate. The combined layers were separated, and the aqueous layer was extracted with ethyl acetate. The combined organic layers were dried over $Na_2SO_4$, filtered, and concentrated. The crude residue was purified via flash column chromatography (ISCO (ELS), Redisep 4 g column, 0-60% EA/Hex gradient) to afford (4S,5S)-5-fluoro-1-(4,4,4-trifluorobutyl)-3-(trifluoromethyl)-4,5,6,7-tetrahydroindazol-4-ol as a clear oil (6 mg, 22%).

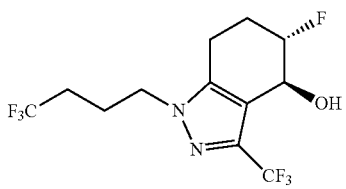 [SMILES: O[C@H]1c2c(C(F)(F)F)nn(CCCC(F)(F)F)c2CC[C@@H]1F]

¹H NMR (400 MHz, Chloroform-d) δ 5.05-4.84 (m, 2H), 4.11 (t, J=6.6 Hz, 2H), 2.80-2.62 (m, 2H), 2.37-2.07 (m, 7H). ¹⁹F NMR (376 MHz, CDCl₃) δ −61.19, −65.99, −192.87. ESI MS [M+H]⁺ for $C_{12}H_{14}F_7N_2O$, calcd 335.1, found 335.1.

Example 53: (4S)-1-(4,4-difluorocyclohexyl)-5,5-difluoro-3-(trifluoromethyl)-4,6-dihydrocyclopenta[c]pyrazol-4-ol C. for two hours. After cooling to room temperature, the reaction was concentrated to dryness. Purification by column chromatography (SiO₂, 0-20% EtOAc/CH₂Cl₂) afforded the desired product (23 g, 39%) as a yellow solid.

Step c: To a solution of the product from step b (24.0 g, 126.2 mmol, 1.0 equiv.) in MeOH (500 mL, 0.25M) was added Selectfluor (67.1 g, 189.3 mmol, 1.5 equiv.) and concentrated H₂SO₄ (0.3 mL). The resulting mixture was heated at reflux for 15 h. After cooling down to room temperature, 0.3 M H₂SO₄ (50 mL) was added to the reaction mixture. The resulting mixture was heated at reflux for 1 h. After cooling down to room temperature, the reaction was quenched with NaHCO₃ sat., the organic phase was separated, and the aqueous layer was extracted with DCM. The combined organic phase was dried over Na₂SO₄, concentrated and the crude residue was purified by column chromatography (SiO₂, EtOAc in DCM, 0 to 30%) to give the 2-F indanone product (11.28 g, 43% yield).

Step d: To a solution of the product from step c (11.0 g, 52.9 mmol, 1.0 equiv.) in THF (350 mL, 0.15M) was added

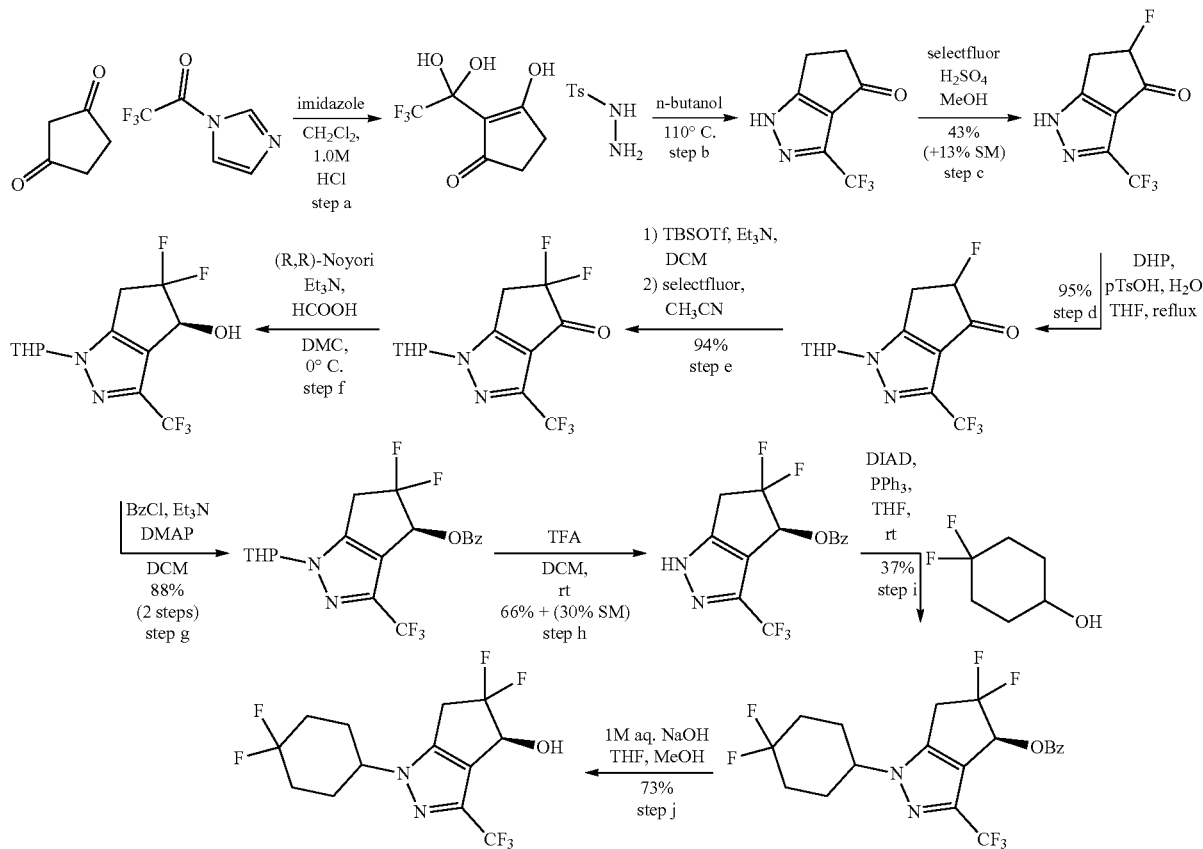

Step a. To a 3-liter 3-neck round bottom flask was added dichloromethane (1.02 L) followed by cyclopentanedione (40.0 g, 408 mmol). 1-(Trifluoroacetyl)imidazole (27.8 g, 408 mmol) was added dropwise via addition funnel maintaining the internal temperature below 25° C. After stirring 4 additional hours the reaction was quenched with 1.0M HCl (800 mL). The precipitate which formed was filtered and washed with water. The cake was suction dried then further dried under high vacuum affording the product as an off-white solid (66.46 g, 77%).

Step b. A suspension of the product from step a (66.46 g, 313 mmol) in n-butanol (782 mL, 0.4M) was heated to 110°

DHP (7.2 mL, 79.3 mmol, 1.5 equiv.) and pTsOH·H₂O (1.0 g, 5.29 mmol, 0.1 equiv.) and the mixture was refluxed overnight. The reaction was quenched with NaHCO₃ sat., the organic phase was separated, and the aqueous layer was extracted with EtOAc. The combined organic phase was dried over Na₂SO₄, concentrated and the crude residue was purified by column chromatography (SiO₂, EtOAc in hexanes, 20 to 60%) to give the THP protected pyrazole (14.7 g, 95% yield).

Step e: To a solution of the product from step d (13.5 g, 46.2 mmol, 1.0 equiv.) and Et₃N (25.0 mL, 185.0 mmol, 4.0 equiv.) in DCM (153 mL, 0.3M) was added TBSOTf (21.0 mL, 92.4 mmol, 2.0 equiv.) dropwise at 0° C. The resulting solution was stirred at 0° C. for 1.5 h, and then quenched with saturated NaHCO₃ (aq.). The organic phase was separated, and the aqueous phase was extracted with DCM, the combined organic phase was then washed with brine, dried over Na₂SO₄ and concentrated to afford the silyl enol ether. The crude material was then dissolved in MeCN (231 mL, 0.2M) and Selectfluor (24.6 g, 69.3 mmol, 1.5 equiv.) was added portion-wise at room temperature. The resulting mixture was stirred at room temperature for 30 min, then water and DCM were added, and the aqueous phase was extracted with DCM. The combined organic phase was dried over Na₂SO₄, concentrated and the crude residue was purified by column chromatography (SiO₂, EtOAc in hexanes, 10 to 40%) to give the difluoro-indanone product (13.6 g, 94% yield).

Step f: To a solution of difluoro-indanone (13.2 g, 42.5 mmol, 1.0 equiv.) in DCM (212 mL, 0.2M) was added HCO₂H (4.8 mL, 127.5 mmol, 3.0 equiv.) and Et₃N (11.6 mL, 85.0 mmol, 2.0 equiv.). After cooling down the solution to 0° C., RuCl(p-cymene)[(R,R)-TsDPEN](811 mg, 1.28 mmol, 0.03 equiv.) was added and the resulting mixture was kept in the fridge overnight (4° C.). The reaction was quenched with NaHCO₃ sat., the organic phase was separated, and the aqueous layer was extracted with DCM. The combined organic phase was dried over Na₂SO₄, concentrated and the crude residue was used without purification.

Step g: The crude residue from step f was dissolved in DCM (212 mL, 0.2M) and Et₃N (11.6 mL, 85.0 mmol, 2 equiv.), BzCl (7.4 mL, 63.8 mmol, 1.5 equiv.) and DMAP (519 mg, 4.25 mmol, 0.1 equiv.) were added. The reaction mixture was refluxed overnight and quenched with NH₄Cl sat. The organic phase was separated, the aqueous layer was extracted with DCM, the combined organic phase was dried over Na₂SO₄, concentrated and the crude residue was purified by column chromatography (SiO₂, EtOAc in hexanes, 0 to 30%) to give the benzoyl protected indanol product (15.6 g, 88% yield over 2 steps).

Step h: The product from step g (15.5 g, 37.2 mmol, 1.0 equiv.) was dissolved in DCM:TFA (9:1, 180 mL, 0.2M) and the reaction mixture was stirred at rt for 4 h. The reaction was quenched with NaHCO₃ sat., the organic phase was separated, the aqueous layer was extracted with DCM, the combined organic phase was dried over Na₂SO₄, concentrated and the crude residue was purified by column chromatography (EtOAc in hexanes, 20 to 50%) to give [(4S)-5,5-difluoro-3-(trifluoromethyl)-4,6-dihydro-1H-cyclopenta[c]pyrazol-4-yl] benzoate (8.24 g, 66% yield) and 4.74 g of recovered starting material.

Step i: To a solution of [(4S)-5,5-difluoro-3-(trifluoromethyl)-4,6-dihydro-1H-cyclopenta[c]pyrazol-4-yl] benzoate (70 mg, 0.211 mmol, 1.0 equiv.) in THF (1.5 mL) was added PPh₃ (100 mg, 0.381 mmol, 1.8 equiv.) and DIAD (75 μL, 0.38 mmol, 1.8 equiv.). The resulting mixture was stirred at room temperature for 30 minutes. The reaction was concentrated onto Celite and purified directly by flash chromatography (SiO₂, hexanes to 40% EtOAc) to furnish the alkylated product (34.9 mg, 37%).

Step j: The product of step i (34.9 mg, 0.077 mmol, 1.0 equiv.) was dissolved in THF (0.5 mL) and MeOH (0.5 mL). 1M aq. NaOH solution (0.40 mL, 0.40 mmol, 5.0 equiv.) was added and the reaction was stirred for 30 min, until LCMS indicated the complete consumption of starting material. The reaction was diluted with EtOAc and quenched with sat. aq. NH₄Cl solution. The aqueous layer was separated and extracted with additional EtOAc. The organic layers were combined and dried over MgSO₄. Concentration under reduced pressure and purification by flash chromatography (SiO₂, hexanes to 40% EtOAc) furnished the title compound as a colorless oil (19.5 mg, 73%). ¹H NMR (400 MHz, CDCl₃) δ 5.06 (dd, J=12.1, 5.5 Hz, 1H), 4.25 (tt, J=10.1, 5.4 Hz, 1H), 3.58-3.24 (m, 2H), 2.41-2.22 (m, 2H), 2.21-2.03 (m, 4H), 2.02-1.81 (m, 2H). ESI MS [M+H]⁺ for C₁₃H₁₃F₇N₂O, calcd 347.1, found 347.1.

Example 54: (4S)-1-(3,3-difluorocyclopentyl)-5,5-difluoro-3-(trifluoromethyl)-4,6-dihydrocyclopenta[c]pyrazol-4-ol

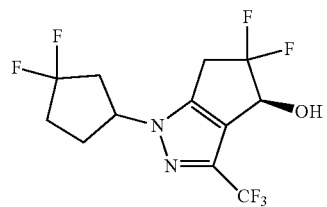

The title compound was prepared in a similar fashion to that described for Example 5 via the reaction of [(4S)-5,5-difluoro-3-(trifluoromethyl)-4,6-dihydro-1H-cyclopenta[c]pyrazol-4-yl] benzoate with the mesylate derived from 3,3-difluorocyclopentan-1-ol. The compound was isolated as a 1:1 mixture of diastereomers at the α-branched cyclopentyl methine. ¹H NMR (400 MHz, CDCl₃) δ 5.06 (dd, J=12.0, 5.5 Hz, 1H), 4.76-4.64 (m, 1H), 3.49-3.24 (m, 2H), 2.77-2.61 (m, 2H), 2.57-2.07 (m, 4H). ESI MS [M+H]⁺ for C₁₂H₁₁F₇N₂O, calcd 333.1, found 333.1.

Example 55: 4-[(4S)-5,5-difluoro-4-hydroxy-3-(trifluoromethyl)-4,6-dihydrocyclopenta[c]pyrazol-1-yl]-2-methylbutanenitrile

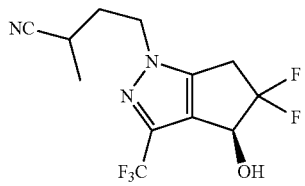

The title compound was prepared in a similar fashion to Example 3 from [(4S)-5,5-difluoro-3-(trifluoromethyl)-4,6-dihydro-1H-cyclopenta[c]pyrazol-4-yl] benzoate. ¹H NMR (400 MHz, CDCl₃) δ 5.05 (ddd, J=11.9, 5.9, 2.1 Hz, 1H), 4.51-4.11 (m, 2H), 3.65-3.22 (m, 2H), 2.87 (ddd, J=11.1, 6.0, 1.8 Hz, 1H), 2.64-2.52 (m, 1H), 2.45-2.21 (m, 1H), 2.21-1.98 (m, 1H), 1.37 (dd, J=7.1, 1.1 Hz, 3H). ESI MS [M+H]⁺ for C₁₂H₁₂F₅N₃O, calcd 310.1, found 310.3.

Example 56: (4S)-5,5-difluoro-1-(2-methylsulfonyl-ethyl)-3-(trifluoromethyl)-4,6-dihydrocyclopenta[c]pyrazol-4-ol

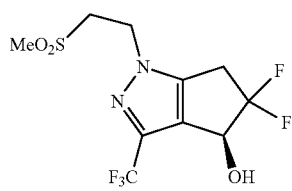

The title compound was prepared in a similar fashion to Example 1 from 1-bromo-2-methylsulfonylethane and [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 5.04 (dd, J=12.1, 5.7 Hz, 1H), 4.55 (t, J=5.9 Hz, 2H), 3.64 (t, J=6.1 Hz, 2H), 3.56-3.33 (m, 2H), 2.97 (d, J=5.8 Hz, 1H), 2.68 (s, 3H). ESI MS [M+H]$^+$ for C$_{10}$H$_{11}$F$_5$N$_2$O$_3$S, calcd 335.1, found 335.0.

Example 57: (4S)-1-[(1,1-dioxothietan-3-yl)methyl]-5,5-difluoro-3-(trifluoromethyl)-4,6-dihydrocyclopenta[c]pyrazol-4-ol

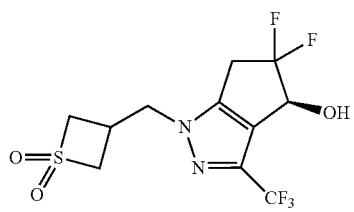 [SMILES: O=S1(=O)CC(Cn2nc(C(F)(F)F)c3c2CC(F)(F)[C@H]3O)C1]

The title compound was prepared in a similar fashion to that described for Example 5 using the mesylate derived from (1,1-dioxothietan-3-yl)methanol and [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 5.09 (dd, J=11.8, 5.4 Hz, 1H), 4.36 (dd, J=7.7, 1.3 Hz, 2H), 4.35-4.26 (m, 2H), 3.90-3.81 (m, 2H), 3.49-3.27 (m, 2H), 3.27-3.15 (m, 1H), 2.48 (dd, J=5.4, 2.0 Hz, 1H). ESI MS [M+Na]$^+$ for C$_{11}$H$_{11}$F$_5$N$_2$O$_3$SNa, calcd 369.0, found 369.0.

Example 58: (4S)-1-[2-(2,2-difluorocyclopropyl)ethyl]-5,5-difluoro-3-(trifluoromethyl)-4,6-dihydrocyclopenta[c]pyrazol-4-ol

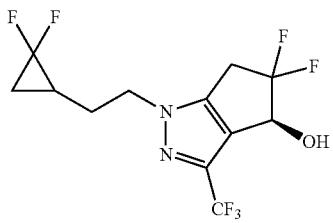 [SMILES: O[C@H]1c2c(C(F)(F)F)nn(CCC3CC3(F)F)c2CC1(F)F]

The title compound was prepared in a similar fashion to that described for Example 1 from 2-(2-bromoethyl)-1,1-difluorocyclopropane and [(4S)-5,5-difluoro-3-(trifluoromethyl)-4,6-dihydro-1H-cyclopenta[c]pyrazol-4-yl] benzoate. $^1$H NMR (400 MHz, Chloroform-d) δ 5.07 (dd, J=12.0, 5.6 Hz, 1H), 4.29-4.01 (m, 2H), 3.59-3.08 (m, 2H), 2.48-2.23 (m, 1H), 2.24-2.04 (m, 1H), 2.03-1.80 (m, 1H), 1.42 (d, J=12.6 Hz, 2H), 1.00-0.76 (m, 1H). ESI MS [M+H]$^+$ for C$_{12}$H$_{11}$F$_7$N$_2$O, calcd 333.1, found 333.1.

Example 59: (4S)-5,5-difluoro-3-(trifluoromethyl)-1-[[2-(trifluoromethyl)cyclopropyl]methyl]-6,7-dihydro-4H-indazol-4-ol

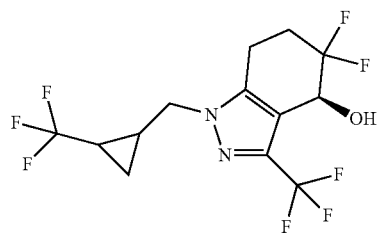 [SMILES: O[C@H]1c2c(C(F)(F)F)nn(CC3CC3C(F)(F)F)c2CCC1(F)F]

The title compound was prepared in a similar fashion to that described for Example 2 from [2-(trifluoromethyl)cyclopropyl]methanol and [(4S)-5,5-difluoro-3-(trifluoromethyl)-1,4,6,7-tetrahydroindazol-4-yl] benzoate. $^1$H NMR (400 MHz, Chloroform-d) δ 4.89 (s, 1H), 4.18-3.83 (m, 3H), 2.86 (s, 2H), 2.54 (s, 2H), 2.30 (s, 1H), 1.81-1.43 (m, 2H), 1.11 (s, 1H), 0.88 (d, J=14.3 Hz, 1H). ESI MS [M+H]$^+$ for C$_{13}$H$_{12}$F$_8$N$_2$O, calcd 365.1, found 365.1.

Example 60: (4S)-5,5-difluoro-1-[2-(trifluoromethoxy)ethyl]-3-(trifluoromethyl)-6,7-dihydro-4H-indazol-4-ol

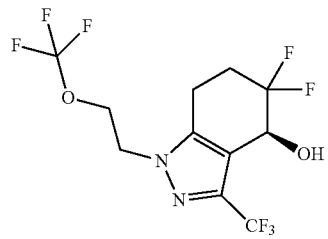

The title compound was prepared in a similar fashion to that described for Example 2 from 2-(trifluoromethoxy)ethanol and [(4S)-5,5-difluoro-3-(trifluoromethyl)-1,4,6,7-tetrahydroindazol-4-yl] benzoate. $^1$H NMR (400 MHz, Chloroform-d) δ 4.99-4.76 (m, 1H), 4.41-4.23 (m, 4H), 3.04-2.70 (m, 2H), 2.66-2.39 (m, 2H), 2.41-2.13 (m, 1H). ESI MS [M+H]$^+$ for C$_{11}$H$_{10}$F$_8$N$_2$O$_2$, calcd 355.1, found 355.0.

Example 61: (4S)-5,5-difluoro-1-[(3R)-4,4,4-trifluoro-3-methoxybutyl]-3-(trifluoromethyl)-4,6-dihydrocyclopenta[c]pyrazol-4-ol

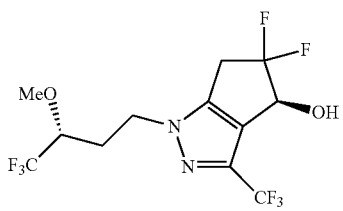 [SMILES: CO[C@H](CCn1nc(C(F)(F)F)c2c1CC(F)(F)[C@H]2O)C(F)(F)F]

The title compound was prepared in a similar fashion to Example 12 from [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 5.16-5.01 (m, 1H), 4.34-4.16 (m, 2H), 3.59-3.47 (m, 4H), 3.47-3.20 (m, 2H), 2.53 (dd, J=5.8, 2.0 Hz, 1H), 2.28 (dddd, J=15.2, 8.6, 6.9, 3.4 Hz, 1H), 2.10 (dddd, J=14.7, 9.6, 6.4, 5.1 Hz, 1H). ESI MS [M+H]$^+$ for C$_{12}$H$_{15}$F$_8$N$_2$O$_2$, calcd 368.1, found 368.0.

Example 62: (4S,5R)-5-fluoro-1-[3-(trifluoromethoxy)propyl]-3-(trifluoromethyl)-5,6-dihydro-4H-cyclopenta[c]pyrazol-4-ol 12.3 mmol, 2.0 equiv.). At room temperature, RuCl(p-cymene)[(R,R)-TsDPEN] (196 mg, 0.31 mmol, 0.05 equiv.) was added and the resulting mixture was stirred at rt for 3 days. The reaction was quenched with sat. aq. NaHCO$_3$ solution, the organic phase was separated, and the aqueous layer was extracted with DCM. The combined organic phase was dried over Na$_2$SO$_4$, concentrated and the crude residue was purified by column chromatography (SiO$_2$, EtOAc in DCM, 0 to 10%) to give the indanol product (1.61 g, 89% yield, 2:1 d.r.).

Step b: The product from step a (1.50 g, 5.1 mmol, 1.0 equiv.) was dissolved in DCM (25 mL, 0.2M) and Et$_3$N (1.4 mL, 10.2 mmol, 2 equiv.), BzCl (0.89 mL, 7.65 mmol, 1.5 equiv.) and DMAP (62 mg, 0.51 mmol, 0.1 equiv.) were added. The reaction mixture was refluxed overnight and quenched with sat. aq. NH$_4$Cl solution. The organic phase was separated, the aqueous layer was extracted with DCM, the combined organic phase was dried over Na$_2$SO$_4$, concentrated and the crude residue was purified by column chromatography (SiO$_2$, EtOAc in hexanes, 0 to 20%) to give the [(4S,5R)-5-fluoro-1-(oxan-2-yl)-3-(trifluoromethyl)-5,6-dihydro-4H-cyclopenta[c]pyrazol-4-yl] benzoate (1.11 g, 55%) and [(4S,5S)-5-fluoro-1-(oxan-2-yl)-3-(trifluoromethyl)-5,6-dihydro-4H-cyclopenta[c]pyrazol-4-yl] benzoate (456 mg, 22%).

Step c: [(4S,5R)-5-fluoro-1-(oxan-2-yl)-3-(trifluoromethyl)-5,6-dihydro-4H-cyclopenta[c]pyrazol-4-yl] benzoate (1.05 g, 2.64 mmol, 1.0 equiv.) was dissolved in DCM:TFA

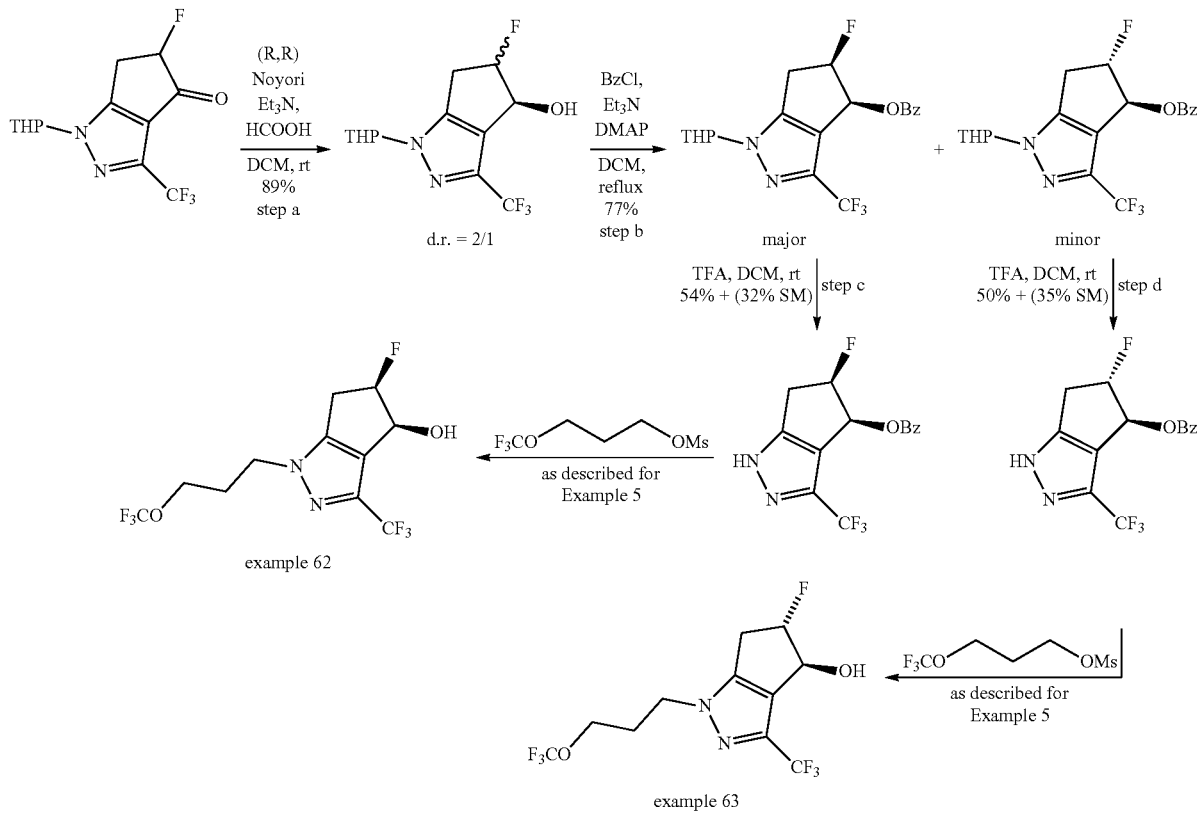

Step a: To a solution of 5-fluoro-1-(oxan-2-yl)-3-(trifluoromethyl)-5,6-dihydrocyclopenta[c]pyrazol-4-one (1.80 g, 6.16 mmol, 1.0 equiv.) in DCM (30 mL, 0.2M) was added HCO$_2$H (0.70 mL, 18.5 mmol, 3.0 equiv.) and Et$_3$N (1.7 mL, (9:1, 13 mL, 0.2M) and the reaction mixture was stirred at rt for 4 h. The reaction was quenched with sat. aq. NaHCO$_3$ solution, the organic phase was separated, the aqueous layer was extracted with DCM, the combined organic phase was dried over Na$_2$SO$_4$, concentrated and the crude residue was purified by column chromatography (SiO$_2$, EtOAc in hexanes, 20 to 50%) to give [(4S,5R)-5-fluoro-3-(trifluoromethyl)-1,4,5,6-tetrahydrocyclopenta[c]pyrazol-4-yl] benzoate (411 mg, 50% yield) and 367 mg of recovered starting material.

Step d: [(4S,5S)-5-fluoro-1-(oxan-2-yl)-3-(trifluoromethyl)-5,6-dihydro-4H-cyclopenta[c]pyrazol-4-yl] benzoate (440 mg, 1.10 mmol, 1.0 equiv.) was dissolved in DCM:TFA (9:1, 5.5 mL, 0.2M) and the reaction mixture was stirred at rt for 4 h. The reaction was quenched with sat. aq. NaHCO$_3$ solution, the organic phase was separated, the aqueous layer was extracted with DCM, the combined organic phase was dried over Na$_2$SO$_4$, concentrated and the crude residue was purified by column chromatography (SiO$_2$, EtOAc in hexanes, 20 to 50%) to give [(4S,5S)-5-fluoro-3-(trifluoromethyl)-1,4,5,6-tetrahydrocyclopenta[c]pyrazol-4-yl]benzoate (188 mg, 54% yield) and 141 mg of recovered starting material.

(4S,5R)-5-fluoro-1-[3-(trifluoromethoxy)propyl]-3-(trifluoromethyl)-5,6-dihydro-4H-cyclopenta[c]pyrazol-4-ol was prepared in a similar fashion to that described for Example 5 from [(4S,5R)-5-fluoro-3-(trifluoromethyl)-1,4,5,6-tetrahydrocyclopenta[c]pyrazol-4-yl] benzoate and the mesylate derived from 3-(trifluoromethoxy)propan-1-ol

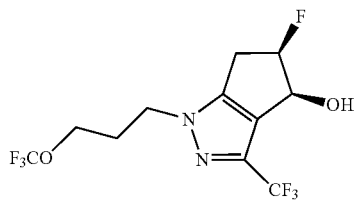

$^1$H NMR (400 MHz, Chloroform-d) δ 5.43 (ddt, J=50.1, 6.1, 4.7 Hz, 1H), 5.15 (q, J=5.5 Hz, 1H), 4.16 (t, J=6.7 Hz, 2H), 3.98-3.86 (m, 2H), 3.18-2.99 (m, 2H), 2.35-2.23 (m, 3H). ESI MS [M+H]$^+$ for C$_{11}$H$_{11}$F$_7$N$_2$O$_2$, calcd 337.1, found 337.0.

Example 63: (4S,5S)-5-fluoro-1-[3-(trifluoromethoxy)propyl]-3-(trifluoromethyl)-5,6-dihydro-4H-cyclopenta[c]pyrazol-4-ol (4S,5S)-5-fluoro-1-[3-(trifluoromethoxy)propyl]-3-(trifluoromethyl)-5,6-dihydro-4H-cyclopenta[c]pyrazol-4-ol was prepared in a similar fashion to that described for Example 5 from [(4S,5S)-5-fluoro-3-(trifluoromethyl)-1,4,5,6-tetrahydrocyclopenta[c]pyrazol-4-yl] benzoate and the mesylate derived from 3-(trifluoromethoxy)propan-1-ol

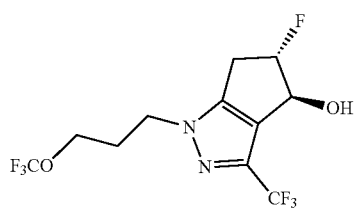

$^1$H NMR (400 MHz, Chloroform-d) δ 5.55-5.38 (m, 1H), 5.19 (dd, J=17.4, 4.2 Hz, 1H), 4.15 (t, J=6.3 Hz, 2H), 3.94 (dd, J=5.6, 6.0 Hz, 2H), 3.35 (ddd, J=20.2, 16.9, 6.0 Hz, 1H), 2.85 (ddd, J=24.0, 17.0, 2.3 Hz, 1H), 2.28 (p, J=6.0 Hz, 2H), 2.11 (d, J=4.8 Hz, 1H). ESI MS [M+H]$^+$ for C$_{11}$H$_{11}$F$_7$N$_2$O$_2$, calcd 337.1, found 337.0.

Example 64: (4S)-5,5-difluoro-1-[(3r,5r)-1,1-difluorospiro[2.3]hexan-5-yl]-3-(trifluoromethyl)-4,6-dihydrocyclopenta[c]pyrazol-4-ol

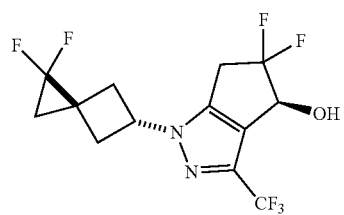

The title compound was prepared in a similar fashion to that described for Example 53 from (3s,5s)-2,2-difluorospiro[2.3]hexan-5-ol and [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 5.07 (dd, J=12.0, 5.6 Hz, 1H), 4.96 (tt, J=8.6, 7.1 Hz, 1H), 3.53-3.26 (m, 2H), 3.04-2.92 (m, 2H), 2.64-2.53 (m, 2H), 2.37 (dd, J=5.6, 2.0 Hz, 1H), 1.40 (t, J=8.3 Hz, 2H). ESI MS [M+H]$^+$ for C$_{13}$H$_{12}$F$_7$N$_2$O, calcd 345.1, found 345.1.

Example 65: (4S)-5,5-difluoro-1-[(3s,5s)-1,1-difluorospiro[2.3]hexan-5-yl]-3-(trifluoromethyl)-4,6-dihydrocyclopenta[c]pyrazol-4-ol

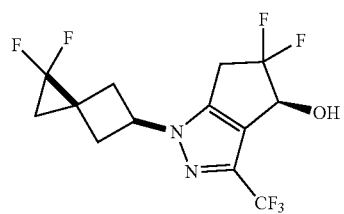

The title compound was prepared in a similar fashion to that described for Example 53 from (3r,5r)-2,2-difluorospiro[2.3]hexan-5-ol and [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 5.07 (dd, J=11.9, 5.6 Hz, 1H), 4.75 (p, J=8.0 Hz, 1H), 3.49-3.24 (m, 2H), 2.99-2.87 (m, 2H), 2.78-2.66 (m, 2H), 2.37 (dd, J=5.6, 2.1 Hz, 1H), 1.36 (t, J=8.3 Hz, 2H). ESI MS [M+H]$^+$ for C$_{13}$H$_{12}$F$_7$N$_2$O, calcd 345.1, found 345.1.

Example 66: (4S)-1-{6,6-difluorospiro[3.3]heptan-2-yl}-5,5-difluoro-3-(trifluoromethyl)-4,6-dihydrocyclopenta[c]pyrazol-4-ol

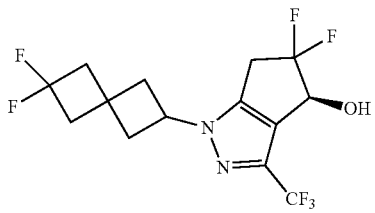 [SMILES: O[C@H]1c2c(C(F)(F)F)nn(C3CC4(C3)CC(F)(F)C4)c2CC1(F)F]

The title compound was prepared in a similar fashion to that described for Example 53 from 2,2-difluorospiro[3.3]heptan-6-ol and [(4S)-5,5-difluoro-3-(trifluoromethyl)-4,6-dihydro-1H-cyclo-penta[c]pyrazol-4-yl] benzoate. $^1$H NMR (400 MHz, CDCl$_3$) δ 5.05 (dd, J=11.9, 5.6 Hz, 1H), 4.58 (p, J=8.2 Hz, 1H), 3.45-3.20 (m, 2H), 2.86-2.75 (m, 2H), 2.75-2.58 (m, 6H), 2.32 (dd, J=5.6, 2.1 Hz, 1H). ESI MS [M+H]$^+$ for C$_{14}$H$_{14}$F$_7$N$_2$O, calcd 359.1, found 359.1.

Example 67: (4S,5R)-1-{6,6-difluorospiro[3.3]heptan-2-yl}-5-fluoro-3-(trifluoromethyl)-4,6-dihydrocyclopenta[c]pyrazol-4-ol

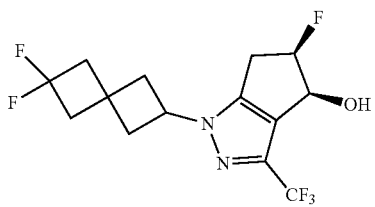 [SMILES: O[C@H]1c2c(C(F)(F)F)nn(C3CC4(C3)CC(F)(F)C4)c2C[C@H]1F]

The title compound was prepared in a similar fashion to that described for Example 53 from 2,2-difluorospiro[3.3]heptan-6-ol and [(4S,5R)-5-fluoro-3-(trifluoromethyl)-1,4,5,6-tetrahydrocyclo-penta[c]pyrazol-4-yl] benzoate. $^1$H NMR (400 MHz, CDCl$_3$) δ 5.42 (ddt, J=50.7, 6.3, 4.8 Hz, 1H), 5.14 (q, J=5.5 Hz, 1H), 4.58 (p, J=8.2 Hz, 1H), 3.19-3.03 (m, 2H), 2.84-2.76 (m, 2H), 2.74-2.54 (m, 6H), 2.28 (dd, J=6.2, 3.8 Hz, 1H). ESI MS [M+H]$^+$ for C$_{14}$H$_{15}$F$_6$N$_2$O, calcd 341.1, found 341.1.

Example 68: (4S)-5,5-difluoro-3-(trifluoromethyl)-1-[6-(trifluoromethyl)pyridin-3-yl]-4,6-dihydrocyclopenta[c]pyrazol-4-ol

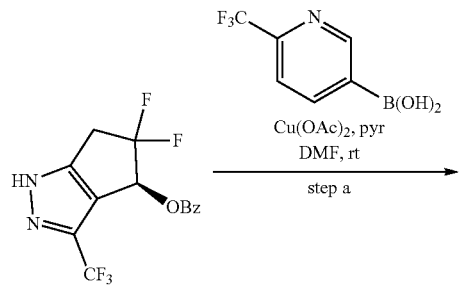

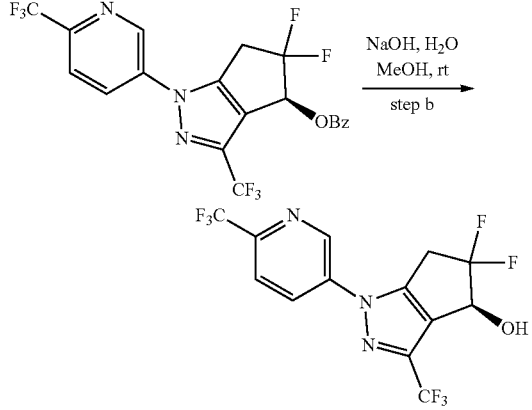

Step a: To a solution of [(4S)-5,5-difluoro-3-(trifluoromethyl)-4,6-dihydro-1H-cyclopenta[c]pyrazol-4-yl] benzoate (107 mg, 0.32 mmol, 1.0 equiv.) in DMF (2.1 mL, 0.15 M) was added [6-(trifluoromethyl)pyridin-3-yl]boronic acid (122 mg, 0.64 mmol, 2 equiv.), Cu(OAc)$_2$ (87 mg, 0.48 mmol, 1.5 equiv.), and pyridine (51 uL, 0.64 mmol, 2.0 equiv.). The reaction mixture was stirred at room temperature under air for 16 hours at which point it was diluted with DCM, filtered over Celite, and concentrated under vacuum. The crude residue was purified via silica gel flash chromatography (0 to 80% EtOAc/hexanes) to afford the product (70 mg, 46% yield).

Step b: To a solution of [(4S)-5,5-difluoro-3-(trifluoromethyl)-1-[6-(trifluoromethyl)pyridin-3-yl]-4,6-dihydrocyclopenta[c]pyrazol-4-yl] benzoate (70 mg, 0.15 mmol, 1.0 equiv.) in MeOH (3 mL, 0.05 M) was added 1.0 M NaOH (0.75 mL, 0.75 mmol, 5.0 equiv.). The reaction was stirred at room temperature for 2 hours, at which point it was quenched with saturated aqueous NH$_4$Cl (10 mL) and extracted with EtOAc (2×10 mL). The combined organics were dried over Na$_2$SO$_4$, filtered, and concentrated under vacuum. The crude residue was purified via silica gel flash chromatography (0 to 80% EtOAc/hexanes) to afford the product (19 mg, 34% yield). $^1$H NMR (400 MHz, Chloroform-d) δ 8.95 (d, J=2.5 Hz, 1H), 8.24 (dd, J=8.6, 2.6 Hz, 1H), 7.87 (d, J=8.5 Hz, 1H), 5.17 (dd, J=11.9, 3.9 Hz, 1H), 3.85-3.52 (m, 2H), 2.66 (d, J=3.7 Hz, 1H). ESI MS [M+H]$^+$ for C$_{13}$H$_7$F$_8$N$_3$O, calcd 374.1, found 374.1.

Example 69a and 69b: (4S)-5,5-difluoro-1-[(1R,2S)-2-methoxycyclohexyl]-3-(trifluoromethyl)-4,6-dihydrocyclopenta[c]pyrazol-4-ol and (4S)-5,5-difluoro-1-[(1S,2R)-2-methoxycyclohexyl]-3-(trifluoromethyl)-4,6-dihydrocyclopenta[c]pyrazol-4-ol 69a

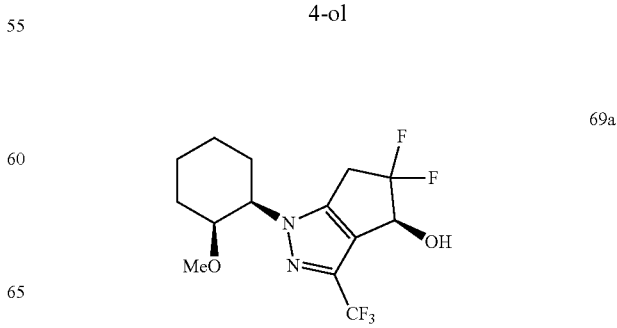

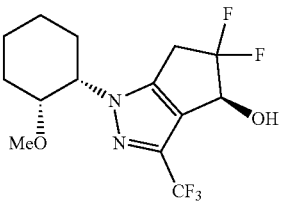

The title compounds were prepared as an inseparable mixture of diastereomers in a similar fashion to that described for Example 53 from trans-2-methoxycyclohexan-1-ol. $^1$H NMR (400 MHz, Chloroform-d) δ 5.03 (d, J=12.1 Hz, 2H), 4.43-4.35 (m, 2H), 3.71-3.65 (m, 2H), 3.64-3.54 (m, 2H), 3.49-3.27 (m, 2H), 3.18 (s, 3H), 3.14 (s, 3H), 2.16-2.06 (m, 4H), 1.94-1.88 (m, 1H), 1.87-1.76 (m, 1H), 1.68-1.29 (m, 10H). ESI MS [M+H]$^+$ for $C_{14}H_{17}F_5N_2O_2$, calcd 341.1, found 341.2.

Example 70: (4S)-5,5-difluoro-1-[(3R,5S)-3,4,5-trifluorocyclohexyl]-3-(trifluoromethyl)-4,6-dihydrocyclopenta[c]pyrazol-4-ol

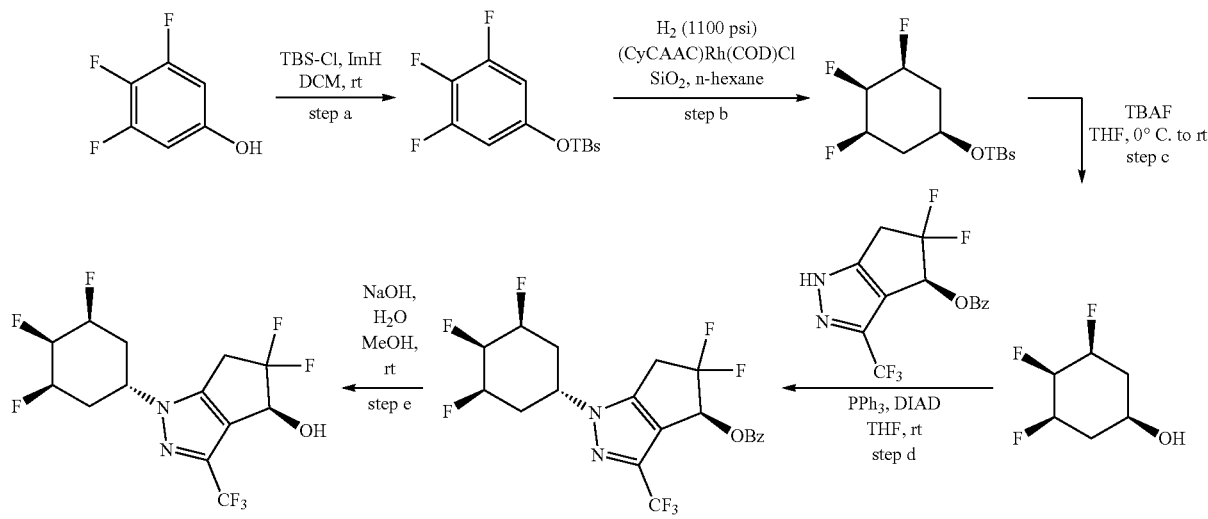

Step a: To a solution of 3,4,5-trifluorophenol (5.5 g, 37.1 mmol, 1.0 equiv.) in DCM (75 mL, 0.5 M) was added imidazole (5.1 g, 74.3 mmol, 2.0 equiv.) followed by TBS-Cl (6.7 g, 44.6 mmol, 1.2 equiv.). The reaction mixture was stirred at room temperature for two hours at which point it was quenched with water (150 mL) and extracted with DCM (100 mL). The combined organics were washed with brine (100 mL), dried over $Na_2SO_4$, filtered, and concentrated under vacuum. The crude residue was purified by silica gel flash column chromatography (0 to 10% EtOAc/hexanes) to afford the product (8.6 g, 88% yield).

Step b: Tert-butyl-dimethyl-(3,4,5-trifluorophenoxy)silane (3.4 g, 13.0 mmol, 1.0 equiv.) was dissolved in n-hexane (26 mL, 0.5 M) in a steel Parr bomb lined with a Teflon insert and equipped with a mechanical stirrer. $SiO_2$ (5.8 g, 0.45 g/mmol) was added, followed by (CyCAAC)Rh(COD)Cl (150 mg, 0.25 mmol, 0.02 equiv.). The Parr bomb was pressurized with 500 psi $H_2$ and vented three times before being pressurized to 1100 psi $H_2$. The reaction mixture was stirred at –300 rpm under 1100 psi $H_2$ for 72 hours at which point it was depressurized and the reaction mixture was filtered over Celite. The filtrate was directly concentrated under vacuum and the crude residue was purified via silica gel flash chromatography (0 to 80% DCM/hexanes) to afford the product (891 mg, 26% yield).

Step c: A solution of tert-butyl-dimethyl-[cis-3,4,5-trifluorocyclohexyl]oxysilane (890 mg, 3.32 mmol, 1.0 equiv.) in THF (17 mL, 0.2 M) was cooled to 0° C. and TBAF (1.0 M in THF, 5 mL, 5 mmol, 1.5 equiv.) was added dropwise. The reaction mixture was stirred for 3 hours as the ice bath expired and the reaction was quenched with saturated aqueous $NH_4Cl$ (50 mL), diluted with EtOAc (100 mL) and partitioned. The organics were washed with water and brine, dried over $Na_2SO_4$, filtered, and concentrated under vacuum. The crude residue was purified via silica gel flash chromatography (0 to 100% EtOAc/hexanes) to afford the product (380 mg, 74% yield)

Step d: To a solution of [(4S)-5,5-difluoro-3-(trifluoromethyl)-4,6-dihydro-1H-cyclopenta[c]pyrazol-4-yl] benzoate (78 mg, 0.23 mmol, 1.0 equiv.) in THF (2.3 mL, 0.1 M) was added cis-3,4,5-trifluorocyclohexan-1-ol (71 mg, 0.46 mmol, 2.0 equiv.), $PPh_3$ (110 mg, 0.42 mmol, 1.8 equiv.), and diisopropyl azodicarboxylate (91 uL, 0.46 mmol, 2.0 equiv.). The reaction was stirred at room temperature for 16 hours at which point it was directly concentrated under vacuum. The crude residue was purified by silica gel flash column chromatography (0 to 50% EtOAc/hexanes) to afford the product to afford the product (49 mg, 46% yield).

Step e: To a solution of [(4S)-5,5-difluoro-1-[(3R,5S)-3,4,5-trifluorocyclohexyl]-3-(trifluoromethyl)-4,6-dihydrocyclopenta[c]pyrazol-4-yl] benzoate (49 mg, 0.10 mmol, 1.0 equiv.) in MeOH (2 mL, 0.05 M) was added 1.0 M NaOH (0.5 mL, 0.5 mmol, 5.0 equiv.). The reaction was stirred for 3 hours at room temperature at which point it was quenched with saturated aqueous $NH_4Cl$ (10 mL) and extracted with EtOAc (2×10 mL). The combined organics were dried over $Na_2SO_4$, filtered, and concentrated under vacuum. The crude residue was purified by silica gel flash column chromatography (0 to 80% EtOAc/hexanes) to afford the product (26 mg, 71% yield). $^1$H NMR (400 MHz, Chloroform-d) δ 5.35-5.11 (m, 2H), 5.07 (d, J=12.0 Hz, 1H), 5.01-4.72 (m, 1H), 4.67 (tt, J=8.7, 4.7 Hz, 1H), 3.53-3.24 (m, 2H), 2.66-2.23 (m, 4H). ESI MS [M+H]$^+$ for $C_{13}H_{12}F_8N_2O$, calcd 365.1, found 365.1.

Example 71: (4S)-1-[(3R,5S)-3,5-difluorocyclohexyl]-5,5-difluoro-3-(trifluoromethyl)-4,6-dihydrocyclopenta[c]pyrazol-4-ol

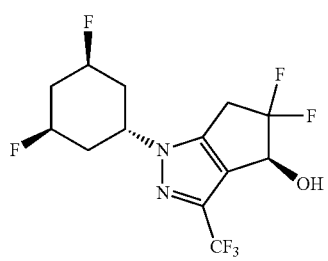 [SMILES: O[C@H]1c2c(C(F)(F)F)nn([C@H]3C[C@H](F)C[C@H](F)C3)c2CC1(F)F]

The title compound was prepared in a similar fashion to that described for Example 70 from cis-3,5-difluorocyclohexan-1-ol. $^1$H NMR (400 MHz, Chloroform-d) δ 5.23-5.02 (m, 3H), 4.69 (tt, J=12.0, 3.9 Hz, 1H), 3.54-3.23 (m, 2H), 2.67-2.38 (m, 4H), 2.38-2.15 (m, 2H), 1.96-1.61 (m, 1H). ESI MS [M+H]$^+$ for $C_{13}H_{13}F_7N_2O$, calcd 347.1, found 347.1.

Examples 72 and 73: (4S)-1-[(1R,3S,4R)-3,4-difluorocyclohexyl]-5,5-difluoro-3-(trifluoromethyl)-4,6-dihydrocyclopenta[c]pyrazol-4-ol and (4S)-1-[(1S,3R,4S)-3,4-difluorocyclohexyl]-5,5-difluoro-3-(trifluoromethyl)-4,6-dihydrocyclopenta[c]pyrazol-4-ol

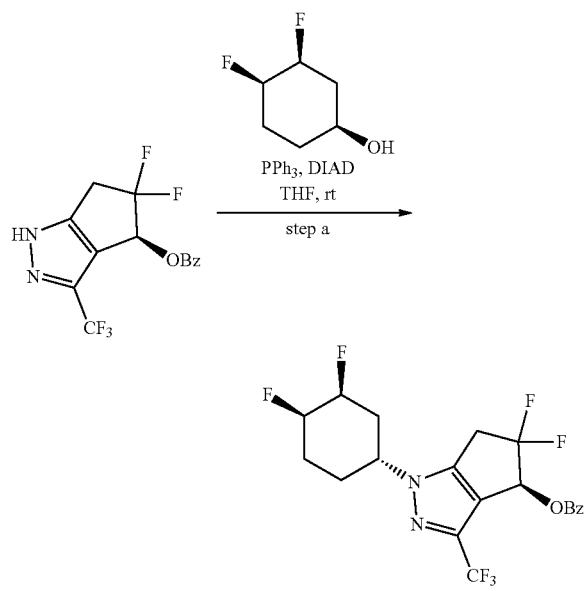

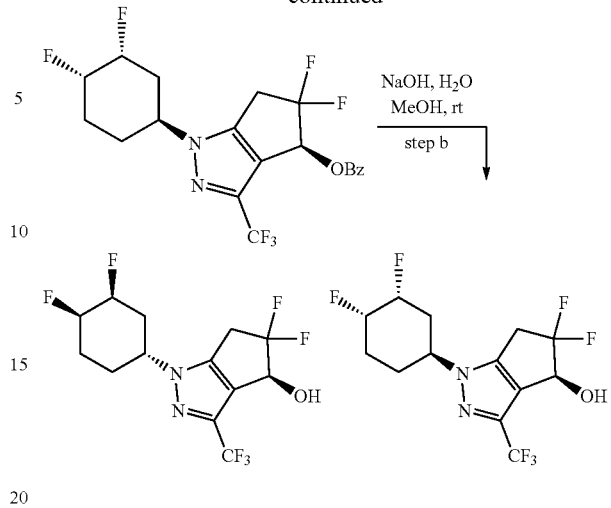

Step a: To a solution of [(4S)-5,5-difluoro-3-(trifluoromethyl)-4,6-dihydro-1H-cyclopenta[c]pyrazol-4-yl] benzoate (475 mg, 1.43 mmol, 1.0 equiv.) in THF (14.3 mL, 0.1 M) was added cis-3,4-difluorocyclohexan-1-ol (390 mg, 2.86 mmol, 2.0 equiv., prepared in a similar fashion to that described for Example 70), triphenylphosphine (676 mg, 2.58 mmol, 1.8 equiv.), and diisopropyl azodicarboxylate (0.56 mL, 2.86 mmol, 2.0 equiv.). The reaction mixture was stirred for 16 hours at room temperature at which point it was directly concentrated under vacuum. The crude residue was purified by silica gel flash column chromatography (0 to 50% EtOAc/hexanes) to afford a mixture of the desired products and the corresponding N2 alkylation regioisomers in a ~2:1 ratio. The N1/N2 regioisomers were separated by reverse phase prep-HPLC (Phenomenex C18 column, 20 to 100% MeCN/H$_2$O) to afford a pure sample of the desired N1 regioisomers as a 1:1 mixture of diastereomers (155 mg, 24% yield). This mixture of diastereomers was used in the subsequent benzoate deprotection without further purification.

Step b: To a solution of [(4S)-1-[(1R,3S,4R)-3,4-difluorocyclohexyl]-5,5-difluoro-3-(trifluoromethyl)-4,6-dihydrocyclopenta[c]pyrazol-4-yl] benzoate and [(4S)-1-[(1S,3R,4S)-3,4-difluorocyclohexyl]-5,5-difluoro-3-(trifluoromethyl)-4,6-dihydrocyclopenta[c]pyrazol-4-yl] benzoate (155 mg, 0.34 mmol, 1.0 equiv.) in ~13.5:1 MeOH/THF (~7.5 mL, ~0.05 M) was added 1.0 M NaOH (1.7 mL, 1.7 mmol, 5.0 equiv.). The reaction was stirred for 1.5 hours at room temperature, at which point it was quenched with saturated aqueous NH$_4$Cl (50 mL) and extracted with EtOAc (2×25 mL). The combined organics were dried over Na$_2$SO$_4$, filtered, and concentrated under vacuum. The crude residue was purified via silica gel flash column chromatography (0 to 60% EtOAc/hexanes) to afford the product as a 1:1 mixture of diastereomers (100 mg, 85% yield). The diastereomers were separated normal phase prep-HPLC (Waters SunFire Silica column, 5% IPA/hexanes) to afford pure samples of (4S)-1-[(1R,3S,4R)-3,4-difluorocyclohexyl]-5,5-difluoro-3-(trifluoromethyl)-4,6-dihydrocyclopenta[c]pyrazol-4-ol and (4S)-1-[(1S,3R,4S)-3,4-difluorocyclohexyl]-5,5-difluoro-3-(trifluoromethyl)-4,6-dihydrocyclopenta[c]pyrazol-4-ol.

First eluting diastereomer (DIAST-1, 30 mg, 25% yield): $^1$H NMR (400 MHz, Chloroform-d) δ 5.23-5.03 (m, 1H), 5.07 (dd, J=12.1, 5.4 Hz, 1H), 4.83-4.55 (m, 1H), 4.38 (tt, J=10.6, 4.2 Hz, 1H), 3.51-3.20 (m, 2H), 2.53-2.41 (m, 1H), 2.39 (dd, J=5.5, 2.0 Hz, 1H), 2.37-1.98 (m, 5H). ESI MS [M+H] for $C_{13}H_{13}F_7N_2O$, calcd 347.1, found 347.1.

Second eluting diastereomer (DIAST-2, 30 mg, 25% yield): $^1$H NMR (400 MHz, Chloroform-d) δ 5.24-5.03 (m, 1H), 5.07 (d, J=11.9 Hz, 1H), 4.82-4.55 (m, 1H), 4.38 (tt, J=10.7, 4.1 Hz, 1H), 3.51-3.23 (m, 2H), 2.54-2.40 (m, 1H), 2.40-2.17 (m, 1H), 2.17-1.94 (m, 4H). ESI MS [M+H]$^+$ for $C_{13}H_{13}F_7N_2O$, calcd 347.1, found 347.1.

Example 74: (4S)-5,5-difluoro-2-(2-phenylethyl)-3-(trifluoromethyl)-4,6-dihydrocyclopenta[c]pyrazol-4-ol

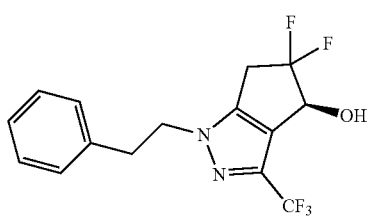 [SMILES: O[C@H]1c2c(C(F)(F)F)nn(CCc3ccccc3)c2CC1(F)F]

The title compound was prepared in a similar fashion to that described for Example 1 from (4S)-5,5-difluoro-3-(trifluoromethyl)-4,6-dihydro-1H-cyclopenta[c]pyrazol-4-ol and 2-phenylethyl bromide. $^1$HNMR (400 MHz, CDCl$_3$) δ 7.33-7.22 (m, 3H), 7.18-7.15 (m, 2H), 5.08 (dd, J=5.6, 5.6 Hz, 1H), 4.40-4.36 (m, 2H), 3.95 (td, J=16.8, 10.8 Hz, 1H), 3.27 (td, J=16.5, 5.7 Hz, 1H), 3.16 (m, 2H), 2.40 (dd, J=5.6, 2.4 Hz, 1H). ESI MS [M+H]$^+$ for $C_{15}H_{13}F_5N_2O$, calcd=333.1, found 333.1.

Example 75: (4S)-5,5-difluoro-1-[2-(1,2-oxazol-4-yl)ethyl]-3-(trifluoromethyl)-4,6-dihydrocyclopenta[c]pyrazol-4-ol

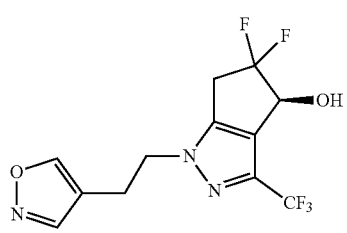 [SMILES: O[C@H]1c2c(C(F)(F)F)nn(CCc3cnoc3)c2CC1(F)F]

The title compound was prepared in a similar fashion to that described for Example 1 from (4S)-5,5-difluoro-3-(trifluoromethyl)-4,6-dihydro-1H-cyclopenta[c]pyrazol-4-ol and 4-(2-bromoethyl)isoxazole. $^1$HNMR (400 MHz, CDCl$_3$) δ 8.13 (s, 1H), 7.97 (s, 1H), 5.06-5.01 (m, 1H), 4.23-4.18 (m, 2H), 3.21-2.96 (m, 4H), 2.41-2.38 (m, 1H). ESI MS [M+H]$^+$ for $C_{12}H_{10}F_5N_3O_2$, calcd=324.1, found 324.1.

Example 76: (4S)-5,5-difluoro-1-(2-thiophen-3-ylethyl)-3-(trifluoromethyl)-4,6-dihydrocyclopenta[c]pyrazol-4-ol

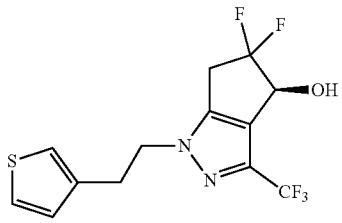 [SMILES: O[C@H]1c2c(C(F)(F)F)nn(CCc3ccsc3)c2CC1(F)F]

The title compound was prepared in a similar fashion to that described for Example 1 from (4S)-5,5-difluoro-3-(trifluoromethyl)-4,6-dihydro-1H-cyclopenta[c]pyrazol-4-ol and 3-(2-bromoethyl)thiophene. T HNMR (400 MHz, CDCl$_3$) δ 7.26 (dd, J=4.8, 2.9 Hz, 1H), 6.79-6.78 (m, 1H), 6.70 (d, J=5.0 Hz, 1H), 4.97 (dd, J=11.9, 5.9 Hz, 1H), 4.23 (t, J=6.5 Hz, 2H), 3.15 (t, J=6.5 Hz, 2H), 2.74 (td, J=16.7, 15.1, 10.4 Hz, 1H), 2.60 (td, J=16.4, 15.5, 4.9 Hz, 1H), 2.30 (ddd, J=5.9, 2.1, 0.7 Hz, 1H). ESI MS [M+H]$^+$ for $C_{13}H_{11}F_5N_2OS$, calcd=339.1, found 339.1.

Example 77: (4S)-5,5-difluoro-1-[2-(furan-2-yl)ethyl]-3-(trifluoromethyl)-1H,4H,5H,6H-cyclopenta[c]pyrazol-4-ol

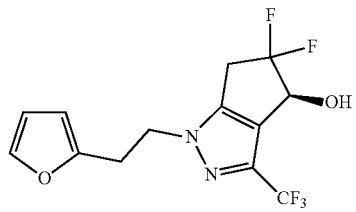 [SMILES: O[C@H]1c2c(C(F)(F)F)nn(CCc3ccco3)c2CC1(F)F]

The title compound was prepared in a similar fashion to that described for Example 53 via the reaction of [(4S)-5,5-difluoro-3-(trifluoromethyl)-4,6-dihydro-1H-cyclopenta[c]pyrazol-4-yl] benzoate with 2-Furanethanol. $^1$H NMR (400 MHz, CDCl$_3$) δ 7.35 (d, J=1.8 Hz, 1H), 6.29 (dd, J=3.2, 1.9 Hz, 1H), 5.92 (d, J=3.1 Hz, 1H), 5.00 (dd, J=12.0, 5.5 Hz, 1H), 4.33 (t, J=6.4 Hz, 2H), 3.16 (t, J=6.4 Hz, 2H), 2.95 (ddd, J=16.5, 15.0, 10.4 Hz, 1H), 2.80 (td, J=16.0, 5.0 Hz, 1H), 2.32 (dd, J=6.0, 2.0 Hz, 1H). ESI MS [M+H]$^+$ for $C_{13}H_{11}F_5N_2O_2$, calcd 323.2, found 323.1.

Example 78: (4S)-5,5-difluoro-1-[2-(furan-3-yl)ethyl]-3-(trifluoromethyl)-1H,4H,5H,6H-cyclopenta[c]pyrazol-4-ol

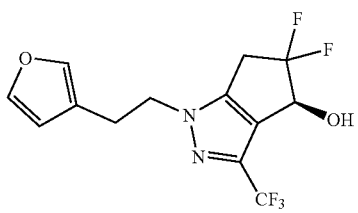 [SMILES: O[C@H]1c2c(C(F)(F)F)nn(CCc3ccoc3)c2CC1(F)F]

The title compound was prepared in a similar fashion to Example 53 from [(4S)-5,5-difluoro-3-(trifluoromethyl)-4,6-dihydro-1H-cyclopenta[c]pyrazol-4-yl] benzoate with 3-Furanethanol. ¹H NMR (400 MHz, CDCl₃) δ 7.36 (d, J=1.7 Hz, 1H), 7.11 (s, 1H), 6.12-5.87 (m, 1H), 5.02 (dd, J=11.9, 5.6 Hz, 1H), 4.21 (t, J=6.7 Hz, 2H), 3.11-3.02 (m, 1H), 2.99 (t, J=6.7 Hz, 2H), 2.91 (td, J=16.0, 4.8 Hz, 1H), 2.38 (dd, J=5.8, 2.0 Hz, 1H). ESI MS [M+H]⁺ for $C_{13}H_{11}F_5N_2O_2$, calcd 323.2, found 323.1.

Example 79: (4S)-5,5-difluoro-1-[2-(3-fluorophenyl)ethyl]-3-(trifluoromethyl)-1H,4H,5H,6H-cyclopenta[c]pyrazol-4-ol

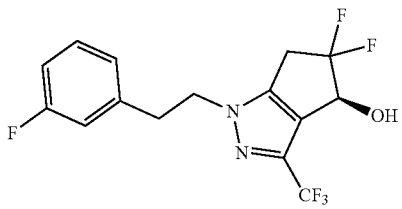 [SMILES: O[C@H]1c2c(C(F)(F)F)nn(CCc3cccc(F)c3)c2CC1(F)F]

The title compound was prepared in a similar fashion to Example 1 from [(4S)-5,5-difluoro-3-(trifluoromethyl)-4,6-dihydro-1H-cyclopenta[c]pyrazol-4-yl] benzoate and 3-Fluorophenethyl bromide. ¹H NMR (400 MHz, CDCl₃) δ 7.23 (dd, J=7.9, 5.9 Hz, 1H), 6.97 (td, J=8.5, 2.6 Hz, 1H), 6.72 (d, J=7.6 Hz, 1H), 6.67 (dt, J=9.5, 2.1 Hz, 1H), 4.98 (dd, J=11.9, 5.8 Hz, 1H), 4.27 (td, J=6.6, 2.7 Hz, 2H), 3.14 (t, J=6.6 Hz, 2H), 2.73 (ddd, J=16.4, 15.1, 10.3 Hz, 1H), 2.56 (td, J=16.0, 4.8 Hz, 1H), 2.27 (dd, J=5.9, 2.1 Hz, 1H). ESI MS [M+H]⁺ for $C_{15}H_{12}F_6N_2O$, calcd 351.3, found 351.1.

Example 80: (4S)-5,5-difluoro-3-(trifluoromethyl)-1-[(1R)-3-(trifluoromethyl)cyclohexyl]-1H,4H,5H,6H-cyclopenta[c]pyrazol-4-ol

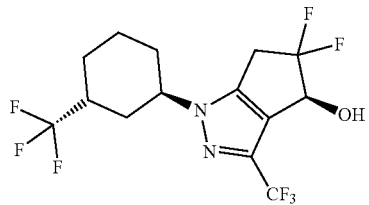

The title compound was prepared in a similar fashion to that described for Example 53 from rel-(1R,3S)-3-(Trifluoromethyl)cyclohexanol and [(4S)-5,5-difluoro-3-(trifluoromethyl)-4,6-dihydro-1H-cyclopenta[c]pyrazol-4-yl] benzoate. ¹H NMR (400 MHz, CDCl₃) δ 5.07 (dd, J=12.1, 4.8 Hz, 1H), 4.41 (td, J=6.3, 3.2 Hz, 1H), 3.56-3.18 (m, 2H), 2.80 (ddq, J=13.4, 9.2, 4.6 Hz, 1H), 2.44-2.25 (m, 2H), 2.01 (ddd, J=13.8, 8.7, 4.3 Hz, 2H), 1.89 (ddq, J=13.1, 8.8, 4.6 Hz, 2H), 1.77 (ddd, J=16.3, 8.8, 4.5 Hz, 1H), 1.66 (dtd, J=12.6, 8.5, 3.7 Hz, 1H). ESI MS [M+H]⁺ for $C_{14}H_{14}F_8N_2O$, calcd 379.3, found 379.1.

Example 81: (4S)-5,5-difluoro-3-(trifluoromethyl)-1-[(1S,3S)-3-(trifluoromethyl)cyclohexyl]-1H,4H,5H,6H-cyclopenta[c]pyrazol-4-ol

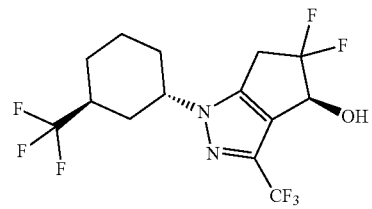 [SMILES: O[C@H]1c2c(C(F)(F)F)nn([C@H]3CCC[C@H](C(F)(F)F)C3)c2CC1(F)F]

The title compound was prepared in a similar fashion to that described for Example 53 from rel-(1R,3S)-3-(Trifluoromethyl)cyclohexanol and [(4S)-5,5-difluoro-3-(trifluoromethyl)-4,6-dihydro-1H-cyclopenta[c]pyrazol-4-yl] benzoate. ¹H NMR (400 MHz, Chloroform-d) δ 5.07 (d, J=12.1 Hz, 1H), 4.41 (p, J=5.7 Hz, 1H), 3.43 (ddd, J=16.6, 15.1, 10.2 Hz, 1H), 3.30 (ddd, J=16.5, 15.6, 4.6 Hz, 1H), 2.75 (ddp, J=13.8, 9.5, 4.7 Hz, 1H), 2.31 (dt, J=14.3, 5.8 Hz, 1H), 2.04 (dddd, J=18.7, 13.9, 9.5, 5.5 Hz, 2H), 1.89 (ddt, J=13.4, 8.1, 4.3 Hz, 2H), 1.73 (dddd, J=41.8, 17.0, 8.8, 4.4 Hz, 2H). ESI MS [M+H]⁺ for $C_{14}H_{14}F_8N_2O$, calcd 379.3, found 379.1.

Example 82: (4S)-5,5-difluoro-3-(trifluoromethyl)-1-[(1R,3S)-3-(trifluoromethyl)cyclohexyl]-1H,4H,5H,6H-cyclopenta[c]pyrazol-4-ol

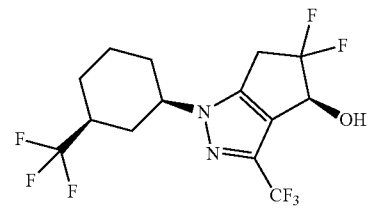 [SMILES: O[C@H]1c2c(C(F)(F)F)nn([C@@H]3CCC[C@H](C(F)(F)F)C3)c2CC1(F)F]

The title compound was prepared in a similar fashion to that described for Example 53 from 3-(Trifluoromethyl)cyclohexanol and [(4S)-5,5-difluoro-3-(trifluoromethyl)-1,4,6,7-tetrahydroindazol-4-yl] benzoate. ¹H NMR (400 MHz, Chloroform-d) δ 5.06 (dd, J=12.0, 5.6 Hz, 1H), 4.13 (tt, J=12.3, 3.8 Hz, 1H), 3.45 (ddd, J=16.6, 15.1, 10.2 Hz, 1H), 3.32 (ddd, J=16.5, 15.5, 4.7 Hz, 1H), 2.34 (dd, J=5.6, 2.1 Hz, 1H), 2.23 (dtt, J=11.6, 7.3, 3.7 Hz, 1H), 2.17-1.97 (m, 3H), 1.97-1.72 (m, 2H), 1.46 (dt, J=13.0, 3.2 Hz, 1H), 1.38 (td, J=12.7, 12.0, 2.9 Hz, 1H). ESI MS [M+H]⁺ for $C_{14}H_{14}F_8N_2O$, calcd 379.3, found 379.1.

Example 83: (2S)-4-[(4S,5R)-5-fluoro-4-hydroxy-3-(trifluoromethyl)-1H,4H,5H,6H-cyclopenta[c]pyrazol-1-yl]-2-methylbutanenitrile

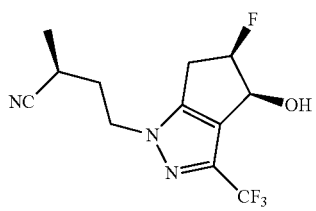 [SMILES: C[C@H](C#N)CCn1nc(C(F)(F)F)c2c1C[C@@H](F)[C@H]2O]

The title compound was prepared in a similar fashion to that described for Example 3 from [(4S,5R)-5-fluoro-1-(oxan-2-yl)-3-(trifluoromethyl)-5,6-dihydro-4H-cyclopenta[c]pyrazol-4-yl] benzoate. $^1$H NMR (400 MHz, Chloroform-d) δ 5.46 (ddt, J=50.7, 6.3, 4.6 Hz, 1H), 5.27-5.06 (m, 1H), 4.37-4.09 (m, 2H), 3.36-3.00 (m, 2H), 2.57 (dddd, J=14.2, 12.1, 6.1, 3.6 Hz, 1H), 2.40 (td, J=6.3, 3.9 Hz, 1H), 2.31 (dtdd, J=14.7, 9.5, 6.7, 5.2 Hz, 1H), 2.19-1.99 (m, 1H), 1.37 (d, J=7.1 Hz, 3H). ESI MS [M+H]$^+$ for $C_{12}H_{13}F_4N_3O$, calcd 292.3, found 292.1.

Example 84: 3-{[(4S,5R)-5-fluoro-4-hydroxy-3-(trifluoromethyl)-1H,4H,5H,6H-cyclopenta[c]pyrazol-1-yl]methyl}-1λ$^6$-thietane-1,1-dione

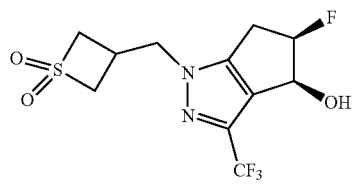 [SMILES: O=S1(=O)CC(Cn2nc(C(F)(F)F)c3c2C[C@@H](F)[C@H]3O)C1]

The title compound was prepared in a similar fashion to Example 62 from [(4S,5R)-5-fluoro-1-(oxan-2-yl)-3-(trifluoromethyl)-5,6-dihydro-4H-cyclopenta[c]pyrazol-4-yl] benzoate. $^1$H NMR (400 MHz, CDCl$_3$) δ 5.47 (dq, J=50.6, 5.1 Hz, 1H), 5.18 (q, J=5.9 Hz, 1H), 4.36-4.20 (m, 4H), 3.92-3.81 (m, 2H), 3.26-3.04 (m, 3H), 2.35 (dd, J=6.5, 4.0 Hz, 1H). ESI MS [M+H]$^+$ for $C_{11}H_{12}F_4N_2O_3S$, calcd 329.3, found 329.1.

Example 85: (4S)-1-(5,5-difluorooxan-3-yl)-5,5-difluoro-3-(trifluoromethyl)-1H,4H,5H,6H-cyclopenta[c]pyrazol-4-ol

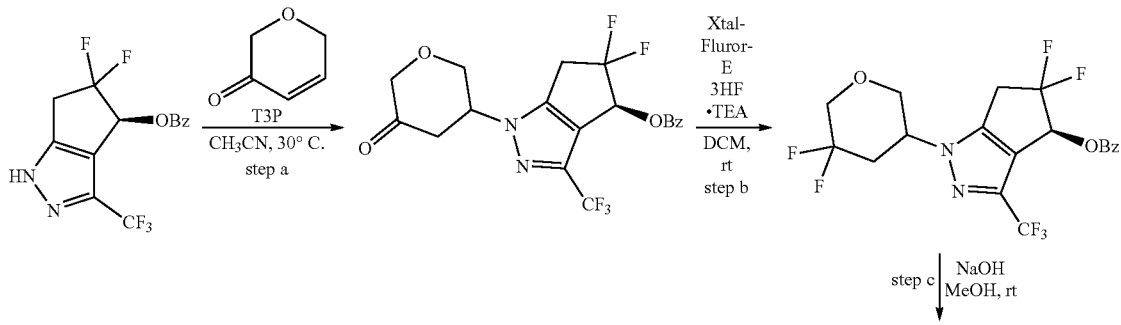

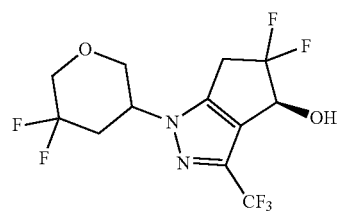

Step a: To a solution of [(4S)-5,5-difluoro-3-(trifluoromethyl)-1,4,6,7-tetrahydroindazol-4-yl] benzoate (250 mg, 0.75 mmol) in CH$_3$CN (2.5 mL) was added 2H-pyran-3 (6H)-one (110 mg, 1.12 mmol) and T3P (propanephosphonic acid anhydride, 360 mg, 1.12 mmol). The resulting mixture was heated to 30° C. for 12 h. After cooling down to room temperature, the reaction was carefully quenched with aq. sat. NaHCO$_3$ (10.0 mL) and diluted with dichloromethane (10.0 mL). The organic phase was separated, and the aqueous layer was additionally extracted with dichloromethane (2×5.0 mL). The combined organic phase was dried over Na$_2$SO$_4$ and concentrated to dryness under reduced pressure to yield the corresponding ketone compound. The crude residue was purified by flash column chromatography (silica gel, hexanes/EtOAc gradient) to afford the product (199 mg, 61%).

Step b: To a solution of the ketone from step a (128 mg, 0.30 mmol) in dichloromethane (2.0 mL) was added XtalFluor-E (N,N-Diethyl-(S,S)-difluorosulfiliminium tetrafluoroborate, 133 mg, 0.60 mmol) and 3HF·TEA (98 mg, 0.60 mmol), and the reaction mixture was stirred at room temperature overnight. The resulting solution was diluted with EtOAc (10.0 mL) and washed with aq. sat. NaHCO$_3$ (10.0 mL). The organic phase was separated, and the aqueous layer was additionally extracted with EtOAc (2×5.0 mL). The combined organic extract was dried over Na$_2$SO$_4$, concentrated to dryness under reduced pressure and the crude product was purified by column chromatography (silica gel, hexanes/EtOAc gradient) to give the title compound (46 mg, 2.9 mmol, 34%) as a colorless oil.

Step c: To a solution of the alkylation product of step b (25.0 mg, 0.055 mmol) in MeOH (2.0 mL) and THF (1.0 mL) was added aq. 1M NaOH solution (0.6 mL, 0.55 mmol) at ambient temperature. The resulting mixture was stirred for 1 h. Once TLC analysis indicated complete consumption of the starting material the reaction was diluted with EtOAc (10.0 mL). The combined organic phase was dried over Na$_2$SO$_4$, concentrated to dryness, and the crude product was purified by column chromatography (silica gel, hexanes/EtOAc gradient) to give the title compound (8.1 mg, 0.023 mmol, 42% yield) as a colorless oil. $^1$H NMR (400 MHz, CDCl$_3$) δ 5.07 (dd, J=11.9, 5.5 Hz, 1H), 4.47 (td, J=10.1, 4.9 Hz, 1H), 4.07 (d, J=11.8 Hz, 1H), 3.98 (ddt, J=12.8, 9.7, 3.3 Hz, 1H), 3.79 (q, J=10.2 Hz, 1H), 3.70-3.56 (m, 1H), 3.53-3.25 (m, 2H), 2.89-2.54 (m, 2H), 2.53-2.24 (m, 1H). ESI MS [M+H]$^+$ for C$_{11}$H$_{12}$F$_4$N$_2$O$_3$S, calcd 349.3, found 349.1.

Example 86: 3-[(4S)-5,5-difluoro-4-hydroxy-3-(trifluoromethyl)-1H,4H,5H,6H-cyclopenta[c]pyrazol-1-yl]-1λ$^6$-thiane-1,1-dione

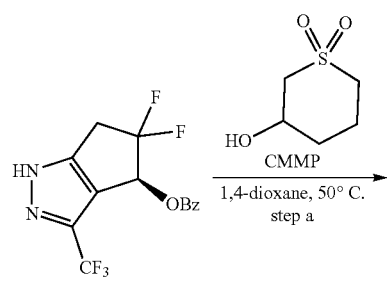

Step a: To a solution of [(4S)-5,5-difluoro-3-(trifluoromethyl)-1,4,6,7-tetrahydroindazol-4-yl] benzoate (160 mg, 0.48 mmol) and 2H-Thiopyran-3-ol, tetrahydro-, 1,1-dioxide (145 mg, 0.96 mmol) in 1,4-dioxane (1.0 mL) was added cyanomethylene trimethylphosphorane (CMMP) (1.9 ml, 1 mol/L). The resulting mixture was heated to 50° C. for 12 h. After cooling down to room temperature, the reaction was carefully quenched with aq. sat. NaHCO$_3$ (10.0 mL) and diluted with dichloromethane (10.0 mL). The organic phase was separated, and the aqueous layer was additionally extracted with dichloromethane (2×5.0 mL). The combined organic phase was dried over Na$_2$SO$_4$ and concentrated to dryness under reduced pressure to yield the corresponding ketone compound. The crude residue was purified by flash column chromatography (silica gel, DCM/MeOH gradient) to afford the product (42 mg, 19%).

Step b: To a solution of the alkylation product of step b (42.0 mg, 0.09 mmol) in MeOH (2.0 mL) and THF (1.0 mL) was added aq. 1M NaOH solution (0.5 mL, 0.45 mmol) at ambient temperature. The resulting mixture was stirred for 1 h. Once TLC analysis indicated complete consumption of the starting material the reaction was diluted with EtOAc (15.0 mL). The combined organic phase was dried over Na$_2$SO$_4$, concentrated to dryness, and the crude product was purified by column chromatography (silica gel, DCM/MeOH gradient) to give the title compound (12.6 mg, 0.035 mmol, 38% yield) as a colorless oil. $^1$H NMR (400 MHz, Chloroform-d) δ 5.07 (dt, J=11.9, 4.7 Hz, 1H), 4.58 (ddt, J=11.9, 8.2, 3.2 Hz, 1H), 3.63 (ddd, J=13.7, 12.0, 6.9 Hz, 1H), 3.49-3.23 (m, 3H), 3.21-3.05 (m, 1H), 3.00 (ddd, J=14.8, 12.3, 4.2 Hz, 1H), 2.63 (d, J=5.4 Hz, 1H), 2.31-2.07 (m, 4H). ESI MS [M+H]$^+$ for C$_{12}$H$_{13}$F$_5$N$_2$O$_3$S, calcd 361.3, found 361.1.

Example 87: (4S)-1-[(3S)-5,5-difluorooxan-3-yl]-5,5-difluoro-3-(trifluoromethyl)-1H,4H,5H,6H-cyclopenta[c]pyrazol-4-ol

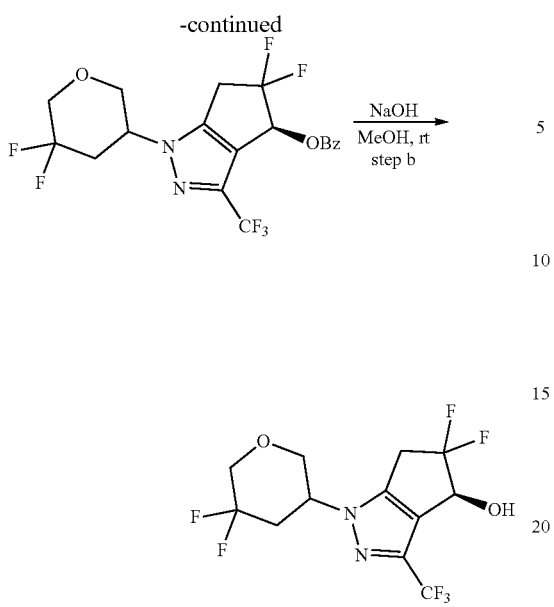

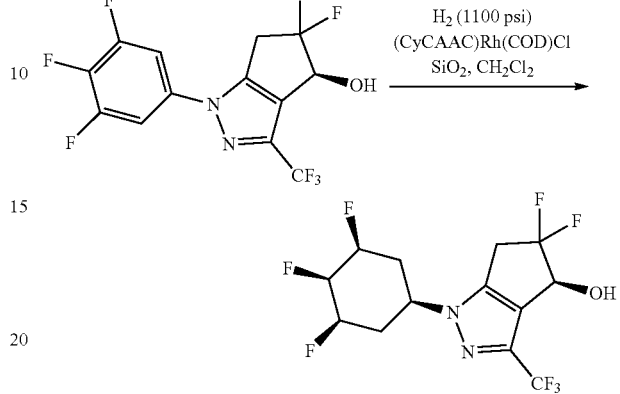

The starting material was prepared according to the protocol described in the synthesis of Example 85.

Step a: To a solution of the ketone (133 mg, 0.31 mmol) in dichloromethane (2.0 mL) was added Deoxo-Fluor (342 mg, 1.54 mmol) and the reaction mixture was stirred at room temperature overnight. The resulting solution was diluted with dichloromethane (10.0 mL) and washed with aq. sat. NaHCO$_3$ (10.0 mL). The organic phase was separated, and the aqueous layer was additionally extracted with dichloromethane (2×5.0 mL). The combined organic extract was dried over Na$_2$SO$_4$, concentrated to dryness under reduced pressure. To a solution of the crude product was added mCPBA (54 mg, 0.31 mmol). The resulting solution was diluted with dichloromethane (10.0 mL) and washed with aq. sat. NaHCO$_3$ (10.0 mL). The organic phase was separated, and the aqueous layer was additionally extracted with dichloromethane (2×5.0 mL). The combined organic extract was dried over Na$_2$SO$_4$, concentrated to dryness under reduced pressure. The crude product was used for the next step without purification.

Step b: To a solution of the alkylation product of step b in MeOH (4.0 mL) and THF (2.0 mL) was added aq. 1M NaOH solution (1.5 mL, 1.5 mmol) at ambient temperature. The resulting mixture was stirred for 1 h. Once TLC analysis indicated complete consumption of the starting material the reaction was diluted with EtOAc (15.0 mL). The combined organic phase was dried over Na$_2$SO$_4$, concentrated to dryness, and the crude product was purified by column chromatography (silica gel, hexanes/EtOAc gradient) to give the title compound (2.1 mg, 0.006 mmol, 11% yield) as a colorless oil. $^1$H NMR (400 MHz, CDCl$_3$) δ 5.07 (d, J=12.0 Hz, 1H), 4.47 (tt, J=10.0, 4.7 Hz, 1H), 4.07 (d, J=12.3 Hz, 1H), 3.98 (ddt, J=12.8, 10.0, 3.1 Hz, 1H), 3.87-3.72 (m, 1H), 3.63 (ddd, J=27.0, 12.3, 2.2 Hz, 1H), 3.45 (td, J=16.0, 9.9 Hz, 1H), 3.34 (td, J=16.1, 4.4 Hz, 1H), 2.86-2.67 (m, 1H), 2.67-2.56 (m, 1H), 2.42 (dd, J=14.4, 4.6 Hz, 2H). ESI MS [M+H]$^+$ for C$_{11}$H$_{12}$F$_4$N$_2$O$_3$S, calcd 349.3, found 349.1.

Example 88: (4S)-5,5-difluoro-1-[(3R,5S)-3,4,5-trifluorocyclohexyl]-3-(trifluoromethyl)-4,6-dihydrocyclopenta[c]pyrazol-4-ol (4S)-5,5-difluoro-3-(trifluoromethyl)-1-(3,4,5-trifluorophenyl)-4,6-dihydrocyclopenta[c]pyrazol-4-ol starting material was prepared similarly to Example 114. This substrate (0.23 g, 0.64 mmol, 1 equiv.) was dissolved in dichloromethane (1.5 mL, 0.4 M) in a stainless steel Parr autoclave lined with a Teflon insert and equipped with a mechanical stirrer. Silica gel (0.29 g, dried in an oven at 180° C.) was added, followed by (CyCAAC)Rh(COD)Cl (7 mg, 0.013 mmol, 0.02 equiv.). The autoclave was pressurized with 500 psi H$_2$ and vented three times before being pressurized to 1100 psi H$_2$. The reaction mixture was stirred at ~300 rpm under 1100 psi H$_2$ for 18 hours at which point it was depressurized and the reaction mixture was filtered over Celite. The filtrate was directly concentrated under vacuum and the crude residue was purified via column chromatography (SiO$_2$, hexanes/EtOAc gradient) to afford the product in a mixture with unknown diastereomer at cyclohexane moiety (4 mg, 2% yield, dr=2:1 favoring the desired product). $^1$H NMR (400 MHz, CDCl$_3$) δ 5.34-5.12 (m, 1H), 5.10-5.01 (m, 1H), 4.78-4.41 (m, 2H), 4.30-4.18 (m, 1H), 3.56-3.40 (m, 1H), 3.36 (ddd, J=16.5, 15.4, 4.4 Hz, 1H), 2.56-2.20 (m, 4H), 2.10-1.94 (m, 1H). $^{19}$F NMR (376 MHz, CDCl$_3$, major epimer) δ −61.86, −95.32 (d, J=235.1 Hz), −101.78 (d, J=234.0 Hz), −193.04 (d, J=14.7 Hz), −218.28 (d, J=14.7 Hz). ESI MS [M+H]$^+$ for C$_{13}$H$_{12}$F$_8$N$_2$O, calcd 365.1, found 365.1.

Example 89: (4S)-1-[(3R,5S)-3,5-difluorocyclohexyl]-5,5-difluoro-3-(trifluoromethyl)-4,6-dihydrocyclopenta[c]pyrazol-4-ol

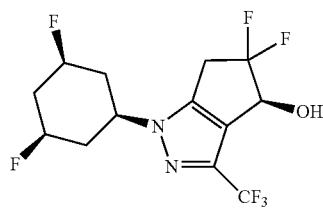 [SMILES: O[C@H]1c2c(C(F)(F)F)nn([C@@H]3C[C@H](F)C[C@H](F)C3)c2CC1(F)F]

The title compound was prepared in a similar fashion to that described for Example 88 from the corresponding aromatic compound. $^1$H NMR (400 MHz, CDCl$_3$) δ 5.07 (dd, J=12.0, 5.3 Hz, 1H), 4.76-4.45 (m, 2H), 4.18-4.04 (m, 1H), 3.45 (ddd, J=16.5, 15.2, 10.1 Hz, 1H), 3.32 (ddd, J=16.5, 15.5, 4.5 Hz, 1H), 2.85-2.68 (m, 1H), 2.61-2.49 (m, 2H), 2.45 (dd, J=5.6, 2.0 Hz, 1H), 2.20-1.98 (m, 2H), 1.91-1.73 (m, 1H). $^{19}$F NMR (376 MHz, CDCl$_3$) δ −61.8, −95.27 (d, J=235.1 Hz), −101.73 (d, J=235.1 Hz), −179.19. ESI MS [M+H]$^+$ for C$_{13}$H$_{13}$F$_7$N$_2$O, calcd 347.1, found 347.2.

Example 90a and 90b, and Example 91a and 91b: (4S)-1-[(rel-1S,3S,4R)-3,4-difluorocyclohexyl]-5,5-difluoro-3-(trifluoromethyl)-4,6-dihydrocyclopenta [c]pyrazol-4-ol and (4S)-5,5-difluoro-1-[(rel-1S, 3R)-3-fluorocyclohexyl]-3-(trifluoromethyl)-4,6-dihydrocyclopenta[c]pyrazol-4-ol

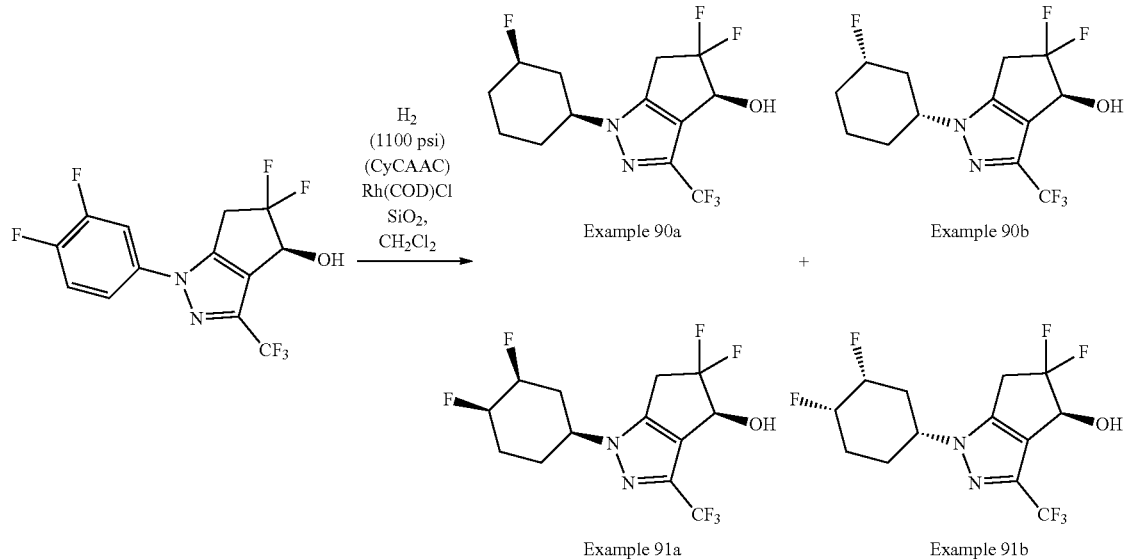

(4S)-1-(3,4-difluorophenyl)-5,5-difluoro-3-(trifluoromethyl)-4,6-dihydrocyclopenta[c]pyrazol-4-ol starting material was prepared similarly to Example 114. This substrate (125 mg, 0.37 mmol, 1 equiv.) was dissolved in dichloromethane (1.5 mL, 0.25 M) in a stainless steel Parr autoclave lined with a Teflon insert and equipped with a mechanical stirrer. Silica gel (165 mg, dried in an oven at 180° C.) was added, followed by (CyCAAC)Rh(COD)Cl (4.2 mg, 0.0073 mmol, 0.02 equiv.). The autoclave was pressurized with 500 psi H$_2$ and vented three times before being pressurized to 1100 psi H$_2$. The reaction mixture was stirred at ~300 rpm under 1100 psi H$_2$ for 18 hours at which point it was depressurized and the reaction mixture was filtered over Celite. The filtrate was directly concentrated under vacuum and the crude residue was purified via column chromatography (SiO$_2$, hexanes/EtOAc gradient) to afford both products separately as diastereomeric mixtures.

First eluting isomers (2) (Example 90a/b, DIAST-1): (4S)-5,5-difluoro-1-[(rel-1S,3R)-3-fluorocyclohexyl]-3-(trifluoromethyl)-4,6-dihydrocyclopenta[c]pyrazol-4-ol (4 mg, 0.012 mmol, 3% yield, colorless oil): $^1$H NMR (400 MHz, CDCl$_3$) δ 5.06 (dd, J=12.1, 5.6 Hz, 1H), 4.79-4.38 (m, 1H), 4.32-3.97 (m, 1H), 3.45 (dddd, J=17.2, 15.3, 10.2, 2.1 Hz, 1H), 3.32 (td, J=16.0, 4.7 Hz, 1H), 2.65-2.47 (m, 1H), 2.39 (dd, J=5.6, 2.0 Hz, 1H), 2.27-2.16 (m, 1H), 2.12-1.88 (m, 3H), 1.79-1.63 (m, 1H), 1.55-1.29 (m, 2H). $^{19}$F NMR (376 MHz, CDCl$_3$) δ −61.68, −95.29 (d, J=234 Hz), −101.86 (d, J=234 Hz), −171.00 (d, J=10.5 Hz). ESI MS [M+H]$^+$ for C$_{13}$H$_{14}$F$_6$N$_2$O, calcd 329.1, found 329.0.

Second eluting isomers (2) (Example 91a/b, DIAST-2): (4S)-1-[(rel-1S,3S,4R)-3,4-difluorocyclohexyl]-5,5-difluoro-3-(trifluoromethyl)-4,6-dihydrocyclopenta[c]pyrazol-4-ol (4 mg, 0.012 mmol, 3% yield, colorless oil): $^1$H NMR (400 MHz, CDCl$_3$) δ 5.12-4.90 (m, 2H), 4.79-4.41 (m, 1H), 4.28 (br. s, 1H), 3.56-3.28 (m, 2H), 2.47-2.25 (m, 3H), 2.21-1.90 (m, 2H), 1.75-1.47 (m, 1H). $^{19}$F NMR (376 MHz, CDCl$_3$) δ −61.75, −95.35 (dd, J=235.1, 20.3 Hz), −101.89 (dd, J=235.1, 13.0 Hz), −178.12--189.21 (m), −199.90--207.17 (m). ESI MS [M+H]$^+$ for C$_{13}$H$_{13}$F$_7$N$_2$O, calcd 347.1, found 347.1.

Example 92 and 93: (4S)-5,5-difluoro-3-(trifluoromethyl)-1-[(2R,4R)-2-(trifluoromethyl)oxan-4-yl]-4,6-dihydrocyclopenta[c]pyrazol-4-ol and (4S)-5,5-difluoro-3-(trifluoromethyl)-1-[(2S,4S)-2-(trifluoromethyl)oxan-4-yl]-4,6-dihydrocyclopenta [c]pyrazol-4-ol

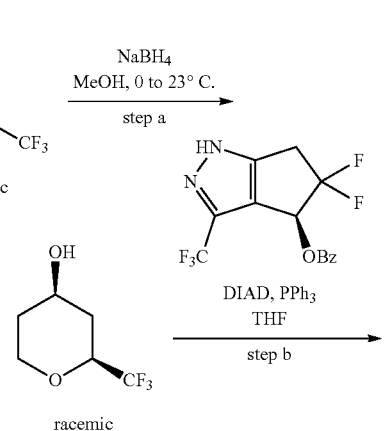

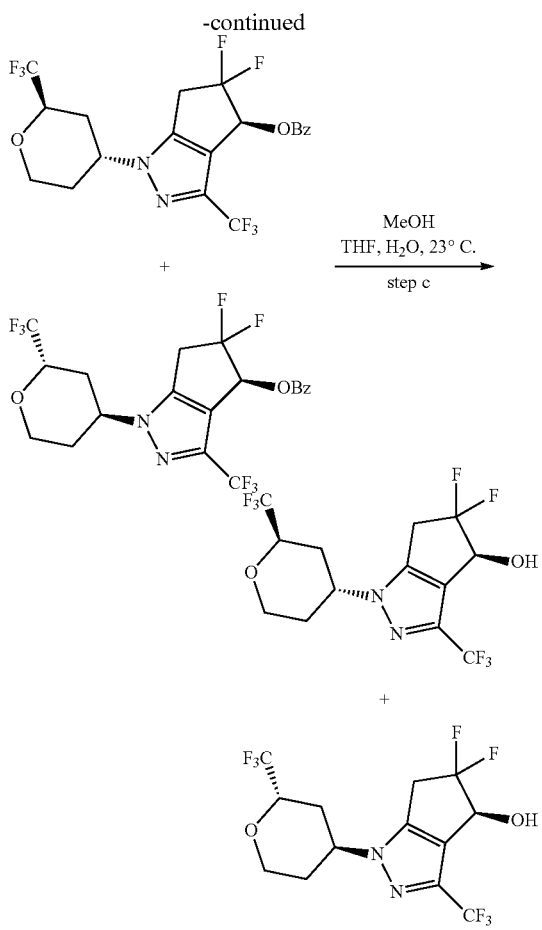

Step a: A solution of 2-(trifluoromethyl)oxan-4-one (1.0 g, 5.9 mmol, 1 equiv.) in dry methanol (15 mL, 0.4 M) was placed in 50 mL round bottom flask equipped with a magnetic stirring bar. The reaction mixture was cooled to 0° C., and NaBH$_4$ (0.27 g, 7.1 mmol, 1.2 equiv.) was added in one portion. The reaction was stirred at 0° C. for 1 h. Once TLC analysis indicated complete disappearance of the initial ketone the reaction was diluted with EtOAc (50 mL) and carefully quenched with 1M aqueous hydrochloric acid (20 mL). The organic phase was separated, and the aqueous layer was additionally extracted with EtOAc (2×30 mL). The combined organic extract was dried over Na$_2$SO$_4$, and the solvent was evaporated under reduced pressure. The dry residue was fractionated by column chromatography (SiO$_2$, hexanes/EtOAc gradient) to yield 2-(trifluoromethyl)oxan-4-ol as a single syn-diastereomer (0.73 g, 4.3 mmol, 72% yield).

Step b: A mixture of [(4S)-5,5-difluoro-3-(trifluoromethyl)-4,6-dihydro-1H-cyclopenta[c]pyrazol-4-yl] benzoate (104.0 mg, 0.31 mmol, 1 equiv.), racemic syn-2-(trifluoromethyl)oxan-4-ol (64.0 mg, 0.38 mmol, 1.2 equiv.) and PPh$_3$ (100.0 mg, 0.38 mmol, 1.2 equiv) in THF (1.5 mL, 0.2 M) was placed in 2 dram vial equipped with a magnetic stirring bar. The mixture was cooled to 0° C. under N$_2$ atmosphere, and DIAD (75 µL, 0.38 mmol, 1.2 equiv.) was added. The resulting solution was allowed to warm to ambient temperature and was stirred overnight. The solution was concentrated to dryness under reduced pressure and directly fractionated by column chromatography (SiO$_2$, hexanes/EtOAc gradient) to produce the desired coupling product (111.0 mg, 0.23 mmol, 74% yield) as a mixture of two diastereomers.

Step c: To a solution of epimers mixture of step b (111.0 mg, 0.23 mmol, 1 equiv.) in MeOH (4.6 mL, 0.05 M) was added aq. 1M NaOH solution (1.2 mL, 1.2 mmol, 5 equiv.) at ambient temperature. The resulting mixture was stirred for 1 h. Once TLC analysis indicated complete consumption of the starting material the reaction was diluted with EtOAc (25.0 mL) and aq. 1M NaOH solution (25.0 mL). The organic phase was separated and washed again with aq. 1M NaOH solution (2×15.0 mL) and brine (15.0 mL) to remove the residual benzoic acid. The combined organic phase was dried over Na$_2$SO$_4$, concentrated to dryness, and the crude product was purified by column chromatography (SiO$_2$, hexanes/EtOAc gradient) to yield (4S)-5,5-difluoro-3-(trifluoromethyl)-1-[(2R,4R)-2-(trifluoromethyl)oxan-4-yl]-4,6-dihydrocyclopenta[c]pyrazol-4-ol and (4S)-5,5-difluoro-3-(trifluoromethyl)-1-[2-(trifluoromethyl)oxan-4-yl]-4,6-dihydrocyclopenta[c]pyrazol-4-ol separately.

First eluting isomer (DIAST-1, 35 mg, 0.092 mmol, 40% yield): $^1$H NMR (400 MHz, CDCl$_3$) δ 5.07 (dd, J=12.0, 5.5 Hz, 1H), 4.65-4.55 (m, 1H), 4.58-4.43 (m, 1H), 4.19-4.05 (m, 1H), 4.05-3.87 (m, 1H), 3.43 (ddd, J=16.5, 15.3, 10.1 Hz, 1H), 3.29 (td, J=16.0, 4.4 Hz, 1H), 2.54 (dd, J=5.6, 2.0 Hz, 1H), 2.33-2.13 (m, 4H), 2.10-1.96 (m, 1H). $^{19}$F NMR (376 MHz, CDCl$_3$) δ −61.75, −77.47, −95.34 (d, J=234.5 Hz), −101.73 (d, J=235.1 Hz). ESI MS [M+H]$^+$ for C$_{13}$H$_{12}$F$_8$N$_2$O$_2$, calcd 381.1, found 381.1.

Second eluting isomer (DIAST-2, 32 mg, 0.084 mmol, 37% yield): $^1$H NMR (400 MHz, CDCl$_3$) δ 5.08 (dd, J=12.0, 5.4 Hz, 1H), 4.77-4.45 (m, 2H), 4.19-3.86 (m, 2H), 3.54-3.21 (m, 2H), 2.49 (dd, J=5.5, 2.0 Hz, 1H), 2.38-2.26 (m, 1H), 2.27-2.12 (m, 2H), 2.06-1.94 (m, 1H). $^{19}$F NMR (376 MHz, CDCl$_3$) δ −61.74, −77.52, −95.39 (d, J=235.0 Hz), −101.66 (d, J=234.6 Hz). ESI MS [M+H]$^+$ for C$_{13}$H$_{12}$F$_8$N$_2$O$_2$, calcd 381.1, found 381.2.

Example 94 and 95: (4S)-5,5-difluoro-3-(trifluoromethyl)-1-[(2R,4S)-2-(trifluoromethyl)oxan-4-yl]-4,6-dihydrocyclopenta[c]pyrazol-4-ol and (4S)-5,5-difluoro-3-(trifluoromethyl)-1-[(2S,4R)-2-(trifluoromethyl)oxan-4-yl]-4,6-dihydrocyclopenta[c]pyrazol-4-ol

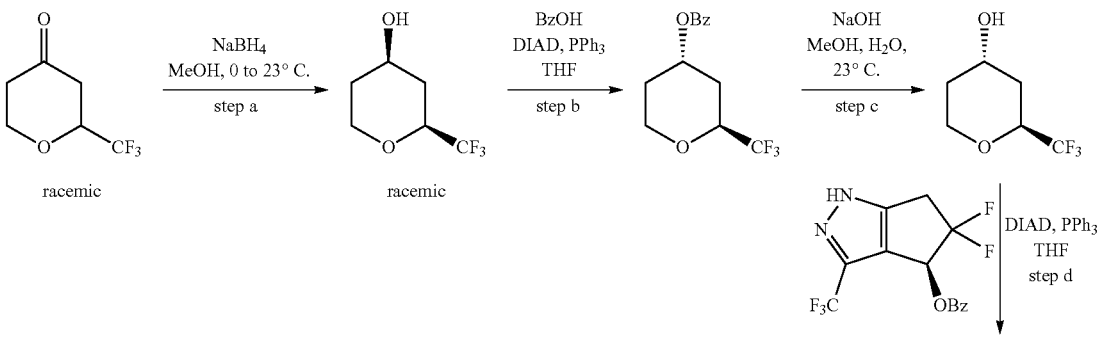

-continued

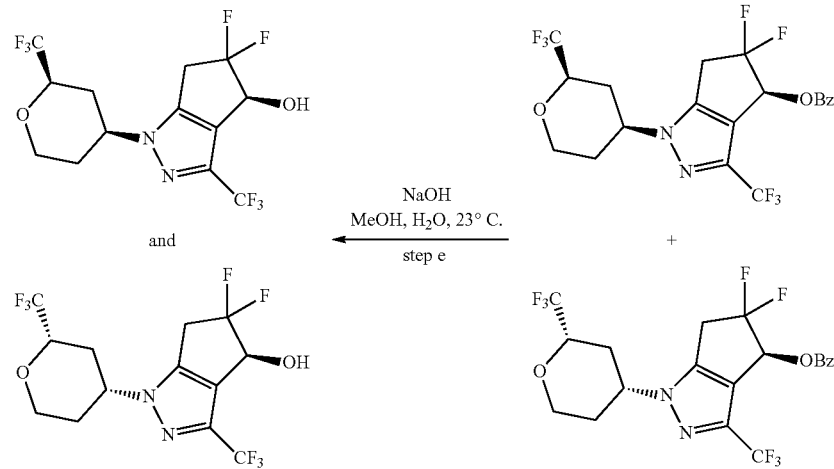

Step a: was performed according to the protocol from Example 92.

Step b: A mixture of racemic syn-2-(trifluoromethyl) oxan-4-ol (0.67 mg, 3.94 mmol, 1.0 equiv.), benzoic acid (0.58 g, 4.73 mmol, 1.2 equiv.) and $PPh_3$ (1.24 g, 4.73 mmol, 1.2 equiv) in THF (20.0 mL, 0.2 M) was placed in 100 mL round-bottom flask equipped with magnetic stirring bar. The mixture was cooled to 0° C. under $N_2$ atmosphere, and DIAD (0.93 mL, 4.73 mmol, 1.2 equiv.) was added dropwise over 10 min period to maintain the reaction temperature below +10° C. The resulting solution was allowed to warm to ambient temperature and was stirred for 2 h. The solution was concentrated to dryness under reduced pressure and directly fractionated by column chromatography ($SiO_2$, hexanes/EtOAc gradient) to produce the desired coupling product (1.02 g, 0.23 mmol, 3.72 mmol, 94% yield) as a yellowish oil.

Step c: To a solution of benzoate of step b (1.02 g, 3.72 mmol, 1 equiv.) in MeOH (25.0 mL, 0.15 M) was added aq. 1M NaOH solution (18.0 mL, 18.0 mmol, 5 equiv.) at ambient temperature. The resulting mixture was stirred for 1 h. Once TLC analysis indicated complete consumption of the starting material the reaction mixture was concentrated to 20 mL under reduced pressure and was diluted with EtOAc (50 mL). The organic phase was separated and washed again with aq. 1M NaOH solution (2×20.0 mL) and brine (20.0 mL) to remove the residual benzoic acid. The combined organic phase was dried over $Na_2SO_4$, concentrated to dryness, and the crude product was purified by column chromatography ($SiO_2$, hexanes/EtOAc gradient) to the desired alcohol (0.5 g, 2.94 mmol, 79% yield) as a colorless liquid.

Step d: A mixture of [(4S)-5,5-difluoro-3-(trifluoromethyl)-4,6-dihydro-1H-cyclopenta[c]pyrazol-4-yl] benzoate (200.0 mg, 0.6 mmol, 1 equiv.), racemic anti-2-(trifluoromethyl)oxan-4-ol (100.0 mg, 0.72 mmol, 1.2 equiv.) and $PPh_3$ (190.0 mg, 0.72 mmol, 1.2 equiv) in THF (3.0 mL, 0.2 M) was placed in 2 dram vial equipped with a magnetic stirring bar. The mixture was cooled to 0° C. under N2 atmosphere, and DIAD (140 μL, 0.72 mmol, 1.2 equiv.) was added. The resulting solution was allowed to warm to ambient temperature and was stirred for 4 h. The solution was concentrated to dryness under reduced pressure and directly fractionated by column chromatography ($SiO_2$, hexanes/EtOAc gradient) to produce the desired alkylation product as a mixture of two diastereomers (80 mg, 0.17 mmol, 27% yield) as a white solid.

Step e: To a solution of epimers mixture of step d (80.0 mg, 0.17 mmol, 1 equiv.) in MeOH (3.3 mL, 0.05 M) was added aq. 1M NaOH solution (0.8 mL, 1.2 mmol, 5 equiv.) at ambient temperature. The resulting mixture was stirred for 1 h. Once TLC analysis indicated complete consumption of the starting material the reaction was diluted with EtOAc (20.0 mL) and aq. 1M NaOH solution (20.0 mL). The organic phase was separated and washed again with aq. 1M NaOH solution (2×10.0 mL) and brine (10.0 mL) to remove the residual benzoic acid. The combined organic phase was dried over $Na_2SO_4$, concentrated to dryness, and the crude product was purified by column chromatography ($SiO_2$, hexanes/EtOAc gradient) to yield (4S)-5,5-difluoro-3-(trifluoromethyl)-1-[(2R, 4S)-2-(trifluoromethyl)oxan-4-yl]-4,6-dihydrocyclopenta[c]pyrazol-4-ol and (4S)-5,5-difluoro-3-(trifluoromethyl)-1-[(2S, 4R)-2-(trifluoromethyl)oxan-4-yl]-4,6-dihydrocyclopenta[c]pyrazol-4-ol separately.

First eluting isomer (DIAST-1, 23 mg, 0.060 mmol, 36% yield): $^1$H NMR (400 MHz, $CDCl_3$) δ 5.06 (dd, J=12.0, 5.5 Hz, 1H), 4.50-4.34 (m, 1H), 4.31 (ddd, J=12.1, 4.9, 1.6 Hz, 1H), 3.96-3.81 (m, 1H), 3.63 (td, J=12.2, 2.4 Hz, 1H), 3.47 (ddd, J=16.6, 15.3, 10.0 Hz, 1H), 3.42-3.27 (m, 1H), 2.59-2.46 (m, 1H), 2.37-2.25 (m, 1H), 2.27-2.11 (m, 1H), 2.12-2.01 (m, 2H). $^{19}$F NMR (376 MHz, $CDCl_3$) δ −61.79, −78.85, −95.34 (d, J=235.3 Hz), −101.79 (d, J=235.0 Hz). ESI MS [M+H]$^+$ for $C_{13}H_{12}F_8N_2O_2$, calcd 381.1, found 381.3.

Second eluting isomer (DIAST-2, 25 mg, 0.066 mmol, 40% yield): $^1$H NMR (400 MHz, $CDCl_3$) δ 5.06 (dd, J=12.1, 5.5 Hz, 1H), 4.50-4.33 (m, 1H), 4.30 (ddd, J=12.1, 4.9, 1.5 Hz, 1H), 3.87 (ddt, J=11.8, 8.1, 4.1 Hz, 1H), 3.63 (td, J=12.2, 2.3 Hz, 1H), 3.47 (td, J=15.9, 10.0 Hz, 1H), 3.34 (td, J=16.0, 4.3 Hz, 1H), 2.60 (dd, J=5.5, 2.0 Hz, 1H), 2.38-2.25 (m, 1H), 2.24-1.97 (m, 2H). ESI MS [M+H]$^+$ for $C_{13}H_{12}F_8N_2O_2$, calcd 381.1, found 381.1.

Example 96: (4S)-5,5-difluoro-1-(4-fluorocyclohexyl)-3-(trifluoromethyl)-4,6-dihydrocyclopenta[c]pyrazol-4-ol

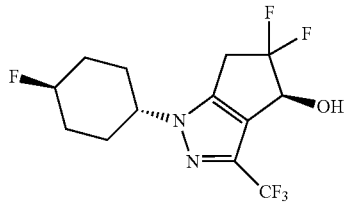 [SMILES: O[C@H]1c2c(C(F)(F)F)nn([C@H]3CC[C@H](F)CC3)c2CC1(F)F]

The title compound was prepared in a similar fashion to that described for Example 1 from cis-4-fluorocyclohexan-1-ol. $^1$H NMR (400 MHz, CDCl$_3$) δ 5.05 (dd, J=12.1, 5.5 Hz, 1H), 4.87-4.37 (m, 1H), 4.36-3.64 (m, 1H), 3.43 (td, J=16.0, 10.2 Hz, 1H), 3.30 (td, J=16.1, 4.5 Hz, 1H), 2.54 (dd, J=5.7, 1.9 Hz, 1H), 2.37-2.20 (m, 1H), 2.20-2.08 (m, 1H), 2.00-1.80 (m, 2H), 1.76-1.57 (m, 2H). $^{19}$F NMR (376 MHz, CDCl$_3$) δ −61.64, −95.36 (d, J=234.8 Hz), −101.82 (d, J=235.0 Hz), −174.69. ESI MS [M+H]$^+$ for C$_{13}$H$_{14}$F$_6$N$_2$O, calcd 329.1, found 329.1.

Example 97 and 98: (4S)-1-[(1R,2R,4R)-2,4-difluorocyclohexyl]-5,5-difluoro-3-(trifluoromethyl)-4,6-dihydrocyclopenta[c]pyrazol-4-ol and (4S)-1-[(1S,2S,4S)-2,4-difluorocyclohexyl]-5,5-difluoro-3-(trifluoromethyl)-4,6-dihydrocyclopenta[c]pyrazol-4-ol

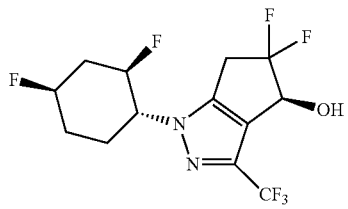

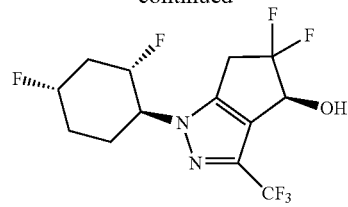

The title compounds were prepared in a similar fashion to that described for Example 1 from cis-4-fluorocyclohexan-1-ol. The crude product was purified by column chromatography (SiO$_2$, hexanes/EtOAc gradient, 0 to 30% over 30 minutes) to yield (4S)-1-[(1R,2R,4R)-2,4-difluorocyclohexyl]-5,5-difluoro-3-(trifluoromethyl)-4,6-dihydrocyclopenta[c]pyrazol-4-ol and (4S)-1-[(1S,2S,4S)-2,4-difluorocyclohexyl]-5,5-difluoro-3-(trifluoromethyl)-4,6-dihydrocyclopenta[c]pyrazol-4-ol separately.

First eluting isomer (DIAST-1): $^1$H NMR (400 MHz, CDCl$_3$) δ 5.05 (dd, J=12.2, 5.9 Hz, 1H), 4.88-4.46 (m, 2H), 4.06-3.84 (m, 1H), 3.45 (td, J=16.2, 10.2 Hz, 1H), 3.27 (ddd, J=16.7, 15.7, 4.3 Hz, 1H), 2.91-2.65 (m, 1H), 2.46 (dd, J=6.1, 1.9 Hz, 1H), 2.39-2.26 (m, 1H), 2.23-2.11 (m, 2H), 1.96-1.78 (m, 1H), 1.78-1.56 (m, 1H). $^{19}$F NMR (376 MHz, CDCl$_3$) δ −61.74, −95.22 (d, J=234.7 Hz), −101.77 (d, J=234.9 Hz), −176.39, −179.25. ESI MS [M+H]$^+$ for C$_{13}$H$_{13}$F$_7$N$_2$O, calcd 347.1, found 347.1.

Second eluting isomer (DIAST-2): $^1$H NMR (400 MHz, CDCl$_3$) δ 5.09 (ddd, J=11.9, 5.7, 1.4 Hz, 1H), 4.87-4.48 (m, 2H), 4.06-3.92 (m, 1H), 3.56-3.24 (m, 2H), 2.90-2.67 (m, 1H), 2.51 (d, J=6.2 Hz, 1H), 2.39-2.25 (m, 1H), 2.27-2.10 (m, 2H), 1.97-1.79 (m, 1H), 1.77-1.62 (m, 1H). 19F NMR (376 MHz, CDCl$_3$) δ −61.76, −95.17 (d, J=234.1 Hz), −101.92 (d, J=233.5 Hz), −176.41 (d, J=4.1 Hz), −179.68 (d, J=4.0 Hz). ESI MS [M+H]$^+$ for C$_{13}$H$_{13}$F$_7$N$_2$O, calcd 347.1, found 347.1.

Example 99: (2R)-4-[(4S)-5,5-difluoro-4-hydroxy-3-(trifluoromethyl)-6,7-dihydro-4H-indazol-1-yl]-2-methylbutanenitrile

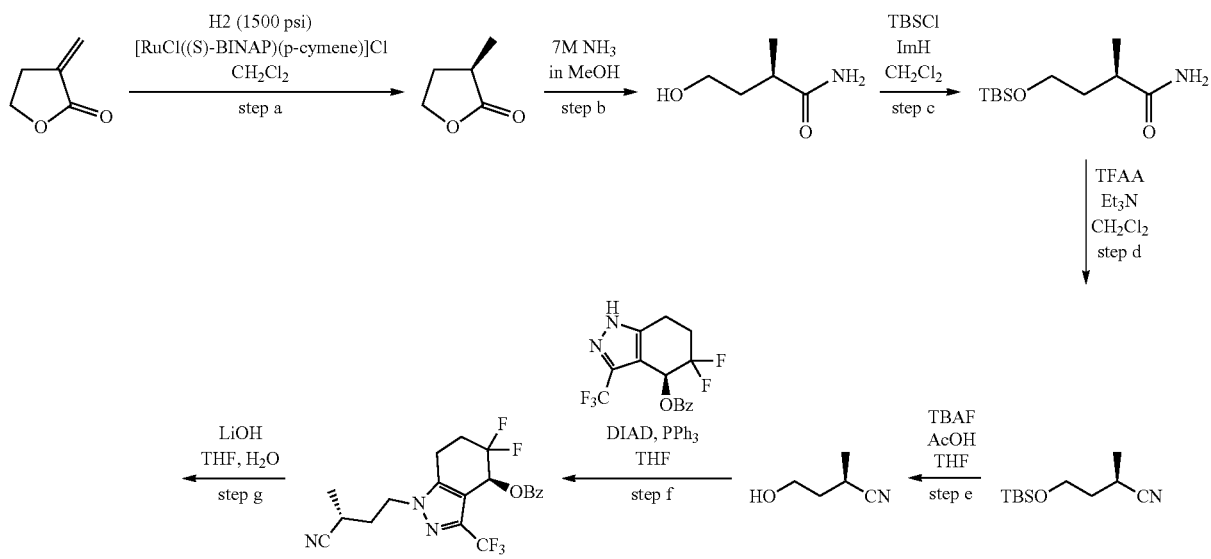

-continued

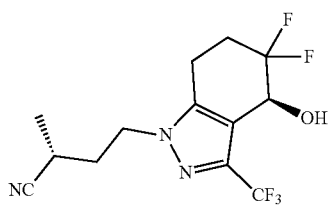

Step a: A mixture of α-methylene-γ-butyrolactone (10.0 g, 0.1 mol, 1 equiv.) and [RuCl((S)-BINAP)(p-cymene)]Cl (0.95 g, 1.0 mmol, 0.01 equiv.) in dichloromethane (20 mL, 5 M) was placed in a 100 mL round-bottom flask equipped with stirring bar, nitrogen inlet needle, submersed into the solution, and a nitrogen outlet needle above the solution. Nitrogen gas was bubbled through the solution for 20 min. Then the resulting homogenous mixture was transferred to stainless steel autoclave and stirred under atmosphere of hydrogen (1500 psi) for 48 h at ambient temperature. Once hydrogen gas was released from the autoclave, the material was directly fractionated by column chromatography (SiO$_2$, CH$_2$Cl$_2$/MTBE gradient) to yield the desired product (10.0 g, 0.1 mol, 100% yield). The enantioselectivity of the reduction (80% ee) was determined by $^1$H NMR analysis of diastereomeric mixture upon coupling of the alcohol with pyrazole moiety on step f.

Step b: The lactone of step a (10.0 g, 0.1 mol) was mixed with 7M NH$_3$ in MeOH (100 mL) and stirred at ambient temperature for 48 h. Once $^1$H NMR analysis indicated complete consumption of the starting material the reaction was concentrated under reduced pressure, the residual solvent and ammonia were removed by co-evaporation with dichloromethane (2×100 mL) and the residue was dried on vacuum to yield the desired primary amide (11.8 g, 0.1 mol, 97% yield) as colorless waxy oil.

Step c: A solution of the primary amide of step b (1.0 g, 8.5 mmol, 1 equiv.) and imidazole (17.9 mmol) in dichloromethane (43.0 mL, 0.2 M) was cooled to 0° C. Then TBSCl (1.35 g, 9.0 mmol, 1.05 equiv.) was added, and the reaction was stirred at ambient temperature for 2 h. The resulting solution was diluted with dichloromethane (50 mL) and washed with water (2×100 mL). The organic extract was dried over sodium sulfate, and the solvent was removed under reduced pressure. The resulting crude product was directly used for the next step without purification.

Step d. The product of step c was dissolved in dichloromethane (43 mL, 0.2 M), triethylamine (5.9 mL, 42.5 mmol, 5 equiv.) was added, and the resulting solution was cooled to 0° C. Trifluoroacetic anhydride (3.5 mL, 25.5 mmol, 3 equiv.) was added dropwise over 20 min period, and the reaction mixture was stirred at 0° C. for additional 20 min. Once TLC analysis indicated complete consumption of the starting material the reaction was diluted with dichloromethane (40 mL), washed with aq. 1M HCl (2×70 mL), water (70 ml) and aq. saturated NaHCO$_3$ solution (2×70 mL). The organic extract was dried over sodium sulfate and concentrated to dryness under reduced pressure. The crude product was purified by column chromatography (SiO$_2$, hexanes/EtOAc gradient) to yield the desired nitrile (1.1 g, 5.2 mmol, 62% yield over two steps) as a colorless liquid.

Step e. To a cooled to 0° C. solution of AcOH (8.7 mL, 0.152 mol, 2.05 equiv.) in THF (200 mL) TBAF solution in THF (147 mL, 0.147 mol, 2.0 equiv., 1M solution) was added. The mixture was stirred for 5 min at 0° C., then a solution of TBS-ether of step d (15.7 g, 7.4 mmol, 1 equiv)

was added dropwise over 20 min. The resulting solution was allowed to warm to room temperature and stirred for 18 h. The reaction mixture was diluted with EtOAc (300 mL), washed with water (2×200 mL), aq. saturated NaHCO$_3$ (2×150 mL) and brine (200 mL). The organic extract was dried over sodium sulfate and concentrated to dryness under reduced pressure. The liquid residue was fractionated by column chromatography (SiO$_2$, hexanes/EtOAc gradient) to yield the desired alcohol (4.4 g, 0.044 mol, 60% yield) as a colorless liquid.

Step f. A mixture of [(4S)-5,5-difluoro-3-(trifluoromethyl)-1,4,6,7-tetrahydroindazol-4-yl] benzoate (300.0 mg, 0.87 mmol, 1 equiv.), alcohol of step e (95.0 mg, 0.95 mmol, 1.1 equiv.) and PPh$_3$ (250.0 mg, 0.95 mmol, 1.1 equiv) in THF (4.5 mL, 0.2 M) was placed in 2 dram vial equipped with a magnetic stirring bar. The mixture was cooled to 0° C. under N$_2$ atmosphere, and DIAD (190 μL, 0.95 mmol, 1.1 equiv.) was added. The resulting solution was allowed to warm to ambient temperature and was stirred for 16 h. The solution was concentrated to dryness under reduced pressure and directly fractionated by column chromatography (SiO$_2$, hexanes/EtOAc gradient) to produce the desired alkylation product (151 mg, 0.35 mmol, 41% yield) as a colorless oil.

Step g: To a solution of the product from step f (150.0 mg, 0.35 mmol, 1 equiv.) in THF (2.2 mL) and water (1.2 mL) was added lithium hydroxide monohydrate (74 mg, 1.8 mmol, 5 equiv.) at ambient temperature. The resulting mixture was stirred for 2 h. Once TLC analysis indicated complete consumption of the starting material the reaction was diluted with EtOAc (20.0 mL) and aq. 1M NaOH solution (20.0 mL). The organic phase was separated and washed again with aq. 1M NaOH solution (2×10.0 mL) and brine (10.0 mL) to remove the residual benzoic acid. The combined organic phase was dried over Na$_2$SO$_4$, concentrated to dryness, and the crude product was purified by column chromatography (SiO$_2$, hexanes/EtOAc gradient) to yield the title compound (94 mg, 0.29 mmol, 83% yield) as a colorless oil. $^1$H NMR (400 MHz, CDCl$_3$) δ 5.01-4.68 (m, 1H), 4.45-4.05 (m, 2H), 2.98 (ddd, J=16.5, 6.8, 2.3 Hz, 1H), 2.93-2.72 (m, 2H), 2.72-2.42 (m, 2H), 2.38-2.21 (m, 2H), 2.16-2.02 (m, 1H), 1.37 (d, J=7.1 Hz, 3H). ESI MS [M+H]$^+$ for C$_{13}$H$_{14}$F$_5$N$_3$O, calcd 324.1, found 324.3.

Example 100: (2S)-4-[(4S)-5,5-difluoro-4-hydroxy-3-(trifluoromethyl)-6,7-dihydro-4H-indazol-1-yl]-2-methylbutanenitrile

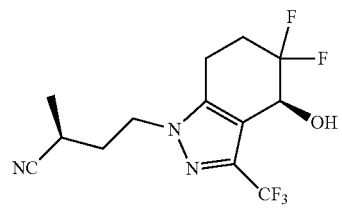 [SMILES: C[C@H](C#N)CCn1nc(C(F)(F)F)c2c1CCC(F)(F)[C@H]2O]

The title compound was prepared in a similar fashion to that described for Example 99 using [RuCl((R)-BINAP)(p-cymene)]Cl for the reduction of α-methylene-γ-butyrolactone. $^1$H NMR (400 MHz, CDCl$_3$) δ 4.94-4.79 (m, 1H), 4.27-4.09 (m, 2H), 2.97-2.80 (m, 3H), 2.69-2.41 (m, 2H), 2.36-2.21 (m, 2H), 2.15-2.00 (m, 1H), 1.37 (d, J=7.1 Hz, 3H). ESI MS [M+H]$^+$ for C$_{13}$H$_{14}$F$_5$N$_3$O, calcd 324.1, found 324.1.

Example 101: (4S)-1-[(3R)-3-ethoxy-4,4,4-trifluorobutyl]-5,5-difluoro-3-(trifluoromethyl)-4,6-dihydrocyclopenta[c]pyrazol-4-ol

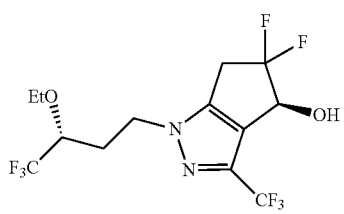 [SMILES: CCO[C@H](CCn1nc(C(F)(F)F)c2c1CC(F)(F)[C@H]2O)C(F)(F)F]

The title compound was prepared according to the protocol described for Example 61 using iodoethane in step d. $^1$H NMR (400 MHz, CDCl$_3$) δ 5.08 (dd, J=11.9, 5.7 Hz, 1H), 4.33-4.15 (m, 2H), 3.92-3.77 (m, 1H), 3.67 (dtd, J=12.8, 6.2, 3.1 Hz, 1H), 3.57 (dq, J=9.1, 7.0 Hz, 1H), 3.48-3.22 (m, 2H), 2.47-2.37 (m, 1H), 2.27 (dtd, J=15.2, 7.6, 3.4 Hz, 1H), 2.19-2.07 (m, 1H), 1.22 (t, J=7.0 Hz, 3H). ESI MS [M+H]$^+$ for C$_{13}$H$_{14}$F$_8$N$_2$O$_2$, calcd 383.1, found 383.1.

Example 102: (4S)-1-[3-(difluoromethoxymethyl)cyclobutyl]-5,5-difluoro-3-(trifluoromethyl)-4,6-dihydrocyclopenta[c]pyrazol-4-ol and brine (30.0 mL). The organic solution was dried over Na$_2$SO$_4$, filtered, and concentrated to dryness under reduced pressure. The crude residue was used in the subsequent step without further purification.

Step b: Product from step a (17.0 g) was dissolved in THF (168 mL) and the solution was cooled to 0° C. LiAlH$_4$ (2.0 M in THF, 18.4 mL, 36.9 mmol) was added dropwise and the reaction was stirred at room temperature for 15 min. The reaction mixture was cooled to 0° C. and quenched with water (10 mL). 1M NaOH (35 mL) was added, and the reaction mixture was stirred at room temperature for 15 minutes. MgSO$_4$ was added, and the reaction mixture was stirred at room temperature for an additional 15 minutes. The reaction mixture was then filtered over celite and concentrated to dryness under reduced pressure. The crude residue was used in the subsequent step without further purification.

Step c: TMSCF$_2$Br (3.40 mL, 22.0 mmol) and KOAc (2.16 g, 22.0 mmol) were added to the solution of the alcohol from step b (1.50 g) in CH$_2$Cl$_2$ (2.20 mL) and water (2.20 mL). The reaction was stirred for 16 h at 23° C. Then it was diluted with CH$_2$Cl$_2$ (5.0 mL) and washed with water (2×8 mL). The combined organic phase was dried over Na$_2$SO$_4$, concentrated and the crude residue was used in the next step without further purification.

Step d: TBAF (6.20 mL, 6.20 mmol, 1M in THF) was added to the solution of the product from step c in THF (22.0 mL) at 0° C. The resulting mixture was stirred at room temperature for 30 min. Upon completion, the mixture was partitioned between Et$_2$O and water. The organic layer was washed with water (3×30.0 mL) and brine (30.0 mL), dried over MgSO$_4$, filtered, and concentrated to dryness under reduced pressure. The crude product was purified by column chromatography (SiO$_2$ EtOAc in hexanes, 0 to 60%) to give the alcohol (0.45 g, 2.96 mmol, 67% yield over 2 steps) as colorless oil.

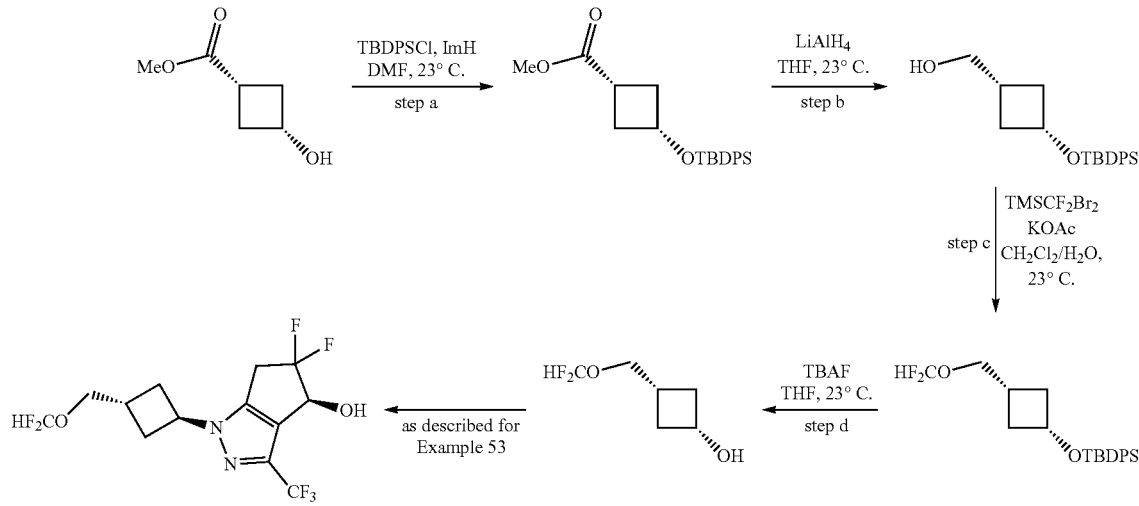

Step a: TBDPSCl (12.0 mL, 46.1 mmol) was added to a solution of cis-methyl-3-hydroxycyclobutane-1-carboxylate (5.0 g, 38.4 mmol) and imidazole (6.0 g, 88.4 mmol) in DMF (38 mL) at 0° C. After 5 min the reaction was warmed up to room temperature and stirred for 1 h. Upon completion, the reaction was diluted with CH$_2$Cl$_2$ (40.0 mL), washed with water (3×15.0 mL), sat. aq. NaHCO$_3$ (30.0 mL)

The title compound was prepared in 2 additional steps in a similar fashion to that described for Example 53. $^1$H NMR (400 MHz, CDCl$_3$) δ 6.24 (t, J=74.6 Hz, 1H), 5.04 (dd, J=12.1, 5.7 Hz, 1H), 4.78-4.46 (m, 1H), 3.91 (d, J=4.7 Hz, 2H), 3.53-3.22 (m, 2H), 2.71-2.55 (m, 2H), 2.55-2.30 (m, 4H). ESI MS [M+H]$^+$ for C$_{13}$H$_{13}$F$_7$N$_2$O$_2$, calcd 363.1, found 363.1.

Example 103: (4S)-1-[3-(difluoromethoxymethyl)cyclobutyl]-5,5-difluoro-3-(trifluoromethyl)-4,6-dihydrocyclopenta[c]pyrazol-4-ol

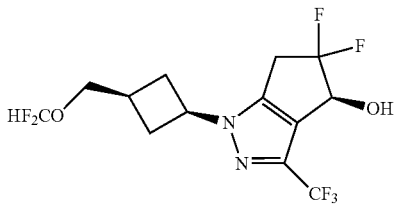

The title compound was prepared in a similar fashion to Example 102 using trans-methyl 3-hydroxycyclobutanecarboxylate. $^1$H NMR (400 MHz, CDCl$_3$) δ 6.24 (t, J=74.6 Hz, 1H), 5.04 (dd, J=12.1, 5.7 Hz, 1H), 4.71-4.48 (m, 1H), 3.91 (d, J=4.7 Hz, 2H), 3.61-3.18 (m, 2H), 2.75-2.53 (m, 2H), 2.53-2.28 (m, 4H). ESI MS [M+H]$^+$ for C$_{13}$H$_{13}$F$_7$N$_2$O$_2$, calcd 363.1, found 363.1.

Example 104: (4S)-1-[3-(difluoromethoxymethyl)cyclobutyl]-5,5-difluoro-3-(trifluoromethyl)-6,7-dihydro-4H-indazol-4-ol

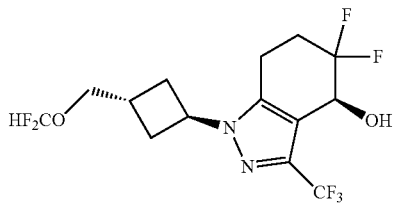

The title compound was prepared in a similar fashion to Example 102 using [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 6.28 (t, J=74.6 Hz, 1H), 4.88 (q, J=5.7 Hz, 1H), 4.70 (p, J=7.7 Hz, 1H), 3.97 (d, J=5.5 Hz, 2H), 3.01-2.66 (m, 5H), 2.63-2.44 (m, 2H), 2.43-2.31 (m, 2H), 2.31-2.17 (m, 1H). ESI MS [M+H]$^+$ for C$_{14}$H$_{15}$F$_7$N$_2$O$_2$, calcd 377.1, found 377.1.

Example 105: (4S)-1-[3-(difluoromethoxymethyl)cyclobutyl]-5,5-difluoro-3-(trifluoromethyl)-6,7-dihydro-4H-indazol-4-ol

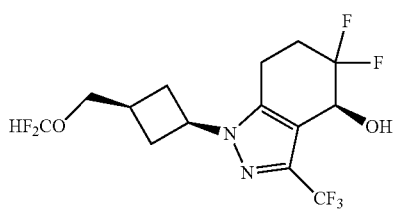

The title compound was prepared in a similar fashion to Example 102 using trans-methyl 3-hydroxycyclobutanecarboxylate and [(4S)-5,5-difluoro-3-(trifluoromethyl)-4,6-dihydro-1H-cyclopenta[c]pyrazol-4-yl] benzoate. $^1$H NMR (400 MHz, CDCl$_3$) δ 6.24 (t, J=74.5 Hz, 1H), 5.05 (dd, J=12.0, 5.6 Hz, 1H), 4.68-4.52 (m, 1H), 3.91 (d, J=4.7 Hz, 2H), 3.61-3.18 (m, 2H), 2.60 (dddd, J=11.3, 8.0, 5.3, 2.9 Hz, 2H), 2.44 (dddd, J=15.5, 13.6, 11.9, 7.5 Hz, 4H). ESI MS [M+H]$^+$ for C$_{14}$H$_{15}$F$_7$N$_2$O$_2$, calcd 377.1, found 377.1.

Example 106: (4S)-1-[3-[(1S)-1-(difluoromethoxy)ethyl]cyclobutyl]-5,5-difluoro-3-(trifluoromethyl)-4,6-dihydrocyclopenta[c]pyrazol-4-ol

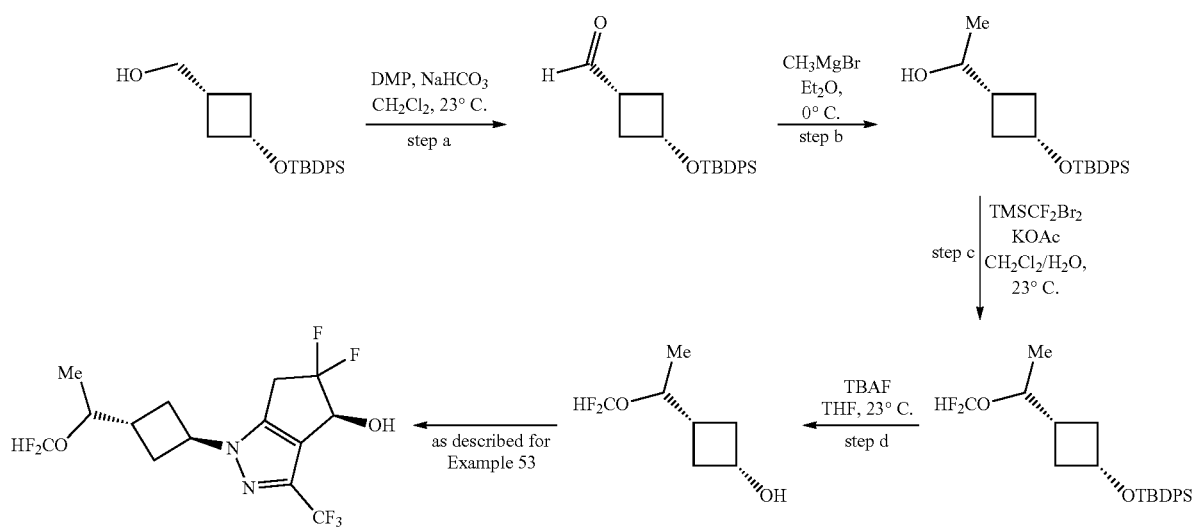

Step a: [3-[tert-butyl(diphenyl)silyl]oxycyclobutyl]methanol was prepared using steps a and b from synthesis of Example 102. [3-[tert-butyl(diphenyl)silyl]oxycyclobutyl]methanol (2.0 g, 5.87 mmol) was dissolved in CH$_2$Cl$_2$ (30.0 mL) and NaHCO₃ (0.54 g, 6.46 mmol) was added followed by DMP (2.80 g, 6.46 mmol). The reaction was stirred for 1 hour at room temperature. The reaction was quenched with saturated aqueous Na₂S₂O₃ (20 mL) and saturated aqueous NaHCO₃ (20 mL) and extracted with CH₂Cl₂ (2×20 mL). The combined organics were dried over Na₂SO₄, filtered, and concentrated in vacuo. The crude product was purified by column chromatography (SiO₂ EtOAc in hexanes, 0 to 25%) to give the alcohol (1.10 g, 3.25 mmol, 55% yield) as colorless oil.

Step b: Methylmagnesium bromide (0.70 mL, 2.11 mmol, 3.0 M in diethyl ether) was added to the solution of the aldehyde from step a (0.55 g, 1.62 mmol) in diethyl ether (8.10 mL) at 0° C. The resulting solution was stirred at 0° C. for 10 min. Upon completion by TLC analysis, the reaction was quenched by addition of aq. sat. NH₄Cl (4.0 mL) and diluted with EtOAc (10.0 mL). The layers were separated, and the organic phase was washed with brine (10.0 mL), dried over Na₂SO₄, filtered, and concentrated to dryness under reduced pressure. The crude residue was used in the next step without further purification.

Step c: TMSCF₂Br (1.30 mL, 8.10 mmol) and KOAc (0.80 g, 8.10 mmol) were added to the solution of the alcohol from step b (0.59 g) in CH₂Cl₂ (0.80 mL) and water (0.80 mL). The reaction was stirred for 16 h at 23° C. Then it was diluted with CH₂Cl₂ (5 mL) and washed with water (2×3 mL). The combined organic phase was dried over Na₂SO₄, filtered and concentrated to dryness under reduced pressure. The crude product was purified by column chromatography (SiO₂ EtOAc in hexanes, 0 to 30%) to give the ether (0.48 g, 1.19 mmol, 74% yield over 2 steps) as colorless oil.

Step d: TBAF (1.70 mL, 1.67 mmol, 1M in THF) was added to the solution of the product from step c (0.48 g, 1.19 mmol) in THF (6.0 mL) at 0° C. The resulting mixture was stirred at room temperature for 30 min. Upon completion the mixture was partitioned between Et₂O and water. The organic layer was washed with water (3×10.0 mL) and brine (10.0 mL), dried over MgSO₄, filtered, and concentrated to dryness under reduced pressure. The crude product was purified by column chromatography (SiO₂ EtOAc in hexanes, 0 to 60%) to give the alcohol (0.16 g, 0.96 mmol, 81% yield) as colorless oil.

The title compound was prepared in 2 additional steps in a similar fashion to that described for Example 53. ¹H NMR (400 MHz, CDCl₃) δ 6.31 (t, J=75.0 Hz, 1H), 5.06 (dd, J=12.0, 5.7 Hz, 1H), 4.68 (tt, J=8.3, 7.0 Hz, 1H), 4.46-4.27 (m, 1H), 3.53-3.13 (m, 2H), 2.86-2.64 (m, 2H), 2.64-2.49 (m, 2H), 2.48-2.32 (m, 2H), 1.27 (d, J=6.3 Hz, 3H). ESI MS [M+H]⁺ for $C_{14}H_{15}F_7N_2O_2$, calcd 377.1, found 377.1.

Example 107a and 107b: (4S)-5,5-difluoro-3-methylsulfonyl-1-[(3R)-4,4,4-trifluoro-3-methoxybutyl]-4,6-dihydrocyclopenta[c]pyrazol-4-ol and (4S)-5,5-difluoro-3-methylsulfonyl-1-[(3S)-4,4,4-trifluoro-3-methoxybutyl]-4,6-dihydrocyclopenta[c]pyrazol-4-ol

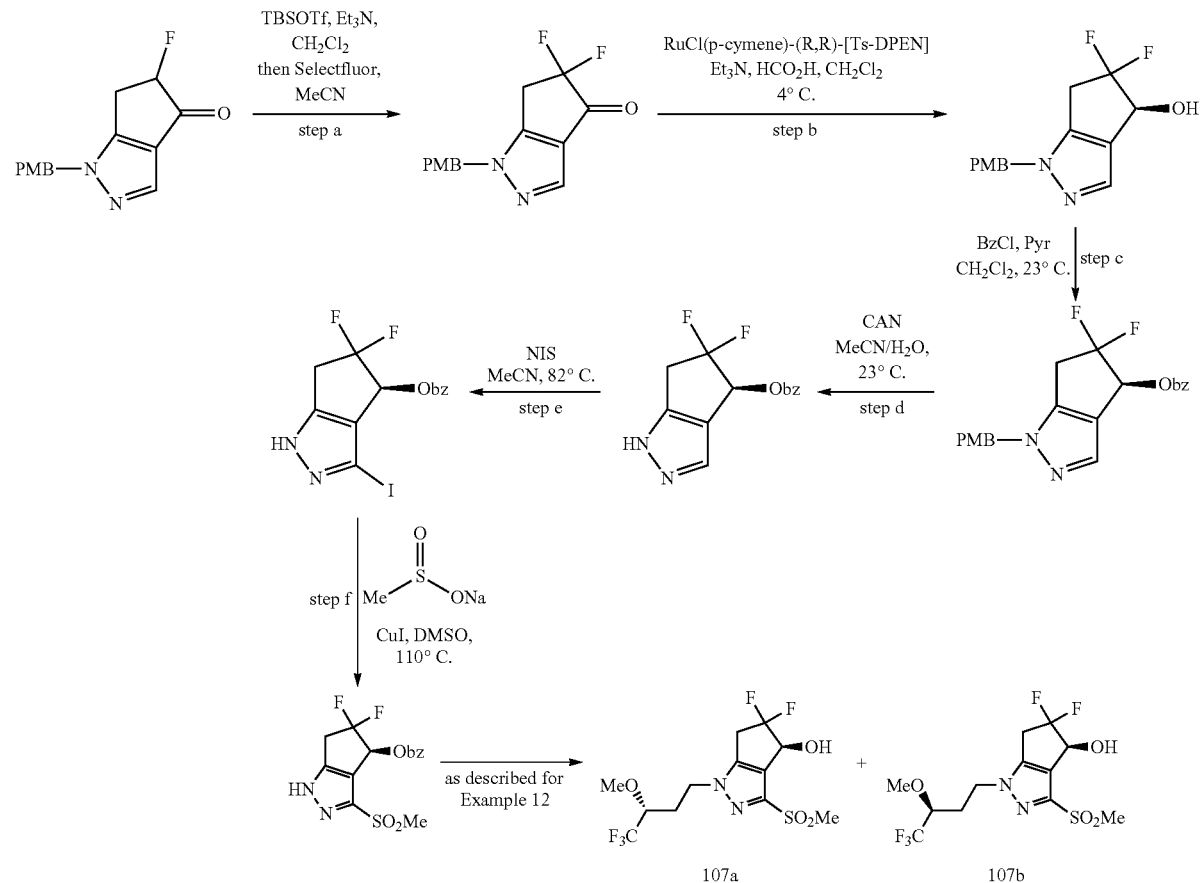

Step a: To a solution of 5-fluoro-1-[(4-methoxyphenyl)methyl]-5,6-dihydrocyclopenta[c]pyrazol-4-one (6.07 g, 23.3 mmol) and Et$_3$N (19.4 mL, 0.14 mol) in dichloromethane (117.0 mL), TBSOTf (21.5 mL, 93.3 mmol) was added dropwise at 0° C. The resulting solution was stirred at room temperature for 1.5 h. Solvent was removed under reduced pressure to afford the crude silyl enol ether. This material was dissolved in acetonitrile (117.0 mL) and Selectfluor (16.5 g, 46.6 mmol) was added portion-wise at 0° C. The resulting mixture was stirred at room temperature for 2 h. Reaction was diluted with EtOAc (150.0 mL), washed with water (2×100 mL), then brine (100 ml). The organic phase was dried over Na$_2$SO$_4$, concentrated to dryness under reduced pressure and the crude product was purified by column chromatography (SiO$_2$ EtOAc in hexanes, 0 to 60%) to give the corresponding α,α-difluoroketone compound (4.31 g, 15.5 mmol, 66% yield).

Step b: To a solution of α,α-difluoroketone from step a (4.86 g, 17.5 mmol) in dichloromethane (88.0 mL) was added formic acid (4.0 mL, 0.105 mol) and triethylamine (9.70 mL, 69.9 mmol). The resulting solution was cooled to 0° C., RuCl(p-cymene)[(R,R)-TsDPEN](0.45 g, 0.67 mmol) was added in one portion, and the resulting mixture was maintained at +4° C. overnight. Once TLC analysis indicated complete disappearance of the starting material, the mixture was diluted with dichloromethane (30.0 mL) and washed with aq. sat. NaHCO$_3$ solution (40.0 mL), dried over Na$_2$SO$_4$ and concentrated to dryness under reduced pressure to provide the crude α,α-difluorohydrin. The crude product was purified by column chromatography (SiO$_2$ EtOAc in hexanes, 0 to 70%) to give the corresponding α,α-difluoroketone compound (2.73 g, 9.74 mmol, 55% yield).

Step c: The alcohol from step b (1.53 g, 5.46 mmol) was dissolved in dichloromethane (55.0 mL), then pyridine (1.10 mL, 13.7 mmol), and benzoyl chloride (1.30 mL, 10.9 mmol) were added sequentially at 0° C. The reaction mixture was warmed up to room temperature and stirred for 6 h. Upon confirming complete reaction by TLC, the mixture was diluted with dichloromethane (20.0 mL) and washed with water (20 mL), then 1 M HCl (20 mL) and finally brine (20 mL). The organic phase was separated, dried over Na$_2$SO$_4$ and concentrated to dryness under reduced pressure. The crude product was purified by column chromatography (SiO$_2$ EtOAc in hexanes, 0 to 40%) to give the corresponding benzoylated alcohol (1.64 g, 4.27 mmol, 78% yield).

Step d: The product of step c (0.60 g, 1.56 mmol) was dissolved in a mixture of MeCN (6.40 mL) and water (1.6 mL), and CAN (3.42 g, 6.24 mmol) was added. Reaction was stirred at room temperature for 30 min. Upon complete PMB group removal (TLC control), reaction was diluted with EtOAc (10 mL), washed with water (2×10 mL), aq. sat. NaHCO$_3$ (10 mL), and brine (10 mL). The organic phase was separated, dried over Na$_2$SO$_4$ and concentrated to dryness under reduced pressure. The crude product was purified by column chromatography (SiO$_2$ EtOAc in hexanes, 0 to 70%) to give the corresponding tetrahydroindazole (0.30 g, 1.13 mmol, 73% yield).

Step e: The tetrahydroindazole from step d (0.90 g, 3.41 mmol) and N-iodosuccinimide (2.30 g, 10.2 mmol) were dissolved in DMF (17 mL), and the reaction mixture was heated at 70° C. for 16 h. Then the mixture was cooled to ambient temperature, diluted with EtOAc (15.0 mL), washed with aq. sat. Na$_2$S$_2$O$_3$ (10.0 mL), then water (2×10 mL), and finally brine (10 mL). The organic phase was separated, dried over Na$_2$SO$_4$ and concentrated to dryness under reduced pressure. The crude product was purified by column chromatography (SiO$_2$ EtOAc in hexanes, 0 to 80%) to give the corresponding iodotetrahydroindazole (1.10 g, 2.82 mmol, 83% yield).

Step f: The iodotetrahydroindazole from step e (0.50 g, 1.28 mmol) was dissolved in DMSO (5.10 mL), and sodium methanesulfinate (0.39 g, 3.84 mmol) and CuI (0.73 g, 3.84 mmol) were added. Reaction was heated to 110° C. for 2.5 h when LCMS showed full consumption of starting material. Reaction was cooled down, diluted with EtOAc (10 mL) and aq. sat. NH$_4$Cl (5 mL) was added. It was stirred for 2 h at room temperature. Organic layer was separated, dried over Na$_2$SO$_4$ and concentrated to dryness under reduced pressure. The crude product was purified by column chromatography (SiO$_2$ EtOAc in hexanes, 0 to 90%) to give the corresponding methyl sulfone (0.25 g, 0.73 mmol, 57% yield).

The title compound was prepared in 2 additional steps in a similar fashion to that described for Example 50 using methyl sulfone from step f. It was isolated as a mixture of diastereomers (dr=1:1). $^1$H NMR (400 MHz, CDCl$_3$) δ 5.22 (overlapping ddt, J=12.2, 3.3, 1.6 Hz, 2H), 4.63 (overlapping td, J=6.6, 6.1, 4.6 Hz, 4H), 3.65 (overlapping dddp, J=12.9, 9.6, 6.4, 3.2 Hz, 2H), 3.57 (overlapping s, 6H), 3.48-3.29 (m, 4H), 3.27 (overlapping s, 6H), 2.88 (overlapping ddd, J=4.5, 3.0, 1.5 Hz, 2H), 2.30 (overlapping dddd, J=20.5, 10.4, 7.4, 3.8 Hz, 2H), 2.23-2.09 (overlapping m, 2H). ESI MS [M+H]$^+$ for C$_{12}$H$_{15}$F$_5$N$_2$O$_4$S, calcd 379.1, found 379.1.

Example 108a and 108b: (4S)-1-[(1S,3S)-3-(difluoromethoxy)cyclohexyl]-5,5-difluoro-3-(trifluoromethyl)-1H,4H,5H,6H-cyclopenta[c]pyrazol-4-ol and (4S)-1-[(1R,3R)-3-(difluoromethoxy)cyclohexyl]-5,5-difluoro-3-(trifluoromethyl)-1H,4H,5H,6H-cyclopenta[c]pyrazol-4-ol

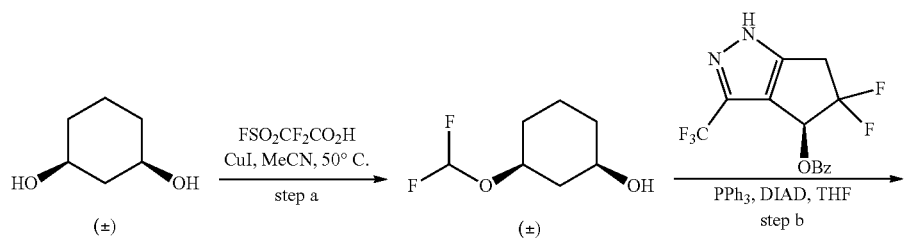

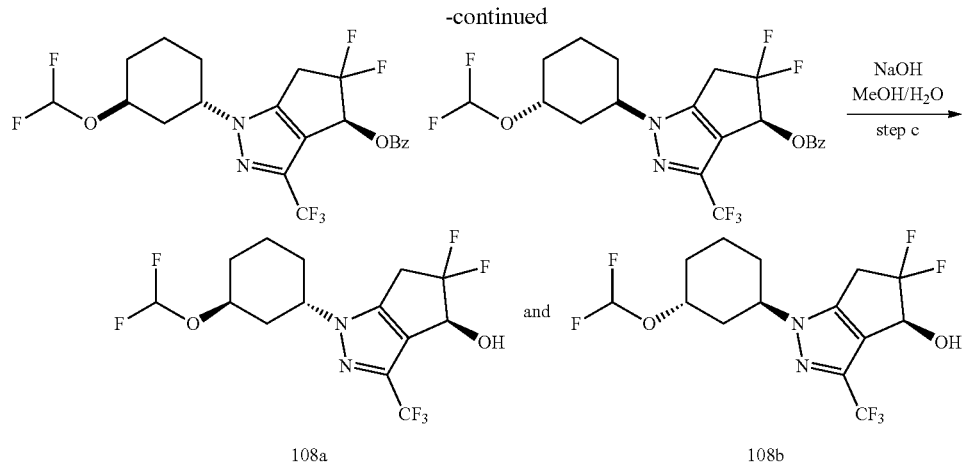

Step a: To a suspension of cis-1,3-cyclohexanediol (359 mg, 3.0 mmol, 1.0 equiv.), CuI (114 mg, 0.60 mmol, 0.20 equiv.) in MeCN (3 mL) was added a solution 2,2-difluoro-2-(fluorosulfonyl)acetic acid (0.641 g, 0.38 mL, 3.6 mmol, 1.2 equiv.) in MeCN (2 mL) at 50° C. over 10 min. The resulting mixture was heated at 50° C. for another 50 min and then cooled to room temperature for another 1 h stirring. The reaction mixture was then carefully quenched by a slow addition of saturated aqueous $NaHCO_3$ solution, and the mixture was diluted with EtOAc. After the layers were separated, the aqueous layer was extracted twice more with EtOAc. The combined organics were dried over $Na_2SO_4$ and concentrated. The crude material was purified by column chromatography using a gradient of 0 to 60% EtOAc in hexanes to afford cis-3-(difluoromethoxy)cyclohexanol (120 mg, 1.0 mmol, 34% yield).

Step b and c: The title compound was prepared in a similar fashion to Example 53 from cis-3-(difluoromethoxy)cyclohexanol, from step a, and [(4S)-5,5-difluoro-3-(trifluoromethyl)-4,6-dihydro-1H-cyclopenta[c]pyrazol-4-yl] benzoate. The compound was isolated as mixture of diastereomers. $^1$H NMR (400 MHz, Chloroform-d) δ 6.27 (t, J=74.8 Hz, 1H), 5.13-5.03 (m, 1H), 4.77-4.67 (m, 1H), 4.61 (tt, J=9.9, 5.0 Hz, 0.3H), 4.49-4.32 (m, 0.7H), 3.56-3.13 (m, 2H), 2.50-2.35 (m, 1H), 2.31-2.07 (m, 3H), 2.00-1.73 (m, 4H). ESI MS [M+H]$^+$ for $C_{14}H_{15}F_7N_2O_2$, calcd 377.1, found 377.1.

Example 109a and 109b: (4S)-1-[(1S,3S)-4,4-difluoro-3-methoxycyclohexyl]-5,5-difluoro-3-(trifluoromethyl)-1H,4H,5H,6H-cyclopenta[c]pyrazol-4-ol and (4S)-1-[(1R,3R)-4,4-difluoro-3-methoxycyclohexyl]-5,5-difluoro-3-(trifluoromethyl)-1H,4H,5H,6H-cyclopenta[c]pyrazol-4-ol

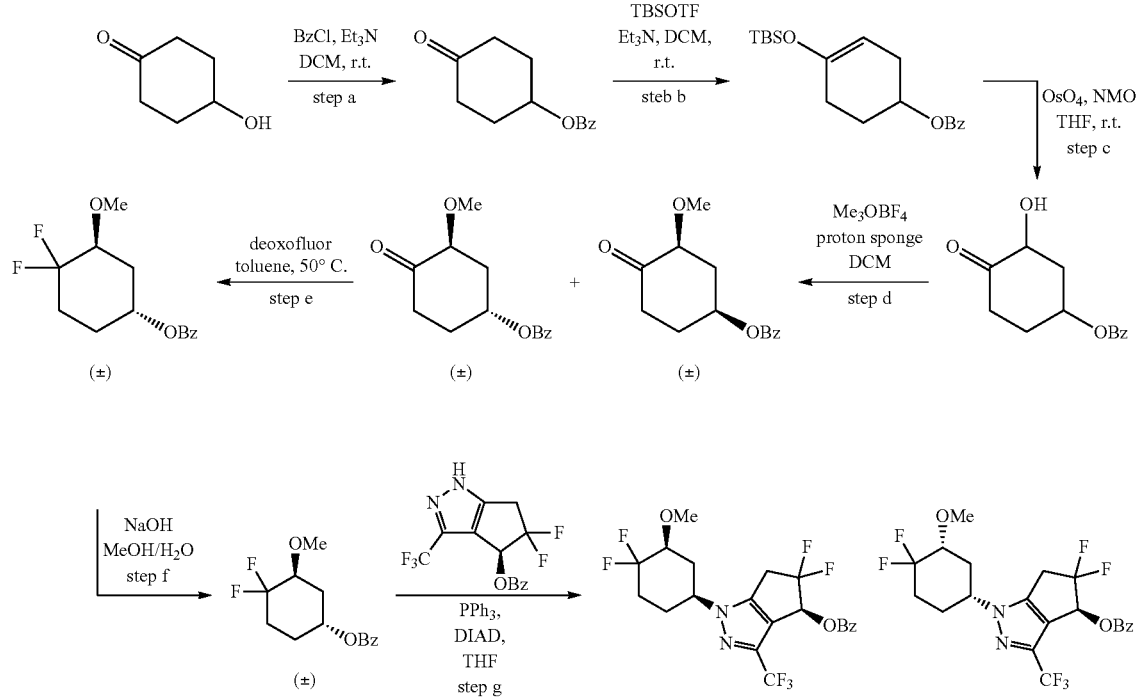

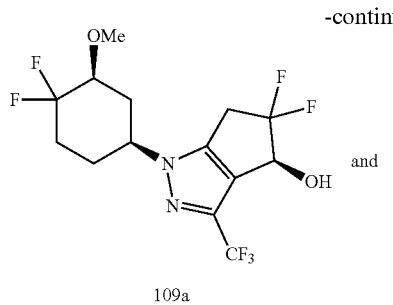
109a and

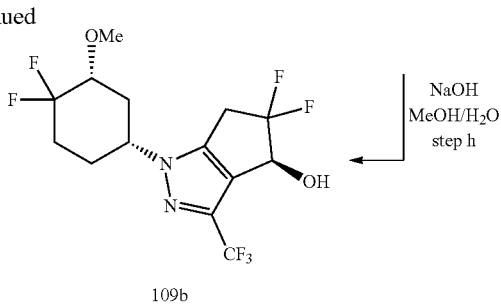
109b

NaOH
MeOH/H₂O
step h

Step a: To a solution of 4-hydroxycyclohexanone (5.00 g, 43.8 mmol, 1.0 equiv.) and triethylamine (6.65 g, 9.2 mL, 65.7 mmol, 1.5 equiv.) in DCM (150 mL) was added benzoyl chloride (6.78 g, 5.6 mL, 48.2 mmol, 1.1 equiv.) at room temperature. The resulting solution was stirred at room temperature for overnight. The reaction mixture was then quenched by a slow addition of saturated aqueous $NaHCO_3$ solution, and the mixture was diluted with DCM. After the layers were separated, the aqueous layer was extracted twice more with DCM. The combined organics were dried over $Na_2SO_4$ and concentrated. The crude material was purified by column chromatography using a gradient of 0 to 20% EtOAc in hexanes to afford the benzoate product (5.23 g, 24.0 mmol, 55% yield).

Step b: To a solution of the benzoate product from step a (4.00 g, 18.3 mmol, 1.0 equiv.) and triethylamine (5.46 g, 7.5 mL, 54.0 mmol, 3.0 equiv.) in DCM (90 mL) was added tert-butyldimethylsilyl trifluoromethanesulfonate (5.81 g, 5.1 mL, 22.0 mmol, 1.2 equiv.) at 0° C. The resulting mixture was kept stirring at this temperature for 30 min before quenched with saturated aqueous $NaHCO_3$ solution. The mixture was diluted with DCM. After the layers were separated, the aqueous layer was extracted once more with DCM. The combined organics were dried over $Na_2SO_4$ and concentrated. The crude material was purified by column chromatography using a gradient of 0 to 10% EtOAc in hexanes to afford silyl enol ether product (6.01 g, 18.0 mmol, 99% yield).

Step c: To a solution of silyl enol ether product from step b (6.01 g, 18.0 mmol, 1.0 equiv.) and N-methylmorpholine N-oxide (3.48 g, 29.7 mmol, 1.65 equiv.) in THF (300 mL) was added a solution of $OsO_4$ (~0.08 M in $H_2O$, 3.3 mL, 0.27 mmol, 1.5 mol %) at room temperature. The resulting mixture was stirred at room temperature for overnight before quenched with saturated aqueous $Na_2S_2O_3$ solution. The mixture was diluted with EtOAc. After the layers were separated, the aqueous layer was extracted twice more with EtOAc. The combined organics were dried over $Na_2SO_4$ and concentrated. The crude material was purified by column chromatography using a gradient of 0 to 50% EtOAc in hexanes to afford the hydroxy ketone product (2.85 g, 12.2 mmol, 68% yield) in a mixture of cis and trans isomers in 1:1 ratio.

Step d: To a solution of the hydroxy ketone product from step c (1.70 g, 7.3 mmol, 1.0 equiv.) and "proton sponge" 1,8-bis(dimethylamino)naphthalene (2.81 g, 13.1 mmol, 1.8 equiv.) in DCM (37 mL) was added trimethyloxonium tetrafluoroborate (1.73 g, 11.7 mmol, 1.6 equiv.) at room temperature. The resulting mixture was stirred at room temperature for overnight. The greenish grey suspension was then quenched with $H_2O$ and diluted with DCM. After the layers were separated, the aqueous layer was extracted once more with DCM. The combined organics were dried over $Na_2SO_4$ and concentrated. The crude material was purified by column chromatography using a gradient of 0 to 20% EtOAc in hexanes to afford trans-isomer of methylated product (1.12 g, 4.5 mmol, 62% yield) and cis-isomer of methylated product (330 mg, 1.3 mmol, 18% yield).

Step e: To a solution of the trans methylated product from step d (45.2 mg, 0.182 mmol, 1.0 equiv.) in toluene (0.34 mL) was added deoxofluor (2.7 M in toluene, 0.34 mL, 0.91 mmol, 5.0 equiv.) at room temperature. The resulting solution was heated at 50° C. for 2 h before being cooled and quenched with saturated aqueous $NaHCO_3$ solution. The mixture was diluted with EtOAc. After the layers were separated, the aqueous layer was extracted twice more with EtOAc. The combined organics were dried over $Na_2SO_4$ and concentrated. The crude material was purified by column chromatography using a gradient of 0 to 15% EtOAc in hexanes to afford the difluorocyclohexane product (35.8 mg, 0.132 mmol, 73% yield).

Step f: To a solution of the difluorocyclohexane product from step e (35.8 mg, 0.132 mmol) in methanol (0.5 mL) was added 1 M NaOH aqueous solution (1.0 mL) at room temperature. The resulting mixture was stirred at room temperature for 2 h before diluted with EtOAc and $H_2O$. After the layers were separated, the aqueous layer was extracted twice more with EtOAc. The combined organics were dried over $Na_2SO_4$ and concentrated. The crude material of trans-4,4-difluoro-3-methoxycyclohexanol (23.0 mg) was directly applied in the next step without further purification.

Step g and h: The title compounds were isolated as a mixture, and were prepared in a similar fashion to Example 53 from trans-4,4-difluoro-3-methoxycyclohexanol and [(4S)-5,5-difluoro-3-(trifluoromethyl)-4,6-dihydro-1H-cyclopenta[c]pyrazol-4-yl] benzoate. $^1$H NMR (400 MHz, Chloroform-d) δ 5.05 (dd, J=12.1, 5.5 Hz, 1H), 4.32 (t, J=12.6 Hz, 1H), 3.55 (s, 3H), 3.54-3.40 (m, 2H), 3.34 (td, J=16.0, 4.4 Hz, 1H), 2.52-2.40 (m, 2H), 2.33 (dddt, J=14.3, 10.8, 7.4, 3.6 Hz, 1H), 2.21-1.97 (m, 3H), 1.83 (dtt, J=32.2, 13.8, 3.8 Hz, 1H). ESI MS [M+H]$^+$ for $C_{14}H_{15}F_7N_2O_2$, calcd 377.1, found 377.1.

Example 110a and 110b: (4S)-1-[(1R,3R)-3-(difluoromethoxy)cyclopentyl]-5,5-difluoro-3-(trifluoromethyl)-1H,4H,5H,6H-cyclopenta[c]pyrazol-4-ol and (4S)-1-[(1S,3S)-3-(difluoromethoxy)cyclopentyl]-5,5-difluoro-3-(trifluoromethyl)-1H,4H,5H,6H-cyclopenta[c]pyrazol-4-ol

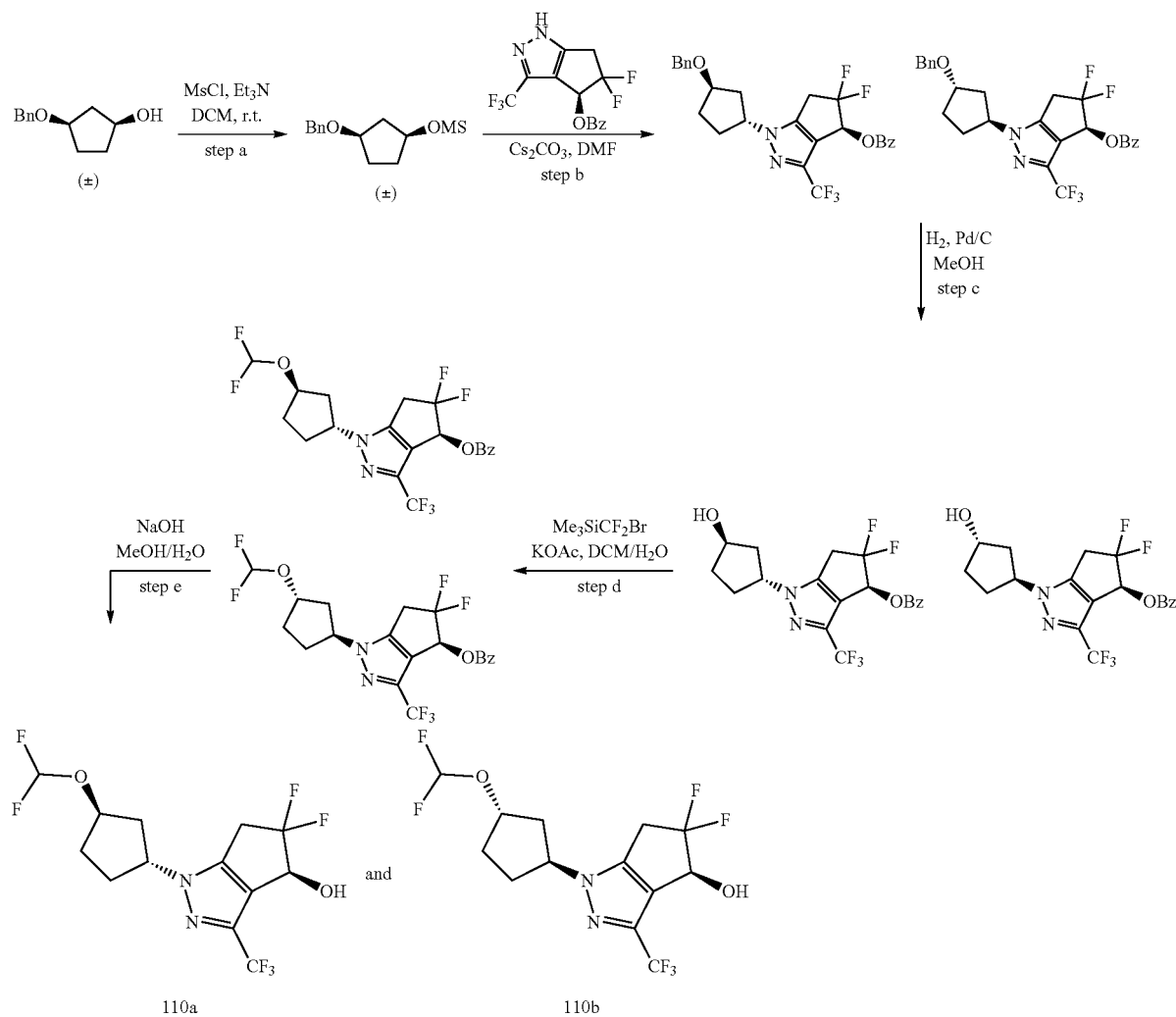

Step a: The mesylate intermediate was prepared in a similar fashion to that described for Example 5 from cis-3-(benzyloxy)cyclopentanol.

Step b: The cyclopentane intermediate was prepared in a similar fashion to that described for Example 1.

Step c: To a solution of the product from step b (144 mg, 0.28 mmol) in methanol (2.8 mL) was added Pd/C (10 wt % Pd, 36 mg). The resulting mixture was purged with $H_2$ and then stirred with $H_2$ balloon at room temperature for overnight. The mixture was filtered through Celite and then concentrated under vacuum. The crude material was directly applied in the next step.

Step d: To a solution of the crude product from step c (128 mg, 0.31 mmol, 1.0 equiv.) and potassium acetate (245 mg, 2.5 mmol, 8.0 equiv.) in DCM/$H_2O$ (1:1 v/v, 1 mL) was added (bromodifluoromethyl)trimethylsilane (508 mg, 0.39 mL, 2.5 mmol, 8.0 equiv.) at room temperature. The resulting mixture was stirred at room temperature for overnight. Additional 10 mL of DCM was added, and the organic layer was separated, dried over $Na_2SO_4$, and concentrated. The crude material was purified by column chromatography using a gradient of 0 to 20% EtOAc in hexanes to afford the difluoromethylated product (121 mg, 0.26 mmol, 84% yield).

Step e: The deprotection step was conducted in a similar fashion to that described for Example 1, affording the title compounds (83.0 mg) as a 1:1 mixture of trans isomers on cyclopentane. $^1$H NMR (400 MHz, Chloroform-d) δ 6.21 (t, J=74.6 Hz, 1H), 5.06 (dd, J=12.0, 5.6 Hz, 1H), 4.91 (tdd, J=5.3, 3.0, 1.7 Hz, 1H), 4.72 (p, J=7.7 Hz, 1H), 3.49-3.20 (m, 2H), 2.53-2.23 (m, 5H), 2.15-1.91 (m, 2H). ESI MS [M+H]$^+$ for $C_{13}H_{13}F_7N_2O_2$, calcd 363.1, found 363.1.

Example 111a and 111b: (4S)-1-[(1R,3S)-4,4-difluoro-3-methoxycyclohexyl]-5,5-difluoro-3-(trifluoromethyl)-1H,4H,5H,6H-cyclopenta[c]pyrazol-4-ol and (4S)-1-[(1S,3R)-4,4-difluoro-3-methoxycyclohexyl]-5,5-difluoro-3-(trifluoromethyl)-1H,4H,5H,6H-cyclopenta[c]pyrazol-4-ol

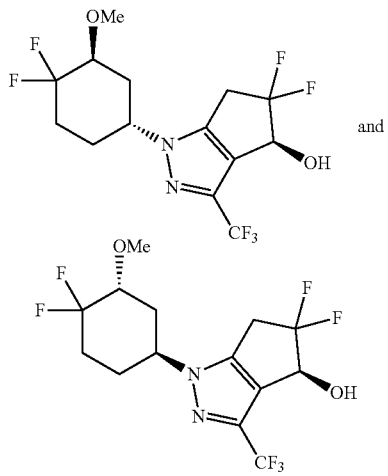

The title compounds were isolated as a mixture, and were prepared in a similar fashion to Example 109 from cis-4,4-difluoro-3-methoxycyclohexanol and [(4S)-5,5-difluoro-3-(trifluoromethyl)-4,6-dihydro-1H-cyclopenta[c]pyrazol-4-yl] benzoate. $^1$H NMR (400 MHz, Chloroform-d) δ 5.05 (dd, J=12.1, 5.4 Hz, 1H), 4.57-4.37 (m, 1H), 3.68-3.60 (m, 1H), 3.57-3.19 (m, 5H), 2.51-2.41 (m, 1H), 2.37-2.22 (m, 2H), 2.19-2.02 (m, 2H). ESI MS [M+H]$^+$ for $C_{14}H_{15}F_7N_2O_2$, calcd 377.1, found 377.1.

Example 112a and 112b: (4S)-1-[(1R,3S)-3-(difluoromethoxy)cyclohexyl]-5,5-difluoro-3-(trifluoromethyl)-1H,4H,5H,6H-cyclopenta[c]pyrazol-4-ol and (4S)-1-[(1S,3R)-3-(difluoromethoxy)cyclohexyl]-5,5-difluoro-3-(trifluoromethyl)-1H,4H,5H,6H-cyclopenta[c]pyrazol-4-ol The title compounds were isolated as a mixture, and prepared in a similar fashion to Example 108 from trans-1,3-cyclohexanediol. $^1$H NMR (400 MHz, Chloroform-d) δ 6.24 (t, J=74.2 Hz, 1H), 5.06 (dd, J=12.1, 5.6 Hz, 1H), 4.29-4.07 (m, 2H), 3.54-3.26 (m, 2H), 2.52-2.40 (m, 1H), 2.38 (dd, J=5.6, 2.0 Hz, 1H), 2.19-2.05 (m, 2H), 2.04-1.88 (m, 2H), 1.79-1.64 (m, 1H), 1.54-1.37 (m, 2H). ESI MS [M+H]$^+$ for $C_{14}H_{15}F_7N_2O_2$, calcd 377.1, found 377.1.

Example 113: (4S)-1-[(4,4-difluorocyclohexyl)methyl]-5,5-difluoro-3-(trifluoromethyl)-1H, 4H, 5H, 6H-cyclopenta[c]pyrazol-4-ol The title compound was prepared in a similar fashion to Example 53 from 4,4-difluorocyclohexanemethanol and [(4S)-5,5-difluoro-3-(trifluoromethyl)-4,6-dihydro-1H-cyclopenta[c]pyrazol-4-yl] benzoate. $^1$H NMR (400 MHz, Chloroform-d) δ 5.08 (dd, J=11.9, 5.6 Hz, 1H), 3.99-3.87 (m, 2H), 3.38 (ddd, J=16.5, 15.3, 10.1 Hz, 1H), 3.25 (td, J=16.0, 4.6 Hz, 1H), 2.55 (dd, J=5.6, 2.0 Hz, 1H), 2.18-2.06 (m, 3H), 1.82-1.62 (m, 4H), 1.42-1.30 (m, 2H). ESI MS [M+H]$^+$ for $C_{14}H_{15}F_7N_2O$, calcd 361.1, found 361.1.

Example 114: (4S)-5,5-difluoro-1-(4-fluorophenyl)-3-(trifluoromethyl)-4,6-dihydrocyclopenta[c]pyrazol-4-ol

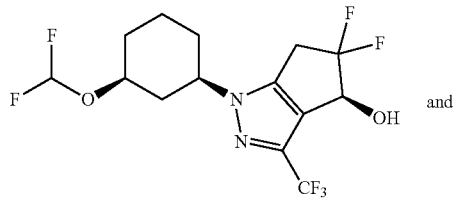

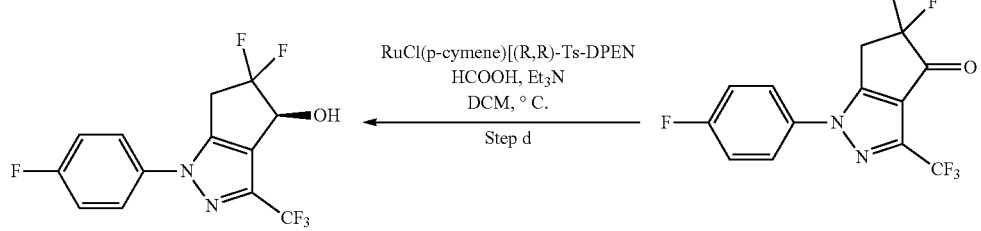

Step a: reaction conducted in a similar fashion to Example 53, step b.

Step b: The starting ketone (380 mg, 1.34 mmol), 3-methoxypropylamine (0.410 mL. 4.02 mmol, 3.0 eq.), and pivalic acid (11 mg, 8 mol %) were dissolved in a 1:1 mixture of toluene/cyclohexane, and the reaction mixture was heated to reflux with a Dean-Stark condenser overnight. The reaction mixture was cooled to room temperature and concentrated. The crude material was used in the next step without purification.

Step c: Crude material from step b was dissolved in acetonitrile (13 mL, 0.1M), Na$_2$SO$_4$ (381 mg, 2.68 mmol, 2 eq) and Selectfluor (1.42 g, 4.02 mmol, 3 eq) were added, and the mixture was heated to 65° C. for 2 hours. The reaction was cooled to room temperature, quenched with 1N aqueous HCl and extracted with EtOAc, the combined organics were dried over Na$_2$SO$_4$ and concentrated. The crude was purified using flash column chromatography (using 0 to 50% EtOAc/hexanes gradient) to obtain the difluoroketone intermediate (247 mg, 0.772 mmol, 58%).

Step d: Reaction conducted in a similar fashion to Example 1, step f.

$^1$H NMR (400 MHz, Chloroform-d) δ 7.61-7.51 (m, 2H), 7.25-7.15 (m, 2H), 5.15 (dd, J=12.0, 5.6 Hz, 1H), 3.72-3.57 (m, 1H), 3.49 (ddd, J=16.8, 15.5, 4.4 Hz, 1H), 2.46 (app d, J=2.5 Hz, 1H). ESI MS [M+H]$^+$ for C$_{13}$H$_9$F$_6$N$_2$O, calcd 323.1, found 323.1.

Example 115: 1-(3,4-difluorophenyl)-5,5-difluoro-3-(trifluoromethyl)-6H-cyclopenta[c]pyrazol-4-one mmol, 1 equiv.) were dissolved in ethanol (8.3 mL) and the solution was heated to reflux overnight. The reaction mixture was cooled to ambient temperature, concentrated, and purified by flash chromatography (100% CH$_2$Cl$_2$) to yield the product as a solid (430 mg, 51%).

Step b: The ketone from step a (430 mg, 1.42 mmol, 1 equiv.) was dissolved in CH$_2$Cl$_2$ (3.6 mL), and triethylamine (0.59 mL, 4.27 mmol, 3 equiv.) was added, followed by TBSOTf (0.65 mL, 2.85 mmol, 2 equiv.). The reaction mixture stirred for 30 minutes, and the solvent was removed under a gentle stream of nitrogen. The crude residue was suspended in MeCN (5.7 mL) and Selectfluor® (629 mg, 1.78 mmol, 1.25 equiv.) was added. The reaction mixture stirred for 15 minutes, and the reaction was quenched with 1M HCl, extracted with EtOAc, washed with brine, dried, and concentrated. Purification by flash chromatography (50-100% CH$_2$Cl$_2$/hexanes) afforded the product as a white solid (398 mg, 87%).

Step c: The ketone from step b (160 mg, 0.5 mmol, 1 equiv.) was converted to the product in analogous fashion to step b to yield the product as a white solid (138 mg, 84%).

Step d: The ketone from step c (135 mg, 0.4 mmol, 1 equiv.) was dissolved in CH$_2$Cl$_2$. Formic acid (0.045 mL, 1.2 mmol, 3 equiv.), triethylamine (0.11 mL, 0.8 mmol, 2 equiv.), and RuCl(p-cymene)[(R,R)-TsDPEN] were added sequentially. The reaction mixture was stirred overnight, concentrated, and purified by flash chromatography (50-100% CH$_2$Cl$_2$/hexanes) to yield the title compound as a

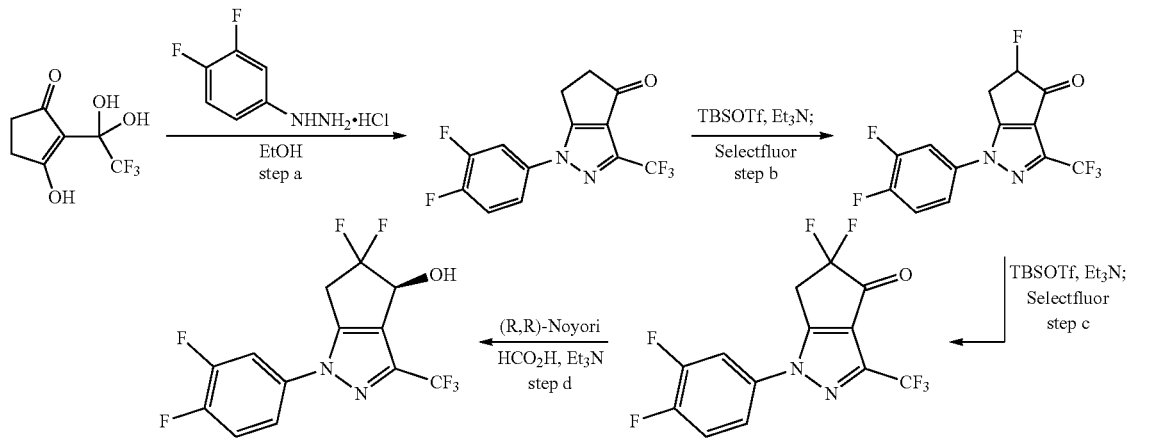

Step a: (3,4-difluorophenyl)hydrazine hydrochloride (500 mg, 2.77 mmol, 1 equiv.) and 3-hydroxy-2-(2,2,2-trifluoro-1,1-dihydroxyethyl)cyclopent-2-en-1-one (587 mg, 2.77 white foam (136 mg, 100%). $^1$H NMR (400 MHz, CDCl$_3$) δ 7.61 (ddd, J=10.6, 6.7, 2.7 Hz, 1H), 7.43 (dddd, J=9.1, 4.0, 2.6, 1.5 Hz, 1H), 7.34 (td, J=9.2, 8.0 Hz, 1H), 3.33-3.25 (m, 2H), 3.25-3.14 (m, 2H). 19F NMR (376 MHz, CDCl$_3$) δ −62.4, −132.6, −136.2. ESI MS [M+H]$^+$ for C$_{13}$H$_7$F$_7$N$_2$O, calcd 341.1, found 341.1.

Example 116: (4S)-1-(4-chlorophenyl)-5,5-difluoro-3-(trifluoromethyl)-4,6-dihydrocyclopenta[c]pyrazol-4-ol

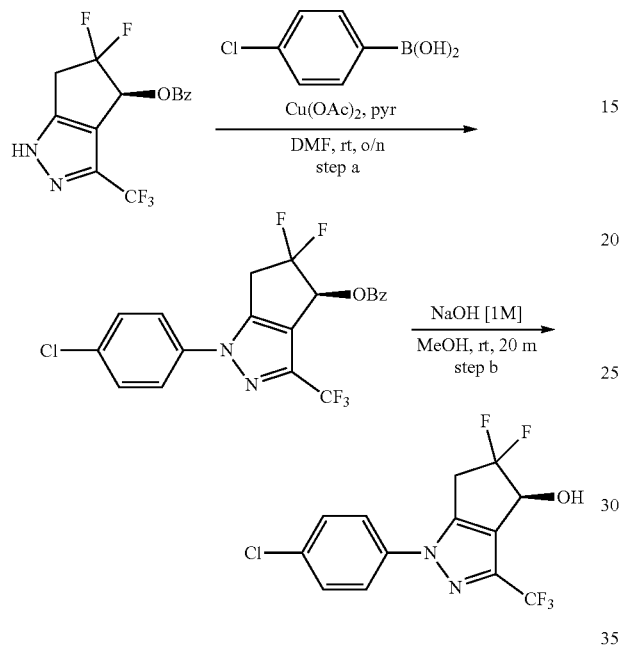

Step a: To [(4S)-5,5-difluoro-3-(trifluoromethyl)-4,6-dihydro-1H-cyclopenta[c]pyrazol-4-yl] benzoate (66 mg, 0.20 mmol, 1.0 eq) in DMF (1.0 mL) at room temperature was added (4-chlorophenyl)boronic acid (62 mg, 0.40 mmol, 2.0 eq), Cu(OAc)$_2$ (55 mg, 0.30 mmol, 1.5 eq), and pyridine (32 µL, 0.40 mmol, 2.0 eq) and the mixture was stirred at room temperature under air overnight. Upon completion, the reaction was diluted with DCM, filtered through a syringe filter, and concentrated. The crude residue was purified via flash column chromatography (ISCO, Redisep 4 g column, 0-40% EA/Hex gradient) to afford [(4S)-1-(4-chlorophenyl)-5,5-difluoro-3-(trifluoromethyl)-4,6-dihydrocyclopenta[c]pyrazol-4-yl]benzoate (26 mg, 30%).

Step b: To the product of step a (26 mg, 0.059 mmol, 1.0 eq) in MeOH (2.25 mL) at room temperature was added 1 M NaOH (0.75 mL, 0.75 mmol, 13 eq) and the mixture was stirred at room temperature for 20 minutes. Upon completion, the reaction was quenched with satd. NH$_4$Cl and diluted with ethyl acetate. The layers were separated, and the aqueous layer was extracted with ethyl acetate. The combined organic layers were dried over Na$_2$SO$_4$, filtered, and concentrated. The crude residue was purified via flash column chromatography (ISCO (ELS), Redisep 4 g column, 0-80% EA/Hex gradient) to afford (4S)-1-(4-chlorophenyl)-5,5-difluoro-3-(trifluoromethyl)-4,6-dihydrocyclopenta[c]pyrazol-4-ol (17 mg, 88%). $^1$H NMR (400 MHz, Chloroform-d) δ 7.58-7.50 (m, 2H), 7.50-7.40 (m, 2H), 5.14 (dd, J=12.1, 5.2 Hz, 1H), 3.75-3.40 (m, 2H), 2.58 (dd, J=5.7, 1.9 Hz, 1H). ESI MS [M+H]$^+$ for C$_{13}$H$_9$ClF$_5$N$_2$O, calcd 339.0, found 339.0.

Example 117: (4S)-5,5-difluoro-3-(trifluoromethyl)-1-[4-(trifluoromethyl)phenyl]-4,6-dihydrocyclopenta[c]pyrazol-4-ol

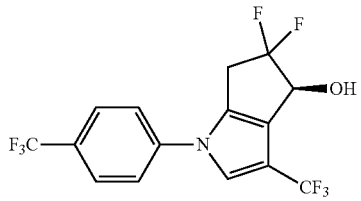

The title compound was prepared in a similar fashion to that described for Example 116 from [4-(trifluoromethyl)phenyl]boronic acid. $^1$H NMR (400 MHz, Chloroform-d) δ 7.84-7.64 (m, 4H), 5.16 (dd, J=12.0, 5.4 Hz, 1H), 3.81-3.49 (m, 2H), 2.55 (dd, J=5.6, 2.0 Hz, 1H). ESI MS [M+H]$^+$ for C$_{13}$H$_9$F$_8$N$_2$O, calcd 373.1, found 373.1.

Example 118: (4S)-1-(3,4-dichlorophenyl)-5,5-difluoro-3-(trifluoromethyl)-4,6-dihydrocyclopenta[c]pyrazol-4-ol

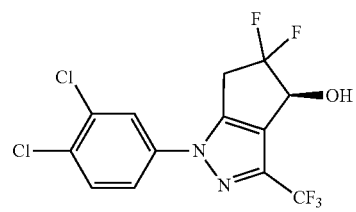

The title compound was prepared in a similar fashion to that described for Example 116 from (3,4-dichlorophenyl)boronic acid. $^1$H NMR (400 MHz, Chloroform-d) δ 7.75 (d, J=2.6 Hz, 1H), 7.58 (d, J=8.7 Hz, 1H), 7.43 (dd, J=8.7, 2.6 Hz, 1H), 5.14 (dd, J=12.0, 5.4 Hz, 1H), 3.78-3.39 (m, 2H), 2.53 (dd, J=5.7, 2.0 Hz, 1H). ESI MS [M+H]$^+$ for C$_{13}$H$_8$Cl$_2$F$_5$N$_2$O, calcd 373.0, found 373.0.

Example 119: (4S)-1-(4-chloro-3-fluorophenyl)-5,5-difluoro-3-(trifluoromethyl)-4,6-dihydrocyclopenta[c]pyrazol-4-ol

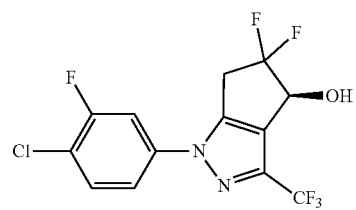

The title compound was prepared in a similar fashion to that described for Example 116 from (4-chloro-3-fluorophenyl)boronic acid. $^1$H NMR (400 MHz, Chloroform-d) δ 7.53 (t, J=8.2 Hz, 1H), 7.49 (dd, J=9.5, 2.6 Hz, 1H), 7.31 (ddd, J=8.8, 2.6, 1.2 Hz, 1H), 5.13 (dd, J=12.1, 5.0 Hz, 1H), 3.77-3.45 (m, 2H), 2.66-2.50 (m, 1H). ESI MS [M+H]$^+$ for C$_{13}$H$_8$ClF$_6$N$_2$O, calcd 357.0, found 357.0.

Example 120: (4S,5R)-5-fluoro-1-[3-(trifluoromethoxy)propyl]-3-(trifluoromethyl)-4,5,6,7-tetrahydroindazol-4-ol

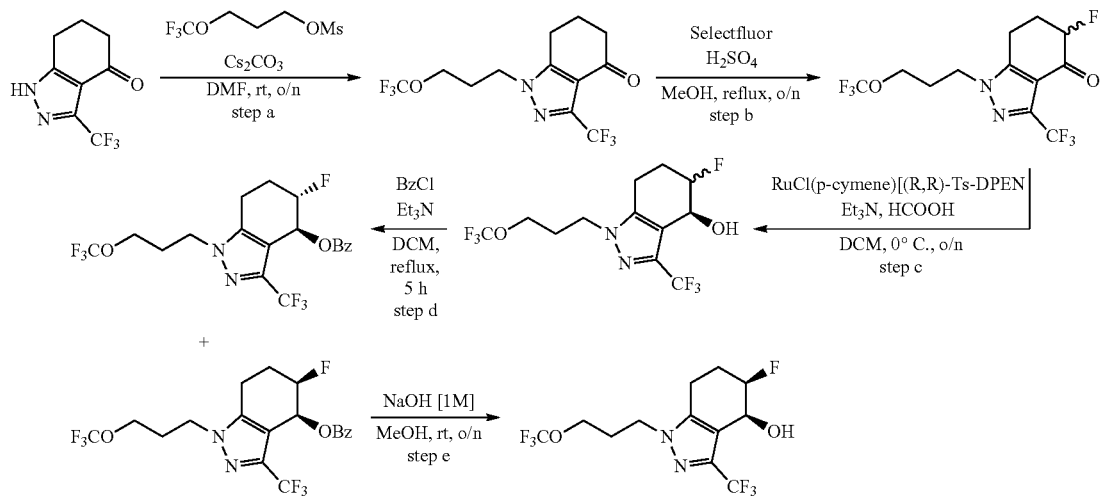

(3-(trifluoromethoxy)propyl methanesulfonate) was prepared in a similar fashion to that described for Example 5.

Step a: To 3-(trifluoromethyl)-1,5,6,7-tetrahydroindazol-4-one (510 mg, 2.50 mmol, 1.0 eq) in DMF (0.25 M, 10 mL) at room temperature was added $Cs_2CO_3$ (1.22 g, 3.75 mmol, 1.5 eq) followed by 3-(trifluoromethoxy)propyl methanesulfonate (666 mg, 3.00 mmol, 1.2 eq) and the mixture was stirred at room temperature overnight. Upon completion, the reaction was quenched with satd. $NH_4Cl$ and diluted with ethyl acetate. The layers were separated, and the aqueous layer was extracted with ethyl acetate. The combined organic layers were washed with water (2×) and then dried over $Na_2SO_4$, filtered, and concentrated. The crude residue was purified via flash column chromatography (ISCO, Redisep 12 g column, 0-100% EA/Hex gradient) to afford 1-[3-(trifluoromethoxy)propyl]-3-(trifluoromethyl)-6,7-dihydro-5H-indazol-4-one as a yellow oil (503 mg, 61%).

Step b: To the product of step a (503 mg, 1.48 mmol, 1.0 eq) in MeOH (0.4 M, 4 mL) at room temperature was added Selectfluor (578 mg, 1.63 mmol, 1.1 eq) followed by conc. $H_2SO_4$ (8 µL, 0.15 mmol, 0.1 eq) and the mixture was heated to reflux overnight. Upon completion, the reaction was cooled to room temperature, quenched with satd. $NaHCO_3$, and diluted with ethyl acetate. The layers were separated and the aqueous layer was extracted with ethyl acetate. The combined organic layers were washed with water (2×) and then dried over $Na_2SO_4$, filtered, and concentrated to afford 5-fluoro-1-[3-(trifluoromethoxy)propyl]-3-(trifluoromethyl)-6,7-dihydro-5H-indazol-4-one as a clear oil (517 mg, quant.).

Step c: To the product of step b (517 mg, 1.48 mmol, 1.0 eq) in DCM (0.1 M, 15 mL) at room temperature was added $Et_3N$ (411 µL, 2.97 mmol, 2.0 eq) followed by formic acid (168 µL, 4.46 mmol, 3.0 eq). The mixture was degassed for −10 minutes, cooled to 0° C., RuCl(p-cymene)[(R,R)-Ts-DPEN] (47 mg, 0.075 mmol, 0.05 eq) was added, and the mixture was stirred at 0° C. overnight. Upon completion, the reaction was concentrated and purified via flash column chromatography (ISCO, Redisep 12 g column, 0-80% EA/Hex gradient) to afford (4S,5R)-5-fluoro-1-[3-(trifluoromethoxy)propyl]-3-(trifluoromethyl)-4,5,6,7-tetrahydroindazol-4-ol and (4S,5S)-5-fluoro-1-[3-(trifluoromethoxy)propyl]-3-(trifluoromethyl)-4,5,6,7-tetrahydroindazol-4-ol (243 mg, 47%) as a clear oil and an inseparable mixture of diastereomers (~1.7:1 cis:trans).

Step d: To the products of step c (233 mg, 0.67 mmol, 1.0 eq) and DMAP (20 mg, 0.17 mmol, 0.25 eq) in DCM (0.1 M, 6.7 mL) at room temperature were added $Et_3N$ (184 µL, 1.33 mmol, 2.0 eq) followed by benzoyl chloride (93 µL, 0.80 mmol, 1.2 eq) and the mixture was heated to reflux for 5 hours. Upon completion, the reaction was cooled to room temperature and quenched with 1 M HCl. The layers were separated, and the aqueous layer was extracted with DCM. The combined organic layers were dried over $Na_2SO_4$, filtered, and concentrated. The crude residue was purified via flash column chromatography (ISCO, Redisep 12 g column, 0-60% EA/Hex gradient) to afford [(4S,5S)-5-fluoro-1-[3-(trifluoromethoxy)propyl]-3-(trifluoromethyl)-4,5,6,7-tetrahydroindazol-4-yl] benzoate as a clear oil (21 mg, 7%, first eluting isomer) and [(4S,5R)-5-fluoro-1-[3-(trifluoromethoxy)propyl]-3-(trifluoromethyl)-4,5,6,7-tetrahydroindazol-4-yl] benzoate as a clear oil (41 mg, 14%, second eluting isomer).

Step e: To [(4S,5R)-5-fluoro-1-[3-(trifluoromethoxy)propyl]-3-(trifluoromethyl)-4,5,6,7-tetrahydroindazol-4-yl] benzoate (41 mg, 0.090 mmol, 1.0 eq) in MeOH (2.25 mL) at room temperature was added 1 M NaOH (0.75 mL, 0.75 mmol, 8.3 eq) and the mixture was stirred at room temperature overnight. Upon completion, the reaction was quenched with satd. $NH_4Cl$ and diluted with ethyl acetate. The layers were separated, and the aqueous layer was extracted with ethyl acetate. The combined organic layers were dried over $Na_2SO_4$, filtered, and concentrated. The crude residue was purified via flash column chromatography (ISCO (ELS), Redisep 4 g column, 0-80% EA/Hex gradient) to afford (4S,5R)-5-fluoro-1-[3-(trifluoromethoxy)propyl]-3-(trifluoromethyl)-4,5,6,7-tetrahydroindazol-4-ol (29 mg, 92%). $^1H$ NMR (400 MHz, Chloroform-d) δ 5.01 (dt, J=9.8, 4.2 Hz, 1H), 4.86 (ddt, J=47.2, 10.4, 3.2 Hz, 1H), 4.17-4.12 (m, 2H), 4.00-3.89 (m, 2H), 2.91-2.79 (m, 1H), 2.71-2.59 (m, 1H), 2.56-2.41 (m, 1H), 2.36 (dd, J=5.0, 2.8 Hz, 1H), 2.33-2.21 (m, 2H), 2.13-1.99 (m, 1H). ESI MS [M+H]$^+$ for $C_{12}H_{14}F_7N_2O_2$, calcd 351.1, found 351.1.

Example 121: (4S)-5,5-difluoro-1-[(1R,3S)-3,4,4-trifluorocyclohexyl]-3-(trifluoromethyl)-4,6-dihydrocyclopenta[c]pyrazol-4-ol

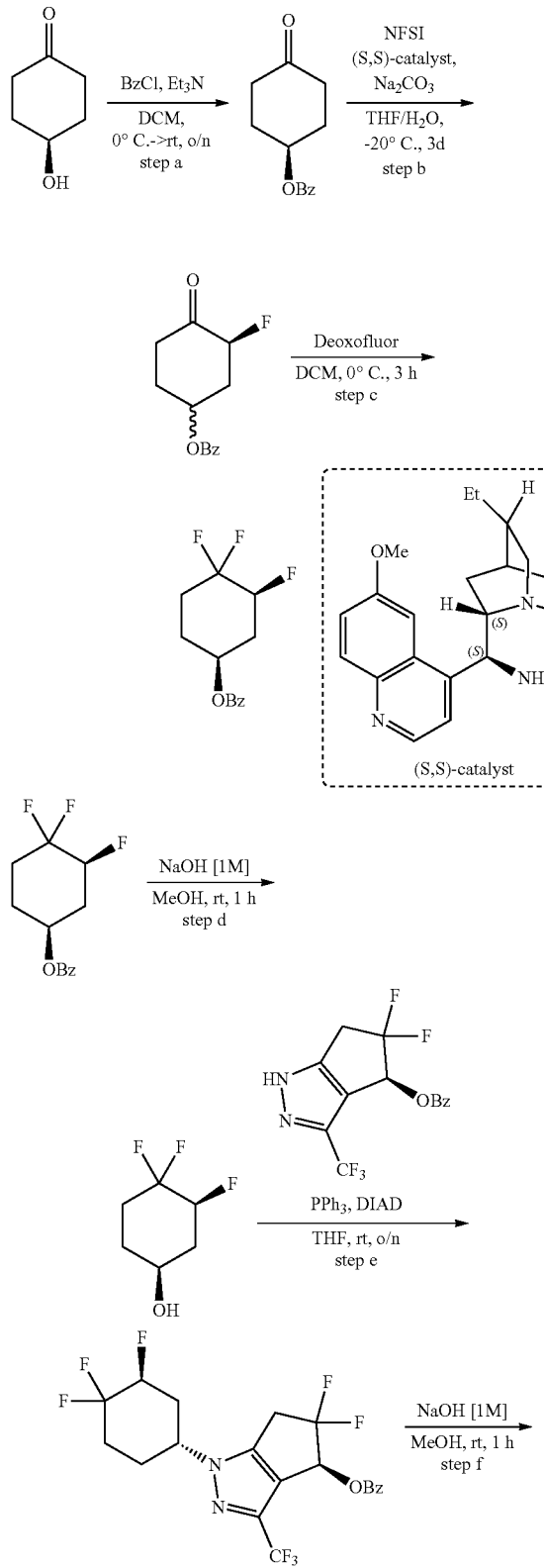

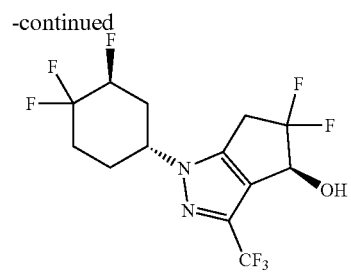

Step a: To 4-hydroxycyclohexan-1-one (11.4 g, 100 mmol, 1.0 eq) in DCM (0.33 M, 300 mL) at 0° C. was added Et₃N (27.7 mL, 120 mmol, 1.2 eq) followed by benzoyl chloride (14.0 mL, 200 mmol, 2.0 eq) and the mixture was warmed to room temperature overnight. Upon completion, the reaction was quenched with 1 M HCl. The layers were separated and the aqueous layer was extracted with DCM. The combined organic layers were dried over Na₂SO₄, filtered, and concentrated. The crude residue was purified via flash column chromatography (ISCO, Redisep 220 g column, 0-40% EA/Hex gradient) to afford (4-oxocyclohexyl) benzoate as a yellowish solid (20.0 g, 92%).

Step b: (S)-[(2S,4S,5R)-5-ethyl-1-azabicyclo[2.2.2]octan-2-yl]-(6-methoxyquinolin-4-yl)methanamine (1.30 g, 4.00 mmol, 20 mol %) was dissolved in THF (40 mL) and trichloroacetic acid (688 mg, 4.20 mmol, 21 mol %) was added followed by water (72 µL). The reaction mixture was stirred at room temperature for 10 minutes. In a separate flask, NFSI (12.6 g, 40.0 mmol, 2.0 eq) and Na₂CO₃ (3.18 g, 30.0 mmol, 1.5 eq) were combined and placed under nitrogen. The solution containing catalyst was added to the flask containing NFSI and Na₂CO₃ and cooled to −20° C. (4-oxocyclohexyl) benzoate (4.36 g, 20.0 mmol, 1.0 eq) was then added all at once and the mixture was stirred at −20° C. under nitrogen for 3 days. Upon completion, the reaction was filtered over a pad of silica and concentrated. The crude residue was purified via flash column chromatography (ISCO, Redisep 40 g column, 0-50% EA/DCM gradient and then ISCO, Redisep 40 g column, 0-80% EA/Hex gradient) to afford [(1S,3S)-3-fluoro-4-oxocyclohexyl] benzoate and [(1R,3S)-3-fluoro-4-oxocyclohexyl] benzoate as a white solid and an inseparable mixture of diastereomers (1.22 g, 26%).

Step c: To the product of step b (1.20 g, 5.08 mmol, 1.0 eq) in DCM (0.1 M, 50 mL) at 0° C. was added Deoxofluor (6.59 mL, 17.8 mmol, 3.5 eq, 2.7 M in PhMe) and the mixture was stirred at 0° C. for 3 hours. Upon completion, the reaction was quenched with satd. NaHCO₃ and extracted with DCM. The combined organic layers were dried over Na₂SO₄, filtered, and concentrated. The crude residue was purified via flash column chromatography (ISCO, Redisep 24 g column, 0-40% EA/Hex gradient) to afford [(1R,3S)-3,4,4-trifluorocyclohexyl] benzoate (0.93 g, 71%, first eluting isomer) as a clear oil and [(1S,3S)-3,4,4-trifluorocyclohexyl] benzoate as a clear oil (0.15 g, 11%, second eluting isomer).

Step d: To [(1S,3S)-3,4,4-trifluorocyclohexyl] benzoate (140 mg, 0.54 mmol, 1.0 eq) in MeOH (7.5 mL) at room temperature was added 1 M NaOH (2.5 mL, 0.05 M total) and the mixture was stirred at room temperature for 1 hour. Upon completion, the reaction was quenched with satd. NH₄Cl and diluted with ethyl acetate. The layers were separated, and the aqueous layer was extracted with ethyl acetate. The combined organic layers were dried over Na₂SO₄, filtered, and concentrated. The crude residue was purified via flash column chromatography (ISCO, Redisep 4 g column, 0-80% EA/Hex gradient) to afford (1S,3S)-3,4,4-trifluorocyclohexan-1-ol (59 mg, 71%).

Step e: 5,5-difluoro-3-(trifluoromethyl)-4,6-dihydro-1H-cyclopenta[c]pyrazol-4-yl] benzoate (85 mg, 0.26 mmol, 1.0 eq) in THF (4.0 mL) at room temperature was added PPh$_3$ (120 mg, 0.46 mmol, 1.8 eq), (1S,3S)-3,4,4-trifluorocyclohexan-1-ol (59 mg, 0.38 mmol, 1.5 eq) and DIAD (100 µL, 0.51 mmol, 2.0 eq) and the mixture was stirred at room temperature overnight. Upon completion, the reaction was concentrated and purified via flash column chromatography (ISCO (ELS), Redisep 4 g column, 0-40% EA/Hex gradient) to afford [(4S)-5,5-difluoro-1-[(1R,3S)-3,4,4-trifluorocyclohexyl]-3-(trifluoromethyl)-4,6-dihydrocyclopenta[c]pyrazol-4-yl] benzoate (9.0 mg, 8%).

Step f: To the product of step e (9.0 mg, 0.019 mmol, 1.0 eq) in MeOH (0.75 mL) at room temperature was added 1 M NaOH (0.25 mL, 0.02 M total) and the mixture was stirred at room temperature for 1 hours. Upon completion, the reaction was quenched with satd. NH$_4$Cl and diluted with ethyl acetate. The layers were separated, and the aqueous layer was extracted with ethyl acetate. The combined organic layers were dried over Na$_2$SO$_4$, filtered, and concentrated. The crude residue was purified via flash column chromatography (ISCO, Redisep 4 g column, 0-60% EA/Hex gradient) to afford (4S)-5,5-difluoro-1-[(1R,3S)-3,4,4-trifluorocyclohexyl]-3-(trifluoromethyl)-4,6-dihydrocyclopenta[c]pyrazol-4-ol (4.6 mg, 66%). $^1$H NMR (400 MHz, Chloroform-d) δ 5.07 (d, J=12.0 Hz, 1H), 4.95-4.76 (m, 1H), 4.50-4.36 (m, 1H), 3.52-3.22 (m, 2H), 2.59-2.06 (m, 7H). ESI MS [M+H]$^+$ for C$_{13}$H$_{13}$F$_8$N$_2$O, calcd 365.1, found 365.1.

Example 122: (4S)-5,5-difluoro-1-[(1S,3R)-3,4,4-trifluorocyclohexyl]-3-(trifluoromethyl)-4,6-dihydrocyclopenta[c]pyrazol-4-ol

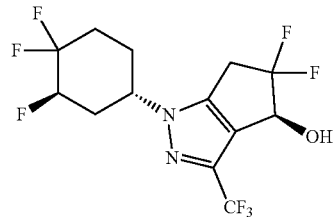

The title compound was prepared in a similar fashion to that described for Example 121 using (R)-[(2R,4S,5R)-5-ethyl-1-azabicyclo[2.2.2]octan-2-yl]-(6-methoxyquinolin-4-yl)methanamine in step b. $^1$H NMR (400 MHz, Chloroform-d) δ 5.15-4.96 (m, 1H), 4.85 (d, J=47.8 Hz, 1H), 4.53-4.37 (m, 1H), 3.52-3.20 (m, 2H), 2.62-2.07 (m, 7H). ESI MS [M+H]$^+$ for C$_{13}$H$_{13}$F$_8$N$_2$O, calcd 365.1, found 365.1.

Example 123 and 124: (4S,6R)-5,5,6-trifluoro-1-(4,4,4-trifluorobutyl)-3-(trifluoromethyl)-1H,4H,5H,6H-cyclopenta[c]pyrazol-4-ol and (4S,6S)-5,5,6-trifluoro-1-(4,4,4-trifluorobutyl)-3-(trifluoromethyl)-1H,4H,5H,6H-cyclopenta[c]pyrazol-4-ol

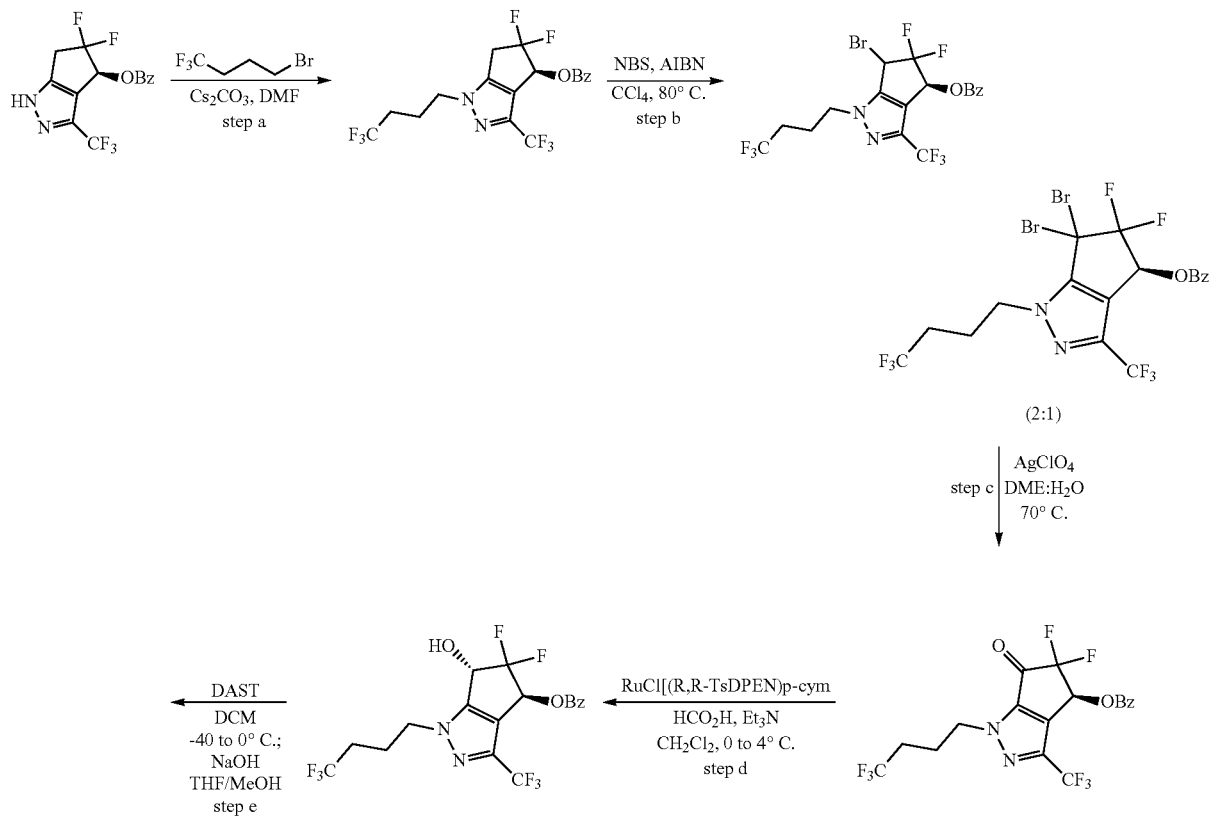

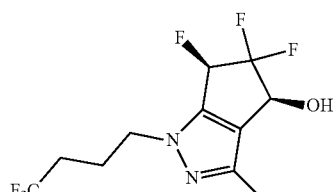

123

+

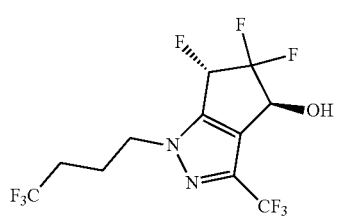

124

Step a: The target compound was prepared in a similar fashion to that described for Example 53.

Step b: To a solution of the product from step a (344 mg, 0.78 mmol) in CCl$_4$ (3.9 mL) was added AIBN (13 mg, 0.08 mmol) and NBS (180 mg, 1.01 mmol). The reaction was heated to 80° C. for 4 hours. After cooling to room temperature, the mixture was partitioned between ethyl acetate and water. The organic layer was washed with brine, dried over MgSO$_4$ and concentrated in vacuo. Purification by column chromatography (SiO$_2$, gradient 25-100 CH$_2$Cl$_2$/hexane) provided a 2:1 mixture of mono- and di-brominated products (263 mg).

Step c: To a solution of the products from step b (219 mg, ~0.4 mmol) in DME/H$_2$O (10:1, 0.1M) was added AgClO$_4$ (261 mg, 1.26 mmol). The mixture was heated to 70° C. overnight. After cooling to room temperature, the mixture was diluted with EtOAc and washed with water and brine. The organics were dried over MgSO$_4$ and concentrated under reduced pressure. The product was isolated following column chromatography (SiO$_2$, 0-40% EtOAc/hexane).

Step d: To a solution of triethylamine (39 μL, 0.28 mmol) and formic acid (16 μL, 0.42 mmol) at 0° C. in dichloromethane (2.8 mL) was added the product from step c followed by RuCl(p-cymene)[(R,R)-Ts-DPEN] (4.5 mg, 0.007 mmol). The mixture was stirred at 2-8° C. overnight then diluted with CH$_2$Cl$_2$ and washed with water. The organics were dried over MgSO$_4$ and concentrated under reduced pressure to afford the target molecule which was used in subsequent reactions without any further purification.

Step e: To a solution of the product from step d (25 mg, 0.055 mmol) in CH$_2$Cl$_2$ (0.55 mL) at −40° C. was added diethylaminosulfur trifluoride (22 μL, 0.165 mmol). The reaction was allowed to slowly warm to 0° C. and stir an addition 30 minutes. The reaction was quenched with saturated aqueous sodium bicarbonate solution the diluted with EtOAc and water. The organic layer was separated, dried over MgSO4, and concentrated under reduced pressure. The residue was taken up in MeOH/THF (1:1, 550 μL) and 1.0M NaOH (330 μL) was added. The mixture was stirred 2 hours then diluted with EtOAc and water. The organics were dried over MgSO$_4$ and concentrated under reduced pressure. The diastereomeric products Ex. 123 (major) and 124 (minor) were separated by C18 (gradient MeCN/H$_2$O with 0.1% formic acid).

Example 123, second eluting isomer: $^1$H NMR (400 MHz, Chloroform-d) δ 5.85 (ddd, J=56.2, 6.8, 2.3 Hz, 1H), 5.38-5.24 (m, 1H), 4.29 (qt, J=13.8, 6.5 Hz, 2H), 2.50 (d, J=6.1 Hz, 1H), 2.34-2.07 (m, 4H), 1.57 (s, 1H). ESI MS [M+H]$^+$ for C$_{11}$H$_9$F$_9$N$_2$O, calcd 357.1, found 357.3.

Example 124, first eluting isomer: $^1$H NMR (400 MHz, Chloroform-d) δ 5.58 (dd, J=55.7, 9.3 Hz, 1H), 5.07 (ddd, J=10.1, 6.6, 2.9 Hz, 1H), 4.31 (ddq, J=20.7, 13.8, 6.6 Hz, 2H), 2.48 (d, J=6.7 Hz, 1H), 2.32-2.05 (m, 3H). ESI MS [M+H]$^+$ for C$_{11}$H$_9$F$_9$N$_2$O, calcd 357.1, found 357.3.

Example 125 and 126: (4S)-5,5-difluoro-1-[(1R,3r,5S)-6,6-difluorobicyclo[3.1.0]hexan-3-yl]-3-(trifluoromethyl)-1H,4H,5H,6H-cyclopenta[c]pyrazol-4-ol and (4S)-1-{6,6-difluorobicyclo[3.1.0]hexan-3-yl}-5,5-difluoro-3-(trifluoromethyl)-1H,4H,5H,6H-cyclopenta[c]pyrazol-4-ol

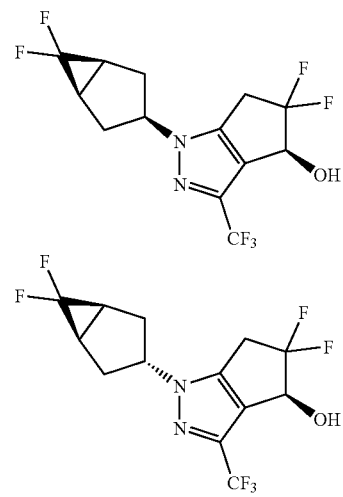

The title compound was prepared in a similar fashion to that described for Example 53 via the reaction of 6,6-Difluorobicyclo[3.1.0]hexan-3-ol.

First eluting diastereomer (DIAST-1) $^1$H NMR (400 MHz, CDCl$_3$) δ 5.15-4.90 (m, 1H), 4.19 (dq, J=13.2, 7.1 Hz, 1H), 3.55-3.17 (m, 2H), 2.71-2.43 (m, 1H), 2.12 (m, 2H), 1.93 (ddd, J=13.6, 4.0, 1.7 Hz, 1H), 1.38-1.16 (m, 2H). ESI MS [M+H]$^+$ for C$_{13}$H$_{11}$F$_5$N$_2$O$_2$, calcd 345.2, found 345.1.

Second eluting diastereomer (DIAST-2) $^1$H NMR (400 MHz, CDCl$_3$) δ 5.06 (dd, J=12.0, 5.5 Hz, 1H), 4.48 (pd, J=8.6, 3.7 Hz, 1H), 3.53-3.16 (m, 2H), 2.78-2.54 (m, 1H), 2.48 (ddq, J=13.7, 8.1, 2.0 Hz, 2H), 2.41 (dd, J=5.6, 2.0 Hz, 1H), 2.15 (ddd, J=13.1, 3.8, 1.7 Hz, 2H). ESI MS [M+H]$^+$ for C$_{13}$H$_{11}$F$_5$N$_2$O$_2$, calcd 345.2, found 345.1.

Example 127: (4S)-1-(2,2-dioxo-2λ$^6$-thiaspiro[3.3]heptan-6-yl)-5,5-difluoro-3-(trifluoromethyl)-4,6-dihydrocyclopenta[c]pyrazol-4-ol

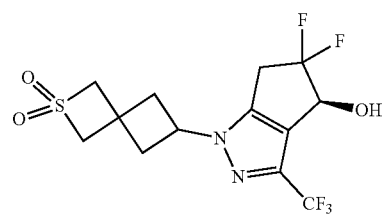 [SMILES: O=S1(=O)CC2(CC(n3nc(C(F)(F)F)c4c3CC(F)(F)[C@H]4O)C2)C1]

The title compound was prepared in a similar fashion to that described for Example 53 from 2,2-dioxo-2λ$^6$-thiaspiro[3.3]heptan-6-ol and [(4S,5R)-5-fluoro-3-(trifluoromethyl)-1,4,5,6-tetrahydro-cyclo-penta[c]pyrazol-4-yl] benzoate. $^1$H NMR (400 MHz, DMSO-d$_6$) δ 6.20 (d, J=7.3 Hz, 1H), 4.94-4.82 (m, 2H), 4.38-4.26 (m, 4H), 3.51 (dd, J=16.3, 8.1 Hz, 2H), 2.86-2.75 (m, 4H). ESI MS [M+H]$^+$ for C$_{13}$H$_{14}$F$_5$N$_2$O$_3$S, calcd 373.1, found 373.0.

Example 128: (4S)-1-[2-(difluoromethylsulfinyl)ethyl]-5,5-difluoro-3-(trifluoromethyl)-6,7-dihydro-4H-indazol-4-ol

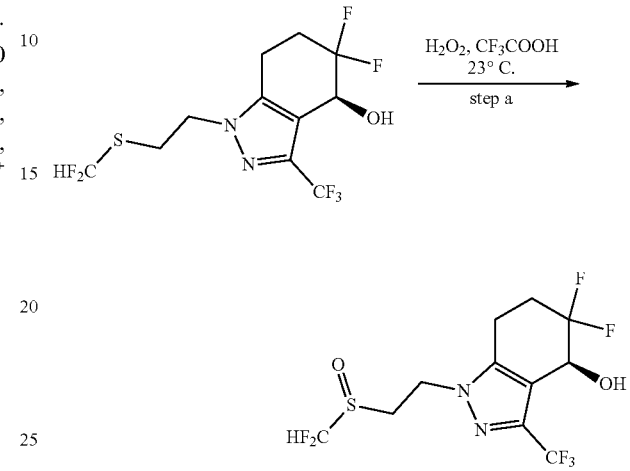

Step a: To the solution of (4S)-1-[2-(difluoromethylsulfanyl)ethyl]-5,5-difluoro-3-(trifluoromethyl)-6,7-dihydro-4H-indazol-4-ol (40 mg, 0.11 mmol, 1.0 equiv.) in CF$_3$COOH (0.17 mL, 0.67M) was added H$_2$O$_2$ (20 µL, 0.11 mmol, 1.0 equiv.) at room temperature. Reaction was let to stir for 2 h when it was diluted with water (1 mL) and quenched with solid NaHCO$_3$ to pH=7. The product was extracted with EtOAc (2×2 mL), and the combined organic layers were washed with water (4 mL), dried over Na$_2$SO$_4$, and evaporated to dryness. The crude residue was purified by column chromatography (SiO2, EtOAc in hexanes, 0 to 70%) to give the sulfoxide (30 mg, 0.082 mmol, 72% yield) as a colorless oil. $^1$H NMR (400 MHz, CDCl$_3$) δ 6.22 (td, J=54.5, 4.9 Hz, 1H), 4.86 (q, J=5.7 Hz, 1H), 4.52 (dd, J=7.4, 5.2 Hz, 2H), 3.63-3.30 (m, 2H), 3.12-2.75 (m, 3H), 2.53 (dddt, J=27.8, 13.8, 10.0, 7.1 Hz, 1H), 2.29 (qd, J=14.0, 11.6, 5.0 Hz, 1H). ESI MS [M+H]$^+$ for C$_{11}$H$_{11}$F$_7$N$_2$O$_2$S, calcd 369.0, found 369.0.

Example 129 and 130: (4S,7S)-5,5,7-trifluoro-1-(4,4,4-trifluorobutyl)-3-(trifluoromethyl)-6,7-dihydro-4H-indazol-4-ol and (4S,7R)-5,5,7-trifluoro-1-(4,4,4-trifluorobutyl)-3-(trifluoromethyl)-6,7-dihydro-4H-indazol-4-ol

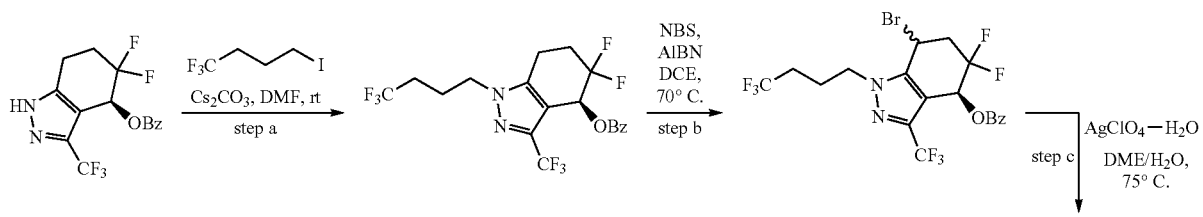

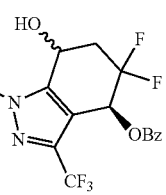 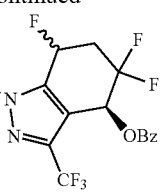 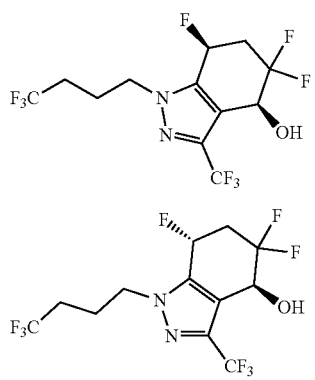

Step a: To a solution of [(4S)-5,5-difluoro-3-(trifluoromethyl)-1,4,6,7-tetrahydroindazol-4-yl] benzoate (322 mg, 0.93 mmol, 1.0 equiv.) in DMF (4.7 mL, 0.2 M) was added Cs$_2$CO$_3$ (606 mg, 1.86 mmol, 2.0 equiv.) and 1,1,1-trifluoro-4-iodobutane (0.14 mL, 1.12 mmol, 1.2 equiv.). The reaction was stirred for 16 hours at room temperature at which point it was quenched with saturated aqueous NH$_4$Cl (30 mL) and extracted with EtOAc (2×30 mL). The combined organics were dried over Na$_2$SO$_4$, filtered, and concentrated under vacuum. The crude residue was purified via silica gel flash column chromatography (0 to 50% EtOAc/hexanes) to afford the product (295 mg, 70% yield).

Step b: To a solution of [(4S)-5,5-difluoro-1-(4,4,4-trifluorobutyl)-3-(trifluoromethyl)-6,7-dihydro-4H-indazol-4-yl] benzoate (269 mg, 0.56 mmol, 1.0 equiv.) in DCE (6 mL, 0.1 M) was added NBS (110 mg, 0.62 mmol, 1.05 equiv.) and AIBN (~1 mg, ~0.006 mmol, ~0.01 equiv.). The reaction was heated to 70° C. and stirred for 1 hour at which point it was cooled to room temperature, quenched with saturated aqueous Na$_2$S$_2$O$_3$ (30 mL), and extracted with DCM (2×30 mL). The combined organics were dried over Na$_2$SO$_4$, filtered, and concentrated under vacuum. The crude residue was purified via silica gel flash column chromatography (0 to 45% EtOAc/hexanes) to afford the product as a 1:1 mixture of diastereomers (169 mg, 53% yield, 89% brsm).

Step c: To a solution of [(4S)-7-bromo-5,5-difluoro-1-(4,4,4-trifluorobutyl)-3-(trifluoromethyl)-6,7-dihydro-4H-indazol-4-yl] benzoate (165 mg, 0.31 mmol, 1.0 equiv.) in 10:1 DME/H$_2$O (3.1 mL, 0.1 M) was added AgClO$_4$—H$_2$O (210 mg, 0.93 mmol, 3.0 equiv.). The reaction was heated to 75° C. and stirred for 1 hour at which point it was cooled to room temperature, quenched with water (20 mL), and extracted with EtOAc (2×20 mL). The combined organics were dried over Na$_2$SO$_4$, filtered, and concentrated under vacuum. The crude residue was carried directly into Step d without further purification.

Step d: A solution of [(4S)-5,5-difluoro-7-hydroxy-1-(4,4,4-trifluorobutyl)-3-(trifluoromethyl)-6,7-dihydro-4H-indazol-4-yl] benzoate (150 mg, 0.32 mmol, 1.0 equiv.) in DCM (3.2 mL, 0.1 M) was cooled to 0° C. and DAST (210 μL, 1.59 mmol, 5.0 equiv.) was added dropwise. The reaction was stirred for 2 hours as the ice bath expired at which point it was quenched with saturated aqueous NaHCO$_3$ (10 mL) and extracted with DCM (2×10 mL). The combined organics were dried over MgSO$_4$, filtered, and concentrated under vacuum. The crude residue was purified via silica gel flash column chromatography (0 to 45% EtOAc/hexanes) to afford the product (105 mg, 69% yield).

Step e: To a solution of [(4S)-5,5,7-trifluoro-1-(4,4,4-trifluorobutyl)-3-(trifluoromethyl)-6,7-dihydro-4H-indazol-4-yl] benzoate (105 mg, 0.22 mmol, 1.0 equiv.) in MeOH (4.5 mL, 0.05 M) was added 1.0 M NaOH in H$_2$O (1.1 mL, 1.1 mmol, 5.0 equiv.). The reaction was stirred at room temperature for 2 hours at which point it was quenched with saturated aqueous NH$_4$Cl (10 mL) and extracted with EtOAc (2×10 mL). The combined organics were dried over Na$_2$SO$_4$, filtered, and concentrated under vacuum. The crude residue was purified via silica gel flash column chromatography (0 to 45% EtOAc/hexanes) to afford diastereomerically pure samples of (4S,7S)-5,5,7-trifluoro-1-(4,4,4-trifluorobutyl)-3-(trifluoromethyl)-6,7-dihydro-4H-indazol-4-ol (Example 129) and (4S,7R)-5,5,7-trifluoro-1-(4,4,4-trifluorobutyl)-3-(trifluoromethyl)-6,7-dihydro-4H-indazol-4-ol (Example 130).

First eluting diastereomer (DIAST-1, white sold, 35 mg, 43% yield): $^1$H NMR (400 MHz, Chloroform-d) δ 5.75 (dt, J=53.0, 7.7 Hz, 1H), 4.95 (q, J=5.6 Hz, 1H), 4.36-4.21 (m, 2H), 2.94-2.73 (m, 2H), 2.61 (d, J=4.3 Hz, 1H), 2.28-2.09 (m, 4H). ESI MS [M+H]$^+$ for C$_{12}$H$_{11}$F$_9$N$_2$O, calcd 371.1, found 371.1.

Second eluting diastereomer (DIAST-2, colorless oil, 25 mg, 31% yield): $^1$H NMR (400 MHz, Chloroform-d) δ 5.78 (ddt, J=52.1, 4.9, 2.2 Hz, 1H), 4.99 (t, J=5.7 Hz, 1H), 4.35-4.18 (m, 2H), 3.01-2.60 (m, 2H), 2.29-2.08 (m, 4H). ESI MS [M+H]$^+$ for C$_{12}$H$_{11}$F$_9$N$_2$O, calcd 371.1, found 371.2.

Example 131: (4S,5S,6R)-5,6-difluoro-1-[(3R)-4,4,4-trifluoro-3-methoxybutyl]-3-(trifluoromethyl)-5,6-dihydro-4H-cyclopenta[c]pyrazol-4-ol

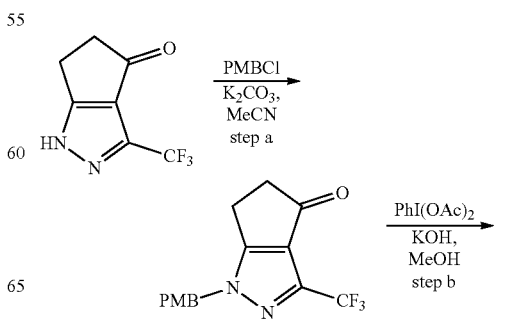

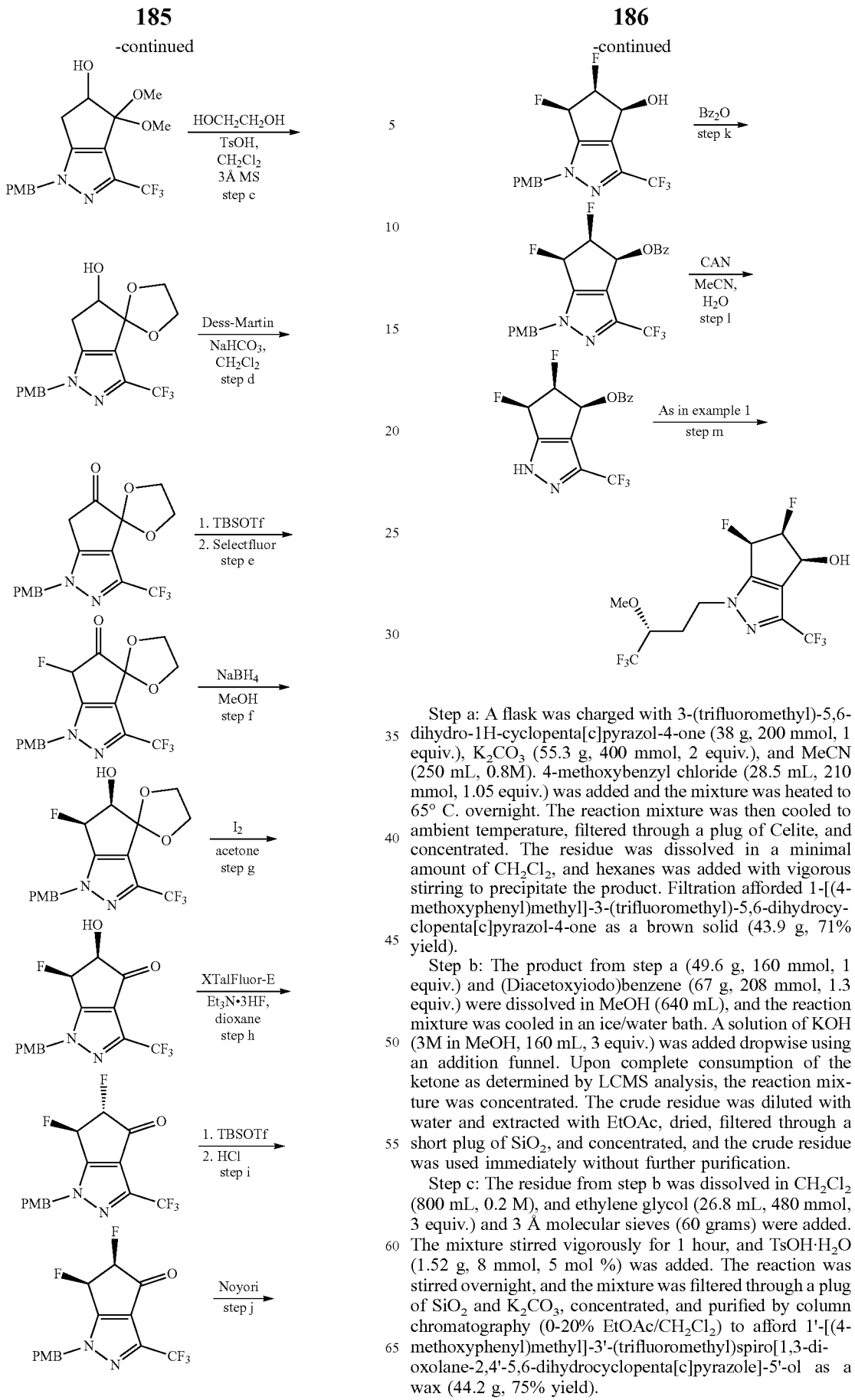

Step a: A flask was charged with 3-(trifluoromethyl)-5,6-dihydro-1H-cyclopenta[c]pyrazol-4-one (38 g, 200 mmol, 1 equiv.), $K_2CO_3$ (55.3 g, 400 mmol, 2 equiv.), and MeCN (250 mL, 0.8M). 4-methoxybenzyl chloride (28.5 mL, 210 mmol, 1.05 equiv.) was added and the mixture was heated to 65° C. overnight. The reaction mixture was then cooled to ambient temperature, filtered through a plug of Celite, and concentrated. The residue was dissolved in a minimal amount of $CH_2Cl_2$, and hexanes was added with vigorous stirring to precipitate the product. Filtration afforded 1-[(4-methoxyphenyl)methyl]-3-(trifluoromethyl)-5,6-dihydrocyclopenta[c]pyrazol-4-one as a brown solid (43.9 g, 71% yield).

Step b: The product from step a (49.6 g, 160 mmol, 1 equiv.) and (Diacetoxyiodo)benzene (67 g, 208 mmol, 1.3 equiv.) were dissolved in MeOH (640 mL), and the reaction mixture was cooled in an ice/water bath. A solution of KOH (3M in MeOH, 160 mL, 3 equiv.) was added dropwise using an addition funnel. Upon complete consumption of the ketone as determined by LCMS analysis, the reaction mixture was concentrated. The crude residue was diluted with water and extracted with EtOAc, dried, filtered through a short plug of $SiO_2$, and concentrated, and the crude residue was used immediately without further purification.

Step c: The residue from step b was dissolved in $CH_2Cl_2$ (800 mL, 0.2 M), and ethylene glycol (26.8 mL, 480 mmol, 3 equiv.) and 3 Å molecular sieves (60 grams) were added. The mixture stirred vigorously for 1 hour, and TsOH·$H_2O$ (1.52 g, 8 mmol, 5 mol %) was added. The reaction was stirred overnight, and the mixture was filtered through a plug of $SiO_2$ and $K_2CO_3$, concentrated, and purified by column chromatography (0-20% EtOAc/$CH_2Cl_2$) to afford 1'-[(4-methoxyphenyl)methyl]-3'-(trifluoromethyl)spiro[1,3-dioxolane-2,4'-5,6-dihydrocyclopenta[c]pyrazole]-5'-ol as a wax (44.2 g, 75% yield).

Step d: A suspension of the product from step c (44.2 g, 119 mmol, 1 equiv.) and NaHCO$_3$ (40.1 g, 477 mmol, 4 equiv.) in CH$_2$Cl$_2$ (476 mL, 0.25 M) was cooled in an ice/water bath. Dess-Martin periodinane (55.7 g, 131 mmol, 1.1 equiv.) was added. Upon complete consumption of the alcohol as determined by LCMS analysis, the reaction was quenched by addition of ~400 mL of half-saturated aqueous NaHCO$_3$. The organic layer was separated, dried, and concentrated. The crude residue was suspended in a minimal amount of CH$_2$Cl$_2$, and hexanes was added with vigorous stirring to precipitate the product. The solid was dissolved in EtOAc and washed with 1M NaOH, and the organic layer was separated, dried, and concentrated to afford 1'-[(4-methoxyphenyl)methyl]-3'-(trifluoromethyl)spiro[1,3-dioxolane-2,4'-6H-cyclopenta[c]pyrazole]-5'-one as a white solid (36.1 g, 82% yield).

Step e: The product from step d (36.1 g, 98 mmol, 1 equiv.) was dissolved in CH$_2$Cl$_2$ (250 mL, 0.4 M), and triethylamine (41 mL, 294 mmol, 3 equiv.) was added. TBSOTf (45 mL, 196 mmol, 2 equiv.) was then added. Upon complete consumption of the ketone as determined by LCMS analysis, the reaction was concentrated under a gentle stream of nitrogen gas. The crude residue was suspended in anhydrous MeCN (400 mL, 0.25 M), and the reaction mixture was cooled in an ice/water bath. Selectfluor (43.4 g, 123 mmol, 1.25 equiv.) was added, and the ice bath was removed after ~5 minutes. Upon complete consumption of the silyl enol ether by LCMS analysis, the reaction was quenched by addition of 400 mL EtOAc and 400 mL of half saturated brine. The layers were separated, and the organic layer was dried, concentrated onto Celite, and purified by column chromatography (0-10% EtOAc/CH$_2$Cl$_2$) to afford 6'-fluoro-1'-[(4-methoxyphenyl)methyl]-3'-(trifluoromethyl)spiro[1,3-dioxolane-2,4'-6H-cyclopenta[c]pyrazole]-5'-one as an orange wax (17.1 g, 45% yield).

Step f: The product from step e (16.8 g, 43.6 mmol, 1 equiv.) was dissolved in EtOH, and the mixture was cooled in an ice/water bath. NaBH$_4$ was added in one portion. Upon complete consumption of the ketone as determined by LCMS analysis, the reaction was quenched by addition of ~8 mL of saturated aqueous NH$_4$Cl and concentrated. The crude residue was extracted with EtOAc, dried, and concentrated to give cis-6'-fluoro-1'-[(4-methoxyphenyl)methyl]-3'-(trifluoromethyl)spiro[1,3-dioxolane-2,4'-5,6-dihydrocyclopenta[c]pyrazole]-5'-ol as an orange wax that was used immediately without further purification.

Step g: The product from step f was dissolved in acetone, and solid I$_2$ (5.5 g, 21.8 mmol, 0.5 equiv) was added. Upon complete consumption of the ketal as determined by LCMS analysis, the reaction mixture was concentrated, reconstituted in EtOAc, washed with a 1:1 mixture of saturated Na$_2$S$_2$O$_3$ and NaHCO$_3$, dried, concentrated onto Celite, and purified by column chromatography (10% EtOAc/CH$_2$Cl$_2$) to afford cis-6-fluoro-5-hydroxy-1-[(4-methoxyphenyl)methyl]-3-(trifluoromethyl)-5,6-dihydrocyclopenta[c]pyrazol-4-one (11.6 g, 78% yield).

Step h: The product from step g (11.6 g, 33.7 mmol, 1 equiv.) was dissolved in dioxane (340 mL, 0.1 M), and XtalFluor-E (15.4 g, 67.4 mmol, 2 equiv.) was added. Upon complete dissolution of solids, Et$_3$N.3HF (11 mL, 67.4 mmol, 2 equiv.) was added. Upon complete consumption of the alcohol as determined by LCMS analysis, the reaction was poured into saturated aqueous NaHCO$_3$, extracted with EtOAc, washed with water, washed with brine, dried, and concentrated. The crude residue was used immediately without further purification.

Step i: The product from step h was dissolved in CH$_2$Cl$_2$ (160 mL, 0.2 M), and 2,6-lutidine (29.8 mL, 259 mmol, 8 equiv.) was added. TBSOTf (28.3 mL, 130 mmol, 4 eq) was added and the reaction was stirred overnight at room temperature under inert atmosphere. Upon complete consumption of the fluoroketone as determined by LCMS analysis, the reaction was concentrated under inert atmosphere and immediately reconstituted in THF (1.0 L, 0.033 M). 1 M HCl (250 mL) was added and the reaction was stirred overnight at room temperature. Upon complete consumption of the silyl enol ether as determined by LCMS analysis, the reaction was concentrated to half volume, diluted with EtOAc, and the organic layer was separated. The aqueous layer was extracted with EtOAc, and the combined organic layers were washed with brine, dried, concentrated, and purified by column chromatography (0-60% EtOAc/Hex) to afford trans-5,6-difluoro-1-[(4-methoxyphenyl)methyl]-3-(trifluoromethyl)-5,6-dihydrocyclopenta[c]pyrazol-4-one (5.90 g, 51% yield over 3 steps, first eluting mixture) and cis-5,6-difluoro-1-[(4-methoxyphenyl)methyl]-3-(trifluoromethyl)-5,6-dihydrocyclopenta[c]pyrazol-4-one (1.74 g, 15% yield over 3 steps, second eluting mixture).

Step j: To cis-5,6-difluoro-1-[(4-methoxyphenyl)methyl]-3-(trifluoromethyl)-5,6-dihydrocyclopenta[c]pyrazol-4-one (1.74 g, 5.03 mmol, 1.0 eq) in CH$_2$Cl$_2$ (0.1 M, 50 mL) was added Et$_3$N (1.39 mL, 10.1 mmol, 2.0 eq) followed by formic acid (948 µL, 25.1 mmol, 5.0 eq). The mixture was degassed for ~20 minutes, cooled to 0° C., RuCl(p-cymene)[(R,R)-Ts-DPEN](96 mg, 0.15 mmol, 0.05 eq) was added, and the mixture was stirred at 0° C. overnight. Upon complete consumption of the ketone as determined by LCMS analysis, the reaction was concentrated and purified by column chromatography (0-60% EtOAc/Hex) to afford (4S,5S,6R)-5,6-difluoro-1-[(4-methoxyphenyl)methyl]-3-(trifluoromethyl)-5,6-dihydro-4H-cyclopenta[c]pyrazol-4-ol (1.04 g, 59% yield, 64% ee).

Step k: The product from step j (1.00 g, 2.87 mmol, 1 equiv.) was dissolved in CH$_2$Cl$_2$ (30 mL, 0.1 M), and pyridine (463 µL, 5.75 mmol, 2 equiv.), 4-pyrrolidinylpyridine (0.11 g, 0.72 mmol, 0.25 equiv.), and benzoic anhydride (779 mg, 3.45 mmol, 1.2 equiv.) were added sequentially. Upon complete consumption of the alcohol as determined by LCMS analysis, the reaction was quenched with 1 M HCl and extracted with CH$_2$Cl$_2$. The combined organic layers were washed with satd. NaHCO$_3$, dried, concentrated, and purified by column chromatography (0-40% EtOAc/Hex) to afford [(4S,5S,6R)-5,6-difluoro-1-[(4-methoxyphenyl)methyl]-3-(trifluoromethyl)-5,6-dihydro-4H-cyclopenta[c]pyrazol-4-yl] benzoate (0.95 g, 73% yield).

Step l: The product from step k (0.95 g, 2.1 mmol, 1 equiv.) was dissolved in 3:1 MeCN:H$_2$O (40 mL, 0.05 M) and CAN (3.46 g, 6.31 mmol, 3.0 equiv.) was added. Upon complete consumption of the starting material as determined by LCMS analysis, the reaction was diluted with EtOAc/H$_2$O, the organic layer was separated, and the aqueous layer was extracted with EtOAc. The combined organic layers were washed with satd. NaHCO$_3$, dried, concentrated onto silica, and purified by column chromatography (0-100% EtOAc/Hex) to afford [(4S,5S,6R)-5,6-difluoro-3-(trifluoromethyl)-1,4,5,6-tetrahydrocyclopenta[c]pyrazol-4-yl] benzoate (0.44 g, 63% yield).

Step m: The title compound was prepared in a similar fashion to that described for Example 1 from the product of step l and [(3R)-4,4,4-trifluoro-3-methoxybutyl] 4-methylbenzenesulfonate. $^1$H NMR (400 MHz, Chloroform-d) δ 5.88-5.62 (m, 1H), 5.32-5.07 (m, 2H), 4.54-4.29 (m, 2H), 3.62-3.46 (m, 4H), 2.47-2.09 (m, 3H). ESI MS [M+H]+ for C$_{12}$H$_{13}$F$_8$N$_2$O$_2$, calcd 369.1, found 369.1.

Example 132: (4S,5S,6R)-1-(4,4-difluorocyclohexyl)-5,6-difluoro-3-(trifluoromethyl)-5,6-dihydro-4H-cyclopenta[c]pyrazol-4-ol

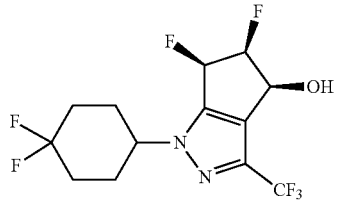 [SMILES: O[C@H]1c2c(C(F)(F)F)nn(C3CCC(F)(F)CC3)c2[C@@H](F)[C@H]1F]

The title compound was prepared in a similar fashion to that described for Example 131 from the product of step 1 and 4,4-difluorocyclohexan-1-ol. ¹H NMR (400 MHz, Chloroform-d) δ 5.77 (dd, J=57.1, 4.6 Hz, 1H), 5.28-5.05 (m, 2H), 4.48-4.32 (m, 1H), 2.48-2.10 (m, 7H), 2.03-1.81 (m, 1H). ESI MS [M+H]+ for C$_{13}$H$_{14}$F$_7$N$_2$O, calcd 347.1, found 347.1.

Example 133: (4S)-1-(2,2-difluorospiro[3.3]heptan-6-yl)-5,5-difluoro-3-(trifluoromethyl)-4,6-dihydrocyclopenta[c]pyrazol-4-ol

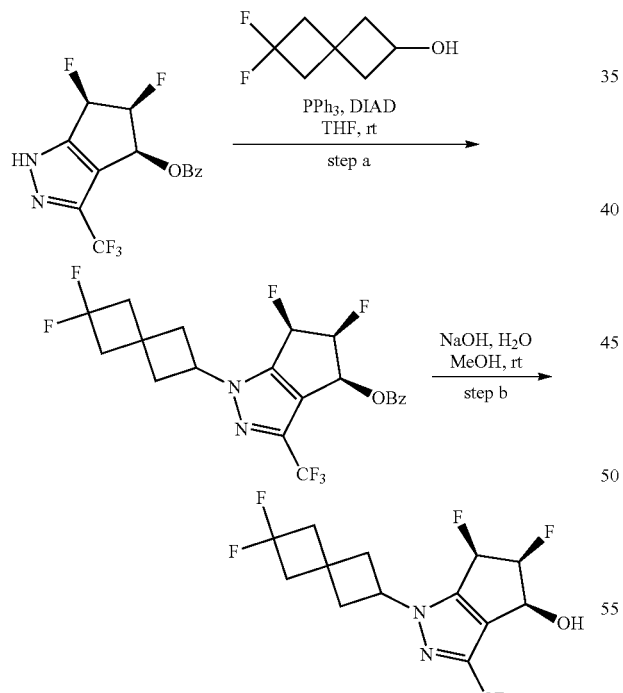

Step a: To a solution of 2,2-difluorospiro[3.3]heptan-6-ol (93 mg, 0.63 mmol, 2.0 equiv.) in THF (3.2 mL, 0.2 M) was added [(4S,5S,6R)-5,6-difluoro-3-(trifluoromethyl)-1,4,5,6-tetrahydrocyclopenta[c]pyrazol-4-yl] benzoate (106 mg, 0.32 mmol, 1.0 equiv.), PPh$_3$ (150 mg, 0.57 mmol, 1.8 equiv.), and DIAD (0.13 mL, 0.63 mmol, 2.0 equiv.). The reaction was stirred at room temperature for 16 hours at which point it was directly concentrated under vacuum. The crude residue was purified by silica gel flash column chromatography (0 to 75% EtOAc/hexanes) to afford the product (39 mg, 26% yield).

Step b: To a solution of [(4S)-1-(2,2-difluorospiro[3.3]heptan-6-yl)-5,5-difluoro-3-(trifluoromethyl)-4,6-dihydrocyclopenta[c]pyrazol-4-yl] benzoate (39 mg, 0.08 mmol, 1.0 equiv.) in MeOH (1.7 mL, 0.05 M) was added 1.0 M aqueous NaOH (0.42 mL, 0.42 mmol, 5.0 equiv.). The reaction was stirred at room temperature for 1 hour, at which point it was quenched with saturated aqueous NH$_4$Cl (10 mL) and extracted with EtOAc (2×10 mL). The combined organics were dried over Na$_2$SO$_4$, filtered, and concentrated under vacuum. The crude residue was purified via silica gel flash chromatography (0 to 75% EtOAc/hexanes) to afford the product (14 mg, 47% yield). ¹H NMR (400 MHz, Chloroform-d) δ 5.72 (dd, J=57.1, 4.9 Hz, 1H), 5.27-5.07 (m, 2H), 4.80 (p, J=8.2 Hz, 1H), 2.90-2.78 (m, 2H), 2.76-2.64 (m, 6H), 2.32 (dd, J=6.6, 2.3 Hz, 1H). ESI MS [M+H]+ for C$_{14}$H$_{13}$F$_7$N$_2$O, calcd 359.1, found 359.1.

Example 134 and 135: (4S,5R,6R)-1-(2,2-difluorospiro[3.3]heptan-6-yl)-5,6-difluoro-3-(trifluoromethyl)-5,6-dihydro-4H-cyclopenta[c]pyrazol-4-ol and (4S,5S,6S)-1-(2,2-difluorospiro[3.3]heptan-6-yl)-5,6-difluoro-3-(trifluoromethyl)-5,6-dihydro-4H-cyclopenta[c]pyrazol-4-ol

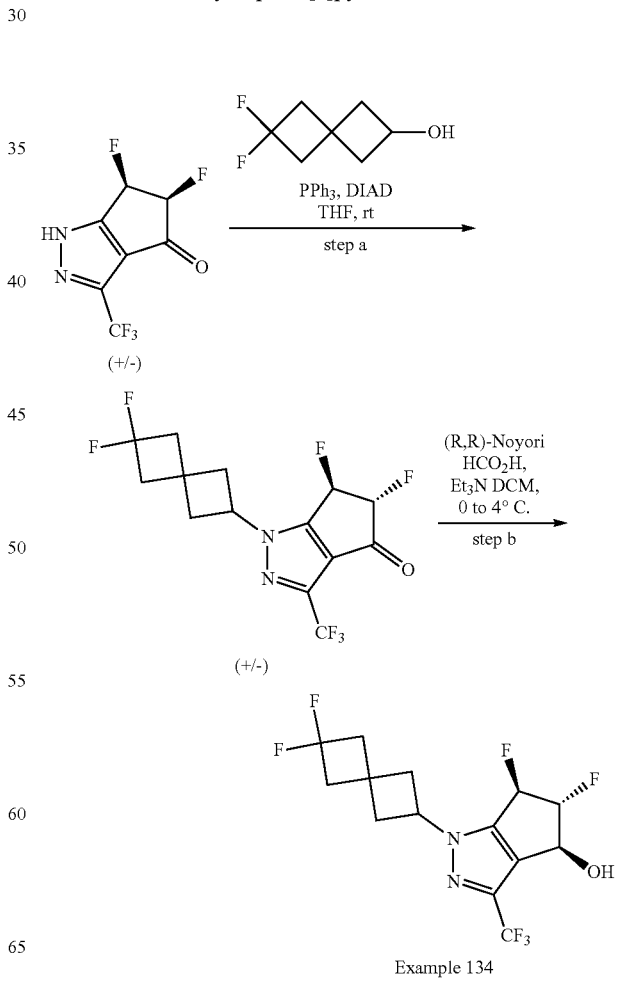

Example 134

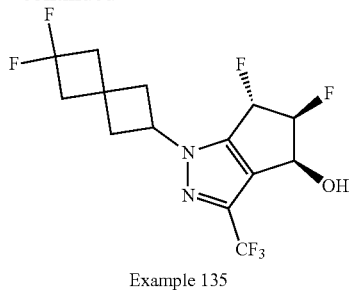

Example 135

Step a: To a solution of 2,2-difluorospiro[3.3]heptan-6-ol (114 mg, 0.77 mmol, 2.0 equiv.) in THF (3.9 mL, 0.2 M) was added cis-5,6-difluoro-3-(trifluoromethyl)-5,6-dihydro-1H-cyclopenta[c]pyrazol-4-one (87 mg, 0.39 mmol, 1.0 equiv.), PPh₃ (182 mg, 0.69 mmol, 1.8 equiv.), and DIAD (0.15 mL, 0.77 mmol, 2.0 equiv.). The reaction was stirred at room temperature for 16 hours at which point it was directly concentrated under vacuum. The crude residue was purified by silica gel flash column chromatography (0 to 100% EtOAc/hexanes) to afford the product (8 mg, 6% yield). ¹H NMR analysis indicated that the cis vicinal difluoride isomerized to the corresponding trans isomer under the reaction conditions.

Step b: trans-1-(2,2-difluorospiro[3.3]heptan-6-yl)-5,6-difluoro-3-(trifluoromethyl)-5,6-dihydrocyclopenta[c]pyrazol-4-one (8 mg, 0.02 mmol, 1.0 equiv.) was dissolved in DCM (0.5 mL, 0.05 M) and the solution was cooled to 0° C. HCO₂H (3 μL, 0.07 mmol, 3.0 equiv.), Et₃N (6 μL, 0.05 mmol, 2.0 equiv.), and RuCl(p-cymene)[(R,R)-Ts-DPEN] (~1 mg, 0.001 mmol, 0.05 equiv.) were added sequentially and the reaction was stirred for 24 hours at 4° C. The reaction was quenched with saturated aqueous NaHCO₃ (10 mL) and extracted with DCM (2×10 mL). The combined organics were dried over Na₂SO₄, filtered, and concentrated under vacuum. The crude residue was purified by silica gel flash column chromatography to afford pure samples of (4S,5R,6R)-1-(2,2-difluorospiro[3.3]heptan-6-yl)-5,6-difluoro-3-(trifluoromethyl)-5,6-dihydro-4H-cyclopenta[c]pyrazol-4-ol and (4S,5S,6S)-1-(2,2-difluorospiro[3.3]heptan-6-yl)-5,6-difluoro-3-(trifluoromethyl)-5,6-dihydro-4H-cyclopenta[c]pyrazol-4-ol.

Example 134, first eluting isomer: (4S,5R,6R)-1-(2,2-difluorospiro[3.3]heptan-6-yl)-5,6-difluoro-3-(trifluoromethyl)-5,6-dihydro-4H-cyclopenta[c]pyrazol-4-ol (2 mg, 25% yield)¹H NMR (400 MHz, Chloroform-d) δ 5.72 (ddd, J=56.0, 15.1, 2.3 Hz, 1H), 5.45 (ddt, J=48.6, 17.3, 2.3 Hz, 1H), 5.08 (dtd, J=17.1, 5.5, 2.4 Hz, 1H), 4.76 (p, J=8.2 Hz, 1H), 2.88-2.61 (m, 8H), 2.41 (d, J=5.9 Hz, 1H). ESI MS [M+H] for C₁₄H₁₃F₇N₂O, calcd 359.1, found 359.1.

Example 135, second eluting isomer: (4S,5S,6S)-1-(2,2-difluorospiro[3.3]heptan-6-yl)-5,6-difluoro-3-(trifluoromethyl)-5,6-dihydro-4H-cyclopenta[c]pyrazol-4-ol (2 mg, 25% yield) ¹H NMR (400 MHz, Chloroform-d) δ 6.08 (ddd, J=57.5, 11.0, 3.3 Hz, 1H), 5.44-5.24 (m, 2H), 4.76 (p, J=8.2 Hz, 1H), 2.86-2.61 (m, 8H), 2.37 (dd, J=4.3, 3.3 Hz, 1H). ESI MS [M+H] for C₁₄H₁₃F₇N₂O, calcd 359.1, found 359.1.

Example 136 and 137: (4S,5S,6R)-1-[(1S)-3,3-difluorocyclohexyl]-5,6-difluoro-3-(trifluoromethyl)-5,6-dihydro-4H-cyclopenta[c]pyrazol-4-ol and (4S,5S,6R)-1-[(1R)-3,3-difluorocyclohexyl]-5,6-difluoro-3-(trifluoromethyl)-5,6-dihydro-4H-cyclopenta[c]pyrazol-4-ol

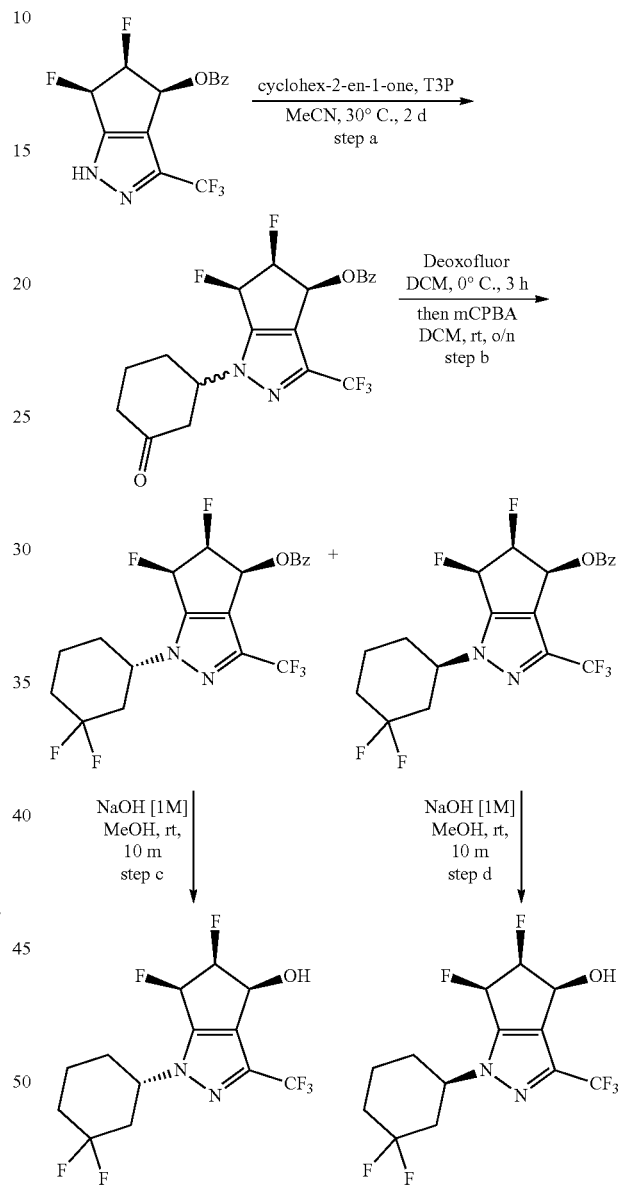

Step a: The product from step 1 of Example 131 (111 mg, 0.33 mmol, 1 equiv.) was dissolved in MeCN (0.2M, 1.7 mL) and cyclohex-2-en-1-one (48 μL, 0.50 mmol, 1.5 equiv.) and propanephosphonic acid anhydride (318 mg, 0.50 mmol, 1.5 equiv., 50 wt % in EtOAc) were added sequentially. Upon stirring the mixture at 30° C. for two days, the reaction was quenched with satd. NaHCO₃ and the aqueous layer was extracted with EtOAc. The combined organic layers were washed with brine, dried, concentrated, and purified by column chromatography (0-60% EtOAc/Hex) to afford ([(4S,5S,6R)-5,6-difluoro-1-(3-oxocyclohexyl)-3-(trifluoromethyl)-5,6-dihydro-4H-cyclopenta[c]
pyrazol-4-yl] benzoate as a ~1:1 mixture of diastereomers
(127 mg, 89% yield).

Step b: The diastereomeric mixture from step a (127 mg,
0.30 mmol, 1 equiv.) was dissolved in CH$_2$Cl$_2$ (0.1 M, 3.0
mL) and cooled to 0° C. Deoxofluor (385 µL, 1.04 mmol, 3.5
equiv., 2.7 M in PhMe) was added and the mixture was Hz, 1H), 5.33-5.10 (m, 2H), 4.60-4.43 (m, 1H), 2.73-1.64
(m, 9H). ESI MS [M+H]$^+$ for C$_{13}$H$_{14}$F$_7$N$_2$O, calcd 347.1,
found 347.1.

Example 138: (4S,5S,6S)-5,6-difluoro-1-[(3R,5S)-3,
4,5-trifluorocyclohexyl]-3-(trifluoromethyl)-5,6-
dihydro-4H-cyclopenta[c]pyrazol-4-ol

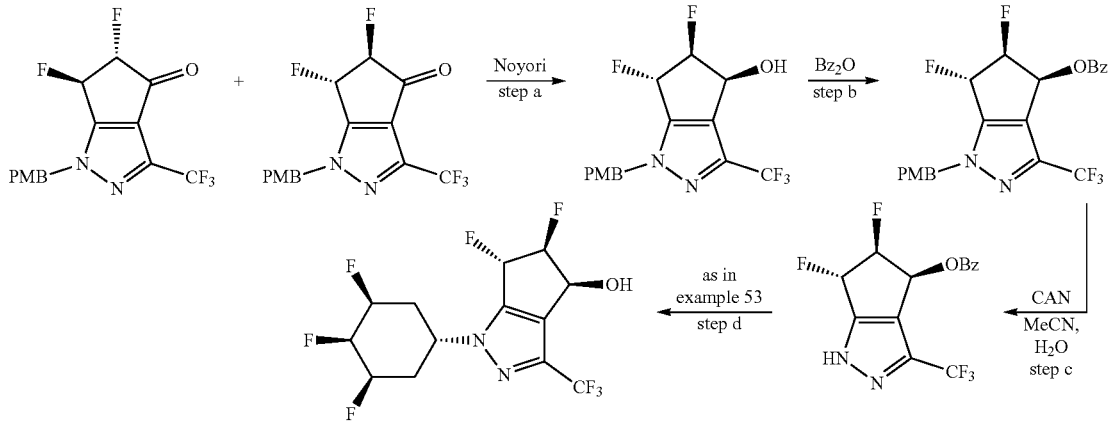

warmed to room temperature over 3 hours. Upon complete
consumption of the ketone as determined by LCMS analysis, the reaction was quenched with satd. NaHCO$_3$ and the
aqueous layer was extracted with CH$_2$Cl$_2$. The combined
organic layers were dried, concentrated, and purified by
column chromatography (0-40% EtOAc/Hex) to afford the
first eluting diastereomer plus inseparable vinyl fluoride
impurities as the first eluting mixture, and the second eluting
diastereomer plus inseparable vinyl fluoride impurities as
the second eluting mixture. The separated compounds plus
their impurities were then each separately dissolved in
CH$_2$Cl$_2$ (~1 mL), treated with mCPBA (~20 mg), and stirred
at room temperature overnight. The reaction mixtures were
then each separately purified by column chromatography
(direct injection, 0-40% EtOAc/Hex) to afford pure first
eluting diastereomer (40 mg, 31% yield) and pure second
eluting diastereomer (32 mg, 25% yield).

Step c: Pure first eluting diastereomer from step b (40 mg,
0.089 mmol, 1 equiv.) was dissolved in MeOH (~3 mL) and
1 M NaOH (~1 mL) was added. Upon complete consumption of the ester after 10 minutes as determined by LCMS
analysis, the reaction was quenched with satd. NH$_4$Cl and
the aqueous layer was extracted with EtOAc. The combined
organic layers were washed with satd. NaHCO$_3$, dried,
concentrated, and purified by HPLC (20-100% MeCN/H$_2$O)
to afford DIAST-1 (7 mg, 23% yield). $^1$H NMR (400 MHz,
Chloroform-d) δ 5.70 (dd, J=57.2, 4.5 Hz, 1H), 5.24-4.98
(m, 2H), 4.47-4.29 (m, 1H), 2.53-1.55 (m, 9H). ESI MS
[M+H]$^+$ for C$_{13}$H$_{14}$F$_7$N$_2$O, calcd 347.1, found 347.1.

Step d: Pure second eluting diastereomer from step b (32
mg, 0.071 mmol, 1 equiv.) was dissolved in MeOH (~3 mL)
and 1 M NaOH (~1 mL) was added. Upon complete
consumption of the ester after 10 minutes as determined by
LCMS analysis, the reaction was quenched with satd.
NH$_4$Cl and the aqueous layer was extracted with EtOAc.
The combined organic layers were washed with satd.
NaHCO$_3$, dried, concentrated, and purified by HPLC (20-100% MeCN/H$_2$O) to afford DIAST-2 (11 mg, 45% yield).
$^1$H NMR (400 MHz, Chloroform-d) δ 5.79 (dd, J=57.2, 4.6

Steps a-c: The compound formed from step c was prepared in a similar fashion to that described in Example 131
starting from the product of step h and using steps j-l
(depicted as steps a-c in this example). The undesired
diastereomer from step a was discarded before performing
step b, as shown in the diagram above.

Step d: The title compound was prepared in a similar
fashion to that described for Example 53 from the product of
steps a-c and (3R,5S)-3,4,5-trifluorocyclohexan-1-ol. $^1$H
NMR (400 MHz, Chloroform-d) δ 6.23-6.00 (m, 1H), 5.58-4.62 (m, 6H), 2.77-2.18 (m, 5H). ESI MS [M+H]$^+$ for
C$_{13}$H$_{13}$F$_8$N$_2$O, calcd 365.1, found 365.1.

Example 139: (4S,5S,6S)-5,6-difluoro-1-(4,4,4-trifluorobutyl)-3-(trifluoromethyl)-5,6-dihydro-4H-cyclopenta[c]pyrazol-4-ol

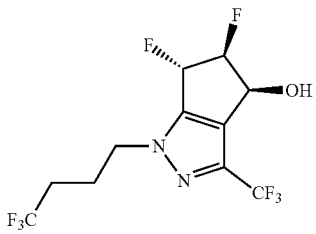 [SMILES: O[C@H]1c2c(C(F)(F)F)nn(CCCC(F)(F)F)c2[C@H](F)[C@H]1F]

The title compound was prepared in a similar fashion to
that described for Example 138 from the product of steps a-c
and 1,1,1-trifluoro-4-iodobutane. $^1$H NMR (400 MHz, Chloroform-d) δ 6.23-5.93 (m, 1H), 5.49-5.22 (m, 2H), 4.40-4.17
(m, 2H), 2.52 (s, 1H), 2.28-2.06 (m, 4H). ESI MS [M+H]$^+$
for C$_{11}$H$_{11}$F$_8$N$_2$O, calcd 339.1, found 339.1.

Example 140: (4S,5S,6R)-5,6-difluoro-1-[(3R,5S)-3,4,5-trifluorocyclohexyl]-3-(trifluoromethyl)-5,6-dihydro-4H-cyclopenta[c]pyrazol-4-ol
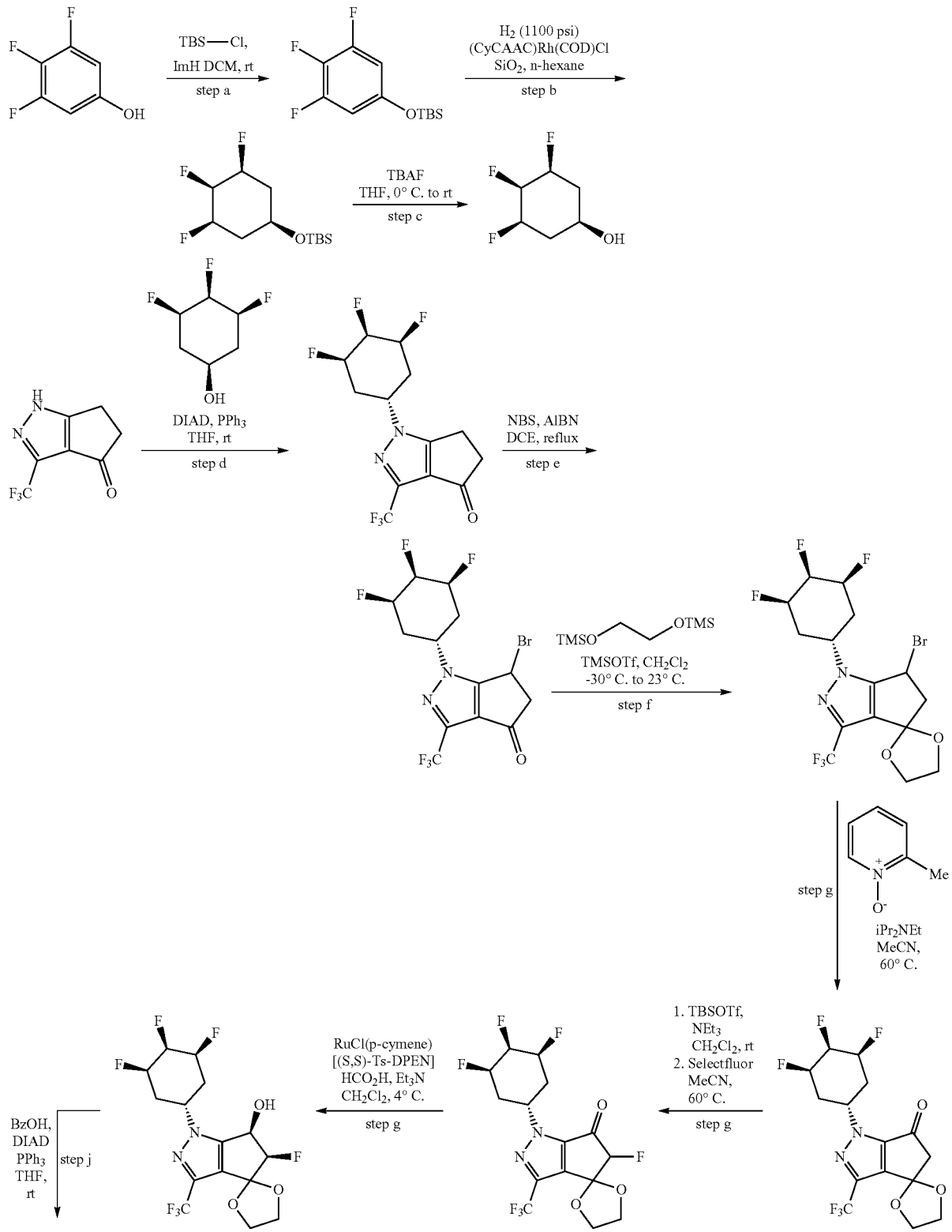

-continued

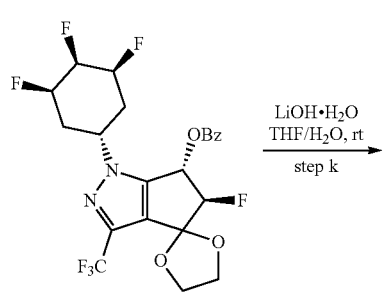
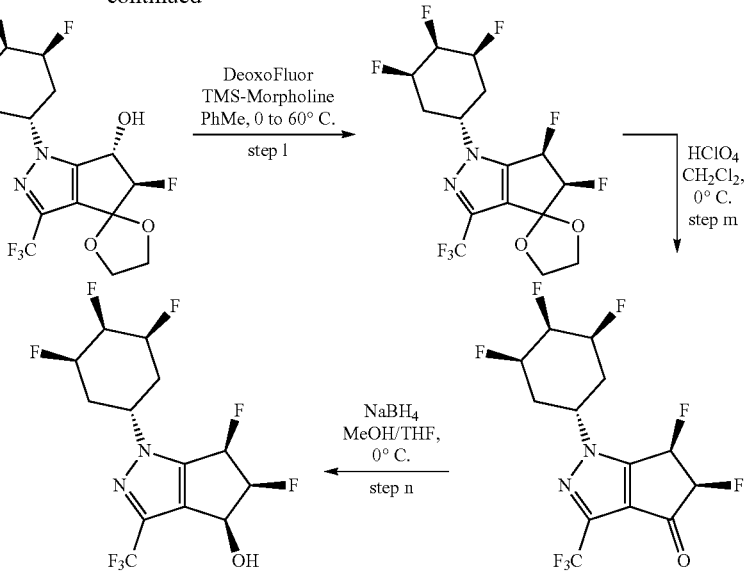

Step a: To a solution of 3,4,5-trifluorophenol (5.5 g, 37.1 mmol, 1.0 equiv.) in DCM (75 mL, 0.5 M) was added imidazole (5.1 g, 74.3 mmol, 2.0 equiv.) followed by TBS-Cl (6.7 g, 44.6 mmol, 1.2 equiv.). The reaction mixture was stirred at room temperature for two hours at which point it was quenched with water (150 mL) and extracted with DCM (100 mL). The combined organics were washed with brine (100 mL), dried over $Na_2SO_4$, filtered, and concentrated under vacuum. The crude residue was purified by silica gel flash column chromatography (0 to 10% EtOAc/hexanes) to afford the product (8.6 g, 88% yield).

Step b: tert-butyl-dimethyl-(3,4,5-trifluorophenoxy)silane (3.4 g, 13.0 mmol, 1.0 equiv.) was dissolved in n-hexane (26 mL, 0.5 M) in a steel Parr bomb lined with a Teflon insert and equipped with a mechanical stirrer. $SiO_2$ (5.8 g, 0.45 g/mmol) was added, followed by (CyCAAC)Rh(COD)Cl (150 mg, 0.25 mmol, 0.02 equiv.). The Parr bomb was pressurized with 500 psi $H_2$ and vented three times before being pressurized to 1100 psi $H_2$. The reaction mixture was stirred at ~300 rpm under 1100 psi $H_2$ for 72 hours at which point it was depressurized and the reaction mixture was filtered over Celite. The filtrate was directly concentrated under vacuum and the crude residue was purified via silica gel flash chromatography (0 to 80% DCM/hexanes) to afford the product (891 mg, 26% yield).

Step c: A solution of tert-butyl-dimethyl-[cis-3,4,5-trifluorocyclohexyl]oxysilane (890 mg, 3.32 mmol, 1.0 equiv.) in THF (17 mL, 0.2 M) was cooled to 0° C. and TBAF (1.0 M in THF, 5 mL, 5 mmol, 1.5 equiv.) was added dropwise. The reaction mixture was stirred for 3 hours as the ice bath expired and the reaction was quenched with saturated aqueous $NH_4Cl$ (50 mL), diluted with EtOAc (100 mL) and partitioned. The organics were washed with water and brine, dried over $Na_2SO_4$, filtered, and concentrated under vacuum. The crude residue was purified via silica gel flash chromatography (0 to 100% EtOAc/hexanes) to afford the product (380 mg, 74% yield)

Step d: To a solution of 3-(trifluoromethyl)-5,6-dihydro-1H-cyclopenta[c]pyrazol-4-one from step c (0.28 g, 1.45 mmol, 1.5 equiv.) and rac-(3R,5S)-3,4,5-trifluorocyclohexan-1-ol (0.15 g, 0.97 mmol, 1.0 eq) in THF (5 mL) was added $PPh_3$ (0.46 g, 1.74 mmol, 1.2 equiv.) and DIAD (0.34 mL, 1.74 mmol, 1.2 equiv.). The resulting mixture was stirred at room temperature for 4 h. The reaction was concentrated onto Celite and purified directly by flash chromatography ($SiO_2$, EtOAc in hexanes, 0 to 60%) to yield the alkylated product (0.24 g, 0.74 mmol, 75% yield) as yellow solid.

Step e: To a solution of product from step d (0.24 g, 0.74 mmol, 1.0 equiv) and NBS (0.20 g, 1.11 mmol, 1.50 equiv.) in DCE (3.70 mL) was added AIBN (18 mg, 0.11 mmol, 0.15 equiv.). The mixture was degassed under vacuum 3 times and back filled with $N_2$. The reaction was heated under reflux for 4 h. Then the mixture was cooled to ambient temperature, diluted with EtOAc (10 mL), washed with aq. sat. $Na_2S_2O_3$ (10 mL), then brine (10 mL). The organic phase was separated, dried over $Na_2SO_4$ and concentrated to dryness under reduced pressure. The crude product was purified by column chromatography ($SiO_2$, EtOAc in hexanes, 0 to 40%) to give the corresponding bromotetrahydroindazole (0.21 g, 0.52 mmol, 70% yield) as a yellow oil.

Step f: Solution of product from step e (0.21 g, 0.52 mmol, 1.0 equiv.) and 1,2-bis(trimethylsiloxy)ethane (0.51 mL, 2.08 mmol, 4.0 equiv.) in $CH_2Cl_2$ (2.60 mL) was cooled to −30° C. and TMSOTf (47 µL, 0.26 mmol, 50 mol %) was added. The mixture was stirred at −30° C. for 1 h, then 0° C. for 1 h, and finally warmed to room temperature and stirred for 16 h. Reaction was quenched with aq. $NaHCO_3$ (2 mL), extracted with $CH_2Cl_2$ (2×5 mL). Combined organic layers were dried over $Na_2SO_4$ and concentrated to dryness under reduced pressure. The crude product was purified by column chromatography ($SiO_2$, EtOAc in hexanes, 0 to 30%) to give the corresponding ketal (0.17 g, 0.38 mmol, 74% yield) as white solid.

Step g: To a solution of product from step f (0.30 g, 0.68 mmol, 1.0 equiv.) in MeCN (3.50 mL) were added 2-methylpyridine N-oxide (0.11 g, 1.0 mmol, 1.50 equiv.) and Hunig's base (0.15 mL, 0.90 mmol, 1.30 equiv.). The mixture was heated at 60° C. for 16 h. It was cooled down to room temperature and diluted with EtOAc (5 mL). The mixture was washed with 1M HCl (7 mL), and then with brine (7 mL). The organic phase was separated, dried over $Na_2SO_4$ and concentrated to dryness under reduced pressure.

The crude product was purified by column chromatography (SiO$_2$, EtOAc in hexanes, 0 to 30%) to give the corresponding ketone (0.24 g, 0.62 mmol, 96% yield) as a pale yellow solid.

Step h: To a solution of the product from step g 0.24, 0.64 mmol, 1.0 equiv.) and Et$_3$N (0.70 mL, 5.12 mmol, 8.0 equiv.) in CH$_2$Cl$_2$ (3.20 mL) was added TBSOTf (0.60 mL, 2.55 mmol, 8.0 equiv.) dropwise at room temperature. The resulting solution was stirred for 16 h and then quenched with sat. aq. NaHCO$_3$ solution. The organic phase was separated, and the aqueous phase was extracted with CH$_2$Cl$_2$, the combined organic phase was then washed with brine, dried over Na$_2$SO$_4$ and concentrated to afford the silyl enol ether. The crude material was then dissolved in MeCN (3.20 mL) and Selectfluor (0.50 g, 1.41 mmol, 2.2 equiv.) was added at room temperature. The resulting mixture was stirred at 60° C. for 30 min, then cooled down to room temperature, and diluted with CH$_2$Cl$_2$ (10 mL). The mixture was washed with water (2×10 mL), and then with brine (10 mL). The organic phase was separated, dried over Na$_2$SO$_4$ and concentrated to dryness under reduced pressure. The crude product was purified by column chromatography (SiO$_2$, EtOAc in hexanes, 0 to 40%) to give the corresponding α-fluoroketone (0.18 g, 0.45 mmol, 70% yield) as a white solid.

Step i: To a solution of the product from step h (0.18 g, 0.45 mmol, 1.0 equiv.) in CH$_2$Cl$_2$ (2.20 mL) was added HCO$_2$H (50 μL, 1.34 mmol, 3.0 equiv.) and Et$_3$N (0.12 mL, 0.89 mmol, 2.0 equiv.). After cooling down the solution to 0° C., RuCl(p-cymene)[(S,S)-TsDPEN] (6 mg, 8.94 μmol, 2 mol %) was added and the resulting mixture was kept in the fridge for 16 h. The reaction was concentrated to dryness and purified directly by flash chromatography (SiO$_2$, EtOAc in hexanes, 0 to 60%) to yield alcohol (0.15 g, 0.37 mmol, 83% yield) as a white solid.

Step j: To a solution of product from step i (0.15 g, 0.37 mmol, 1.0 equiv.) and benzoic acid (54 mg, 0.44 mmol, 1.20 eq) in THF (1.90 mL) was added PPh$_3$ (0.12 g, 0.44 mmol, 1.2 equiv.) and DIAD (87 μL, 0.44 mmol, 1.2 equiv.). The resulting mixture was stirred at room temperature for 16 h. The reaction was concentrated onto Celite and purified directly by flash chromatography (SiO$_2$, EtOAc in hexanes, 0 to 30%) to yield the alkylated product with minor impurities (0.20 g) as a yellow solid.

Step k: The product from step j (0.20 g, 0.39 mmol) was dissolved in THF (1.50 mL) and a solution of LiOH·H$_2$O (83 mg, 1.96 mmol, 5.0 equiv.) in water (0.5 mL) was added at ambient temperature. The resulting mixture was vigorously stirred and monitored by TLC analysis. Upon complete consumption of the starting material the reaction was diluted with EtOAc (5 mL) and water (3 mL). The product was extracted with EtOAc (2×5 mL). Combined organic extract was washed with 1M NaOH (2×10 mL), then brine (10 mL), and dried over Na$_2$SO$_4$. The reaction was concentrated to dryness and purified directly by flash chromatography (SiO$_2$, EtOAc in hexanes, 0 to 60%) to yield alcohol (0.14 g, 0.35 mmol, 94% yield over 2 steps) as a white solid.

Step l: TMS-morpholine (0.42 mL, 2.40 mmol, 7.10 equiv.) was added to Deoxo-Fluor (50% wt solution in PhMe, 1.0 mL, 2.33 mmol, 7.0 eq) at 0° C. The ice bath was subsequently removed, and the mixture was warmed to room temperature, during which time it became increasingly heterogeneous, and a white precipitate formed. After 1 h, the suspension was added to the mixture of product from step k (0.14 g, 0.33 mmol, 1.0 equiv.) in toluene (3.30 mL) at 0° C. The reaction was warmed to room temperature, then heated at 60° C. for 30 min. Upon completion the reaction was quenched with satd. NaHCO$_3$ (3 mL) and diluted with EtOAc (5 mL). The organic layer was separated, and the aqueous layer was extracted with EtOAc (2×5 mL). The combined organic layers were dried over Na$_2$SO$_4$, and concentrated to dryness. The crude material was purified by flash column chromatography (SiO$_2$, EtOAc in hexanes, 0 to 40%) to yield difluoropyrazole (87 mg, 0.21 mmol, 64% yield) as a yellow oil.

Step m: To a cooled solution of product from step l (87 mg, 0.21 mmol, 1.0 equiv.) in CH$_2$Cl$_2$ (5 mL) was added HClO$_4$ (aq. 70%, 0.5 mL, 1M) at 0° C. The mixture was stirred at 0° C. for 1 h when TLC showed complete conversion. The reaction was carefully neutralized with aq. NaHCO$_3$ (2 mL) and the product was extracted with CH$_2$Cl$_2$. The organic phase was separated, dried over Na$_2$SO$_4$ and concentrated to dryness under reduced pressure. The crude material was used in the next step (65 mg, 0.18 mmol, 85% yield).

Step n: To a solution of the crude material from step m (65 mg, 0.18 mmol, 1.0 equiv.) in methanol (0.50 mL) and THF (0.50 mL) was added NaBH$_4$ (7 mg, 0.28 mmol, 1.50 equiv.) at 0° C. The resulting solution was stirred at 0° C. for 30 min. The mixture was diluted with EtOAc (5 mL) and washed with 1M HCl (4 mL). The organic layer was washed with brine (5 mL), dried over Na$_2$SO$_4$, and concentrated to dryness. Purification by flash chromatography (SiO$_2$, 0 to 40% EtOAc in hexanes) furnished the alcohol product (50 mg, 0.14 mmol, 77% yield) as a white solid. $^1$H NMR (400 MHz, CDCl$_3$) δ 5.92-5.68 (m, 1H), 5.43-4.69 (m, 6H), 2.68-2.20 (m, 4H). ESI MS [M+H]$^+$ for C$_{13}$H$_{12}$F$_8$N$_2$O, calcd 365.1, found 364.1.

Example 141 and 142: (4S,5S,6R)-1-[(1R,3S,4R)-3,4-difluorocyclohexyl]-5,6-difluoro-3-(trifluoromethyl)-5,6-dihydro-4H-cyclopenta[c]pyrazol-4-ol and (4S,5S,6R)-1-[(1S,3R,4S)-3,4-difluorocyclohexyl]-5,6-difluoro-3-(trifluoromethyl)-5,6-dihydro-4H-cyclopenta[c]pyrazol-4-ol

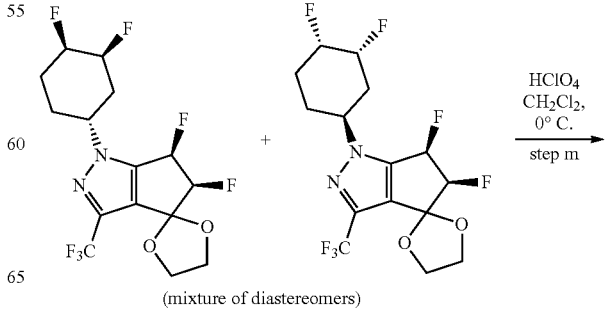

(mixture of diastereomers)

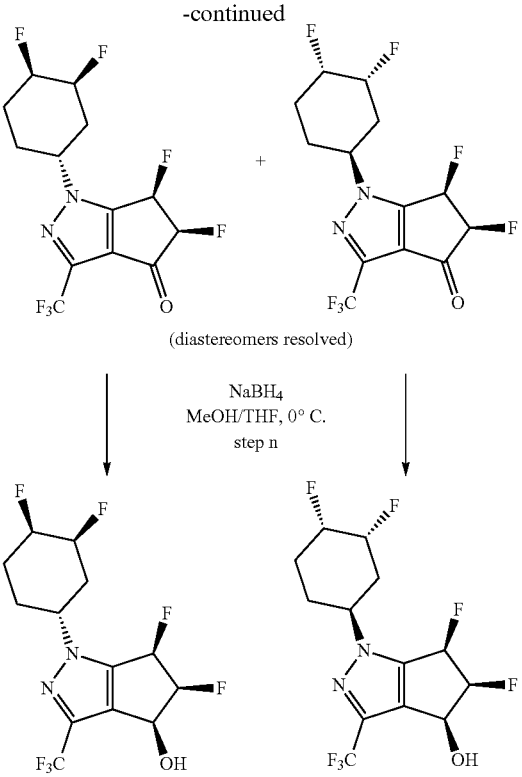

The title compounds were prepared in a similar fashion to Example 140, steps a-l using 3,4-difluorophenol in step a.

Step m: To a cooled solution of the mixture of the substrates (45 mg, 0.12 mmol, 1.0 equiv.) in CH$_2$Cl$_2$ (1.2 mL) was added HClO$_4$ (aq. 70%, 0.12 mL, 1M) at 0° C. The mixture was stirred at 0° C. for 1 h when TLC showed complete conversion. The reaction was carefully neutralized with aq. NaHCO$_3$ (0.3 mL) and the product was extracted with CH$_2$Cl$_2$. The organic phase was separated, dried over Na$_2$SO$_4$ and concentrated to dryness under reduced pressure. Purification by flash chromatography (SiO2, EtOAc in hexanes, 0 to 30%) separated diastereomers: first eluting diasteromer (DIAST-1, 13 mg, 0.038 mmol, 31% yield) and second eluting diastereomer (DIAST-2, 18 mg, 0.052 mmol, 44%)

Step n for DIAST-1: To a solution of the product that eluted first in step m (13 mg, 0.038 mmol, 1.0 equiv.) in methanol (0.20 mL) and THF (0.20 mL) was added NaBH$_4$ (3 mg, 0.076 mmol, 2.0 equiv.) at 0° C. The resulting solution was stirred at 0° C. for 30 min. The mixture was diluted with EtOAc (2 mL) and washed with 1M HCl (2 mL). The organic layer was washed with brine (2 mL), dried over Na$_2$SO$_4$, and concentrated to dryness. Purification by flash chromatography (SiO$_2$, 0 to 40% EtOAc in hexanes) furnished the alcohol product (11 mg, 0.032 mmol, 84% yield) as a white solid. $^1$H NMR (400 MHz, CDCl$_3$) δ 5.77 (dd, J=57.2, 4.6 Hz, 1H), 5.34-5.01 (m, 2H), 4.85-4.54 (m, 2H), 2.63-1.88 (m, 7H). ESI MS [M+H]$^+$ for C$_{13}$H$_{13}$F$_7$N$_2$O, calcd 347.1, found 347.1.

Step n for DIAST-2: To a solution of the product that eluted second in step m (18 mg, 0.052 mmol, 1.0 equiv.) in methanol (0.26 mL) and THE (0.26 mL) was added NaBH$_4$ (4 mg, 0.10 mmol, 2.0 equiv.) at 0° C. The resulting solution was stirred at 0° C. for 30 min. The mixture was diluted with EtOAc (2 mL) and washed with 1M HCl (2 mL). The organic layer was washed with brine (2 mL), dried over Na$_2$SO$_4$, and concentrated to dryness. Purification by flash chromatography (SiO$_2$, 0 to 40% EtOAc in hexanes) furnished the alcohol product (15 mg, 0.043 mmol, 83% yield) as a white solid. $^1$H NMR (400 MHz, CDCl$_3$) δ 5.94-5.64 (m, 1H), 5.40-5.00 (m, 3H), 4.91-4.55 (m, 2H), 2.70-2.46 (m, 1H), 2.45-2.07 (m, 6H). ESI MS [M+H]$^+$ for C$_{13}$H$_{13}$F$_7$N$_2$O, calcd 347.1, found 347.1.

Example 143: (4S,5S,6R)-5,6-difluoro-1-[(3R,5S)-3,4,5-trifluorocyclohexyl]-3-(trifluoromethyl)-5,6-dihydro-4H-cyclopenta[c]pyrazol-4-ol

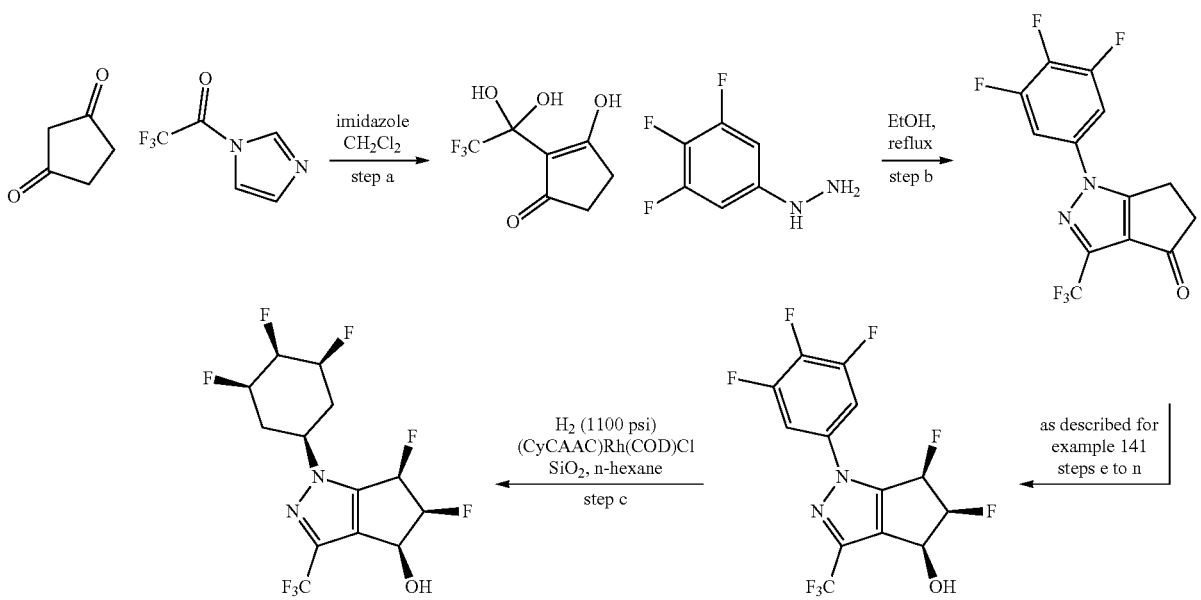

Step a: To a 3-liter 3-neck round bottom flask was added dichloromethane (1.02 L) followed by cyclopentanedione (40.0 g, 408 mmol). 1-(Trifluoroacetyl)imidazole (27.8 g, 408 mmol) was added dropwise via addition funnel maintaining the internal temperature below 25° C. After stirring 4 additional hours the reaction was quenched with 1.0M HCl (800 mL). The precipitate which formed was filtered and washed with water. The cake was suction dried then further dried under high vacuum affording the product as an off-white solid (66.46 g, 77%).

Step b: A mixture of the product from step a (3.3 g, 15.4 mmol, 1.0 equiv.) and (3,4,5-trifluorophenyl)hydrazine (2.50 g, 15.4 mmol, 1.0 equiv.) in ethanol (51 mL) was heated to reflux and stirred for 24 h. After cooling to room temperature, the reaction was concentrated to dryness. Purification by column chromatography (SiO$_2$, 0 to 100% CH$_2$Cl$_2$ in hexanes) afforded the desired product (0.24 g, 0.79 mmol, 34% yield) as a brown solid.

Step c: Syn-2,3-difluoro tetrahydroindazole (95 mg, 0.26 mmol, 1.0 equiv.) was dissolved in CH$_2$Cl$_2$ (3.0 mL) in a steel Parr bomb lined with a Teflon insert and equipped with a mechanical stirrer. SiO$_2$ (0.12 g, 0.45 g/mmol) was added, followed by (CyCAAC)Rh(COD)Cl (7.5 mg, 0.013 mmol, 0.05 equiv.). The Parr bomb was pressurized with 500 psi H$_2$ and vented three times before being pressurized to 1100 psi H$_2$. The reaction mixture was stirred at ~300 rpm under 1100 psi H$_2$ for 72 hours at which point it was depressurized and the reaction mixture was filtered over Celite. The filtrate was directly concentrated under vacuum and the crude residue was purified via silica gel flash chromatography (0 to 70% EtOAc in hexanes) to afford the product (3 mg, 0.008 mmol, 3% yield). $^1$H NMR (400 MHz, CDCl$_3$) δ 5.73 (ddd, J=56.8, 4.6, 1.4 Hz, 1H), 5.32-5.19 (m, 1H), 5.10 (td, J=7.2, 6.6, 3.3 Hz, 2H), 4.73-4.41 (m, 1H), 4.30 (h, J=7.1, 6.0 Hz, 1H), 2.57 (ddd, J=20.6, 12.8, 9.9 Hz, 1H), 2.49-2.34 (m, 3H), 2.27 (dd, J=6.6, 2.5 Hz, 1H). ESI MS [M+H]$^+$ for C$_{13}$H$_{12}$F$_8$N$_2$O, calcd 365.1, found 364.1.

Example 144 and 145: (4S,6S)-1-[(1,1-dioxothietan-3-yl)methyl]-5,5,6-trifluoro-3-(trifluoromethyl)-4,6-dihydrocyclopenta[c]pyrazol-4-ol and (4S,6R)-1-[(1,1-dioxothietan-3-yl)methyl]-5,5,6-trifluoro-3-(trifluoromethyl)-4,6-dihydrocyclopenta[c]pyrazol-4-ol Step a: The product from step h (5.8 g, 16.7 mmol, 1 equiv.) above was dissolved in CH$_2$Cl$_2$ (84 mL, 0.2 M), and 2,6-lutidine (15.4 mL, 134 mmol, 8 equiv.) was added. TBSOTf (15.3 mL, 67 mmol, 4 equiv.) was then added. Upon complete consumption of the ketone as determined by LCMS analysis, the reaction mixture was cooled in an ice/water bath, and NFSI (10.6 g, 33.5 mmol, 2 equiv.) was added. The reaction mixture stirred overnight, and a second portion of NFSI (10.6 g, 33.5 mmol, 2 equiv.) was added. The reaction mixture stirred for 2.5 hours and was quenched by addition of half saturated NaHCO$_3$. The reaction mixture was extracted with CH$_2$Cl$_2$, dried, concentrated, and purified by column chromatography (0-100% CH$_2$Cl$_2$/hexanes) to afford rac-5,5,6-trifluoro-1-[(4-methoxyphenyl)methyl]-3-(trifluoromethyl)-6H-cyclopenta[c]pyrazol-4-one (5.5 g, 90% yield).

Steps b-d ([(4S)-5,5,6-trifluoro-3-(trifluoromethyl)-4,6-dihydro-1H-cyclopenta[c]pyrazol-4-yl] benzoate): The title compound was prepared in a similar fashion to that described in Example 131 starting from the product of step a, above, and using steps j-l from Example 131.

Step e: The title compounds were prepared in a similar fashion to that described for Example 1, steps i and j using the product of steps b-d, above and (1,1-dioxothietan-3-yl) methyl methanesulfonate. The diastereomers were separated via HPLC (20-100% MeCN/H$_2$O).

First eluting isomer (DIAST-1): $^1$H NMR (400 MHz, Methanol-d4) δ 5.82 (dd, J=55.0, 9.7 Hz, 1H), 4.87 (dd, J=11.4, 3.0 Hz, 1H), 4.59-4.42 (m, 2H), 4.24-4.07 (m, 2H), 4.00-3.82 (m, 2H), 3.15-2.99 (m, 1H). ESI MS [M+H]$^+$ for C$_{11}$H$_{11}$F$_6$N$_2$O$_3$S, calcd 365.0, found 365.0.

Second eluting isomer (DIAST-2): $^1$H NMR (400 MHz, Methanol-d4) δ 6.15 (ddd, J=55.5, 7.5, 1.9 Hz, 1H), 5.22 (dd, J=9.1, 3.8 Hz, 1H), 4.67-4.50 (m, 2H), 4.34-4.15 (m, 2H), 4.09-3.93 (m, 2H), 3.23-3.08 (m, 1H). ESI MS [M+H]$^+$ for C$_{11}$H$_{11}$F$_6$N$_2$O$_3$S, calcd 365.0, found 365.0.

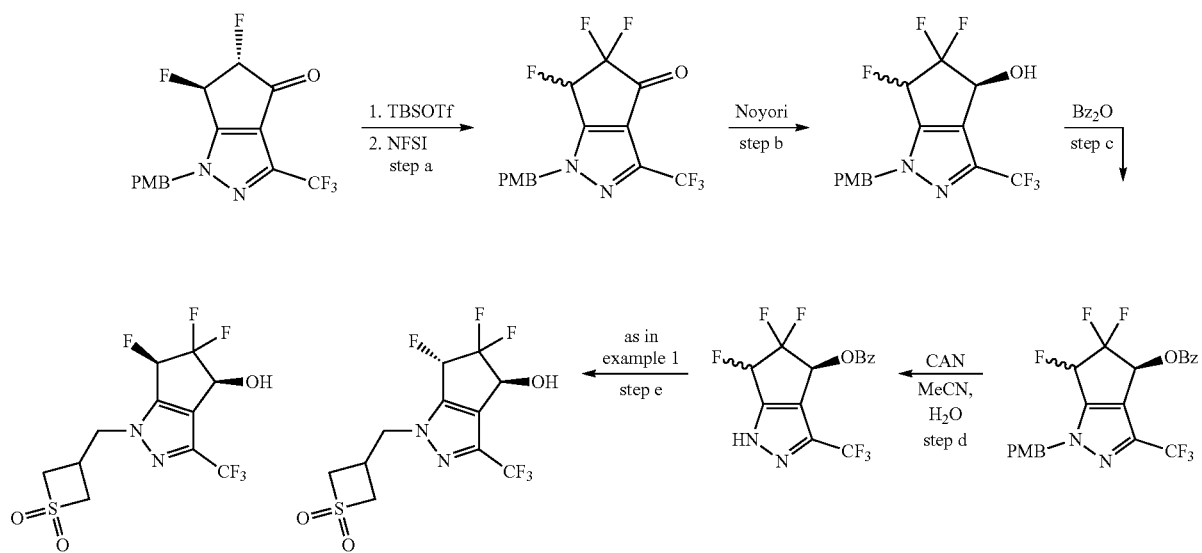

Example 146 and 147: (4S,6S)-5,5,6-trifluoro-1-[(3R,5S)-3,4,5-trifluorocyclohexyl]-3-(trifluoromethyl)-4,6-dihydrocyclopenta[c]pyrazol-4-ol and (4S,6R)-5,5,6-trifluoro-1-[(3R,5S)-3,4,5-trifluorocyclohexyl]-3-(trifluoromethyl)-4,6-dihydrocyclopenta[c]pyrazol-4-ol

Example 148 and 149: (4S,6S)-5,5,6-trifluoro-1-[(3R)-4,4,4-trifluoro-3-methoxybutyl]-3-(trifluoromethyl)-4,6-dihydrocyclopenta[c]pyrazol-4-ol and (4S,6R)-5,5,6-trifluoro-1-[(3R)-4,4,4-trifluoro-3-methoxybutyl]-3-(trifluoromethyl)-4,6-dihydrocyclopenta[c]pyrazol-4-ol

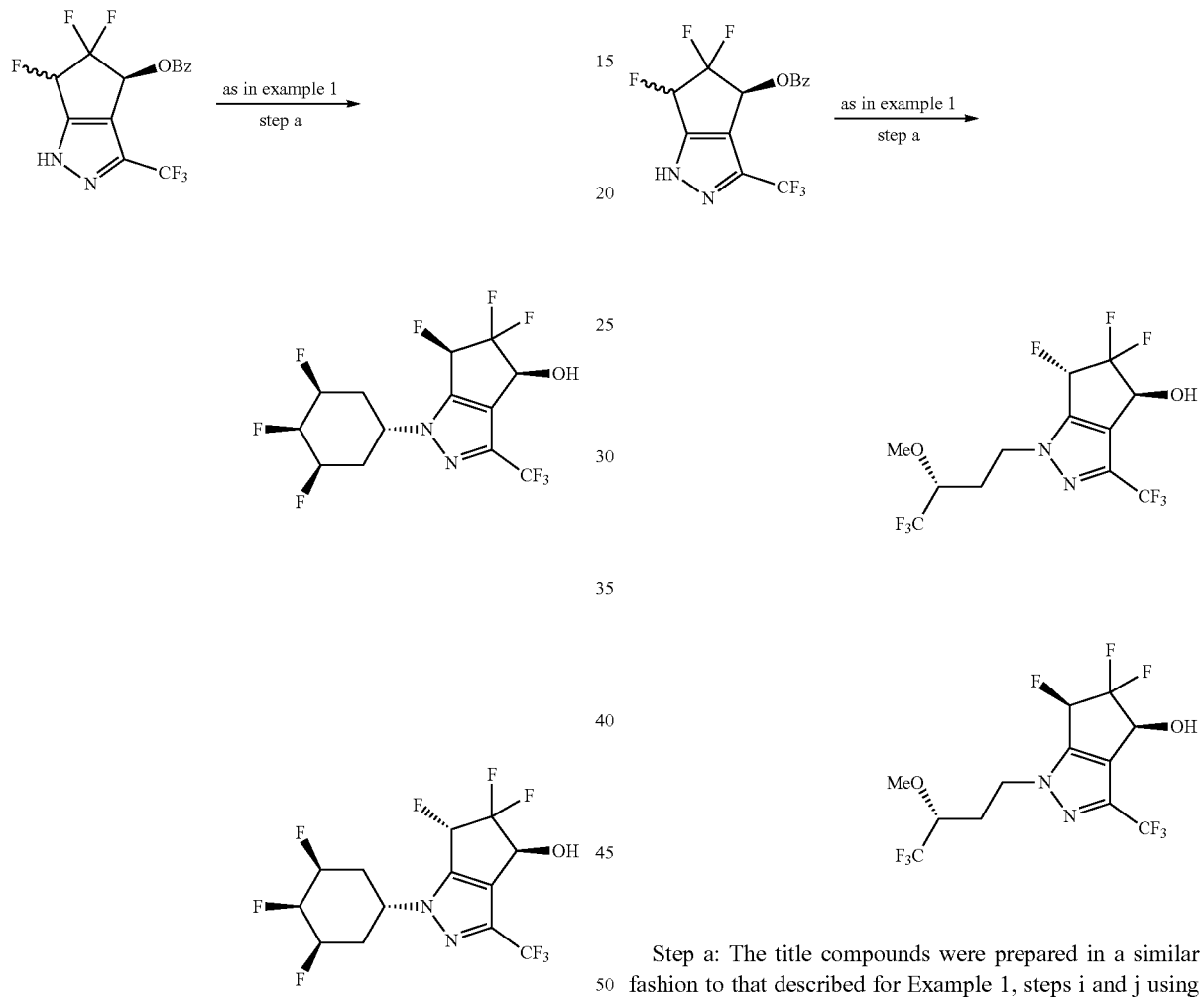

Step a: The title compounds were prepared in a similar fashion to that described for Example 1, steps i and j using the product of steps b-d, as described in Example 144 and (3R,5S)-3,4,5-trifluorocyclohexan-1-ol instead of (1,1-dioxothietan-3-yl)methyl methanesulfonate. The diastereomers were separated via HPLC (20-100% MeCN/H$_2$O).

First eluting isomer (DIAST-1): $^1$H NMR (400 MHz, Methanol-d4) δ 5.86 (dd, J=54.9, 9.8 Hz, 1H), 5.25-4.64 (m, 5H), 2.55-2.12 (m, 4H). ESI MS [M+H]$^+$ for C$_{13}$H$_{12}$F$_9$N$_2$O, calcd 383.1, found 383.1.

Second eluting isomer (DIAST-2): $^1$H NMR (400 MHz, Methanol-d4) δ 6.10 (ddd, J=55.3, 7.3, 2.3 Hz, 1H), 5.26-4.66 (m, 5H), 2.54-2.09 (m, 4H). ESI MS [M+H]$^+$ for C$_{13}$H$_{12}$F$_9$N$_2$O, calcd 383.1, found 383.1.

Step a: The title compounds were prepared in a similar fashion to that described for Example 1, steps i and j using the product of steps b-d, as described in Example 144 and [(3R)-4,4,4-trifluoro-3-methoxybutyl] 4-methylbenzenesulfonate instead of (1,1-dioxothietan-3-yl)methyl methanesulfonate. The diastereomers were separated via HPLC (20-100% MeCN/H$_2$O).

First eluting isomer (DIAST-1): $^1$H NMR (400 MHz, Methanol-d4) δ 5.91 (dd, J=55.1, 9.7 Hz, 1H), 4.99 (dd, J=11.4, 3.0 Hz, 1H), 4.57-4.32 (m, 3H), 3.83-3.62 (m, 1H), 2.42-2.04 (m, 2H). ESI MS [M+H]$^+$ for C$_{12}$H$_{12}$F$_9$N$_2$O$_2$, calcd 387.1, found 387.1.

Second eluting isomer (DIAST-2): $^1$H NMR (400 MHz, Methanol-d4) δ 6.13 (ddd, J=55.5, 7.5, 2.0 Hz, 1H), 5.25 (dd, J=9.1, 3.9 Hz, 1H), 4.56-4.36 (m, 2H), 3.80-3.63 (m, 1H), 2.40-2.04 (m, 2H). ESI MS [M+H]$^+$ for C$_{12}$H$_{12}$F$_9$N$_2$O$_2$, calcd 387.1, found 387.1.

Example 150 and 151: (4S,5S,6R)-5,6-difluoro-3-(trifluoromethyl)-1-[(2R,4S)-2-(trifluoromethyl)oxan-4-yl]-5,6-dihydro-4H-cyclopenta[c]pyrazol-4-ol and (4S,5S,6R)-5,6-difluoro-3-(trifluoromethyl)-1-[(2S,4R)-2-(trifluoromethyl)oxan-4-yl]-5,6-dihydro-4H-cyclopenta[c]pyrazol-4-ol
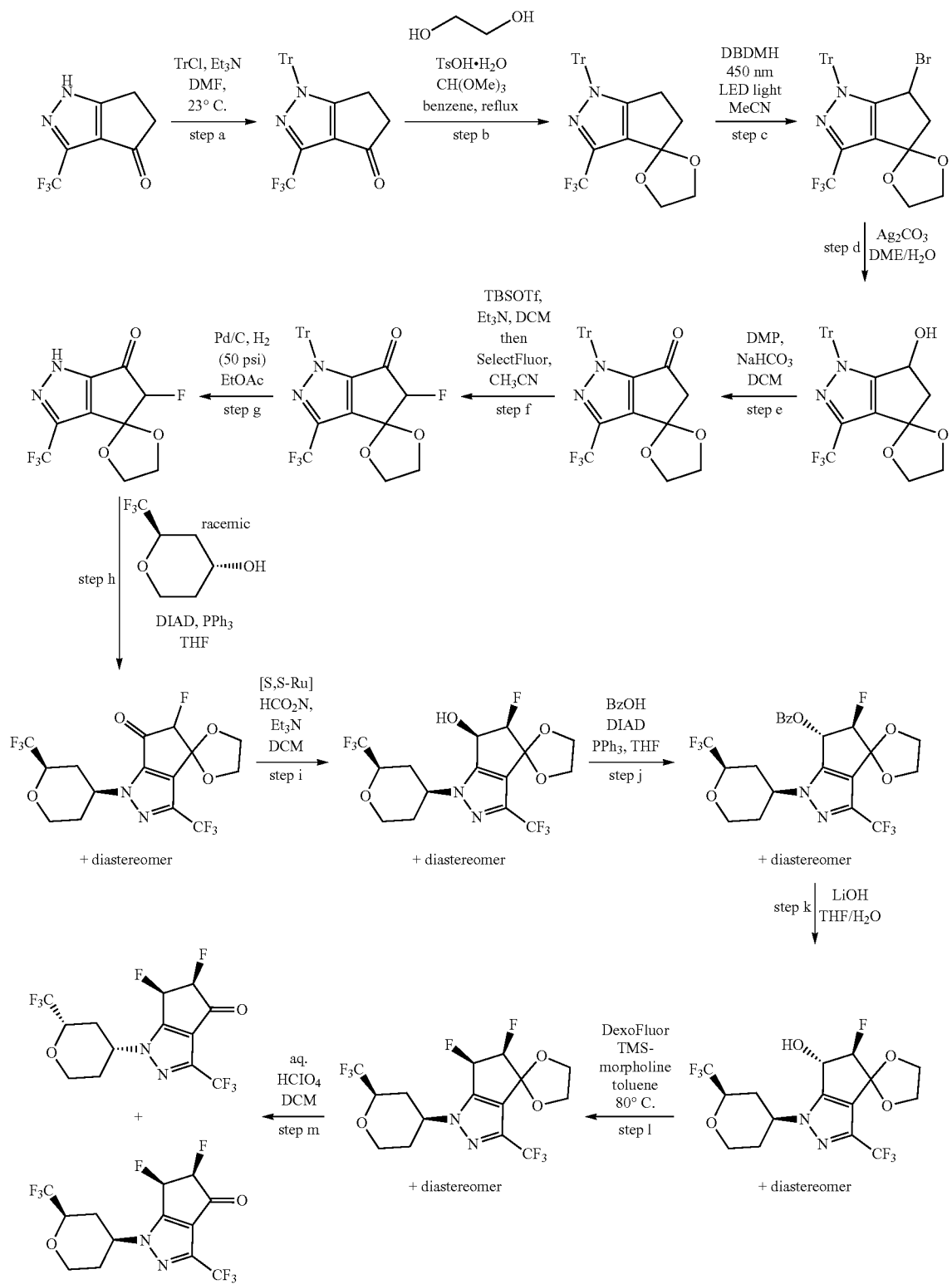

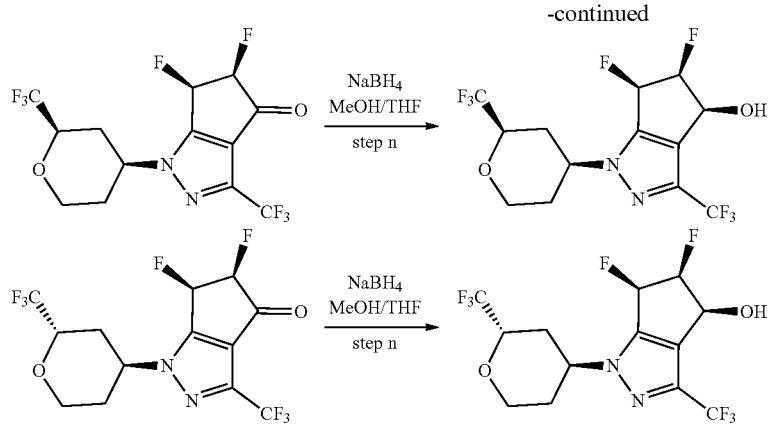

Step a: A solution of 3-(trifluoromethyl)-5,6-dihydro-1H-cyclopenta[c]pyrazol-4-one (34.0 g, 0.18 mol) in DMF (177 mL) was placed in a single-neck round-bottom flask equipped with stirring bar and a drying tube. Triethylamine (50.0 mL, 0.35 mol) was added to the reaction followed by trityl chloride (52.0 g, 0.19 mol) at room temperature. The resulting mixture was stirred at ambient temperature for 1 h. Once TLC analysis of the reaction mixture confirmed complete consumption of the starting material, the reaction was slowly poured in water (600 mL). The formed precipitate was collected by vacuum filtration and washed with Et$_2$O (2×50 mL). The precipitate was dried under vacuum to produce the desired product (75.0 g, 0.17 mol, 96% yield).

Step b: A mixture of the ketone from step a (80.2 g, 0.18 mol), ethylene glycol (51.0 mL, 0.92 mol), trimethyl orthoformate (100.6 mL, 0.92 mol), p-toluenesulfonic acid monohydrate (3.5 g, 0.02 mol) and benzene (920 mL) was placed in a one-neck round-bottom flask equipped with a magnetic stirring bar and reflux condenser with a drying tube. The resulting mixture was stirred at 75° C. for 24 h. The mixture was cooled to room temperature, diluted with EtOAc (300 mL) and washed with aqueous saturated NaHCO$_3$ (500 mL). The organic layer was separated, and the aqueous phase was additionally extracted with EtOAc (2×200 mL). Combined organic extract was washed with brine, dried over Na$_2$SO$_4$ and concentrated to dryness under reduced pressure. The crude concentrate was triturated with small amount of hexanes/MTBE mixture (1:1, v/v) and the first fraction of the desired product was collected by filtration. The filtrate was concentrated to dryness under reduced pressure, and the residue was fractionated by column chromatography (SiO$_2$, hexanes/EtOAc gradient) to isolate the remaining product. These fractions were combined to obtain the corresponding ketal (73.8 g, 0.16 mol, 84% yield).

Step c. A solution of ketal from step b (49.9 g, 0.104 mol) and 1,3-dibromo-5,5-dimethylhydantoin (33.0 g, 0.115 mol) in dichloroethane (520 mL) were placed in a 1 L one-neck round-bottom flask equipped with a magnetic stirring bar. The resulting mixture was irradiated with visible light source (450 nm) for 1.5 h under stirring. Once $^{19}$F NMR analysis indicated complete consumption of the starting material the resulting suspension was diluted with dichloromethane (200 mL) and quenched with a solution of aq. saturated Na$_2$S$_2$O$_3$ (300 mL) and NaHCO$_3$ (300 mL). The organic phase was separated. The aqueous solution was additionally extracted with dichloromethane (2×200 mL). Combined organic extract was dried over Na$_2$SO$_4$ and concentrated to dryness under reduced pressure. The crude product was used for the next step without purification.

Step d. The crude bromide from step c was dissolved in a mixture of dimethoxyethane (350 mL) and water (170 mL) in a 1 L one-neck round-bottom flask equipped with a reflux condenser and a magnetic stirring bar. Then Ag$_2$CO$_3$ (43.0 g, 0.16 mol) was added, and the reaction mixture was refluxed for 1.5 h. Once complete consumption of the starting material was observed by TLC analysis the reaction was cooled to room temperature and filtered through a pad of celite. The filtrate was diluted with water (400 mL) and EtOAc (400 mL). The organic phase was separated, and the aqueous phase was additionally extracted with EtOAc (2×200 mL). Combined organic extract was dried over Na$_2$SO$_4$ and concentrated to dryness under reduced pressure. The crude product was used for the next step without purification.

Step e. A solution of the crude alcohol from step d was dissolved in dichloromethane (520 mL) and placed in a 1 L one-neck round-bottom flask equipped with a magnetic stirring bar and drying tube. The resulting mixture was cooled to 0° C., then sodium bicarbonate (44.0 g, 0.52 mol) was added followed by Dess-Martin periodinane (57.3 g, 0.135 mol). The resulting suspension was stirred at 0° C. for 30 min, then allowed to warm to room temperature and stirred for additional 1.5 h. Once TLC analysis indicated complete consumption of the alcohol starting material the reaction mixture was quenched by slowly pouring into a mixture of saturated aqueous solution of NaHCO$_3$ (200 mL) and Na$_2$S$_2$O$_3$ (200 mL). After vigorously stirring the resulting biphasic mixture for 1 h the organic phase was separated, and the aqueous phase was extracted with dichloromethane (2×200 mL). Combined organic solution was dried over Na$_2$SO$_4$ and concentrated to dryness. The crude product was fractionated by column chromatography (SiO$_2$, hexanes/EtOAc gradient) to provide the desired ketone (50.8 g, 0.104 mol, 100% yield).

Step f. The ketone from step e (47.2 g, 0.10 mol) was dissolved in dichloromethane (480 mL) and triethylamine (107.1 mL, 0.77 mol) was added followed by TBSOTf (88.5 mL, 0.39 mol) at room temperature. The resulting dark brown solution was stirred at room temperature for 6 h. Once TLC analysis indicated a complete consumption of the starting material the reaction mixture was washed with aqueous 1M NaOH solution (2×500 mL), dried over Na$_2$SO$_4$ and concentrated to dryness under reduced pressure. The residue was triturated with MTBE (150 mL), and the precipitate of TBS enol ether was filtered. The remaining product was isolated by concentration of the filtrate to dryness and fractionation of the residue by column chromatography (SiO$_2$, hexanes/EtOAc gradient). Fractions obtained by filtration and column chromatography were combined to provide the desired silyl enol ether that was suspended in acetonitrile (500 mL) and placed in 1 L one-neck round-bottom flask equipped with reflux condenser and magnetic stirring bar. Selectfluor (53.1 g, 0.15 mol) was added and the resulting suspension was heated at 60° C. for 1 hour. Once TLC analysis indicated complete transformation of silyl enol ether, the reaction was cooled to room temperature and concentrated dryness. The residue was partitioned between EtOAc (350 mL) and water (350 mL). Organic phase was separated, and the aqueous phase was additionally extracted with EtOAc (2×200 mL). Combined organic extract was washed with brine, dried over Na$_2$SO$_4$ and concentrated to dryness under reduced pressure. The crude material was triturated with MeOH (100 mL) and the formed precipitate was filtered and dried under vacuum to provide corresponding α-fluoroketone (38.7 g, 0.08 mol, 79% yield).

Step g. A solution of α-fluoroketone from step f (38.7 g, 0.08 mol) in EtOAc (530 mL) was degassed under vacuum and backfilled with nitrogen. Palladium on carbon was added (3.8 g, 10 wt % Pd), and the mixture was agitated in a Parr shaker under hydrogen atmosphere (50 psi) for 72 h. The material was degassed under vacuum and backfilled with nitrogen to remove excess of hydrogen gas. The suspension was filtered through a pad of celite and concentrated to dryness under reduced pressure. The dry residue was fractionated by column chromatography (SiO$_2$, hexanes/EtOAc gradient) to provide 5'-fluoro-3'-(trifluoromethyl)spiro[1,3-dioxolane-2,4'-1,5-dihydrocyclopenta [c]pyrazole]-6'-one (20.2 g, 0.08 mol, 100% yield).

Step h. Diisopropyl azodicarboxylate (0.52 mL, 2.6 mmol) was added dropwise to a cooled to 0° C. solution of α-fluoroketone from step g (0.47 g, 1.8 mmol), trans-2-(trifluoromethyl)oxan-4-ol (0.3 g, 1.8 mmol) and PPh$_3$ (0.69 g, 2.6 mmol) in tetrahydrofuran (6 mL). The cooling bath was removed, and the reaction was stirred at room temperature overnight. The resulting yellow solution was concentrated to dryness under reduced pressure, and the dry residue was purified by column chromatography (SiO$_2$, hexanes/EtOAc gradient) to provide the desired coupling product (0.16 g, 0.38 mmol, 22% yield) as a mixture of diastereomers.

Step i. Product of step h (160 mg, 0.38 mmol) was dissolved in CH$_2$Cl$_2$ (1.9 mL), and the solution was cooled to 0° C. Formic acid (43 μL, 1.14 mmol) and triethylamine (75 μL, 0.76 mmol) were added sequentially, and the solution was purged with nitrogen for 10 min. RuCl(p-cymene)[(R,R)-Ts-DPEN] (5.0 mg, 0.008 mmol) was added and the resulting mixture was stirred at 4° C. for 16 h. Upon completion (TLC monitoring), the reaction mixture was diluted with dichloromethane (10 mL), washed with sat. aq. NaHCO$_3$ (5 mL) and brine (5.0 mL), dried over Na$_2$SO$_4$ and concentrated under reduced pressure. The residue was fractionated using column chromatography (SiO$_2$, hexanes/EtOAc gradient) to produce the desired product (100.0 mg, 0.24 mmol, 63% yield, mixture of diastereomers).

Step j. To a solution of product from step i (100.0 mg, 0.24 mmol) and benzoic acid (35 mg, 0.29 mmol) in THF (1.2 mL) at 0° C. was added PPh$_3$ (76 mg, 0.29 mmol) and DIAD (57 μL, 0.29 mmol). The resulting mixture was allowed to warm to room temperature and stirred for 1 h. Once complete reaction was observed by TLC analysis the solution was concentrated to dryness and was directly fractionated by column chromatography (SiO$_2$, hexanes/EtOAc gradient) to yield the corresponding benzoate (79 mg, 0.15 mmol, 62% yield, mixture of diastereomers).

Step k. The product from step j (79 mg, 0.15 mmol) was dissolved in THF (0.8 mL) and a solution of LiOH H$_2$O (50.0 mg, 1.2 mmol) in water (0.4 mL) was added at room temperature. The resulting mixture was vigorously stirred and monitored by TLC analysis. Upon complete consumption of the starting material the reaction was diluted with EtOAc (5 mL) and water (3 mL). The product was extracted with EtOAc (2×5 mL). Combined organic extract was washed with 1M NaOH (2×10 mL), brine (10 mL) and dried over Na$_2$SO$_4$. Upon concentration the residue was purified by column chromatography (SiO$_2$, hexanes/EtOAc gradient) to yield the corresponding alcohol (53 mg, 0.13 mmol, 89% yield, mixture of diastereomers).

Step l. TMS-morpholine (0.14 mL, 0.89 mmol) was added to a solution of Deoxo-Fluor (0.4 g, 0.88 mmol, 50 wt % solution in PhMe) in toluene (1.0 mL) at 0° C. The ice bath was subsequently removed, and the mixture was warmed to room temperature and stirred for 1 h, during which time it became increasingly heterogeneous, and a white precipitate formed. A solution of alcohol from step k in toluene (0.5 mL) was added, and the reaction mixture was heated at 80° C. for 1 h. Upon completion the reaction was diluted with EtOAc (10 mL) and quenched with sat. aq. NaHCO$_3$ (5 mL). The organic layer was separated, and the aqueous layer was extracted with EtOAc (2×5 mL). The combined organic extract was dried over Na$_2$SO$_4$ and concentrated to dryness. The crude material was purified by column chromatography (SiO$_2$, hexanes/EtOAc gradient) to yield the corresponding fluorinated product (47 mg, 0.11 mmol, 89% yield, mixture of diastereomers).

Step m. To a cooled solution of product from step l (47 mg, 0.11 mmol) in dichloromethane (2 mL) was added HClO$_4$ (aq. 70%, 0.4 mL) at 0° C. The resulting biphasic mixture was stirred at 0° C. for 1 h. Once TLC analysis indicated complete conversion the reaction was carefully neutralized with aq. NaHCO$_3$ (2 mL) and the product was extracted with dichloromethane (2×10 mL). The organic phase was separated, dried over Na$_2$SO$_4$ and concentrated to dryness under reduced pressure. The crude material was fractionated by column chromatography (SiO$_2$, hexanes/EtOAc gradient) to yield corresponding diastereomeric ketones separately (first eluting isomer (DIAST-1)-18.0 mg (0.05 mmol, 45% yield), second eluting isomer (DIAST-2)-15.0 mg (0.04 mmol, 36% yield).

Step n. The protocol is described for DIAST-1. Identical procedure was implemented for the reduction of DIAST-2.

To a solution of the less polar diastereomer of ketone from step n (18.0 mg, 0.05 mmol) in methanol (0.50 mL) and THF (0.50 mL) was added NaBH$_4$ (4.0 mg, 0.1 mmol) at 0° C. The resulting mixture was stirred at 0° C. for 30 min. Then it was diluted with EtOAc (5 mL), washed with 1M HCl (5 mL) and brine (5 mL). The organic phase was dried over Na$_2$SO$_4$ and concentrated to dryness under reduced pressure. Purification by column chromatography (SiO$_2$, hexanes/EtOAc gradient) furnished the alcohol product (15 mg, 0.04 mmol, 83% yield) as a white solid. $^1$H NMR (400 MHz, CDCl$_3$) δ 5.8 (dd, J=56.9, 4.3 Hz, 1H), 5.3-5.1 (m, 2H), 4.5 (dq, J=11.6, 5.9, 4.6 Hz, 1H), 4.3 (dd, J=12.3, 4.8 Hz, 1H), 4.0-3.8 (m, 1H), 3.7 (tt, J=12.3, 2.0 Hz, 1H), 2.5-2.1 (m, 5H). $^{19}$F NMR (376 MHz, CDCl$_3$) δ −61.7, −78.9, −180.7, −199.8.

More polar diastereomer (DIAST-2): $^1$H NMR (400 MHz, CDCl$_3$) δ 5.80 (dd, J=56.8, 4.3 Hz, 1H), 5.33-5.07 (m, 2H), 4.65-4.48 (m, 1H), 4.33 (dd, J=12.2, 4.9 Hz, 1H), 4.02-3.79

(m, 1H), 3.66 (td, J=12.2, 2.1 Hz, 1H), 2.46-2.25 (m, 3H), 2.18-1.98 (m, 2H). ¹⁹F NMR (376 MHz, CDCl₃) δ −61.7, −78.8, −180.4, −199.7.

Example 152: (4S,5S,6R)-1-[2-(2,2-difluorocyclo-propyl)ethyl]-5,6-difluoro-3-(trifluoromethyl)-5,6-dihydro-4H-cyclopenta[c]pyrazol-4-ol

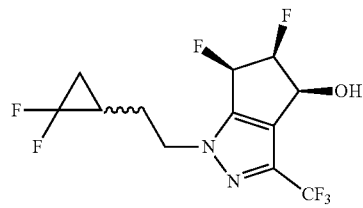 [SMILES: O[C@H]1c2c(C(F)(F)F)nn(CCC3CC3(F)F)c2[C@@H](F)[C@H]1F]

The title compound was prepared in a similar fashion to that described for Example 131 starting from intermediate obtained in step g and racemic 2-(2,2-difluorocyclopropyl)ethanol. 1H NMR (400 MHz, CDCl₃) δ 5.74 (dd, J=57.2, 4.5 Hz, 1H), 5.47-4.94 (m, 2H), 4.32 (t, J=6.6 Hz, 2H), 2.33 (d, J=6.8 Hz, 1H), 2.22-1.88 (m, 2H), 1.58-1.29 (m, 2H), 1.02-0.69 (m, 1H). ¹⁹F NMR (376 MHz, CDCl₃) δ −61.6, −61.7, −128.8 (d, J=21.4 Hz), −129.2 (d, J=21.0 Hz), −144.1, −144.5, −181.5 (d, J=8.3 Hz), −181.7 (d, J=8.2 Hz), −199.3 (d, J=8.3 Hz), −199.5 (d, J=8.3 Hz).

Example 153, 154, and 155: (4S,6S)-1-[(1R,3S,4R)-3,4-difluorocyclohexyl]-5,5,6-trifluoro-3-(trifluoromethyl)-4,6-dihydrocyclopenta[c]pyrazol-4-ol; (4R,6S)-1-[(1S,3R,4S)-3,4-difluorocyclohexyl]-5,5,6-trifluoro-3-(trifluoromethyl)-4,6-dihydrocyclopenta[c]pyrazol-4-ol and (4S,6S)-1-[(1S,3R,4S)-3,4-difluorocyclohexyl]-5,5,6-trifluoro-3-(trifluoromethyl)-4,6-dihydrocyclopenta[c]pyrazol-4-ol

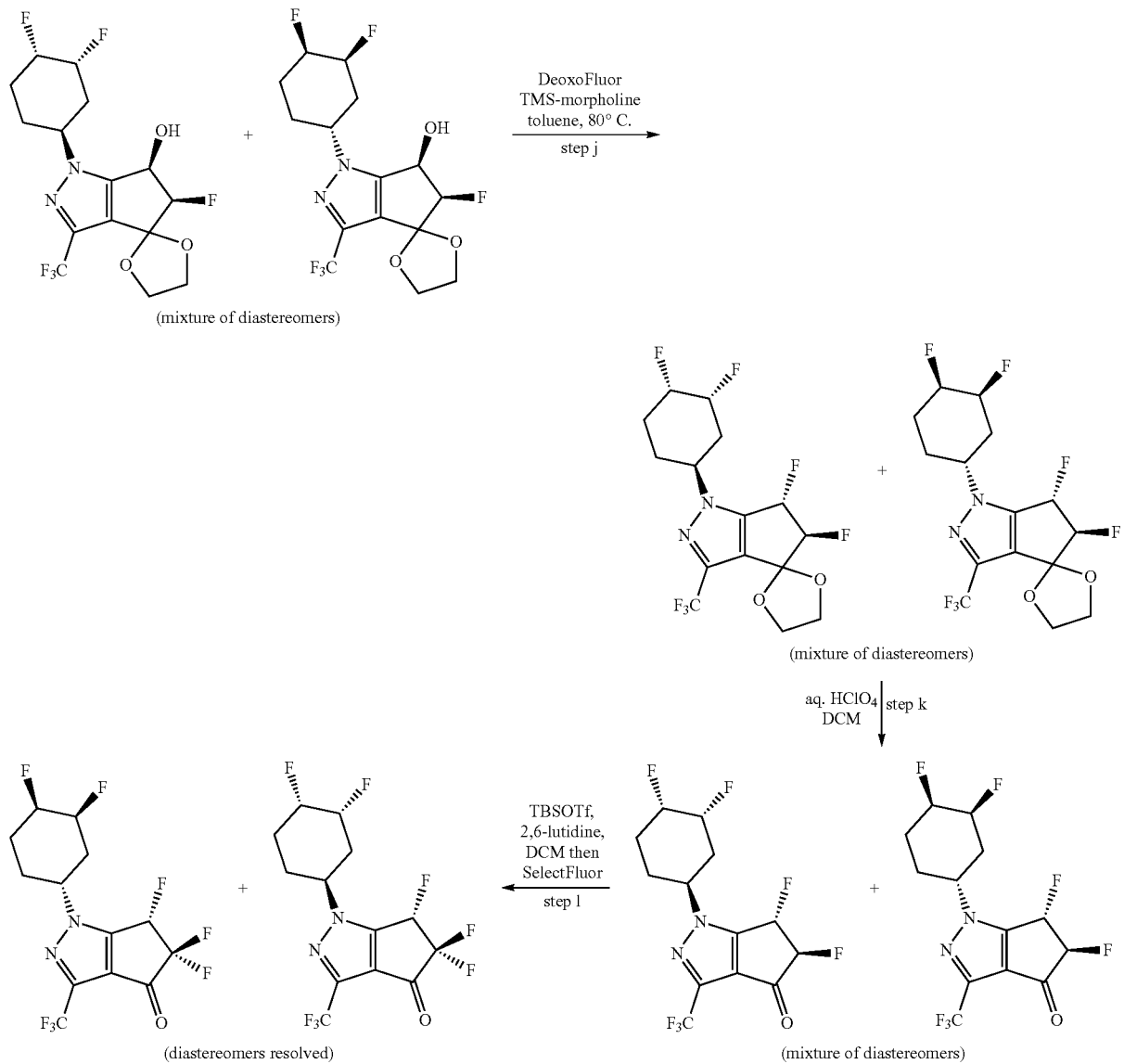

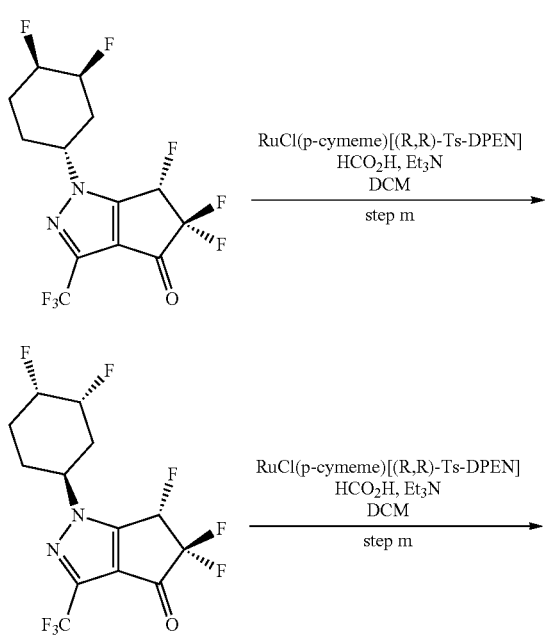

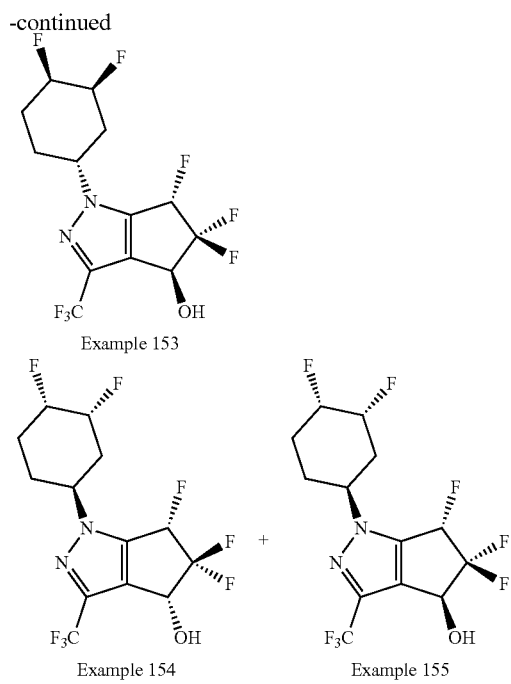

Example 153

Example 154

Example 155

The starting mixture of diastereomers was prepared in a similar fashion to Example 140, steps a-i using 3,4-difluorophenol in step a.

Step j: TMS-morpholine (4.30 mL, 23.9 mmol, 7.10 equiv.) was added to Deoxo-Fluor (50% wt solution in PhMe, 10.4 mL, 23.6 mmol, 7.0 eq) at 0° C. The ice bath was subsequently removed, and the mixture was warmed to room temperature, during which time it became increasingly heterogeneous, and a white precipitate formed. After 1 h, the suspension was added to the mixture of the substrates formed in the previous step (1.30 g, 3.37 mmol, 1.0 equiv.) in toluene (34 mL) at 0° C. The reaction was warmed to room temperature, then heated at 60° C. for 30 min. Upon completion the reaction was quenched with satd. NaHCO$_3$ (30 mL) and diluted with EtOAc (50 mL). The organic layer was separated, and the aqueous layer was extracted with EtOAc (2×50 mL). The combined organic layers were dried over Na$_2$SO$_4$ and concentrated to dryness. The crude material was purified by flash column chromatography (SiO$_2$, EtOAc in hexanes, 0 to 30%) to yield difluoropyrazole (1.00 g, 2.58 mmol, 76% yield).

Step k: To a cooled solution of product from step j (1.00 g, 2.58 mmol, 1.0 equiv.) in CH$_2$Cl$_2$ (26 mL) was added HClO$_4$ (aq. 70%, 2.6 mL, 1M) at 0° C. The mixture was stirred at 0° C. for 1 h when TLC showed complete conversion. The reaction was carefully neutralized with aq. NaHCO$_3$ (10 mL) and the product was extracted with CH$_2$Cl$_2$. The organic phase was separated, dried over Na$_2$SO$_4$ and concentrated to dryness under reduced pressure. The crude material was purified by flash column chromatography (SiO$_2$, EtOAc in hexanes, 0 to 50%) to yield ketone (0.82 g, 2.38 mmol, 92% yield).

Step l: To a solution of the product from step k (0.82 g, 2.38 mmol, 1.0 equiv.) and 2,6-lutidine (2.20 mL, 19.04 mmol, 8.0 equiv.) in CH$_2$Cl$_2$ (12 mL) was added TBSOTf (2.20 mL, 9.52 mmol, 4.0 equiv.) dropwise at room temperature. The resulting solution was stirred for 16 h and then quenched with sat. aq. NaHCO$_3$ solution. The organic phase was separated, and the aqueous phase was washed with 1M HCl (15 mL) and extracted with CH$_2$Cl$_2$. The combined organic phase was then washed with brine, dried over Na$_2$SO$_4$ and concentrated to afford the silyl enol ether. The crude material was then dissolved in MeCN (12 mL) and Selectfluor (1.90 g, 5.24 mmol, 2.2 equiv.) was added at room temperature. The resulting mixture was stirred at 60° C. for 30 min, then cooled down to room temperature, and diluted with EtOAc (30 mL). The mixture was washed with water (2×20 mL), and then with brine (20 mL). The organic phase was separated, dried over Na$_2$SO$_4$ and concentrated to dryness under reduced pressure. The crude product was purified by column chromatography (SiO$_2$, CH$_2$Cl$_2$ in hexanes, 0 to 100%). Second, purification by flash chromatography (SiO$_2$, EtOAc in hexanes, 0 to 30%) separated diastereomers: first eluting diastereomer (DIAST-1, 0.20 g, 0.55 mmol, 23% yield) and second eluting diastereomer (DIAST-2, 0.15 g, 0.41 mmol, 17%).

Step m for DIAST-1: To a solution of the product that eluted first in step 1 (0.20 g, 0.55 mmol, 1.0 equiv.) in DCM (3.0 mL, 0.2M) was added HCO$_2$H (62 μL, 1.65 mmol, 3.0 equiv.) and Et$_3$N (0.15 mL, 1.10 mmol, 2.0 equiv.). After cooling down the solution to 0° C., RuCl(p-cymene)[(R,R)-TsDPEN] (7 mg, 0.011 mmol, 0.02 equiv.) was added and the resulting mixture was kept in the fridge overnight. The reaction was concentrated, and the crude residue was purified by column chromatography (SiO$_2$, CH$_2$Cl$_2$ 100%, then EtOAc in hexanes, 0 to 25%) to give alcohol product, Example 153 (68 mg, 0.19, 34% yield). $^1$H NMR (400 MHz, CDCl$_3$) δ 5.88 (dd, J=56.1, 7.0 Hz, 1H), 5.35-5.27 (m, 1H), 5.27-5.03 (m, 1H), 4.83-4.53 (m, 2H), 2.51 (d, J=11.6 Hz, 1H), 2.46-2.40 (m, 1H), 2.40-2.25 (m, 1H), 2.25-2.09 (m, 3H), 2.04-1.92 (m, 1H). ESI MS [M+H]$^+$ for C$_{13}$H$_{12}$F$_8$N$_2$O, calcd 365.1, found 365.1.

Step m for DIAST-2: To a solution of the product that eluted second in step 1 (0.15 g, 0.41 mmol, 1.0 equiv.) in DCM (2.0 mL, 0.2M) was added HCO$_2$H (46 μL, 1.23 mmol, 3.0 equiv.) and Et$_3$N (0.11 mL, 0.82 mmol, 2.0 equiv.). After cooling down the solution to 0° C., RuCl(p-cymene)[(R,R)-TsDPEN] (6 mg, 0.0082 mmol, 0.02 equiv.)

was added and the resulting mixture was kept in the fridge overnight. The reaction was concentrated, and the purification of the crude residue by column chromatography (SiO$_2$, EtOAc in hexanes, 0 to 20%) separated diastereomers: first eluting diastereomer (DIAST-3, 13.5 mg, 0.037 mmol, 9% yield) and second eluting diastereomer (DIAST-4, 76 mg, 0.21 mmol, 51%). DIAST-3 (Example 154): $^1$H NMR (400 MHz, CDCl$_3$) δ 5.60 (dd, J=55.6, 9.4 Hz, 1H), 5.25-4.97 (m, 2H), 4.83-4.54 (m, 2H), 2.55 (d, J=5.8 Hz, 1H), 2.47 (d, J=6.5 Hz, 1H), 2.31-2.06 (m, 5H). ESI MS [M+H]$^+$ for C$_{13}$H$_{12}$F$_8$N$_2$O, calcd 365.1, found 365.1. DIAST-4 (Example 155): $^1$H NMR (400 MHz, CDCl$_3$) δ 5.86 (ddd, J=56.1, 6.8, 2.0 Hz, 1H), 5.30 (q, J=6.4, 4.9 Hz, 1H), 5.22-5.02 (m, 1H), 4.83-4.55 (m, 2H), 2.67 (d, J=6.7 Hz, 1H), 2.52 (tp, J=8.5, 4.6 Hz, 1H), 2.31-2.05 (m, 5H). ESI MS [M+H]$^+$ for C$_{13}$H$_{12}$F$_8$N$_2$O, calcd 365.1, found 365.1.

Example 156 and 157: (4S,6R)-1-[(1R,3S,4R)-3,4-difluorocyclohexyl]-5,5,6-trifluoro-3-(trifluoromethyl)-4,6-dihydrocyclopenta[c]pyrazol-4-ol and (4S,6R)-1-[(1S,3R,4S)-3,4-difluorocyclohexyl]-5,5,6-trifluoro-3-(trifluoromethyl)-4,6-dihydrocyclopenta[c]pyrazol-4-ol

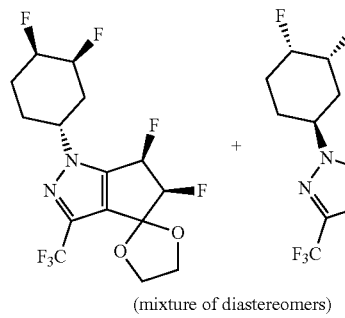

(mixture of diastereomers)

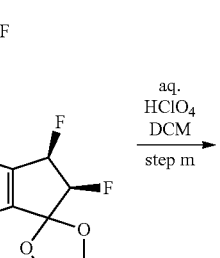

(diastereomers resolved)

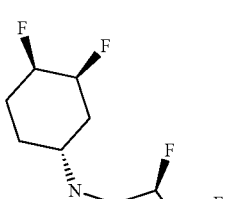

TBSOTf, 2,6-lutidine, DCM then SelectFluor
step n

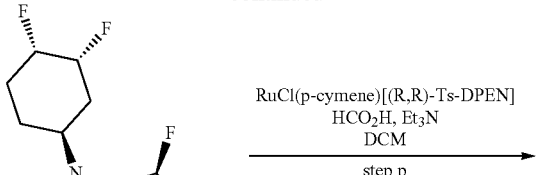

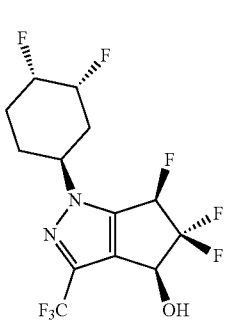

TBSOTf, 2,6-lutidine, DCM then SelectFluor
step n

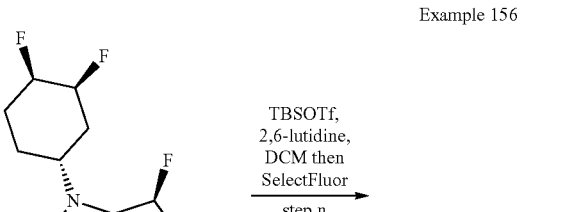

NaBH$_4$
THF/MeOH
step o

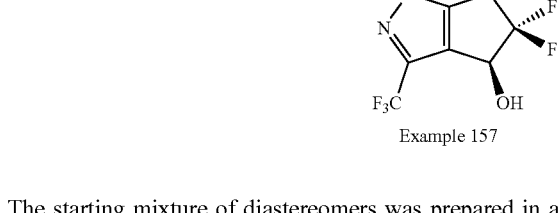

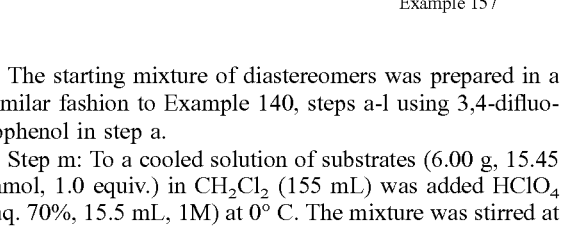

The starting mixture of diastereomers was prepared in a similar fashion to Example 140, steps a-l using 3,4-difluorophenol in step a.

Step m: To a cooled solution of substrates (6.00 g, 15.45 mmol, 1.0 equiv.) in CH$_2$Cl$_2$ (155 mL) was added HClO$_4$ (aq. 70%, 15.5 mL, 1M) at 0° C. The mixture was stirred at 0° C. for 1 h when TLC showed complete conversion. The reaction was carefully neutralized with aq. NaHCO$_3$ (50 mL) and the product was extracted with CH$_2$Cl$_2$. The organic phase was separated, dried over Na$_2$SO$_4$ and concentrated to dryness under reduced pressure. Purification by flash chromatography (SiO$_2$, EtOAc in hexanes, 0 to 50%) separated diastereomers: first eluting diastereomer (DIAST-1, 1.20 g, 3.49 mmol, 23% yield) and second eluting diastereomer (DIAST-2, 1.50 g, 4.36 mmol, 28%).

Step n for DIAST-1: To a solution of the product that eluted first in step m (0.10 g, 0.29 mmol, 1.0 equiv.) and 2,6-lutidine (0.27 mL, 2.32 mmol, 8.0 equiv.) in CH$_2$Cl$_2$ (1.50 mL) was added TBSOTf (0.27 mL, 1.16 mmol, 4.0 equiv.) dropwise at room temperature. The resulting solution was stirred for 16 h and then quenched with sat. aq. NaHCO$_3$ solution. The organic phase was separated, and the aqueous phase was washed with 1M HCl (2 mL) and extracted with CH$_2$Cl$_2$. The combined organic phase was then washed with brine, dried over Na$_2$SO$_4$ and concentrated to afford the silyl enol ether. The crude material was then dissolved in MeCN (1.50 mL) and Selectfluor (0.23 g, 0.64 mmol, 2.2 equiv.) was added at room temperature. The resulting mixture was stirred at 60° C. for 30 min, then cooled down to room temperature, and diluted with EtOAc (5 mL). The mixture was washed with water (2×5 mL), and then with brine (5 mL). The organic phase was separated, dried over Na$_2$SO$_4$ and concentrated to dryness under reduced pressure. The crude product was purified by column chromatography (SiO$_2$, EtOAc in hexanes, 0 to 30%). Second, purification by flash chromatography (SiO$_2$, CH$_2$Cl$_2$ in hexanes, 0 to 100%) yielded ketone (50 mg, 0.14 mmol, 46%).

Step o: To a solution of the product from step n for DIAST-1 (50 mg, 0.14 mmol, 1.0 equiv.) in methanol (0.70 mL, 0.20 M) and THF (0.70 ml, 0.20 M) was added NaBH$_4$ (10 mg, 0.28 mmol, 2.0 equiv.) at 0° C. The resulting solution was stirred at 0° C. for 30 min. The mixture was diluted with EtOAc (3 mL) and washed with 1M HCl (3 mL). The organic layer was washed with brine (3 mL), dried over Na$_2$SO$_4$, and concentrated to dryness. The crude product was purified by column chromatography (SiO$_2$, EtOAc in hexanes, 0 to 50%). Second, purification by flash chromatography (SiO$_2$, CH$_2$Cl$_2$ in hexanes, 0 to 100%) gave the alcohol product, Example 156 (28 mg, 0.077 mmol, 56%). $^1$H NMR (400 MHz, CDCl$_3$) δ 5.61 (dd, J=55.6, 9.4 Hz, 1H), 5.27-4.99 (m, 2H), 4.84-4.55 (m, 2H), 2.63 (d, J=6.5 Hz, 1H), 2.53 (qq, J=8.6, 6.0, 4.8 Hz, 1H), 2.46-2.26 (m, 12H), 2.26-2.06 (m, 3H), 2.06-1.91 (m, 1H). ESI MS [M+H]$^+$ for C$_{13}$H$_{12}$F$_8$N$_2$O, calcd 365.1, found 365.1.

Step n for DIAST-2: To a solution of the product that eluted second in step m (80 mg, 0.23 mmol, 1.0 equiv.) and 2,6-lutidine (0.21 mL, 1.86 mmol, 8.0 equiv.) in CH$_2$Cl$_2$ (1.20 mL) was added TBSOTf (0.21 mL, 0.92 mmol, 4.0 equiv.) dropwise at room temperature. The resulting solution was stirred for 16 h and then quenched with sat. aq. NaHCO$_3$ solution. The organic phase was separated, and the aqueous phase was washed with 1M HCl (2 mL) and extracted with CH$_2$Cl$_2$. The combined organic phase was then washed with brine, dried over Na$_2$SO$_4$ and concentrated to afford the silyl enol ether. The crude material was then dissolved in MeCN (1.20 mL) and Selectfluor (0.18 g, 0.51 mmol, 2.2 equiv.) was added at room temperature. The resulting mixture was stirred at 60° C. for 30 min, then cooled down to room temperature, and diluted with EtOAc (5 mL). The mixture was washed with water (2×5 mL), and then with brine (5 mL). The organic phase was separated, dried over Na$_2$SO$_4$ and concentrated to dryness under reduced pressure. The crude product was purified by column (SiO$_2$, CH$_2$Cl$_2$ in hexanes, 0 to 100%) to yield ketone (30 mg, 0.083 mmol, 36%).

Step p: To a solution of the product from step n for DIAST-2 (30 mg, 0.083 mmol, 1.0 equiv.) in DCM (0.42 mL, 0.2M) was added HCO$_2$H (9.4 µL, 0.25 mmol, 3.0 equiv.) and Et$_3$N (34 µL, 0.25 mmol, 2.0 equiv.). After cooling down the solution to 0° C., RuCl(p-cymene)[(R,R)-TsDPEN] (5 mg, 0.008 mmol, 0.10 equiv.) was added and the resulting mixture was kept in the fridge overnight. The reaction was concentrated, and the crude residue was purified by column chromatography (SiO$_2$, EtOAc in hexanes, 0 to 60%) to give alcohol product, Example 157 (68 mg, 0.19, 34% yield). $^1$H NMR (400 MHz, CDCl$_3$) δ 5.60 (dd, J=55.6, 9.4 Hz, 1H), 5.25-4.98 (m, 3H), 4.85-4.54 (m, 2H), 2.56 (dd, J=15.2, 6.4 Hz, 2H), 2.35-1.98 (m, 6H). ESI MS [M+H]$^+$ for C$_{13}$H$_{12}$F$_8$N$_2$O, calcd 365.1, found 365.1.

Biological Examples

Generation of HIF-2α Luciferase 786-0 Cell Line:

Stable cell lines were generated by transducing 786-0 cells (ATCC, CRL-1932) with Cignal Lenti HIF Luc Reporter lentivirus (CLS-007L, Qiagen) according to the manufacturer's guidelines. In brief, 0.3×106 786-0 cells were transduced with lentivirus at a multiplicity of infection (MOI) of 25 for 24 hours. After transduction, cells were replenished with fresh RPMI 1640 Medium (Cat. No. 11875085, Thermo Fisher) supplemented with 10% FBS (Cat. No. A3160502, Gibco), 2 mM GlutaMAX™ (Cat. No. 35050-061, Invitrogen) and 100 units of penicillin and 100 µg of streptomycin/mL (Cat. No 15070063, Thermo Fisher) for another 24 hours. Antibiotic selection was performed in cell media containing 4 µg/mL of puromycin. After 7 days of antibiotic selection, stable pools of surviving cells were expanded and used in a luciferase reporter assay.

HIF-2α Luciferase Reporter Assay (Serum Free):

On day one, 20 uL of HIF-Luc-786-0 cells in Opti-MEM™ (Cat. No. 31985088, Thermo Fisher) were seeded into each well of a 384 well white opaque plate (Corning 3570) and incubated at 37° C. and 5% CO$_2$. Twenty microliters of 2× test compounds in Opti-MEM™ were added to cells after 4 hours of incubation. Final assay conditions comprised 20,000 cells per well in 1% DMSO with test compound concentrations ranging from 50 uM to 0 uM. After 20 hours incubation at 37° C. and 5% CO$_2$, luciferase activity was determined using ONE-Glo™ Luciferase Assay Reagent (E6110, Promega) following the manufacture's recommended procedure. Briefly, 40 uL of ONE-Glo™ luciferase reagents were added to each well and luciferase signals were measured using an Envision 2102 Multilabel Reader. Percentage maximum activity in each test well was calculated based on DMSO (maximum activity) and no cell control wells (baseline activity). The IC$_{50}$ values of the test compounds were determined from compound dose response curves fitted using a standard four parameter fit equation.

HIF-2α Luciferase Reporter Assay (Serum):

An HRE-luciferase stable reporter 786-0 cell line was maintained in active culture using RPMI 1640 (GIBCO) media supplemented with 1% penicillin-streptomycin, 1% GlutaMAX™, 10% FBS-One Shot (GIBCO) and 4 ug/ml of puromycin (Invitrogen). On the day of the assay, cells were harvested using StemPro™ Accutase™ cell dissociation reagent (GIBCO) and resuspended at 1.5 million cells per milliliter in Opti-MEM™ (GIBCO). 20 ul/well of the resuspended cells were dispensed into a 384 white tissue culture-treated microplate (Corning) and allowed to incubate at 37°

C., 5% $CO_2$ for 3 hours. Compounds were prepared by dispensing 0.8 ul of compound in 100% DMSO into a Greiner plate containing 40 ul/well of 100% human serum (Bioreclamation IVT). After 3 hours, media was removed via centrifugation at 500 RPM for 30 seconds and 30 ul/well of compound diluted in human serum was added. The plate was incubated overnight at 37° C., 5% $CO_2$. The following day, ONE-Glo™ was prepared per vendors instructions. The cell plate was removed from the incubator and the human serum was removed from the plate using centrifugation at 500 RPM for 30 seconds. Following the removal of human serum, 40 ul/well of room temperature Opti-MEM™ was added to the plate and allowed to equilibrate to room temperature for 2 hours. 40 ul/well of ONE-Glo™ reagent was added and allowed to incubate for 10 minutes before reading the luminescence signal on the Envision (PerkinElmer). Data was analyzed using 4-parameter logistic equation to generate $IC_{50}$.

HIF-2α Scintillation Proximity Assay (SPA) Binding Assay:

Tritium labeled compound N-(3-chlorophenyl)-4-nitro-2,1,3-benzoxadiazol-5-amine was obtained from American Radiolabeled Chemicals Inc. and copper chelate PVT SPA beads were from PerkinElmer (Cat #RPNQ0009). Biotin tagged HIF-2α protein containing PAS-B domain (240-350) was prepared and purified in-house.

Compounds solubilized in DMSO were dispensed into a white 384-well polystyrene non-binding flat clear bottom plate (Greiner Bio-One, Cat #781903) using an HP D300 dispenser. Ten microliters of biotinylated HIF-2α protein in buffer (25 mM Tris-HCl, pH 7.4, 150 mM NaCl, 0.15% BSA and 0.001% Tween 20) was added to the compound wells and allowed to incubate for 1 hour at room temperature. Ten microliters of SPA bead mix were added to the wells and incubated for an additional 45 minutes, followed by 10 ul of $^3$H-tracer solution. Final assay conditions comprised 50 nM HIF-2α protein, 25 nM radiolabeled tracer and 3 ug beads per well with compounds in 2% DMSO. The plate was read using a MicroBeta Microplate Counter (PerkinElmer) for luminescence detection. The $IC_{50}$ values of the test compounds were determined from compound dose response curves fitted using a standard four parameter fit equation and are reported in Table 2.

In Table 2, below, when the absolute stereochemistry for particular Example/elution fraction has not yet been determined, the entry lists the tested fraction (e.g., "DIAST-1" or "DIAST-2") as well as the relevant example numbers. With reference to Table 1, Example numbers ending in "a" or "b" refer to elution fractions that have more than one isomer. Therefore, the tested elution fractions for these Examples include more than one isomer and are reported in Table 2 by Example number only.

TABLE 2

Potency of select compounds
For SPA, Luc and Serum Potency: Less than 100 nM (+++), 100 nM to 1 μM (++), greater than 1 μM (+)

| Example # | HIF-2α Scintillation Proximity Assay (SPA) | HIF-2α Luciferase Assay (Luc) | Serum Potency | Serum Shift (approximate) |
|---|---|---|---|---|
| 1 | ++ | + | + | 2 |
| 2 | ++ | ++ | + | 13 |
| 3 | ++ | ++ | ++ | 1 |
| 4 | n.d. | + | — | — |
| 5 | ++ | ++ | + | 18 |
| 6 | n.d. | + | — | — |
| 7 | +++ | +++ | ++ | 5 |
| 8 | n.d. | +++ | ++ | 4 |
| 9 | + | + | — | — |
| 10 | + | + | — | — |
| 11 | n.d. | ++ | +++ | 6 |
| 12 | n.d. | +++ | +++ | 5 |
| 13 | n.d. | ++ | ++ | 2 |
| 14 | n.d. | +++ | +++ | 6 |
| 15 | n.d. | +++ | +++ | 6 |
| 16 | ++ | ++ | + | 22 |
| 17 | +++ | +++ | ++ | 5 |
| 18 | n.d. | ++ | ++ | 4 |
| 19 | n.d. | + | — | — |
| 20 | +++ | +++ | ++ | 7 |
| 21 | ++ | ++ | + | 3 |
| 22 | ++ | ++ | + | 10 |
| 23/24 DIAST-1 | ++ | ++ | + | 6 |
| 23/24 DIAST-2 | ++ | ++ | + | 10 |
| 25 | + | + | — | — |
| 26/27 DIAST-1 | n.d. | + | — | — |
| 26/27 DIAST-2 | n.d. | ++ | + | 10 |
| 28 | n.d. | + | — | — |
| 29 | n.d. | + | — | — |
| 30 | n.d. | +++ | ++ | 8 |
| 31 | ++ | ++ | + | 7 |
| 32 | ++ | +++ | ++ | 10 |
| 33 | ++ | ++ | + | 9 |
| 34 | n.d. | + | — | — |
| 35 | n.d. | + | — | — |
| 36 | ++ | ++ | — | — |
| 37 | + | + | — | — |
| 38 | +++ | ++ | ++ | 8 |
| 39 | ++ | ++ | + | >39 |
| 40 | ++ | ++ | + | 31 |
| 41 | +++ | +++ | ++ | 12 |
| 42 | ++ | ++ | + | 6 |
| 43 | n.d. | ++ | + | 17 |
| 44 | ++ | ++ | + | 6 |
| 45 | ++ | + | — | — |
| 46 | ++ | ++ | ++ | 2 |
| 47 | + | + | — | — |
| 48 | n.d. | + | — | — |
| 49 | ++ | ++ | + | 7 |
| 50 | + | + | — | — |
| 51 | n.d. | ++ | ++ | 3 |
| 52 | n.d. | ++ | + | 7 |
| 53 | n.d. | +++ | ++ | 7 |
| 54 | n.d. | ++ | + | 5 |
| 55 | n.d. | ++ | ++ | 1 |
| 56 | n.d. | ++ | ++ | 2 |
| 57 | n.d. | ++ | ++ | 2 |
| 58 | +++ | +++ | ++ | 3 |
| 59 | n.d. | ++ | + | 7 |
| 60 | + | + | + | 3 |
| 61 | n.d. | +++ | +++ | 5 |
| 62 | n.d. | ++ | ++ | 2 |
| 63 | n.d. | ++ | + | 4 |
| 64 | n.d. | +++ | + | 12 |
| 65 | n.d. | ++ | + | 11 |
| 66 | n.d. | +++ | ++ | 6 |
| 67 | n.d. | ++ | ++ | 7 |
| 68 | n.d. | +++ | — | — |
| 69 | n.d. | + | — | — |
| 70 | n.d. | ++ | ++ | 0 |
| 71 | n.d. | +++ | + | 18 |
| 72/73 DIAST-1 | n.d. | +++ | ++ | 8 |

TABLE 2-continued

Potency of select compounds
For SPA, Luc and Serum Potency: Less than 100 nM (+++),
100 nM to 1 μM (++), greater than 1 μM (+)

| Example # | HIF-2α Scintillation Proximity Assay (SPA) | HIF-2α Luciferase Assay (Luc) | Serum Potency | Serum Shift (approximate) |
|---|---|---|---|---|
| 72/73 DIAST-2 | n.d. | +++ | ++ | 3 |
| 74 | n.d. | +++ | + | 6 |
| 75 | n.d. | +++ | + | 5 |
| 76 | n.d. | ++ | + | 17 |
| 77 | n.d. | +++ | + | 10 |
| 78 | n.d. | +++ | + | 8 |
| 79 | n.d. | +++ | + | 13 |
| 80 | n.d. | ++ | + | >41 |
| 81 | n.d. | ++ | + | 49 |
| 82 | n.d. | ++ | + | 23 |
| 83 | n.d. | ++ | + | 3 |
| 84 | n.d. | ++ | + | 2 |
| 85 | n.d. | ++ | + | 6 |
| 86 | n.d. | ++ | ++ | 3 |
| 87 | n.d. | ++ | + | 7 |
| 88 | n.d. | +++ | ++ | 6 |
| 89 | n.d. | +++ | ++ | 7 |
| 90 DIAST-1 | n.d. | +++ | ++ | 6 |
| 91 DIAST-2 | n.d. | +++ | + | 9 |
| 92/93 DIAST-1 | n.d. | +++ | — | — |
| 92/93 DIAST-1 | n.d. | +++ | — | — |
| 94/95 DIAST-1 | n.d. | +++ | + | 17 |
| 94/95 DIAST-2 | n.d. | +++ | + | 23 |
| 96 | n.d. | +++ | + | 7 |
| 97/98 DIAST-1 | n.d. | ++ | + | 23 |
| 97/98 DIAST-2 | n.d. | +++ | — | — |
| 99 | n.d. | +++ | ++ | 3 |
| 100 | n.d. | ++ | + | 4 |
| 101 | n.d. | +++ | + | 11 |
| 102 | n.d. | ++ | + | 17 |
| 103 | n.d. | + | + | 7 |
| 104 | n.d. | ++ | + | 20 |
| 105 | n.d. | + |  |  |
| 106 | n.d. | ++ | ++ | 1 |
| 107 | n.d. | +++ | — | — |
| 108 | n.d. | +++ | + | 19 |
| 109 | n.d. | ++ | ++ | 4 |
| 110 | n.d. | +++ | + | 225 |
| 111 | n.d. | +++ | + | 9 |
| 112 | n.d. | +++ | + | 17 |
| 113 | n.d. | +++ | + | 14 |
| 114 | n.d. | ++ | + | 27 |
| 115 | n.d. | ++ | + | 45 |
| 116 | n.d. | +++ | + | 73 |
| 117 | n.d. | +++ | + | >62 |
| 118 | n.d. | +++ | + | 119 |
| 119 | n.d. | +++ | + | 73 |
| 120 | n.d. | +++ | ++ | 4 |
| 121 | n.d. | +++ | + | 11 |
| 122 | n.d. | +++ | + | 6 |
| 123 | n.d. | ++ | + | 12 |
| 124 | n.d. | +++ | + | 11 |
| 125/126 DIAST-1 | n.d. | ++ | + | 9 |
| 125/126 DIAST-2 | n.d. | ++ | + | 5 |
| 127 | n.d. | + | + | 3 |
| 128 | n.d. | ++ | + | 4 |
| 129/130 DIAST-1 | n.d. | ++ | + | 18 |
| 129/130 DIAST-2 | n.d. | ++ | + | 17 |
| 131 | n.d. | +++ | +++ | 2 |
| 132 | n.d. | +++ | + | 8 |
| 133 | n.d. | +++ | ++ | 5 |
| 134 | n.d. | +++ | + | 13 |
| 135 | n.d. | +++ | + | 12 |
| 136/137 DIAST-1 | n.d. | +++ | + | 4 |
| 136/137 DIAST-2 | n.d. | +++ | ++ | 7 |
| 138 | n.d. | +++ | + | 9 |
| 139 | n.d. | +++ | + | 6 |
| 140 | n.d. | +++ | ++ | 3 |
| 141/142 DIAST-1 | n.d. | ++ | ++ | 4 |
| 141/142 DIAST-2 | n.d. | ++ | ++ | 3 |
| 143 | n.d. | ++ | + | 9 |
| 144/145 DIAST-1 | n.d. | ++ | + | 3 |
| 144/145 DIAST-2 | n.d. | ++ | ++ | 3 |
| 146/147 DIAST-1 | n.d. | +++ | +++ | 5 |
| 146/147 DIAST-2 | n.d. | +++ | ++ | 8 |
| 148/149 DIAST-1 | n.d. | +++ | +++ | 9 |
| 148/149 DIAST-2 | n.d. | +++ | ++ | 12 |
| 150/151 DIAST-1 | n.d. | ++ | + | 5 |
| 150/151 DIAST-2 | n.d. | + | — | — |
| 152 | n.d. | ++ | ++ | 3 |
| 153 | n.d. | ++ | + | 18 |
| 154 | n.d. | +++ | ++ | 9 |
| 155 | n.d. | + | — | — |
| 156 | n.d. | +++ | ++ | 8 |
| 157 | n.d. | +++ | +++ | 3 |

Although the foregoing disclosure has been described in some detail by way of illustration and example for purposes of clarity of understanding, one of skill in the art will appreciate that certain changes and modifications may be practiced within the scope of the appended claims. Where a conflict exists between the instant application and a reference provided herein, the instant application shall dominate.

What is claimed is:
1. A compound, or a pharmaceutically acceptable salt thereof, having a structure according to Formula I:

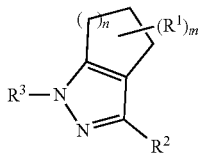

(Formula I)

wherein:
n is 1 or 2;
m is 2, 3, 4, 5, 6, 7, or 8, provided that when n is 1, m is 2, 3, 4, 5, or 6;

each $R^1$ is independently selected from the group consisting of halo, —OH, and —O—($C_1$-$C_3$ alkyl);

$R^2$ is selected from the group consisting of —$C_1$-$C_6$ alkyl, —CN, and —S(O)$_2$—($C_1$-$C_3$ alkyl), wherein the —$C_1$-$C_6$ alkyl and —S(O)$_2$—($C_1$-$C_3$ alkyl) are substituted with 0-3 halo;

$R^3$ is selected from the group consisting of —$C_1$-$C_2$ alkyl substituted with 1-3 $R^4$, —$C_3$-$C_6$ alkyl, —$C_3$-$C_8$ cycloalkyl, -3- to 7-membered heterocycloalkyl having 1-3 heteroatom or heteroatom groups selected from N, O, S, S(=O), and S(=O)$_2$, —Y—($C_3$-$C_6$ cycloalkyl), —Y—O—($C_3$-$C_6$ cycloalkyl), —Y-(3- to 6-membered heterocycloalkyl) having 1-3 heteroatom or heteroatom groups selected from N, O, S, S(=O), and S(=O)$_2$, —X-(phenyl), and —Y-(5- to 6-membered heteroaryl) having 1-3 heteroatoms selected from N, O, and S, wherein the —$C_3$-$C_6$ alkyl, —$C_3$-$C_8$ cycloalkyl, -3- to 7-membered heterocycloalkyl, —Y—($C_3$-$C_6$ cycloalkyl), —Y—O—($C_3$-$C_6$ cycloalkyl), —Y-(3- to 6-membered heterocycloalkyl), —X-(phenyl), and —Y-(5- to 6-membered heteroaryl), are independently substituted with 0-3 $R^4$;

each $R^4$ is independently selected from halo, —$C_1$-$C_6$ alkyl, —CN, —$C_1$-$C_6$ haloalkyl, —OH, —O—($C_1$-$C_6$ alkyl), —Y—O—($C_1$-$C_6$ alkyl), —S—($C_1$-$C_6$ alkyl), —S(O)—($C_1$-$C_6$ alkyl), and —S(O)$_2$—($C_1$-$C_6$ alkyl), wherein the —O—($C_1$-$C_6$ alkyl), —Y—O—($C_1$-$C_6$ alkyl), —S—($C_1$-$C_6$ alkyl), —S(O)—($C_1$-$C_6$ alkyl), and —S(O)$_2$—($C_1$-$C_6$ alkyl) are independently substituted with 0-3 halo;

X is —$C_2$-$C_3$ alkylene-; and

Y is —$C_1$-$C_3$ alkylene-.

2. The compound, or a pharmaceutically acceptable salt thereof, according to claim 1 wherein:

n is 1 or 2;

m is 2, 3, 4, 5, 6, 7, or 8, provided that when n is 1, m is 2, 3, 4, 5 or 6;

each $R^1$ is independently selected from the group consisting of halo, —OH, and —O—($C_1$-$C_3$ alkyl);

$R^2$ is selected from the group consisting of —$C_1$-$C_6$ alkyl, —CN, and —S(O)$_2$—($C_1$-$C_3$ alkyl), wherein the —$C_1$-$C_6$ alkyl and —S(O)$_2$—($C_1$-$C_3$ alkyl) are substituted with 0-3 halo;

$R^3$ is selected from the group consisting of —$C_1$-$C_2$ alkyl substituted with 1-3 $R^4$, —$C_3$-$C_6$ alkyl, —$C_3$-$C_6$ cycloalkyl, —Y—($C_3$-$C_6$ cycloalkyl), —Y—O—($C_3$-$C_6$ cycloalkyl), —Y-(3- to 6-membered heterocycloalkyl) having 1-3 heteroatom or heteroatom groups selected from N, O, S, S(=O), and S(=O)$_2$, and —Y-(5- to 6-membered heteroaryl) having 1-3 heteroatoms selected from N, O, and S, wherein the —$C_3$-$C_6$ alkyl, —$C_3$-$C_6$ cycloalkyl, —Y—($C_3$-$C_6$ cycloalkyl), —Y—O—($C_3$-$C_6$ cycloalkyl), —Y-(3- to 6-membered heterocycloalkyl), and —Y-(5- to 6-membered heteroaryl) are independently substituted with 0-3 $R^4$;

each $R^4$ is independently selected from halo, —$C_1$-$C_6$ alkyl, —CN, —$C_1$-$C_6$ haloalkyl, —OH, —O—($C_1$-$C_6$ alkyl), —S—($C_1$-$C_6$ alkyl), and —S(O)$_2$—($C_1$-$C_6$ alkyl), wherein the —O—($C_1$-$C_6$ alkyl), —S—($C_1$-$C_6$ alkyl), and —S(O)$_2$—($C_1$-$C_6$ alkyl) are independently substituted with 0-3 halo; and Y is —$C_1$-$C_3$ alkylene-.

3. The compound, or pharmaceutically acceptable salt thereof, according to claim 1, wherein the compound of Formula I has a structure according to Formula II:

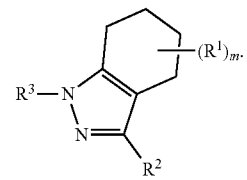

(Formula II)

4. The compound, or pharmaceutically acceptable salt thereof, according to claim 3, wherein the compound of Formula II has a structure according to Formula IIa:

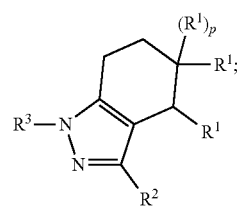

(Formula IIa)

p is 0 or 1.

5. The compound, or pharmaceutically acceptable salt thereof, according to claim 1, wherein:

each $R^1$ is independently halo or —OH;

$R^2$ is —$C_1$-$C_6$ alkyl substituted with 0-3 halo;

$R^3$ is —$C_1$-$C_6$ alkyl, —$C_3$-$C_8$ cycloalkyl, tetrahydropyranyl, or —Y—($C_3$-$C_6$ cycloalkyl), each of which is independently substituted with 1-3 $R^4$;

each $R^4$ is independently halo, —$C_1$-$C_6$ haloalkyl, —O—($C_1$-$C_6$ alkyl), —Y—O—($C_1$-$C_6$ alkyl), —S—($C_1$-$C_6$ alkyl), or —S(O)$_2$—($C_1$-$C_6$ alkyl), wherein the —O—($C_1$-$C_6$ alkyl), —Y—O—($C_1$-$C_6$ alkyl), —S—($C_1$-$C_6$ alkyl), and —S(O)$_2$—($C_1$-$C_6$ alkyl) are independently substituted with 0-3 halo; and Y is —$C_1$-$C_3$ alkylene-.

6. The compound, or pharmaceutically acceptable salt thereof, according to claim 5, wherein each $R^4$ is independently selected from the group consisting of halo, —CN, —O—($C_1$-$C_3$ alkyl), —S—($C_1$-$C_3$ alkyl), and —S(O)$_2$—($C_1$-$C_3$ alkyl), wherein the —O—($C_1$-$C_3$ alkyl), —S—($C_1$-$C_3$ alkyl), and —S(O)$_2$—($C_1$-$C_3$ alkyl) are independently substituted with 0-3 halo.

7. The compound, or pharmaceutically acceptable salt thereof, according to claim 6, wherein each $R^4$ is independently selected-from —F, —CN, —OCH$_3$, —OCF$_2$H, —OCF$_3$, —SCF$_3$, and —S(O)$_2$CF$_3$.

8. The compound, or pharmaceutically acceptable salt thereof, according to claim 5, wherein each $R^4$ is independently halo, —$C_1$-$C_6$ haloalkyl, —O—($C_1$-$C_6$ alkyl), or —Y—O—($C_1$-$C_6$ alkyl), wherein the —O—($C_1$-$C_6$ alkyl), or —Y—O—($C_1$-$C_6$ alkyl) are independently substituted with 0-3 halo.

9. The compound, or pharmaceutically acceptable salt thereof, according to claim 8, wherein each $R^4$ is independently —F, —CF$_3$, —OCH$_3$, —OCF$_3$, or —CH(CH$_3$)—O—CF$_3$.

10. The compound, or pharmaceutically acceptable salt thereof, according to claim 1, wherein the compound has a structure according to Formula III, Formula IIIa, Formula IIIc, or Formula IIId:

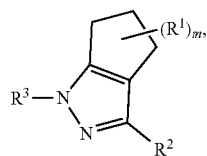
(Formula III)

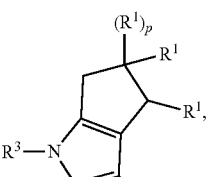
(Formula IIIa)

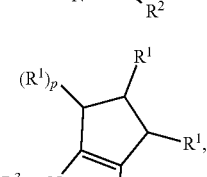
(Formula IIIc)

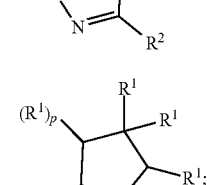
(Formula IIIe)

wherein:
each R¹ is independently halo or —OH;
R² is —$C_1$-$C_6$ alkyl substituted with 0-3 halo, or —S(O)$_2$—($C_1$-$C_3$ alkyl);
R³ is —$C_1$-$C_6$ alkyl substituted with 1-3 R⁴, —$C_3$-$C_6$ cycloalkyl, -6 to 7-membered heterocycloalkyl having one heteroatom or heteroatom group selected from O and S(=O)$_2$, —$C_1$-$C_2$ alkylene-($C_3$-$C_4$ cycloalkyl), —$C_1$-$C_2$ alkylene-(4- to 5-membered heterocycloalkyl) having 1 heteroatom or heteroatom group selected from O and S(=O)$_2$, —$C_2$-$C_3$ alkylene-(phenyl), and —$C_1$-$C_2$ alkylene-(5-membered heteroaryl) having 1-2 heteroatoms selected from N, O, and S, wherein the —$C_3$-$C_6$ cycloalkyl, -6 to 7-membered heterocycloalkyl, —$C_1$-$C_2$ alkylene-($C_3$-$C_4$ cycloalkyl), —$C_1$-$C_2$ alkylene-(4- to 5-membered heterocycloalkyl), —$C_2$-$C_3$ alkylene-(phenyl), and —$C_1$-$C_2$ alkylene-(5-membered heteroaryl) are independently substituted with 0-3 R⁴;
each R⁴ is independently selected from halo, —ON, —$C_1$-$C_6$ haloalkyl, —OH, —O—($C_1$-$C_6$ alkyl), —($C_1$-$C_2$ alkylene)—O—($C_1$-$C_6$ alkyl), —S(O)—($C_1$-$C_6$ alkyl), and —S(O)$_2$—($C_1$-$C_6$ alkyl), wherein the —O—($C_1$-$C_6$ alkyl), —($C_1$-$C_2$ alkylene)—O—($C_1$-$C_6$ alkyl), —S(O)—($C_1$-$C_6$ alkyl), and —S(O)$_2$—($C_1$-$C_6$ alkyl) are independently substituted with 0-3 halo; and
for each of Formula IIIa, Formula IIIc, and Formula IIIe, p is 0 or 1.

11. The compound, or pharmaceutically acceptable salt thereof, according to claim 1, wherein R² is —CF$_3$.

12. The compound, or pharmaceutically acceptable salt thereof, according to claim 1, wherein at least one R¹ is —F.

13. The compound, or pharmaceutically acceptable salt thereof, according to claim 1, wherein at least one R¹ is —OH.

14. The compound, or pharmaceutically acceptable salt thereof, according to claim 1, selected from the group consisting of:

Example 1
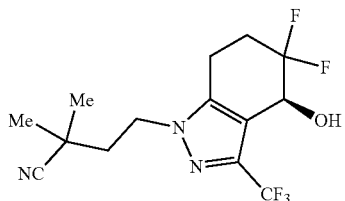

Example 2
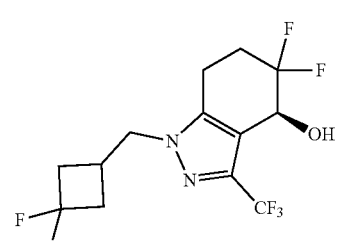

Example 3
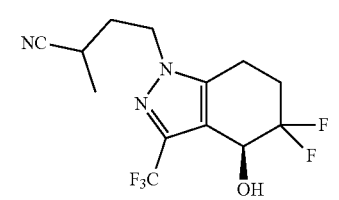

Example 4
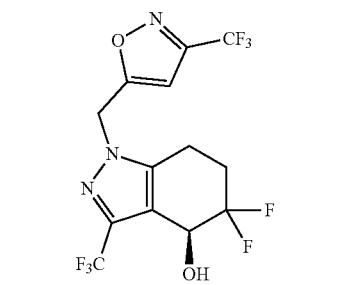

Example 5
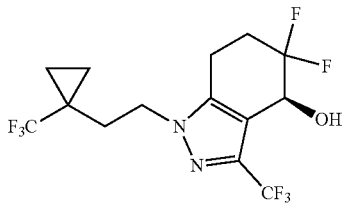

Example 6
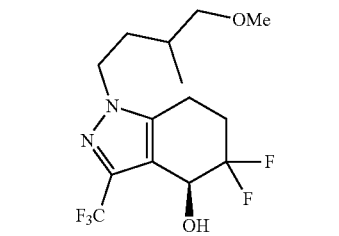

Example 7
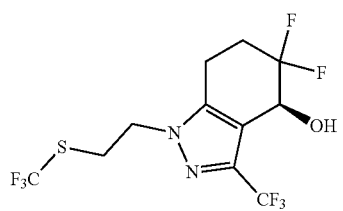
Example 8
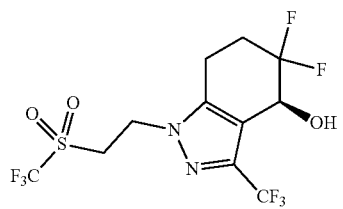
Example 9
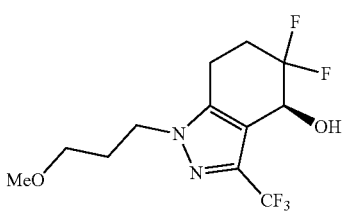
Example 10
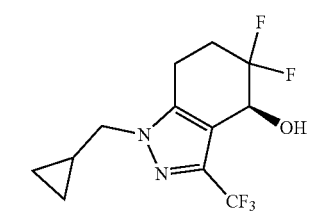
Example 11
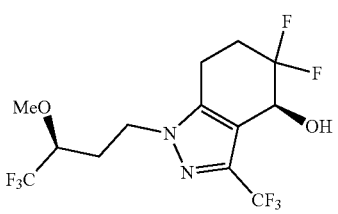
Example 12
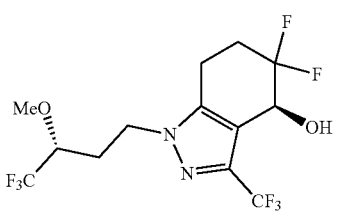
Example 13
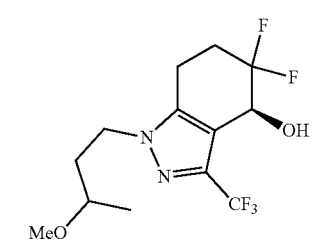
Example 14
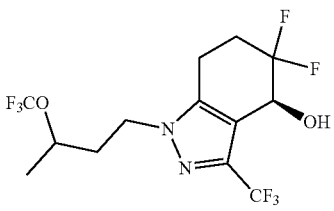
Example 15
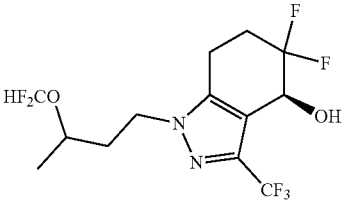
Example 16
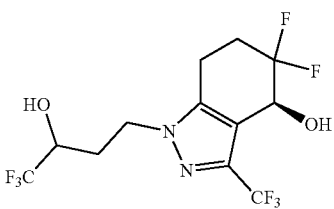
Example 17
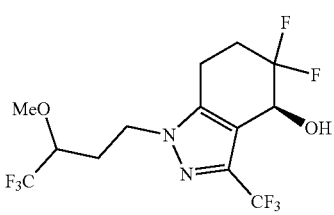
Example 18
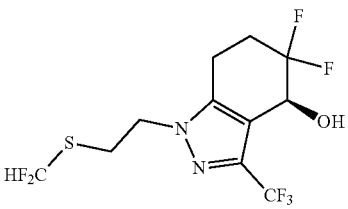
Example 19
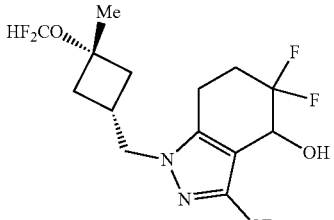
Example 20
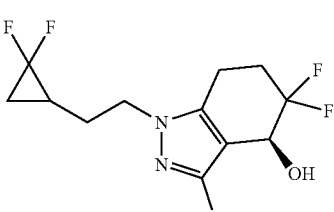

Example 21
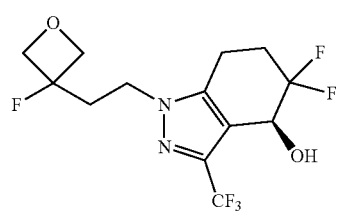
Example 22
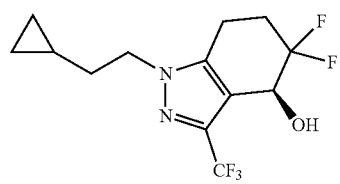
Example 23 and 24
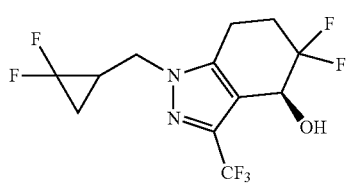
Example 25
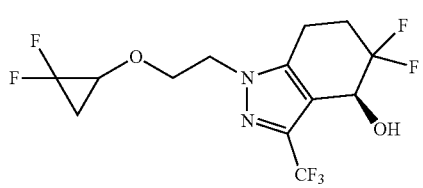
Example 26 and 27
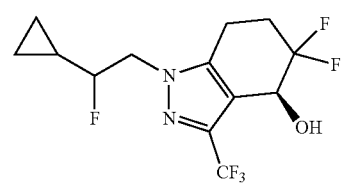
Example 28
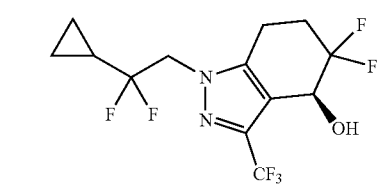
Example 29
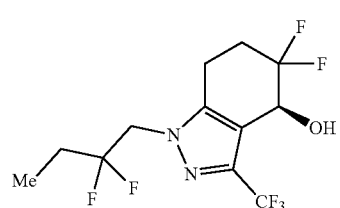
Example 30
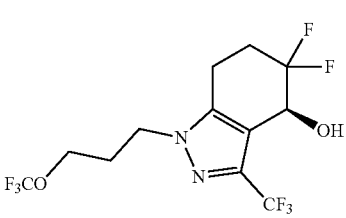
Example 31
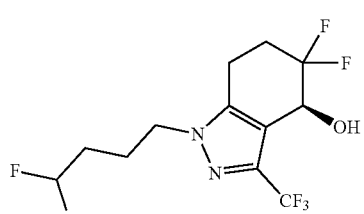
Example 32
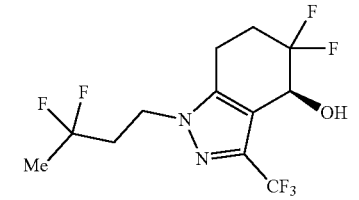
Example 33
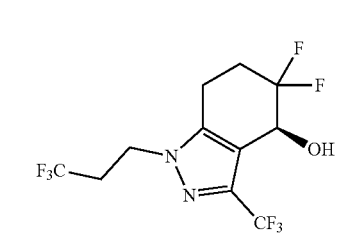
Example 34
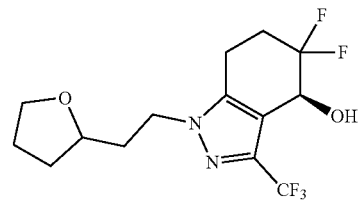
Example 35
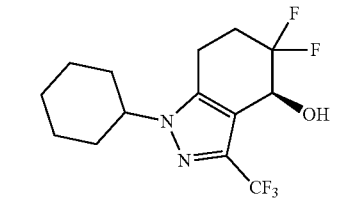
Example 36
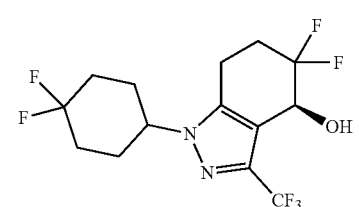
Example 37
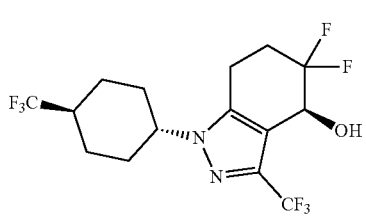

-continued
Example 38
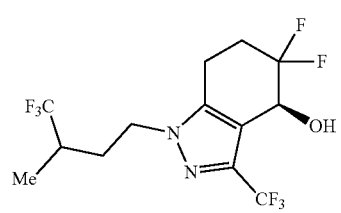
Example 39
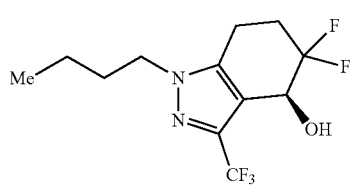
Example 40
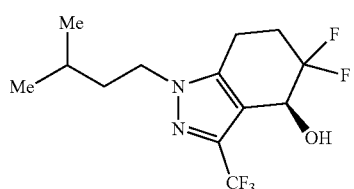
Example 41
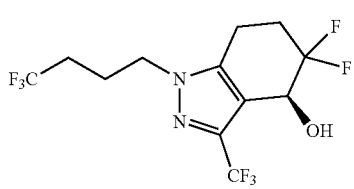
Example 42
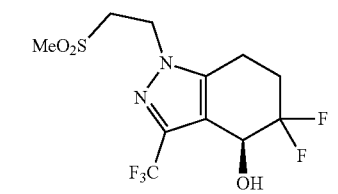
Example 43
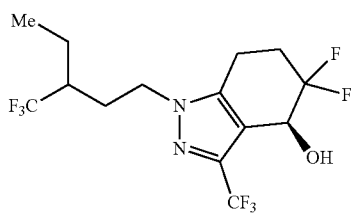
Example 44
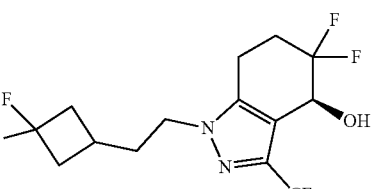
Example 45
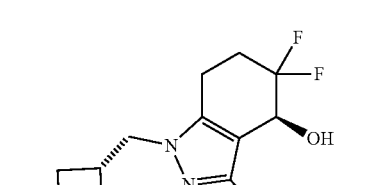
-continued
Example 46
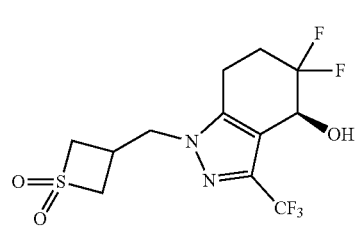
Example 47
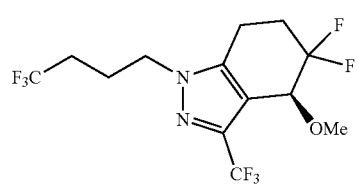
Example 48
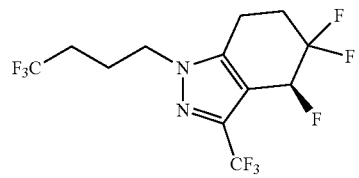
Example 49
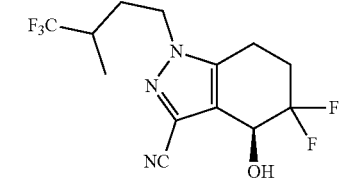
Example 50
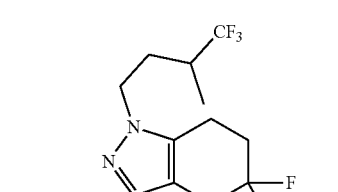
Example 51
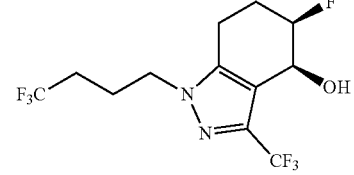
Example 52
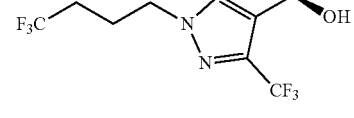

Example 53
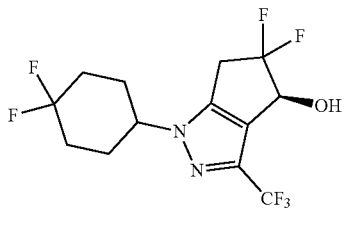
Example 54
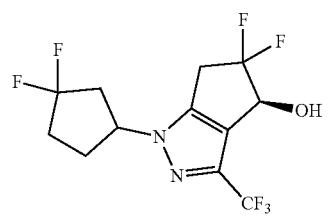
Example 55
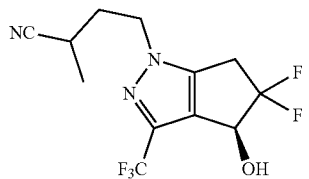
Example 56
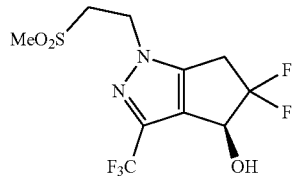
Example 57
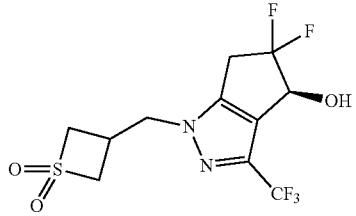
Example 58
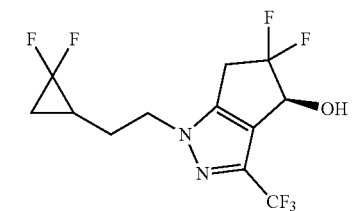
Example 59
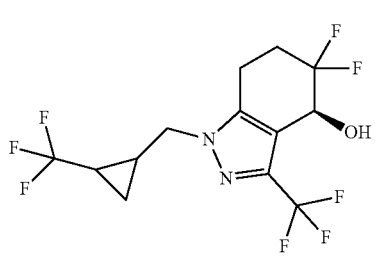
Example 60
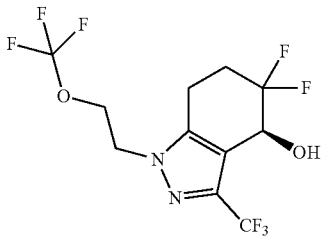
Example 61
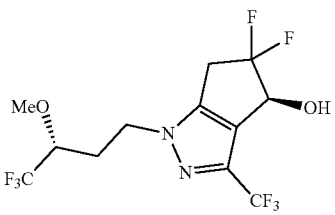
Example 62
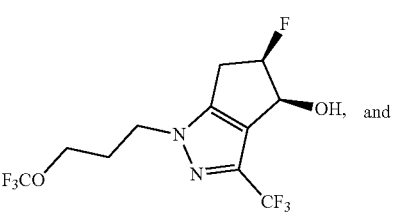
Example 63
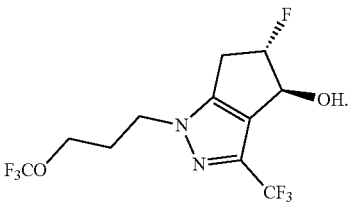
15. The compound, or pharmaceutically acceptable salt thereof, according to claim 1, selected from the group consisting of:
Example 64
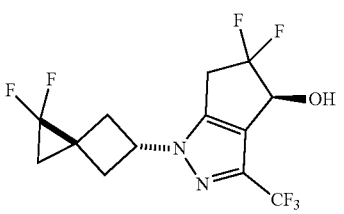
Example 65
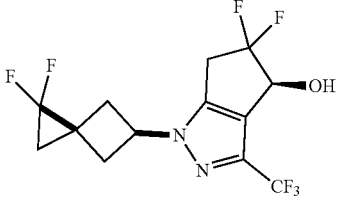

| | |
|---|---|
| Example 66 | 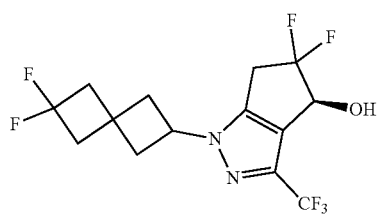 |
| Example 67 | 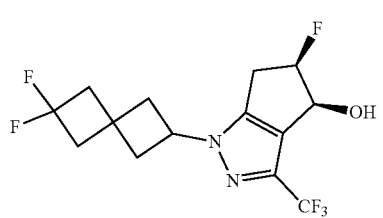 |
| Example 69a | 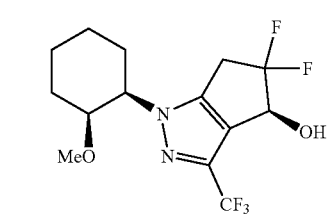 |
| Example 69b | 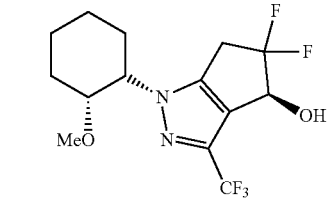 |
| Example 70 | 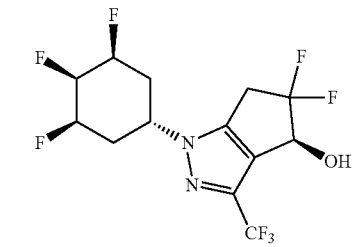 |
| Example 71 | 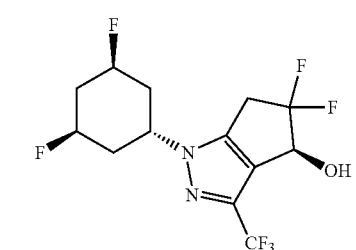 |
| Example 72/73 | 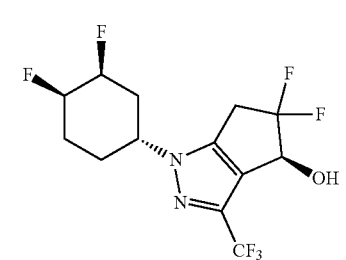 |
| Example 72/73 | 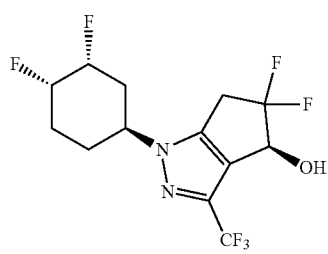 |
| Example 74 | 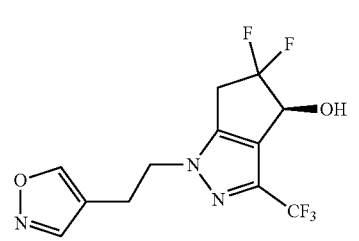 |
| Example 75 | 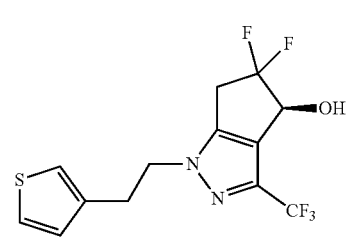 |
| Example 76 | 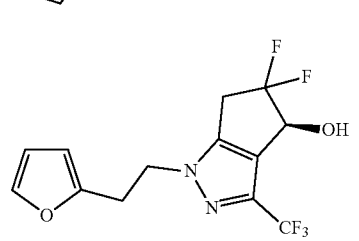 |
| Example 77 | 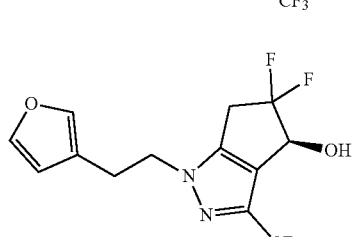 |
| Example 78 | 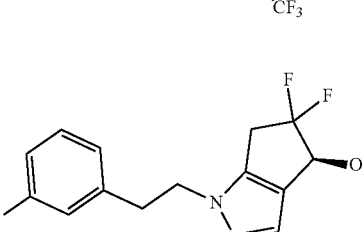 |
| Example 79 | 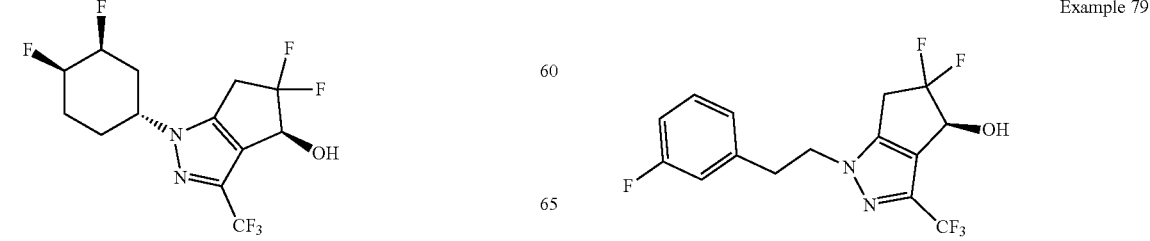 |

Example 80
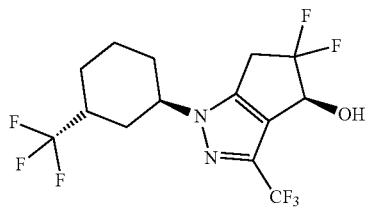
Example 81
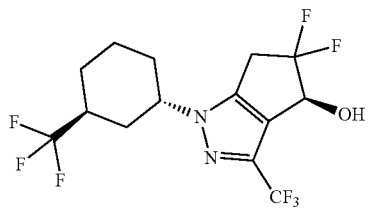
Example 82
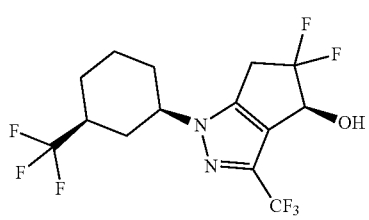
Example 83
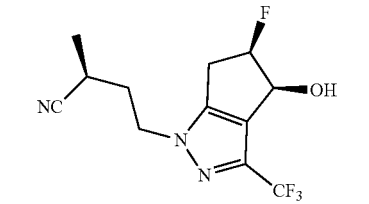
Example 84
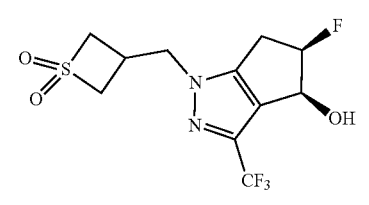
Example 85
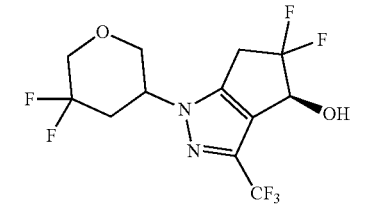
Example 86
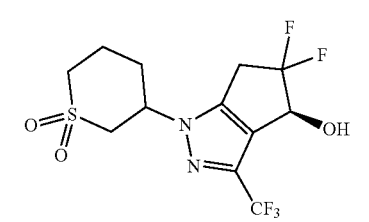
Example 87
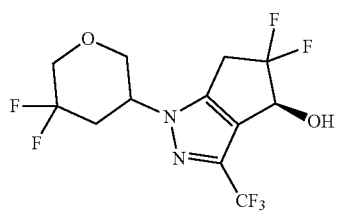
Example 88
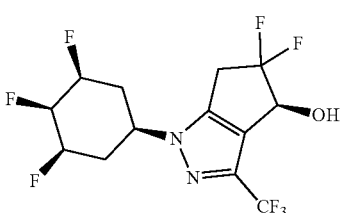
Example 89
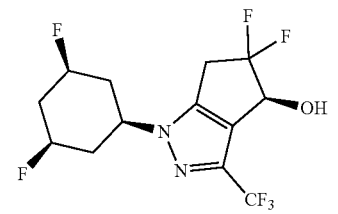
Example 90a
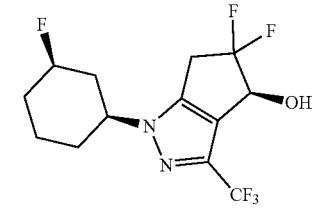
Example 90b
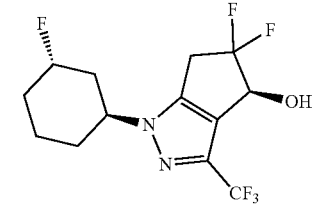
Example 91a
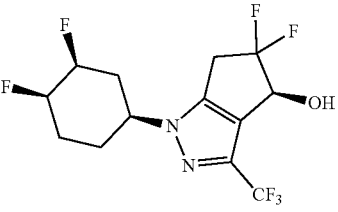
Example 91b
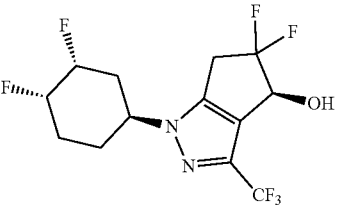

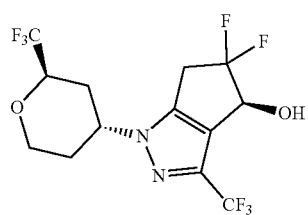
Example 92/93
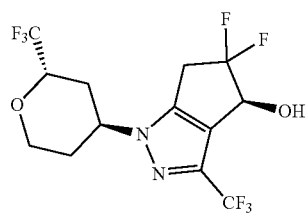
Example 92/93
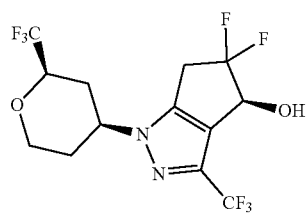
Example 94/95
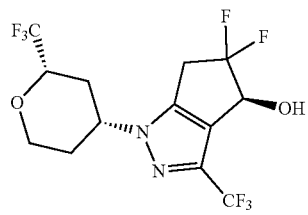
Example 94/95
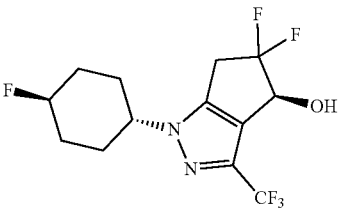
Example 96
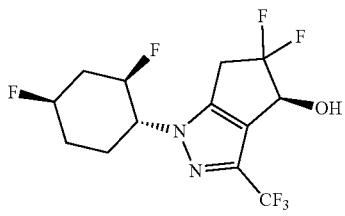
Example 97/98
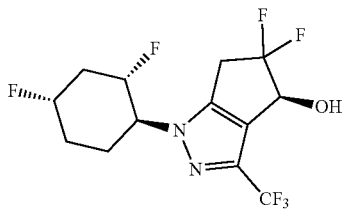
Example 97/98
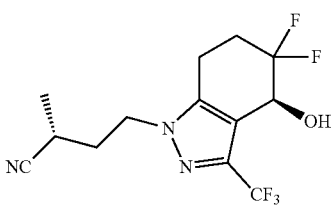
Example 99
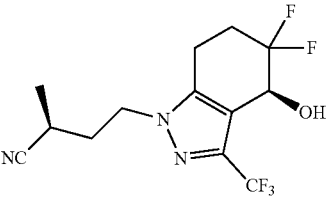
Example 100
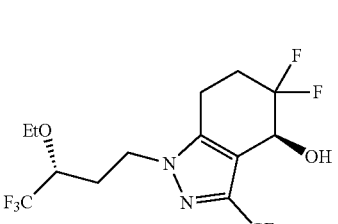
Example 101
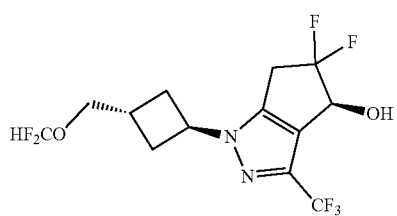
Example 102
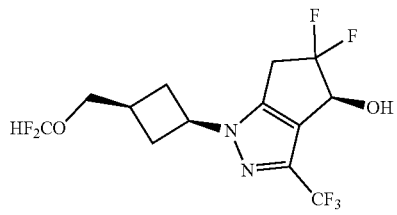
Example 103
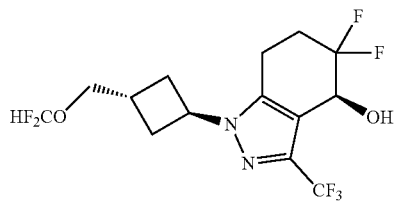
Example 104
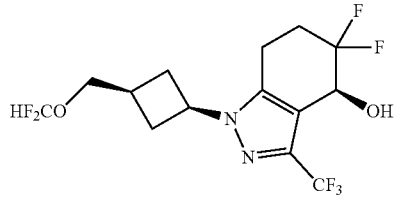
Example 105

-continued
Example 106
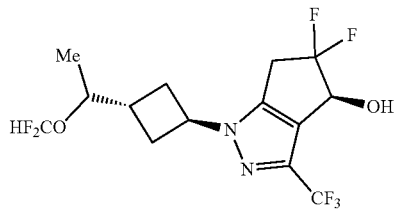
Example 107a
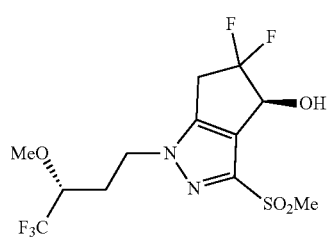
Example 107b
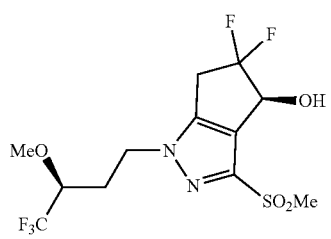
Example 108a
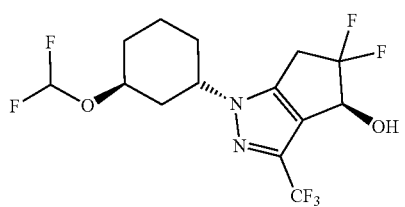
Example 108b
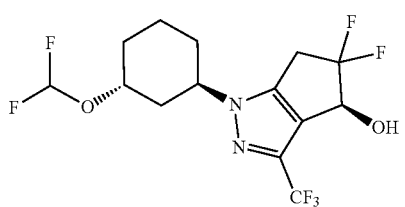
Example 109a
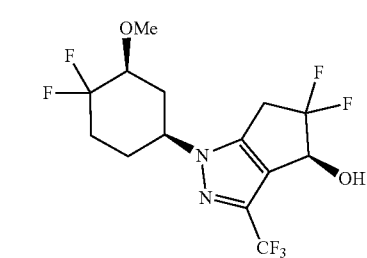
Example 109b
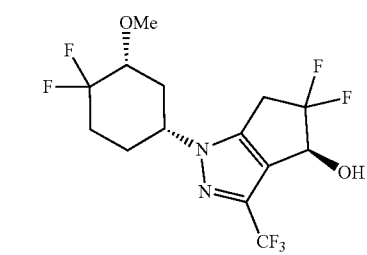
-continued
Example 110a
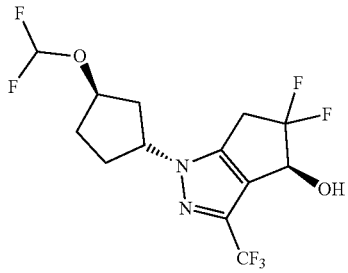
Example 110b
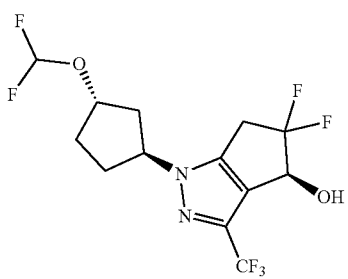
Example 111a
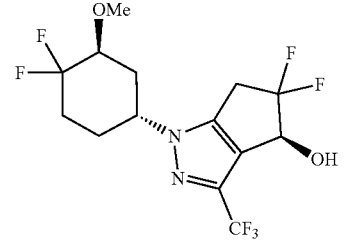
Example 111b
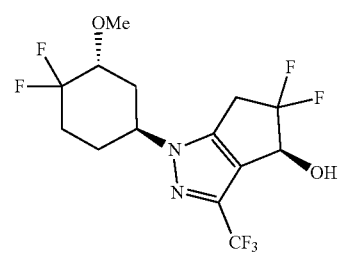
Example 112a
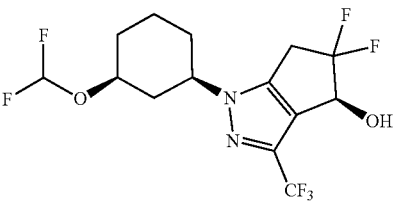
Example 112b
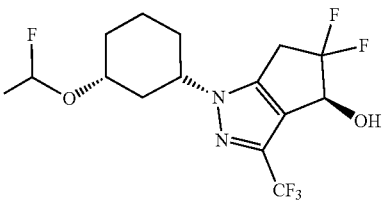

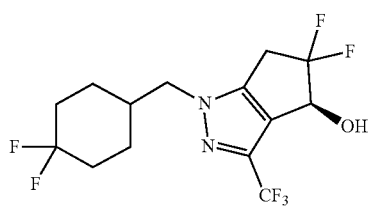
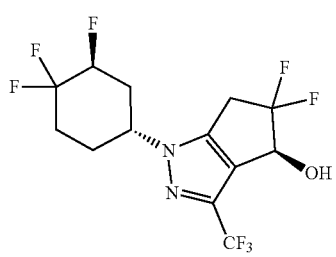
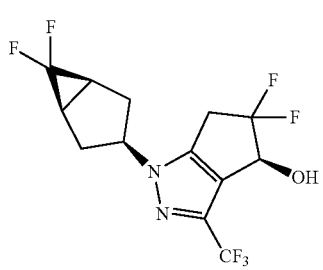

Example 131
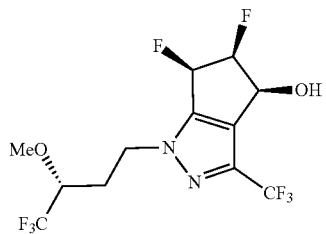
Example 132
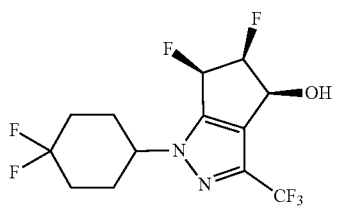
Example 133
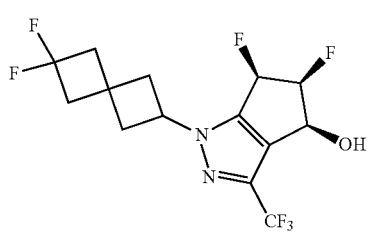
Example 134
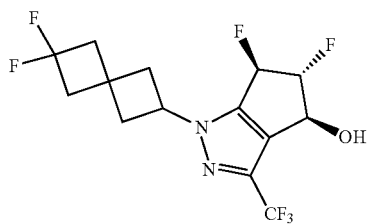
Example 135
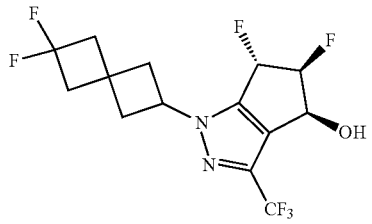
Example 136/137
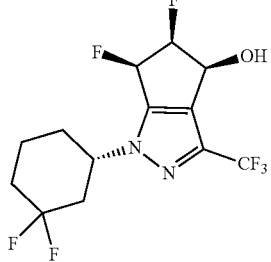
Example 136/137
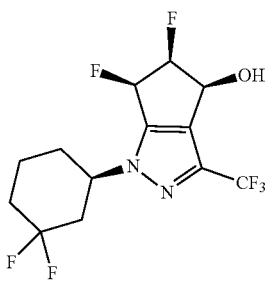
Example 138
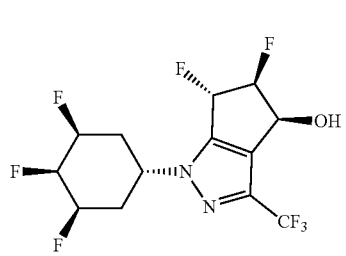
Example 139
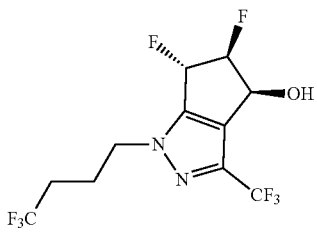
Example 140
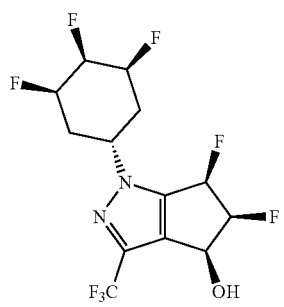
Example 141/142
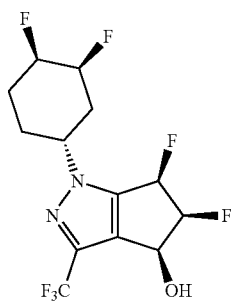

Example 141/142
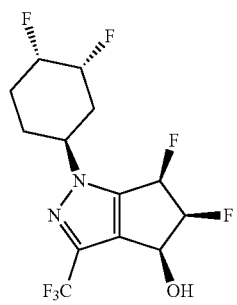
Example 143
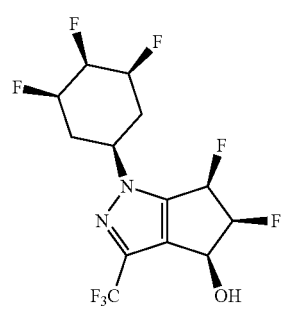
Example 144/145
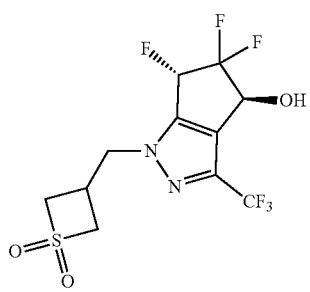
Example 144/145
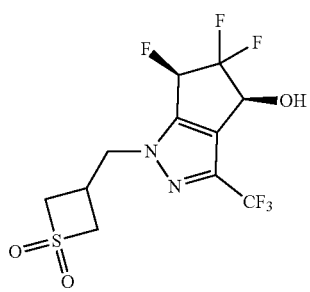
Example 146/147
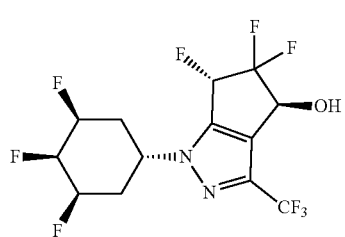
Example 146/147
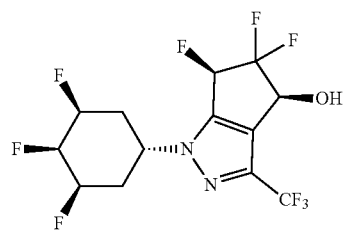
Example 148/149
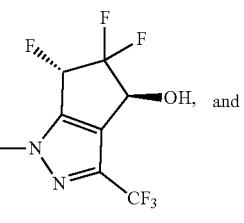
Example 148/149
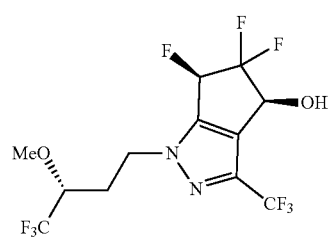
OH, and
Example 148/149
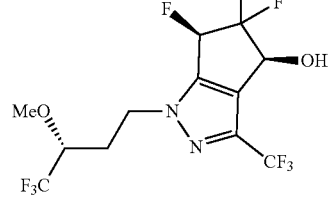
16. The compound, or pharmaceutically acceptable salt thereof, according to claim 1, selected from the group consisting of:
Example 150/151
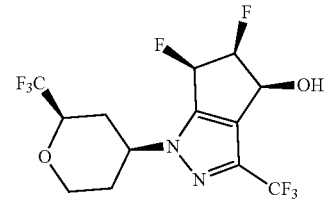
Example 150/151
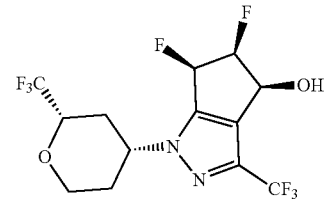
Example 152
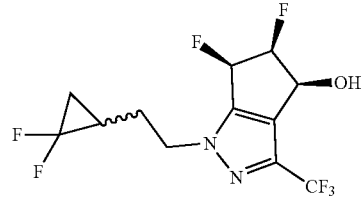

-continued

Example 153

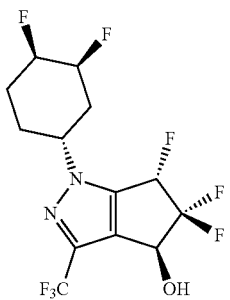

Example 154

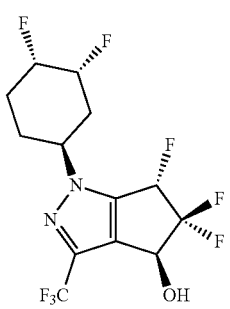

Example 155

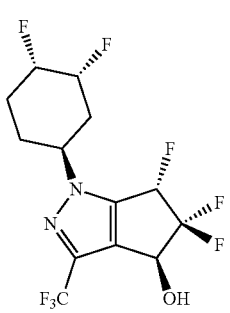

Example 156

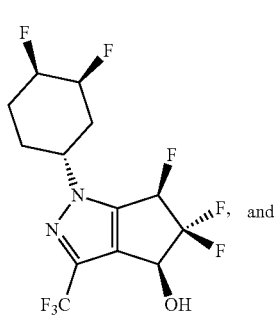

Example 157

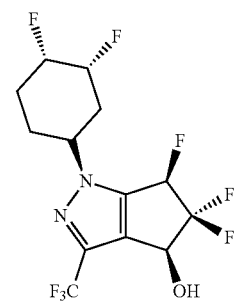

17. A pharmaceutical composition comprising a compound of claim 1, or a pharmaceutically acceptable salt thereof, and a pharmaceutically acceptable excipient.

18. A method of treating a disease, disorder, or condition, mediated at least in part by HIF-2α, said method comprising administering a therapeutically effective amount of a compound or pharmaceutically acceptable salt thereof according to claim 1 to a human subject in need thereof.

19. The method of claim 18, wherein the disease, disorder, or condition is von Hippel-Lindau (VHL) disease.

20. The method of claim 19, wherein the von Hippel-Lindau (VHL) disease is associated with renal cell carcinoma (RCC), central nervous system (CNS) hemangioblastomas, or pancreatic neuroendocrine tumors (pNET).

21. The method of claim 18, wherein the disease, disorder, or condition is cancer.

22. The method of claim 7, wherein the cancer is a cancer of the prostate, colon, rectum, pancreas, cervix, stomach, endometrium, uterus, brain, liver, bladder, ovary, testis, head, neck, skin, mesothelial lining, white blood cell, esophagus, breast, muscle, connective tissue, intestine, lung, adrenal gland, thyroid, kidney, or bone; or is glioblastoma, mesothelioma, renal cell carcinoma, gastric carcinoma, sarcoma, choriocarcinoma, cutaneous basocellular carcinoma, or testicular seminoma.

23. The method of claim 21, wherein the cancer is chosen from melanoma, basal carcinoma, colorectal cancer, pancreatic cancer, liver cancer, breast cancer, prostate cancer, lung cancer, leukemia, a brain tumor, lymphoma, ovarian cancer, Kaposi's sarcoma, renal cell carcinoma, head and neck cancer, esophageal cancer, and urothelieal carcinoma.

24. The method of claim 18, further comprising administering one or more additional therapeutic agents.

25. The method of claim 24, wherein the one or more additional therapeutic agents comprise one or more agents chosen from a tyrosine kinase inhibitor, a cytokine therapy, an antiangiogenic agent, an mTOR inhibitor, an immune checkpoint inhibitor, an inhibitor of CDK-4, an inhibitor of CDK-6, an agent that targets the extracellular production of adenosine, radiation therapy, and a chemotherapeutic agent.

26. The compound or pharmaceutically acceptable salt according to claim 1, wherein the compound of Formula I has a structure according to Formula III:

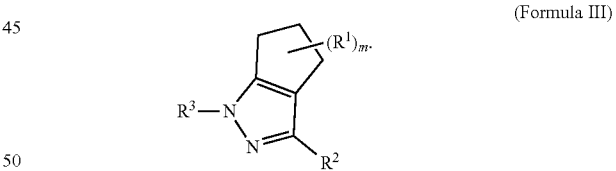

(Formula III)

27. The compound or pharmaceutically acceptable salt according to claim 26, wherein the compound of Formula III has a structure according to Formula IIIa, Formula IIIc, or Formula IIIe:

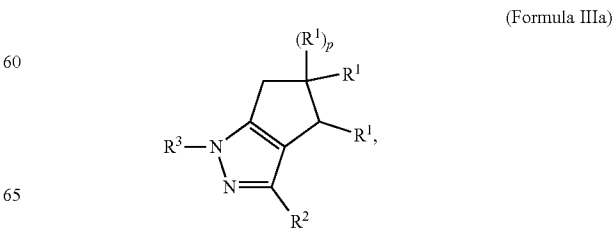

(Formula IIIa)

253
-continued

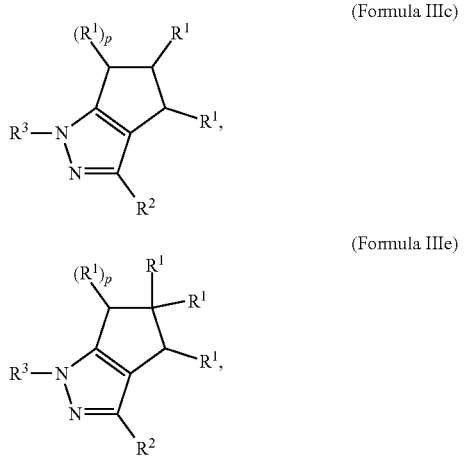

wherein for each of Formula IIIa, Formula IIIc, and Formula IIIe, p is 0 or 1.

28. A compound chosen from:

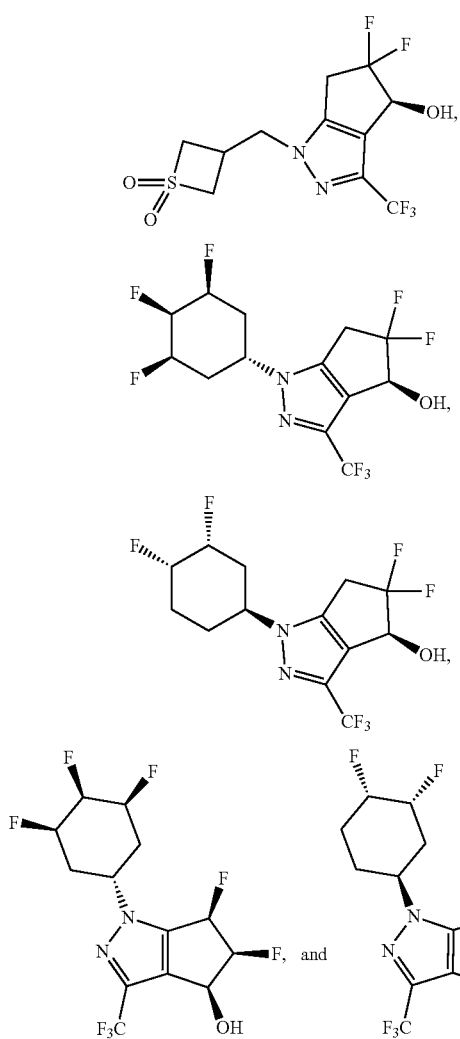

29. A compound having the structure:

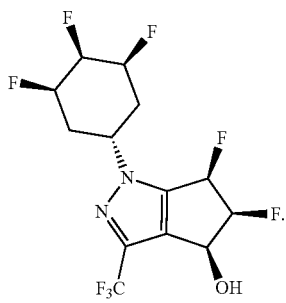 [SMILES: O[C@H]1c2c(C(F)(F)F)nn([C@@H]3C[C@@H](F)[C@@H](F)[C@@H](F)C3)c2[C@@H](F)[C@H]1F]

30. A compound having the structure:

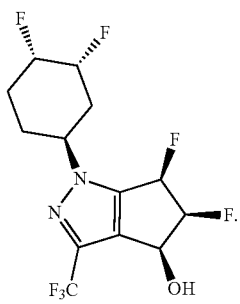 [SMILES: O[C@H]1c2c(C(F)(F)F)nn([C@H]3CC[C@H](F)[C@H](F)C3)c2[C@@H](F)[C@H]1F]

31. A compound having a structure according to Formula I:

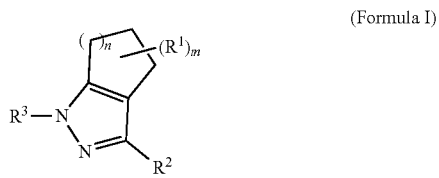

wherein:
n is 1 or 2;
m is 2, 3, 4, 5, 6, 7, or 8, provided that when n is 1, m is 2, 3, 4, 5, or 6;
each $R^1$ is independently chosen from halo, —OH, and —O—($C_1$-$C_3$ alkyl);
$R^2$ is chosen from —$C_1$-$C_6$ alkyl, —CN, and —S(O)$_2$—($C_1$-$C_3$ alkyl), wherein the —$C_1$-$C_6$ alkyl and —S(O)$_2$—($C_1$-$C_3$ alkyl) are substituted with 0-3 halo;
$R^3$ is chosen from —$C_1$-$C_2$ alkyl substituted with 1-3 $R^4$, —$C_3$-$C_6$ alkyl, —$C_3$-$C_8$ cycloalkyl, -3- to 7-membered heterocycloalkyl having 1-3 heteroatom or heteroatom groups chosen from N, O, S, S(=O), and S(=O)$_2$, —Y—($C_3$-$C_6$ cycloalkyl), —Y—O—($C_3$-$C_6$ cycloalkyl), —Y-(3- to 6-membered heterocycloalkyl) having 1-3 heteroatom or heteroatom groups chosen from N, O, S, S(=O), and S(=O)$_2$, —X-(phenyl), and —Y-(5- to 6-membered heteroaryl) having 1-3 heteroatoms chosen from N, O, and S, wherein the —$C_3$-$C_6$ alkyl, —$C_3$-$C_8$ cycloalkyl, -3- to 7-membered heterocycloalkyl, —Y—($C_3$-$C_6$ cycloalkyl), —Y—O—($C_3$-$C_6$ cycloalkyl), —Y-(3- to 6-membered heterocycloalkyl), —X-(phenyl), and —Y-(5- to 6-membered heteroaryl), are independently substituted with 0-3 $R^4$;

each $R^4$ is independently chosen from halo, —$C_1$-$C_6$ alkyl, —CN, —$C_1$-$C_6$ haloalkyl, —OH, —O—($C_1$-$C_6$ alkyl), —Y—O—($C_1$-$C_6$ alkyl), —S—($C_1$-$C_6$ alkyl), —S(O)—($C_1$-$C_6$ alkyl), and —S(O)$_2$—($C_1$-$C_6$ alkyl), wherein the —O—($C_1$-$C_6$ alkyl), —Y—O—($C_1$-$C_6$ alkyl), —S—($C_1$-$C_6$ alkyl), —S(O)—($C_1$-$C_6$ alkyl), and —S(O)$_2$—($C_1$-$C_6$ alkyl) are independently substituted with 0-3 halo;

X is —$C_2$-$C_3$ alkylene-; and

Y is —$C_1$-$C_3$ alkylene-.

\* \* \* \* \*

UNITED STATES PATENT AND TRADEMARK OFFICE
CERTIFICATE OF CORRECTION

PATENT NO. : 12,071,411 B2
APPLICATION NO. : 18/050557
DATED : August 27, 2024
INVENTOR(S) : Joel Worley Beatty et al.

It is certified that error appears in the above-identified patent and that said Letters Patent is hereby corrected as shown below:

In the Claims

Claim 10, Column 227, Line 55 should read:
each R4 is independently selected from halo, -CN, Claim 22, Column 252, Line 15 should read:
The method of claim 21, wherein the cancer is a cancer Signed and Sealed this
Tenth Day of December, 2024

Katherine Kelly Vidal
*Director of the United States Patent and Trademark Office*